(12) United States Patent
Arbuthnot et al.

(10) Patent No.: US 8,293,974 B2
(45) Date of Patent: Oct. 23, 2012

(54) USE OF DOUBLE STRANDED RNA HAIRPIN DUPLEXES IN GENE SILENCING

(75) Inventors: Patrick Arbuthnot, Kensington (ZA); Marc Saul Weinberg, Midrand (ZA); Marie Emma Christine Rey, Johannesburg (ZA); Johan Harmse, Meyersdal (ZA); Sarah Helen Taylor, Edenvale (ZA)

(73) Assignee: University of Witwatersrand, Johannesburg (ZA)

( * ) Notice: Subject to any disclaimer, the term of this patent is extended or adjusted under 35 U.S.C. 154(b) by 259 days.

(21) Appl. No.: 12/524,909

(22) PCT Filed: Jan. 29, 2008

(86) PCT No.: PCT/IB2008/050316
§ 371 (c)(1), (2), (4) Date: Nov. 20, 2009

(87) PCT Pub. No.: WO2008/093283
PCT Pub. Date: Aug. 7, 2008

(65) Prior Publication Data
US 2010/0152282 A1    Jun. 17, 2010

(30) Foreign Application Priority Data
Jan. 29, 2007   (ZA) .................................. 2007-00815

(51) Int. Cl.
| C12N 15/113 | (2010.01) |
| C12N 5/10 | (2006.01) |
| C12N 15/01 | (2006.01) |
| C12N 15/34 | (2006.01) |
| C12N 15/82 | (2006.01) |
| C12P 19/34 | (2006.01) |

(52) U.S. Cl. ....... 800/285; 435/91.1; 435/468; 435/440; 435/91.2; 536/24.5; 536/23.72; 800/279

(58) Field of Classification Search .................. 800/285
See application file for complete search history.

(56) References Cited

U.S. PATENT DOCUMENTS
6,468,745 B1   10/2002   Fitzmaurice et al.
2006/0200878 A1*  9/2006   Lutfiyya et al. ............... 800/285

FOREIGN PATENT DOCUMENTS
WO    WO-95/03404 A1    2/1995
WO    WO-03/042385 A2   5/2003

OTHER PUBLICATIONS

Watanbe et al. Intacellular-diced dsRNA has enhanced efficacy for silencing HCV RNA and overcomes varaiation in the viral genotype (2006) Gene Therapy 13: 883-892.*
Clark et al. High sensativity mapping of methylatedd cytosines (1994) Nucleic Acids Res. 22: 2992-2997.*
Meyerhans et al. Strand-specific PCR amplification of low copy number DNA (1992) Nucleic Acids Res. 20: 521-523.*
Zhang et al. Resistance to cassava mosaic disease in transgenic cassava expressing antisense RNAs targeting virus replication genes (2005) Plant Biotechnol. J. 3: 385-397.*
Dalzel et al. Short interfering RNA-mediated gene silencing in *Globodera pallida* and *Meloidogyne incognita* infective stage juveniles (2010) Int. J. Parasitol. (2010) 40: 91-100.*
Mallory et al. MicroRNA control of *PHABULOSA* in leaf development: importance of pairing to the microRNA 5 region (2004) EMBO J. 23: 3356-3364.*
Jing Qu et al., "Artificial MicroRNA-Mediated Virus Resistance in Plants," *Journal of Virology*, Jun. 2007, vol. 81, No. 12, pp. 6690-6699.
T. Watanabe et al., "Intracellular-diced dsRNA has enhanced efficacy for silencing HCV RNA and overcomes variation in the viral genotype," *Gene Therapy*, 2006, vol. 13, pp. 883-892.
P. Konstantinova et al., "Inhibition of human immunodeficiency virus type 1 by RNA interference using long-hairpin RNA," *Gene Therapy*, 2006, vol. 13, pp. 1403-1413.
J. Wang et al., "Rice ubiquitin promoters: deletion analysis and potential usefulness in plant transformation systems," *Plant Cell Rep.*, 2003, vol. 22, pp. 129-134.
Matthew R. Giese et al., "Stability of RNA Hairpins Closed by Wobble Base Pairs," *Biochemistry*, 1998, vol. 37, pp. 1094-1100.
Michael Smith, "In Vitro Mutagenesis," *Ann. Rev. Genet.*, 1985, vol. 19, pp. 423-462.
Christian Zwieb et al., "Point mutation in the middle of 16S ribosomal RNA of *E. coli* produced by deletion loop mutagenesis," *Nucleic Acid Research*, 1984, vol. 12, No. 10, pp. 4361-4375.
Nakano et al., Rearrangements of Large-Insert T-DNAs in Transgenic Rice, *Mol. Genet. Genomics* 273(2):123-9 (2005).

* cited by examiner

*Primary Examiner* — David T Fox
*Assistant Examiner* — Steven Bernacki
(74) *Attorney, Agent, or Firm* — RatnerPrestia

(57) ABSTRACT

A DNA polynucleotide is described herein having a modified sequence of a target gene, wherein any one type of nucleotide in the target gene sequence has been chemically modified to another type of nucleotide; and a complementary sequence of the unmodified target gene; wherein either one of the modified sequence or the complementary sequence is in a reverse orientation to the other sequence; and wherein the RNA sequence transcribed from the DNA polynucleotide forms a duplex between the modified sequence and the complementary sequence so that a long double stranded RNA (IdsRNA) duplex forms between the modified and complementary sequences with base pair mismatches where the nucleotides have been modified, the IdsRNA duplex being capable of inhibiting expression of the target gene. RNA polynucleotides and IdsRNA duplexes transcribed by the DNA polynucleotide are also described, as is a method for producing the IdsRNA duplexes. These IdsRNA duplexes can be used in gene silencing.

12 Claims, 63 Drawing Sheets

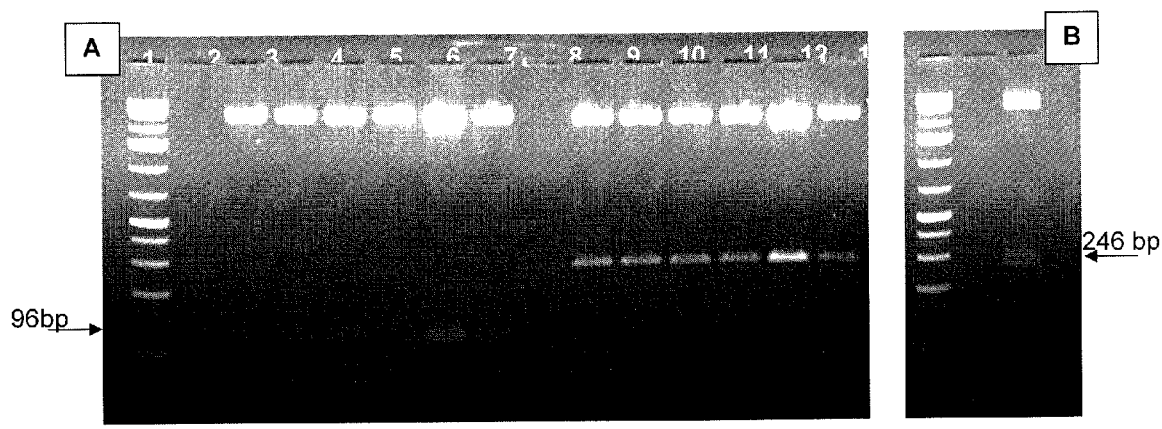
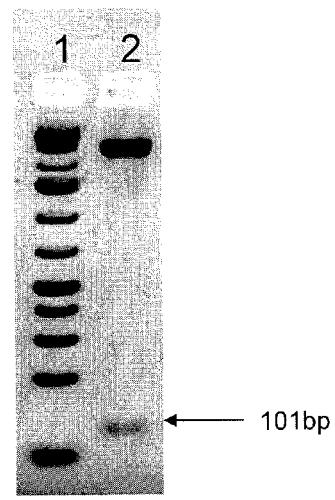
Fig 8A and B
Fig 8C

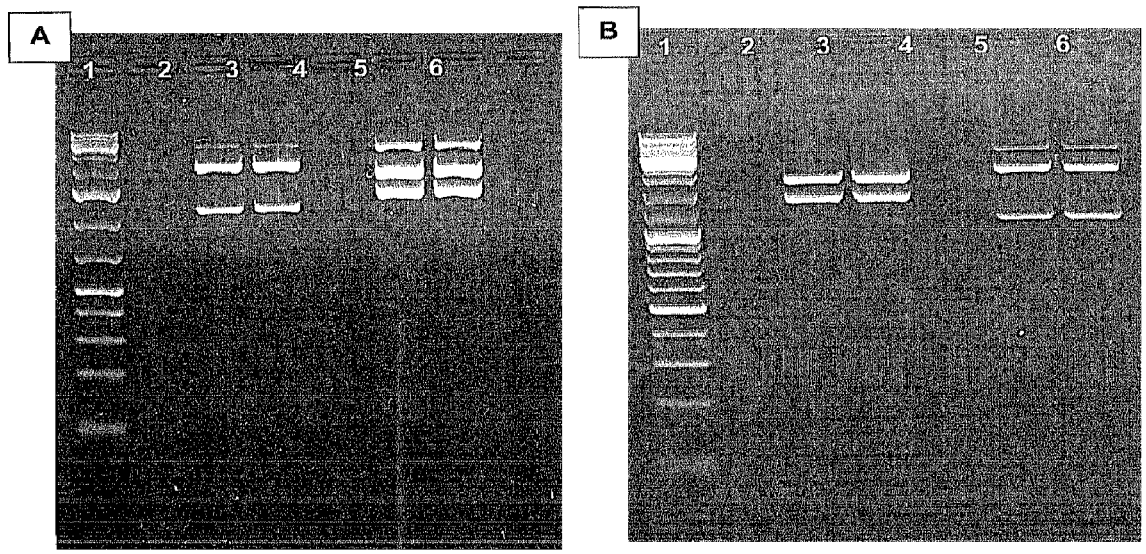
Fig 9A and B
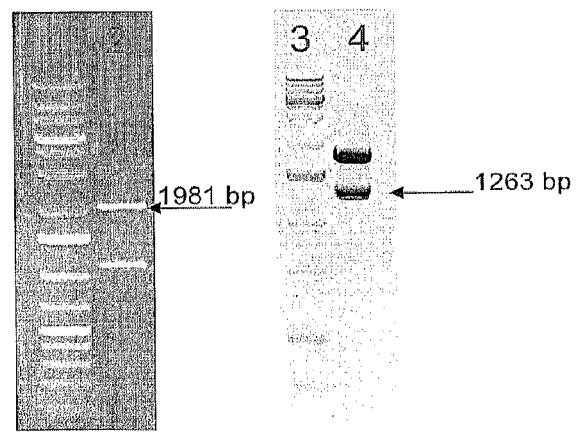
Fig 9C

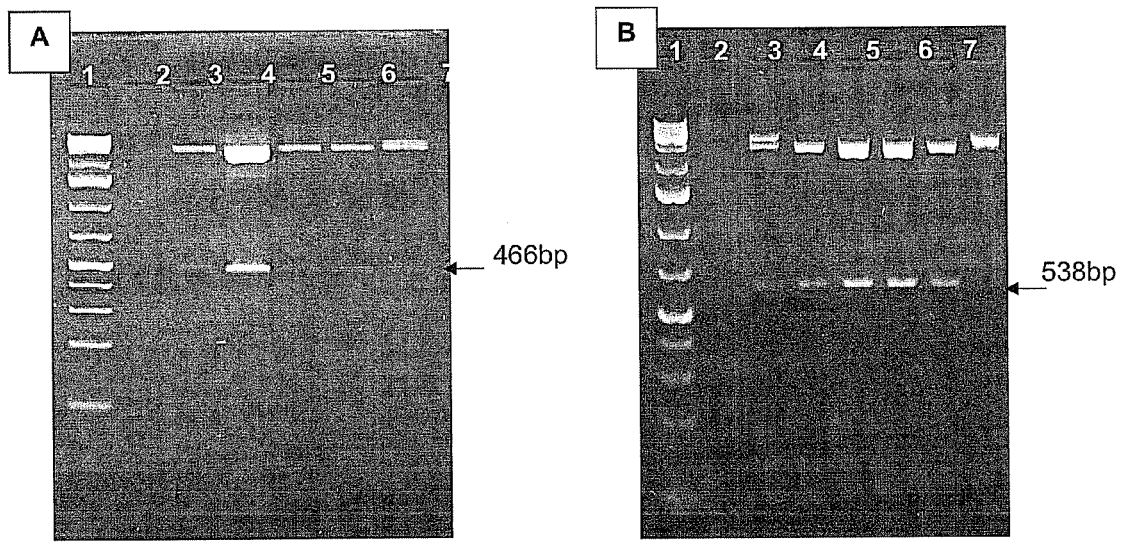
Fig 10A and B
Fig 10C

BC1 Sequence with targeted area indicated

```
  1 caattgttta ttacaattgc cttggtgcgt cggatttat tttgtagaga cacttgttta
 61 tggtactctc aagcagtgtc tcgaggtcct ttctggagac ggagtcggat tgggcctgtg
121 atatcgagtc ccctgggtcc aaatcgggtg tgtgtaatct gtgtagtttc tggtaaggat
181 attctgtgga gtcgttgtct aagtccgttg gtgttgtcga tgggtccatt ctcatggact
241 gtgaacgaaa gtgttccagc tgtgctgggc ctaatgagct tggtagccca atctgagacc
301 ttgtggccca tgtttcgcct ggatggatgg tgatgggcct gtgggttatg ggttgttgac
361 tacgagcagt tggagtggga tttaataatc gtcgtcttgt ttctccttt tccacggacc
421 agaagtctat gcagtctttt gtgtatccct tggataagat gttaattgtt gggggtttga
481 aacgtatgtc cgtggaatgt ttggccgatg ataatcggag cttggccttg atggatgcga
541 atttcacgcc ttctatgacg tttgagtctt cgactctgta catgattctc aaggggaag
601 gttcagaaat cgaaaaatat gtagaagaga agtagtggag gtccacgttg aagcgatgg
661 ggaaagtgaa tgctgcctga gctgcgtcgt caaggctgac gcgattgtct ctgatttcta
721 cgataaccga cccagttgcg ttaaatggga cctggttt cg gtattcaatt ataatgtggt
781 cgattttcat acatcggcct ttgagtcgca tggtagcctg ctcgaatgag cctgggaatt
841 ggagattgat tggtgcagca tcgtttgtta atgcgtactc ggtgcgtttg ctgttgatgt
901 aattattgtc tgtgacggta aatt
```

MSV repA Sequence with targeted area indicated

```
  1 ctaggcttct ggcccaagta gattttccgg ttcttgttgg ccgacgatg tagaggctct
 61 gctttcttga tctttcatct gatgactgga tacagaatcc atccattgga ggtcagaaat
121 tgcatcctcg agggtataac aggtaggttg aaggagcatg taagcttcgg gactaacctg
181 gaagatgtta ggctggagcc aatcgttgat tgactcatta caaagtaaat caggtgagga
241 gggtggatga ggattggtga actcttcctg aatctcagga aaaagcttat ttgcagagta
301 ttcaaaatac tgcaattttg tggaccaatc aaaggggagc tctttctgga tcatggagag
361 gtactcttct ttggaggtag cgtgtgaaat aatgtctcgc attatttcat ctttagaagg
421 cttttttcc tttacctctg aatcagattt tcctaggaag ggggacttcc taggaatgaa
481 agtacctctc tcaaacacag ccagaggttc cttgagaatg taatccctca ctctgttaac
541 tgacttggca ctctgaatat tgggtgaaa cccatttata tcaaagaacc ttgagtcaga
601 tatccttatc ggcttctctg gctgaagcaa tgcatgtaaa tgcaaacttc catctttatg
661 tgcctctcgg gcacatagaa tatatttggg aatccaacga acgacgagct cccagatcat
721 ctgacaggcg atttcaggat tttctggaca ctttggatag gttaggaacg tgttagcgtt
781 cctgtgtgag aactgacggt tggatgagga ggaggccat
```

Fig 12

SACMV AC1 sequence with targeted area indicated

```
1    tacgtctgag ggccctagtc ttcgcggtgc ggtgttggac tttgatgggc acttgagaac
61   aatggctcgt ggagggtgat gaaggttgca ttctttaaag cccaggcttt aagggactgg
121  ttctttcct  cgtccagaaa ctctttatat gatgatgtcg gtcctggatt gcataggaag
181  atagtgggaa tgccgccttt aatttgaatc ggcttcccgt acttggtatt gctttgccag
241  tccctttggg cccccatgaa ttctttgaag tgcttgaggt aatgggggtc gacgtcatca
301  atgacgttgt accatgcgtc gttgctgtaa acctttggac tgagatccaa atgtccacat
361  aagtagttgt gtggtcccag agatcgggcc cacatcgtct tccctgtcct actatcgccc
421  tcgatgacga tactactcgg tctccatggc cgcgcagcga aacccatcac gttctcggaa
481  acccagtctt caagttcctc aggaacatga gtgaaagaag aagaaagaaa gggagaaata
541  taaggaatcg gaggctcctg aaaaatccta tctaaattgc tatttaaatt atgaaactgt
601  aaaacaaaat cctttggggc tagttcccgg attacattaa gagcctctgt tttacttgct
661  gcgttaagag ccttggcgta agcgtcattg gcggattgtt gtccgccgcg agcagatcgt
721  ccgtcgatct gaaactcgcc ccattggatg gtgctccgt  ccttgtccaa ataggacttg
781  acgtcagaac tggatttagc tccctgaatg tttggatgga aatgtgttga cctggaaggg
841  gatatgaggt cgaagaatcg ttggttggta caattgtact tgccctcgaa ctgaatgagg
901  gcatgcaaat gaggttcccc attttcatgg agttctctgc agatcttgat gaacaattta
961  tttgttgggg tttggagttg tcggagttga tctaatgccg cttctttcga gagagtgcat
1021 ttcggatacg tgaggaaata atttttggct tttatgctaa aacgaccagc cctcggcat
```

Fig 13

SACMV BC1

SEQ: SACMV BC1_target gene sequence: 2760 bp;
Composition  770  A;  454  C;  741  G;  795  T;  0 OTHER
Percentage:   28%  A;  16%  C;  27%  G;  29%  T;  0%OTHER Molecular Weight (kDa): ssDNA: 857.68    dsDNA: 1701.4
ORIGIN

```
1     ACCGGATGGC CGCGCCCGAA AAAGCAGATG GACCCCACAA TGGTCCCCAC GCACTAAATA
61    ATGTCAGCCA ATCAATTGCA AGACTGGAAG ACTCGGTAGT GACGCATGGA GTATTAAGTG
121   GTTTCTGCAC TAATTTGGAC AGGCAATTTT ATTGCTATGT GTGTATCATA TTTTTATAGG
181   TGTGCTACTG GCCAATCAAA GTTAGGTGAT GGGGCCTACC ATAAAAACGC AAAATATAGG
241   TACGTATGTA CATATTGATT ATATTTTTAG GTGCGGATAT AAGAGGCGCC ACGTGTTTAC
301   AATGGATATG GATTGTCCTA TAAATATTGT GCATGTCTCC CGTTCGTTAA TGCAAGATGT
361   ATTCAGTTTA CAGACGTGGG TATAAGACTC CGTATAGGAG TCCGTATGGC GCTCGTGTAA
421   CACCATATGT ATATCGTAAG ACCTCTGGTA ACAGACGTC  TAAATCTCGT GTACCGCGAA
481   AGTTGGTGTA TGAATCGCCA AAAGGTCTAT ATACGCGACG CTCATTGGAG GATATCCATA
541   ATGGGGCTTC CTTGAAGTTG TCTCAACAGG GGGATTATAC GTCCTACGTG TCACTCCCTT
601   GTCGAGGTAT CGAAGGTAAT GGGGGTAGGT CTGTTGATCA CATAAAATTA TTAAACTTGA
661   GGGTTTCTGG GACCGTCAAC GTCAGTCAAG TCGGTGGTGA TGATAATATG GGAGAGAGAA
721   CGACCATGAG GGGTATCTTC TTCATGGCTT GTCTTGTTGA TAAGAAACCT TTCGTTCCAG
781   AGGGGGTCAG TATATTGCCG ACGTTCAATG AGTTGTTCGG GGAATATGAA TCCGTGTACG
841   GCATGCCTAG GTTGAAGGAA AACGTCCGTC ACCGGTATCG CGTTATTGGG ACATCGAAAT
901   TATATATAAC GACGGATGAA GATCACATCC AAAAGCCCTT TAGTTTACGT CGAAGACTAA
961   GTGGAGGGAA ATATCCTATT TGGTCGTCGT TCAAGGATGT GGATAATAGT AGTACAGGTG
1021  GTAACTATAA AAATATAAAT AAGAACGCTA TACTAGTGAG TTATGTGTGG GTATCGCTAT
1081  GTCGGACCAC GTGTGATGTG TATTCGCAGT TTGTACTGAA TTACGTCGGT TGATAATAAA
1141  AAGAGATAAG TGTGTTGACA GGAATTATGT TTGAACTAAT GAAACATGAG ATGAACATTA
1201  ATTGAAAGCA TATATAGTTT GATTATGCTT TTAAGCAAAT ATGGTACATA TCAATTGTTT
1261  ATTACAATTG CCTTGGTGCG TCGGATTTTA TTTTGTAGAG ACACTTGTTT ATGGTACTCT
1321  CAAGCAGTGT CTCGAGGTCC TTTCTGGAGA CGGAGTCGGA TTGGGCCTGT GATATCGAGT
1381  CCCCTGGGTC CAAATCGGGT GTGTGTAATC TGTGTAGTTT CTGGTAAGGA TATTCTGTGG
1441  AGTCGTTGTC TAAGTCCGTT GGTGTTGTCG ATGGGTCCAT TCTCATGGAC TGTGAACGAA
1501  AGTGTTCCAG CTGTGCTGGG CCTAATGAGC TTGGTAGCCC AATCTGAGAC CTTGTGGCCC
1561  ATGTTTCGCC TGGATGGATG GTGATGGGCC TGTGGGTTAT GGGTTGTTGA CTACGAGCAG
1621  TTGGAGTGGG ATTTAATAAT CGTCGTCTTG TTTCTCCTTT TTCCACGGAC CAGAAGTCTA
1681  TGCAGTCTTT TGTGTATCCC TTGGATAAGA TGTTAATTGT TGGGGGTTTG AAACGTATGT
1741  CCGTGGAATG TTTGGCCGAT GATAATCGGA GCTTGGCCTT GATGGATGCG AATTTCACGC
1801  CTTCTATGAC GTTTGAGTCT TCGACTCTGT ACATGATTCT CCAAGGGGAA GGTTCAGAAA
1861  TCGAAAAATA TGTAGAAGAG AAGTAGTGGA GGTCCACGTT GCAAGCGATG GGGAAAGTGA
1921  ATGCTGCCTG AGCTGCGTCG TCAAGGCTGA CGCGATTGTC TCTGATTTCT ACGATAACCG
1981  ACCCAGTTGC GTTAAATGGG ACCTGGTTTC GGTATTCAAT TATAATGTGG TCGATTTTCA
2041  TACATCGGCC TTTGAGTCGC ATGGTAGCCT GCTCGAATGA GCCTGGGAAT TGGAGATTGA
2101  TTGGTGCAGC ATCGTTTGTT AATGCGTACT CGGTGCGTTT GCTGTTGATG TAATTATTGT
2161  CTGTGACGGT AAATTGGGCG TCCATTCTAT GAAGCAAAAA AACAAAGGTT AGTAAACGGA
2221  GAGACGAGAG GTATAAAAGT CAGAACAAAG TTGAAAAAAT ATCGTGTAGA CATGGAAGCA
2281  TATATGCATT TGTTATATAG AATAACACAC GAGATCAGAA CAAGGATCAT ATATGTTGAA
2341  CCGGCCGCGC AGCGGATAGG AAGTCAGATA AATCGGCGAA CAAAGAAAAC AGTCGAATGG
2401  GGTGATGTGA TGTAAACCAC TTACAGAAGC GCCGAAGAAG CAGTTCGAAG TGAATTCCTG
2461  TGCTAATTAG GCGAAGACAA AGAAATAAAA GTAGAACTTA TTGCGAAAAA AGGAAAGGGA
2521  GCAGATGTTA CGCGTGGTGT CGTGAAATGA TATGTTATTA GGTGTTTATA TAGGCGTGAA
2581  TAAGCTACAC GTGGTAGAGA GAGAAAGAAG AGAGAGGCGA GAGCAATCGG GGGCACTCA
2641  AAGTTCCTAG CAATCGGGGG AATGGGGGC  AATTTATATG ATGCCCCCA  AATGGCATTT
2701  GTGTAATTTC TTAATGAAAT TTGAATTGCG AACGTGGAAA GCGGCCATCC GTATAATATT
```

Fig. 16 (SEQ ID NO:11)

SEQ  SACMV BC1_target region: 222 bp;
Composition   40   A;  37   C;  66   G;  79   T;  0 OTHER
Percentage:   18%  A;  17%  C;  30%  G;  36%  T;  0%OTHER Molecular Weight (kDa): ssDNA: 68.94      dsDNA: 136.9
ORIGIN
1       TGGTAGCCCA  ATCTGAGACC  TTGTGGCCCA  TGTTTCGCCT  GGATGGATGG  TGATGGGCCT
61      GTGGGTTATG  GGTTGTTGAC  TACGAGCAGT  TGGAGTGGGA  TTTAATAATC  GTCGTCTTGT
121     TTCTCCTTTT  TCCACGGACC  AGAAGTCTAT  GCAGTCTTTT  GTGTATCCCT  TGGATAAGAT
181     GTTAATTGTT  GGGGGTTTGA  AACGTATGTC  CGTGGAATGT  TT Fig. 17 (SEQ ID NO:12)

SEQ  SACMV BC1_target region_modified (C to T modification): 222 bp;
Composition   40   A;  0   C;  66   G;  116   T;  0 OTHER
Percentage:   18%  A;  0%  C;  30%  G;  53%   T;  0%OTHER Molecular Weight (kDa): ssDNA: 68.94      dsDNA: 136.9
ORIGIN
1       TGGTAGTTTA  ATTTGAGATT  TTGTGGTTTA  TGTTTTGTTT  GGATGGATGG  TGATGGGTTT
61      GTGGGTTATG  GGTTGTTGAT  TATGAGTAGT  TGGAGTGGGA  TTTAATAATT  GTTGTTTTGT
121     TTTTTTTTTT  TTTATGGATT  AGAAGTTTAT  GTAGTTTTTT  GTGTATTTTT  TGGATAAGAT
181     GTTAATTGTT  GGGGGTTTGA  AATGTATGTT  TGTGGAATGT  TT Fig. 18 (SEQ ID NO:13)

SEQ  SACMV BC1_target gene sequence_complement: 2760 bp;
Composition   795  A;  741  C;  454  G;  770  T;  0 OTHER
Percentage:   29%  A;  27%  C;  16%  G;  28%  T;  0%OTHER Molecular Weight (kDa): ssDNA: 846.43    dsDNA: 1701.4
ORIGIN

```
1      TGGCCTACCG GCGCGGGCTT TTTCGTCTAC CTGGGGTGTT ACCAGGGGTG CGTGATTTAT
61     TACAGTCGGT TAGTTAACGT TCTGACCTTC TGAGCCATCA CTGCGTACCT CATAATTCAC
121    CAAAGACGTG ATTAAACCTG TCCGTTAAAA TAACGATACA CACATAGTAT AAAAATATCC
181    ACACGATGAC CGGTTAGTTT CAATCCACTA CCCCGGATGG TATTTTTGCG TTTTATATCC
241    ATGCATACAT GTATAACTAA TATAAAAATC CACGCCTATA TTCTCCGCGG TGCACAAATG
301    TTACCTATAC CTAACAGGAT ATTTATAACA CGTACAGAGG GCAAGCAATT ACGTTCTACA
361    TAAGTCAAAT GTCTGCACCC ATATTCTGAG GCATATCCTC AGGCATACCG CGAGCACATT
421    GTGGTATACA TATAGCATTC TGGAGACCAT TTGTCTGCAG ATTTAGAGCA CATGGCGCTT
481    TCAACCACAT ACTTAGCGGT TTTCCAGATA TATGCGCTGC GAGTAACCTC CTATAGGTAT
541    TACCCCGAAG GAACTTCAAC AGAGTTGTCC CCCTAATATG CAGGATGCAC AGTGAGGGAA
601    CAGCTCCATA GCTTCCATTA CCCCATCCA GACAACTAGT GTATTTTAAT AATTTGAACT
661    CCCAAAGACC CTGGCAGTTG CAGTCAGTTC AGCCACCACT ACTATTATAC CCTCTCTCTT
721    GCTGGTACTC CCCATAGAAG AAGTACCGAA CAGAACAACT ATTCTTTGGA AAGCAAGGTC
781    TCCCCCAGTC ATATAACGGC TGCAAGTTAC TCAACAAGCC CCTTATACTT AGGCACATGC
841    CGTACGGATC CAACTTCCTT TTGCAGGCAG TGGCCATAGC GCAATAACCC TGTAGCTTTA
901    ATATATATTG CTGCCTACTT CTAGTGTAGG TTTTCGGGAA ATCAAATGCA GCTTCTGATT
961    CACCTCCCTT TATAGGATAA ACCAGCAGCA AGTTCCTACA CCTATTATCA TCATGTCCAC
1021   CATTGATATT TTTATATTTA TTCTTGCGAT ATGATCACTC AATACACACC CATAGCGATA
1081   CAGCCTGGTG CACACTACAC ATAAGCGTCA AACATGACTT AATGCAGCCA ACTATTATTT
1141   TTCTCTATTC ACACAACTGT CCTTAATACA AACTTGATTA CTTTGTACTC TACTTGTAAT
1201   TAACTTTCGT ATATATCAAA CTAATACGAA AATTCGTTTA TACCATGTAT AGTTAACAAA
1261   TAATGTTAAC GGAACCACGC AGCCTAAAAT AAAACATCTC TGTGAACAAA TACCATGAGA
1321   GTTCGTCACA GAGCTCCAGG AAAGACCTCT GCCTCAGCCT AACCCGGACA CTATAGCTCA
1381   GGGGACCCAG GTTTAGCCCA CACACATTAG ACACATCAAA GACCATTCCT ATAAGACACC
1441   TCAGCAACAG ATTCAGGCAA CCACAACAGC TACCCAGGTA AGAGTACCTG ACACTTGCTT
1501   TCACAAGGTC GACACGACCC GGATTACTCG AACCATCGGG TTAGACTCTG AACACCGGG
1561   TACAAAGCGG ACCTACCTAC CACTACCCGG ACACCCAATA CCCAACAACT GATGCTCGTC
1621   AACCTCACCC TAAATTATTA GCAGCAGAAC AAAGAGGAAA AAGGTGCCTG GTCTTCAGAT
1681   ACGTCAGAAA ACACATAGGG AACCTATTCT ACAATTAACA ACCCCCAAAC TTTGCATACA
1741   GGCACCTTAC AAACCGGCTA CTATTAGCCT CGAACCGGAA CTACCTACGC TTAAAGTGCG
1801   GAAGATACTG CAAACTCAGA AGCTGAGACA TGTACTAAGA GGTTCCCCTT CCAAGTCTTT
1861   AGCTTTTTAT ACATCTTCTC TTCATCACCT CCAGGTGCAA CGTTCGCTAC CCCTTTCACT
1921   TACGACGGAC TCGACGCAGC AGTTCCGACT GCGCTAACAG AGACTAAAGA TGCTATTGGC
1981   TGGGTCAACG CAATTTACCC TGGACCAAAG CCATAAGTTA ATATTACACC AGCTAAAAGT
2041   ATGTAGCCGG AAACTCAGCG TACCATCGGA CGAGCTTACT CGGACCCTTA ACCTCTAACT
2101   AACCACGTCG TAGCAAACAA TTACGCATGA GCCACGCAAA CGACAACTAC ATTAATAACA
2161   GACACTGCCA TTTAACCCGC AGGTAAGATA CTTCGTTTTT TTGTTTCCAA TCATTTGCCT
2221   CTCTGCTCTC CATATTTTCA GTCTTGTTTC AACTTTTTTA TAGCACATCT GTACCTTCGT
2281   ATATACGTAA ACAATATATC TTATTGTGTG CTCTAGTCTT GTTCCTAGTA TATACAACTT
2341   GGCCGGCGCG TCGCCTATCC TTCAGTCTAT TTAGCCGCTT GTTTCTTTTG TCAGCTTACC
2401   CCACTACACT ACATTTGGTG AATGTCTTCG CGGCTTCTTC GTCAAGCTTC ACTTAAGGAC
2461   ACGATTAATC CGCTTCTGTT TCTTTATTTT CATCTTGAAT AACGCTTTTT TCCTTTCCCT
2521   CGTCTACAAT GCGCACCACA GCACTTTACT ATACAATAAT CCACAAATAT ATCCGCACTT
2581   ATTCGATGTG CACCATCTCT CTCTTTCTTC TCTCTCCGCT CTCGTTAGCC CCCCGTGAGT
2641   TTCAAGGATC GTTAGCCCCC TTACCCCCCG TTAAATATAC TACGGGGGGT TTACCGTAAA
2701   CACATTAAAG AATTACTTTA AACTTAACGC TTGCACCTTT CGCCGGTAGG CATATTATAA
```

Fig. 19 (SEQ ID NO:14)

```
SEQ  SACMV BC1_target region_complement: 222 bp;
Composition  79   A;  66   C;  37   G;  40   T;  0 OTHER
Percentage:  36%  A;  30%  C;  17%  G;  18%  T;  0%OTHER Molecular Weight (kDa): ssDNA: 68.13      dsDNA: 136.9
ORIGIN
1       ACCATCGGGT TAGACTCTGG AACACCGGGT ACAAAGCGGA CCTACCTACC ACTACCCGGA
61      CACCCAATAC CCAACAACTG ATGCTCGTCA ACCTCACCCT AAATTATTAG CAGCAGAACA
121     AAGAGGAAAA AGGTGCCTGG TCTTCAGATA CGTCAGAAAA CACATAGGGA ACCTATTCTA
181     CAATTAACAA CCCCCAAACT TTGCATACAG GCACCTTACA AA
```

Fig. 20 (SEQ ID NO:15)

```
SEQ  SACMV BC1_target gene sequence_reverse: 2760 bp;
Composition   770  A;  454  C;  741  G;  795  T;  0 OTHER
Percentage:   28%  A;  16%  C;  27%  G;  29%  T;  0%OTHER Molecular Weight (kDa): ssDNA: 857.68

```
SEQ  SACMV BC1_target region_reverse: 222 bp;
Composition  40   A; 37   C; 66   G; 79   T; 0 OTHER
Percentage:  18%  A; 17%  C; 30%  G; 36%  T; 0%OTHER Molecular Weight (kDa): ssDNA: 68.94     dsDNA: 136.9
ORIGIN
1       TTTGTAAGGT GCCTGTATGC AAAGTTTGGG GGTTGTTAAT TGTAGAATAG GTTCCCTATG
61      TGTTTTCTGA CGTATCTGAA GACCAGGCAC CTTTTTCCTC TTTGTTCTGC TGCTAATAAT
121     TTAGGGTGAG GTTGACGAGC ATCAGTTGTT GGGTATTGGG TGTCCGGGTA GTGGTAGGTA
181     GGTCCGCTTT GTACCCGGTG TTCCAGAGTC TAACCCGATG GT
```

Fig. 22 (SEQ ID NO:17)

```
SEQ  SACMV BC1_target region_modified_reverse: 222 bp;
Composition  40   A; 0    C; 66   G; 116  T; 0 OTHER
Percentage:  18%  A; 0%  C; 30%  G; 52%  T; 0%OTHER Molecular Weight (kDa): ssDNA: 69.50     dsDNA: 136.8
ORIGIN
1       TGGTAGTTTA ATTTGAGATT TTGTGGTTTA TGTTTTGTTT GGATGGATGG TGATGGGTTT
61      GTGGGTTATG GGTTGTTGAT TATGAGTAGT TGGAGTGGGA TTTAATAATT GTTGTTTTGT
121     TTTTTTTTTT TTTATGGATT AGAAGTTTAT GTAGTTTTTT GTGTATTTTT TGGATAAGAT
181     GTTAATTGTT GGGGGTTTGA AATGTATGTT TGTGGAATGT TT
```

Fig. 23 (SEQ ID NO:18)

```
SEQ  SACMV BC1_target gene sequence_complement_reverse: 2760 bp;
Composition  795  A;  741  C;  454  G;  770  T;  0 OTHER
Percentage:  29%  A;  27%  C;  16%  G;  28%  T;  0%OTHER Molecular Weight (kDa): ssDNA: 846.43    dsDNA: 1701.4
ORIGIN
1     AATATTATAC GGATGGCCGC TTTCCACGTT CGCAATTCAA ATTTCATTAA GAAATTACAC
61    AAATGCCATT TGGGGGGCAT CATATAAATT GCCCCCCATT CCCCCGATTG CTAGGAACTT
121   TGAGTGCCCC CCGATTGCTC TCGCCTCTCT CTTCTTTCTC TCTCTACCAC GTGTAGCTTA
181   TTCACGCCTA TATAAACACC TAATAACATA TCATTTCACG ACACCACGCG TAACATCTGC
241   TCCCTTTCCT TTTTTCGCAA TAAGTTCTAC TTTTATTTCT TTGTCTTCGC CTAATTAGCA
301   CAGGAATTCA CTTCGAACTG CTTCTTCGGC GCTTCTGTAA GTGGTTTACA TCACATCACC
361   CCATTCGACT GTTTTCTTTG TTCGCCGATT TATCTGACTT CCTATCCGCT GCGCGGCCGG
421   TTCAACATAT ATGATCCTTG TTCTGATCTC GTGTGTTATT CTATATAACA AATGCATATA
481   TGCTTCCATG TCTACACGAT ATTTTTTCAA CTTTGTTCTG ACTTTTATAC CTCTCGTCTC
541   TCCGTTTACT AACCTTTGTT TTTTTGCTTC ATAGAATGGA CGCCCAATTT ACCGTCACAG
601   ACAATAATTA CATCAACAGC AAACGCACCG AGTACGCATT AACAAACGAT GCTGCACCAA
661   TCAATCTCCA ATTCCCAGGC TCATTCGAGC AGGCTACCAT GCGACTCAAA GGCCGATGTA
721   TGAAAATCGA CCACATTATA ATTGAATACC GAAACCAGGT CCCATTTAAC GCAACTGGGT
781   CGGTTATCGT AGAAATCAGA GACAATCGCG TCAGCCTTGA CGACGCAGCT CAGGCAGCAT
841   TCACTTTCCC CATCGCTTGC AACGTGGACC TCCACTACTT CTCTTCTACA TATTTTTCGA
901   TTTCTGAACC TTCCCCTTGG AGAATCATGT ACAGAGTCGA AGACTCAAAC GTCATAGAAG
961   GCGTGAAATT CGCATCCATC AAGGCCAAGC TCCGATTATC ATCGGCAAAA CATTCCACGG
1021  ACATACGTTT CAAACCCCCA ACAATTAACA TCTTATCCAA GGGATACACA AAGACTGCA
1081  TAGACTTCTG GTCCGTGGAA AAAGGAGAAA CAAGACGACG ATTATTAAAT CCCACTCCAA
1141  CTGCTCGTAG TCAACAACCC ATAACCCACA GGCCCATCAC CATCCATCCA GGCGAAACAT
1201  GGGCCACAAG GTCTCAGATT GGGCTACCAA GCTCATTAGG CCCAGCACAG CTGGAACACT
1261  TTCGTTCACA GTCCATGAGA ATGGACCCAT CGACAACACC AACGGACTTA CAACGACT
1321  CCACAGAATA TCCTTACCAG AAACTACACA GATTACACAC ACCCGATTTG GACCCAGGGG
1381  ACTCGATATC ACAGGCCAA TCCGACTCCG TCTCCAGAAA GGACCTCGAG ACACTGCTTG
1441  AGAGTACCAT AAACAAGTGT CTCTACAAAA TAAAATCCGA CGCACCAAGG CAATTGTAAT
1501  AAACAATTGA TATGTACCAT ATTTGCTTAA AAGCATAATC AAACTATATA TGCTTTCAAT
1561  TAATGTTCAT CTCATGTTTC ATTAGTTCAA ACATAATTCC TGTCAACACA CTTATCTCTT
1621  TTTATTATCA ACCGACGTAA TTCAGTACAA ACTGCGAATA CACATCACAC GTGGTCCGAC
1681  ATAGCGATAC CCACACATAA CTCACTAGTA TAGCGTTCTT ATTTATATTT TTATAGTTAC
1741  CACCTGTACT ACTATTATCC ACATCCTTGA ACGACGACCA AATAGGATAT TTCCCTCCAC
1801  TTAGTCTTCG ACGTAAACTA AAGGGCTTTT GGATGTGATC TTCATCCGTC GTTATATATA
1861  ATTTCGATGT CCCAATAACG CGATACCGGT GACGGACGTT TTCCTTCAAC CTAGGCATGC
1921  CGTACACGGA TTCATATTCC CCGAACAACT CATTGAACGT CGGCAATATA CTGACCCCCT
1981  CTGGAACGAA AGGTTTCTTA TCAACAAGAC AAGCCATGAA GAAGATACCC CTCATGGTCG
2041  TTCTCTCTCC CATATTATCA TCACCACCGA CTTGACTGAC GTTGACGGTC CCAGAAACCC
2101  TCAAGTTTAA TAATTTTATG TGATCAACAG ACCTACCCCC ATTACCTTCG ATACCTCGAC
2161  AAGGGAGTGA CACGTAGGAC GTATAATCCC CCTGTTGAGA CAACTTCAAG GAAGCCCCAT
2221  TATGGATATC CTCCAATGAG CGTCGCGTAT ATAGACCTTT GGCGATTCA TACACCAACT
2281  TTCGCGGTAC ACGAGATTTA GACGTCTGTT TACCAGAGGT CTTACGATAT ACATATGGTG
2341  TTACACGAGC GCCATACGGA CTCCTATACG GAGTCTTATA CCCACGTCTG TAAACTGAAT
2401  ACATCTTGCA TTAACGAACG GGAGACATGC ACAATATTTA TAGGACAATC CATATCCATT
2461  GTAAACACGT GGCGCCTCTT ATATCCGCAC CTAAAAATAT AATCAATATG TACATACGTA
2521  CCTATATTTT GCGTTTTTAT GGTAGGCCCC ATCACCTAAC TTTGATTGGC CAGTAGCACA
2581  CCTATAAAAA TATGATACAC ACATAGCAAT AAAATTGCCT GTCCAAATTA GTGCAGAAAC
2641  CACTTAATAC TCCATGCGTC ACTACCGAGT CTTCCAGTCT TGCAATTGAT TGGCTGACAT
2701  TATTTAGTGC GTGGGGACCA TTGTGGGGTC CATCTGCTTT TTCGGGCGCG GCCATCCGGT
```

Fig. 24 (SEQ ID NO:19)

SEQ SACMV BC1_target region_complement_reverse: 222 bp;
Composition 79   A;  66   C;  37   G;  40   T;  0 OTHER
Percentage:  36%  A;  30%  C;  17%  G;  18%  T;  0%OTHER Molecular Weight (kDa): ssDNA: 68.13     dsDNA: 136.9
ORIGIN
1      AAACATTCCA CGGACATACG TTTCAAACCC CCAACAATTA ACATCTTATC CAAGGGATAC
61     ACAAAAGACT GCATAGACTT CTGGTCCGTG GAAAAAGGAG AAACAAGACG ACGATTATTA
121    AATCCCACTC CAACTGCTCG TAGTCAACAA CCCATAACCC ACAGGCCCAT CACCATCCAT
181    CCAGGCGAAA CATGGGCCAC AAGGTCTCAG ATTGGGCTAC CA Fig. 25 (SEQ ID NO:20)

SEQ SACMV BC1_hairpin: 183 bp;
Composition 41   A;  30   C;  53   G;  59   T;  0 OTHER
Percentage:  22%  A;  16%  C;  29%  G;  32%  T;  0%OTHER Molecular Weight (kDa): ssDNA: 56.88     dsDNA: 112.8
ORIGIN
1      GACCTGGAAG GGGATATGAG GTCGAAGAAT CGTTGGTTGG TACAATTGTA CTTGCCCTCG
61     AACTGAATGA GGGCATGCAA ATGAGGTTCC CCATTTTCAT GGAGTTCTCT GCAGATCTTG
121    ATGAACAATT TATTTGTTGG GGTTTGGAGT TGTCGGAGTT GATCTAATGC CGCTTCTTTC
181    GAG Fig. 26 (SEQ ID NO:21)

SEQ  SACMV BC1_Target gene RNA sequence: 2760 bases;
Composition  770  A;  454  C;  741  G;  795  U;  0 OTHER
Percentage:  28%  A;  16%  C;  27%  G;  29%  U;  0%OTHER Molecular Weight: 890.71kDa

```
1     ACCGGAUGGC CGCGCCCGAA AAAGCAGAUG GACCCCACAA UGGUCCCCAC GCACUAAAUA
61    AUGUCAGCCA AUCAAUUGCA AGACUGGAAG ACUCGGUAGU GACGCAUGGA GUAUUAAGUG
121   GUUUCUGCAC UAAUUGGAC  AGGCAAUUUU AUUGCUAUGU GUGUAUCAUA UUUUUAUAGG
181   UGUGCUACUG GCCAAUCAAA GUUAGGUGAU GGGGCCUACC AUAAAAACGC AAAAUAUAGG
241   UACGAUGUA  CAUAUUGAUU AUAUUUUUAG GUCGGAUAU  AAGAGGCGCC ACGUGUUUAC
301   AAUGGAUAUG GAUUGUCCUA UAAAUAUUGU GCAUGUCUCC CGUUCGUUAA UGCAAGAUGU
361   AUUCAGUUUA CAGACGUGGG UAUAAGACUC CGUAUAGGAG UCCGUAUGGC GCUCGUGUAA
421   CACCAUAUGU AUAUCGUAAG ACCUCUGGUA AACAGACGUC UAAAUCUCGU GUACCGCGAA
481   AGUUGGUGUA UGAAUCGCCA AAAGGUCUAU AUACGCGACG CUCAUUGGAG GAUAUCCAUA
541   AUGGGGCUUC CUUGAAGUUG UCUCAACAGG GGGAUUAUAC GUCCUACGUG UCACUCCCUU
601   GUCGAGGUAU CGAAGGUAAU GGGGGUAGGU CUGUUGAUCA CAUAAAAUUA UUAAACUUGA
661   GGGUUUCUGG GACCGUCAAC GUCAGUCAAG UCGGUGGUGA UGAUAAUAUG GGAGAGAGAA
721   CGACCAUGAG GGGUAUCCUU CUCAUGGCUU GUCUGGUUGA UAAGAAACCU UUCGUUCCAG
781   AGGGGGUCAG UAUAUUGCCG ACGUUCAAUG AGUUGUUCGG GGAAUAUGAA UCCGUGUACG
841   GCAUGCCUAG GUUGAAGGAA AACGUCCGUC ACCGGUAUCG CGUUAUUGGG ACAUCGAAAU
901   UAUAUAUAAC GACGGAUGAA GAUCACAUCC AAAAGCCCUU UAGUUUACGU CGAACACUAA
961   GUGGAGGGAA AUACCUAUU  UGGUCGUCGU UCAAGGAUGU GGAUAAUAGU AGUACAGGUG
1021  GUAACUAUAA AAAUAUAAAU AAGAACGCUA UACUAGUGAG UUAUGUGUGG GUAUCGCUAU
1081  GUCGGACCAC GUGUGAUGUG UAUUCGCAGU UUGUACUGAA UUACGUCGGU UGAUAAUAAA
1141  AAGAGAUAAG UGUGUUGACA GGAAUUAUGU UUGAACUAAU GAAACAUGAG AUGAACAUUA
1201  AUUGAAAGCA UAUAUAGUUU GAUUAUGCUU UUAAGCAAAU AUGGUACAUA UCAAUUGUUU
1261  AUUACAAUUG CCUUGGUGCG UCGGAUUUUA UUUUGUAGAG ACACUUGUUU AUGGUACUCU
1321  CAAGCAGUGU CUCGAGGUCC UUUCUGGAGA CGGAGUCGGA UUGGGCCUGU GAUAUCGAGU
1381  CCCCUGGGUC CAAAUCGGGU GUGUGUAAUC UGUGUAGUUU CUGGUAAGGA UAUUCUGUGG
1441  AGUCGUUGUC UAAGUCCGUU GGUGUUGUCG AUGGGUCCAU UCUCAUGGAC UGUGAACGAA
1501  AGUGUUCCAG CUGUGCUGGG CCUAAUGAGC UUGGUAGCCC AAUCUGAGAC CUUGUGGCCC
1561  AUGUUUCGCC UGGAUGGAUG GUGAUGGGCC UGUGGGUUAU GGGUUGUUGA CUACGAGCAG
1621  UUGGAGUGGG AUUUAAUAAU CGUCGUCUUG UUUCUCCUUU UUCCACGGAC CAGAAGUCUA
1681  UGCAGUCUUU UGUGUAUCCC UUGGAUAAGA UGUUAAUUGU UGGGGGUUUG AAACGUAUGU
1741  CCGUGGAAUG UUUGGCCGAU GAUAACGGA  GCUUGGCCUU GAUGGAUGCG AAUUUCACGC
1801  CUUCUAUGAC GUUUGAGUCU UCGACUCUGU ACAUGAUUCU CCAAGGGGAA GGUUCAGAAA
1861  UCGAAAAAUA UGUAGAAGAG AAGUAGUGGA GGUCCACGUU GCAAGCGAUG GGGAAAGUGA
1921  AUGCUGCCUG AGCUGCGUCG UCAAGGCUGA CGCGAUUGUC UCUGAUUUCU ACGAUAACCG
1981  ACCCAGUUGC GUUAAAUGGG ACCUGGUUUC GGUAUUCAAU UAUAAUGUGG UCGAUUUUCA
2041  UACAUCGGCC UUUGAGUCGC AUGGUAGCCU GCUCGAAUGA GCCUGGGAAU UGGAGAUUGA
2101  UUGGUGCAGC AUCGUUUGUU AAUGCGUACU CGGUGCGUUU GCUGUUGAUG UAAUUAUUGU
2161  CUGUGACGGU AAAUUGGGCG UCCAUUCUAU GAAGCAAAAA AACAAAGGUU AGUAAACGGA
2221  GAGACGAGAG GUAUAAAAGU CAGAACAAAG UUGAAAAAAU AUCGUGUAGA CAUGGAAGCA
2281  UAUAUGCAUU UGUUAUAUAG AAUAACACAC GAGAUCAGAA CAAGGAUCAU AUAUGUUGAA
2341  CCGGCCGCGC AGCGGAUAGG AAGUCAGAUA AAUCGGCGAA CAAAGAAAAC AGUCGAAUGG
2401  GGUGAUGUGA UGUAAACCAC UUACAGAAGC GCCGAAGAAG CAGUUCGAAG UGAAUUCCUG
2461  UGCUAAUUAG GCGAAGACAA AGAAAUAAAA GUAGAACUUA UUGCGAAAAA AGGAAAGGGA
2521  GCACAUGUUA CGCGUGGUGU CGUGAAAUGA UAUGUUAUUA GGUGUUUAUA UAGGCGUGAA
2581  UAAGCUACAC GUGGUAGAGA GAGAAAGAAG AGAGAGGCGA GAGCAAUCGG GGGGCACUCA
2641  AAGUUCCUAG CAAUCGGGGG AAUGGGGGGC AAUUUAUAUG AUGCCCCCCA AAUGGCAUUU
2701  GUGUAAUUUC UUAAUGAAAU UUGAAUUGCG AACGUGGAAA GCGGCCAUCC GUAUAAUAUU
```

Fig. 27 (SEQ ID NO:22)

SEQ  SACMV BC1_Target gene RNA region: 222 bases;
Composition   40   A;  37   C;  66   G;  79   U;  0 OTHER
Percentage:   18%  A;  17%  C;  30%  G;  36%  U;  0%OTHER Molecular Weight: 71.39 kDa

```
1      UGGUAGCCCA AUCUGAGACC UUGUGGCCCA UGUUUCGCCU GGAUGGAUGG UGAUGGGCCU
61     GUGGGUUAUG GGUUGUUGAC UACGAGCAGU UGGAGUGGGA UUUAAUAAUC GUCGUCUUGU
121    UUCUCCUUUU UCCACGGACC AGAAGUCUAU GCAGUCUUUU GUGUAUCCCU UGGAUAAGAU
181    GUUAAUUGUU GGGGGUUUGA AACGUAUGUC CGUGGAAUGU UU
```

Fig. 28 (SEQ ID NO:23)

SEQ  SACMV BC1_Target gene RNA region_modified: 222 bases;
Composition   40   A;   0   C;  66   G;  116  U;  0 OTHER
Percentage:   18%  A;   0%  C;  30%  G;  52%  U;  0%OTHER Molecular Weight: 71.43 kDa

```
1      UGGUAGUUUA AUUUGAGAUU UUGUGGUUUA UGUUUUGUUU GGAUGGAUGG UGAUGGGUUU
61     GUGGGUUAUG GGUUGUUGAU UAUGAGUAGU UGGAGUGGGA UUUAAUAAUU GUUGUUUUGU
121    UUUUUUUUUU UUUAUGGAUU AGAAGUUUAU GUAGUUUUUU GUGUAUUUUU UGGAUAAGAU
181    GUUAAUUGUU GGGGGUUUGA AAUGUAUGUU UGUGGAAUGU UU
```

Fig. 29 (SEQ ID NO:24)

SEQ   SACMV BC1_Target gene complement_RNA: 2760 bases;
Composition   795 A; 741 C; 454 G; 770 U; 0 OTHER
Percentage:   29% A; 27% C; 16% G; 28% U; 0%OTHER Molecular Weight: 879.81kDa

```
   1    UGGCCUACCG GCGCGGGCUU UUUCGUCUAC CUGGGGUGUU ACCAGGGGUG CGUGAUUUAU
  61    UACAGUCGGU UAGUUAACGU UCUGACCUUC UGAGCCAUCA CUGCGUACCU CAUAAUUCAC
 121    CAAAGACGUG AUUAAACCUG UCCGUUAAAA UAACGAUACA CACAUAGUAU AAAAAUAUCC
 181    ACACGAUGAC CGGUUAGUUU CAAUCCACUA CCCCGGAUGG UAUUUUUGCG UUUUAUAUCC
 241    AUGCAUACAU GUAUAACUAA UAUAAAAAUC CACGCCUAUA UUCUCCGCGG UGCACAAAUG
 301    UUACCUAUAC CUAACAGGAU AUUUAUAACA CGUACAGAGG GCAAGCAAUU ACGUUCUACA
 361    UAAGUCAAAU GUCUGCACCC AUAUUCUGAG GCAUACCUC AGGCAUACCG CGAGCACAUU
 421    GUGGUAUACA UAUAGCAUUC UGGAGACCAU UUGUCUGCAG AUUUAGAGCA CAUGGCGCUU
 481    UCAACCACAU ACUUAGCGGU UUUCCAGAUA UAUGCGCUGC GAGUAACCUC CUAUAGGUAU
 541    UACCCCGAUG GAACUUCAAC AGAGUUGUCC CCCUAAUAUG CAGGAUGCAC AGUGAGGGAA
 601    CAGCUCCAUA GCUUCCAUUA CCCCCAUCCA GACAACUAGU GUAUUUAAU AAUUUGAACU
 661    CCCAAAGACC CUGGCAGUUG CAGUCAGUUC AGCCACCACU ACUAUUAUAC CCUCUCUCUU
 721    GCUGGUACUC CCCAUAGAAG AAGUACCGAA CAGAACAACU AUUCUUUGGA AGCAAGGUC
 781    UCCCCCAGUC AUAUAACGGC UGCAAGUUAC UCAACAAGCC CCUUAUACUU AGGCACAUGC
 841    CGUACGGAUC CAACUUCCUU UUGCAGGCAG UGGCCAUAGC GCAAUAACCC UGUAGCUUUA
 901    AUAUAUAUUG CUGCCUACUU CUAGUGUAGG UUUUCGGGAA UCAAAUGCA GCUUCUGAUU
 961    CACCUCCCUU UAUAGGAUAA ACCAGCAGCA AGUUCCUACA CCUAUUAUCA UCAUGUCCAC
1021    CAUUGAUAUU UUUAUAUUUA UUCUUGCGAU AUGAUCACUC AAUACACACC CAUAGCGAUA
1081    CAGCCUGGUG CACACUACAC AUAAGCGUCA AACAUGACUU AAUGCAGCCA ACUAUUAUUU
1141    UUCUCUAUUC ACACAACUGU CCUUAAUACA AACUUGAUUA CUUUGUACUC UACUUGUAAU
1201    UAACUUUCGU AUAUAUCAAA CUAAUACGAA AAUUCGUUUA UACCAUGUAU AGUUAACAAA
1261    UAAUGUUAAC GGAACCACGC AGCCUAAAAU AAAACAUCUC UGUAACAAA UACCAUGAGA
1321    GUUCGUCACA GAGCUCCAGG AAAGACCUCU GCCUCAGCCU AACCCGGACA CUAUAGCUCA
1381    GGGGACCCAG GUUUAGCCCA CACACAUUAG ACACAUCAAA GACCAUUCCU AUAAGACACC
1441    UCAGCAACAG AUUCAGGCAA CCACAACAGC UACCCAGGUA AGAGUACCUG ACACUUGCUU
1501    UCACAAGGUC GACACGACCC GGAUUACUCG AACCAUCGGG UUAGACUCUG AACACCGGG
1561    UACAAAGCGG ACCUACCUAC CACUACCCGG ACACCCAAUA CCCAACAACU GAUGCUCGUC
1621    AACCUCACCC UAAAUUAUUA GCAGCAGAAC AAAGAGGAAA AAGGUGCCUG GUCUUCAGAU
1681    ACGUCAGAAA ACACAUAGGG AACCUAUUCU ACAAUUAACA ACCCCCAAAC UUUGCAUACA
1741    GGCACCUUAC AAACCGGCUA CUAUUAGCCU CGAACCGGAA CUACCUACGC UUAAAGUGCG
1801    GAAGAUACUG CAAACUCAGA AGCUGAGACA UGUACUAAGA GGUUCCCCUU CCAAGUCUUU
1861    AGCUUUUUAU ACAUCUUCUC UUCAUCACCU CCAGGUGCAA CGUUCGCUAC CCCUUUCACU
1921    UACGACGGAC UCGACGCAGC AGUUCCGACU GCGCUAACAG AGACUAAAGA UGCUAUUGGC
1981    UGGGUCAACG CAAUUUACCC UGGACCAAAG CCAUAAGUUA AUAUUACACC AGCUAAAAGU
2041    AUGUAGCCGG AAACUCAGCG UACCAUCGGA CGAGCUUACU CGGACCCUUA CCUCUAACU
2101    AACCACGUCG UAGCAAACAA UUACGCAUGA GCCACGCAAA CGACAACUAC AUUAAUAACA
2161    GACACUGCCA UUUAACCCGC AGGUAAGAUA CUUCGUUUUU UGUUUCCAA UCAUUUGCCU
2221    CUCUGCUCUC CAUAUUUUCA GUCUUGUUUC AACUUUUUUA UAGCACAUCU GUACCUUCGU
2281    AUAUACGUAA ACAAUAUAUC UUAUUGUGUG CUCUAGUCUU GUUCCUAGUA UAUACAACUU
2341    GGCCGGCGCG UCGCCUAUCC UUCAGUCUAU UUAGCCGCUU GUUUCUUUUG UCAGCUUACC
2401    CCACUACACU ACAUUGGUG AAUGUCUUCG CGGCUUCUUC GUCAAGCUUC ACUUAGGAC
2461    ACGAUUAAUC CGCUUCUGUU UCUUUAUUUU CAUCUUGAAU AACGCUUUUU UCCUUUCCCU
2521    CGUCUACAAU GCGCACCACA GCACUUACU AUACAAUAAU CCACAAAUAU AUCCGCACUU
2581    AUUCGAUGUG CACCAUCUCU CUCUUUCUUC UCUCUCCGCU CUCGUUAGCC CCCCGUGAGU
2641    UUCAAGGAUC GUUAGCCCCC UUACCCCCG UUAAAUAUAC UACGGGGGGU UUACCGUAAA
2701    CACAUUAAAG AAUUACUUUA AACUUAACGC UUGCACCUUU CGCCGGUAGG CAUAUUAUAA
```

Fig. 30 (SEQ ID NO:25)

```
SEQ  SACMV BC1_Target region complement_RNA: 222 bases;
Composition  79   A;  66   C;  37   G;  40   U;  0 OTHER
Percentage:  36%  A;  30%  C;  17%  G;  18%  U;  0%OTHER Molecular Weight: 71.13 kDa 1       ACCAUCGGGU  UAGACUCUGG  AACACCGGGU  ACAAAGCGGA  CCUACCUACC  ACUACCCGGA
61      CACCCAAUAC  CCAACAACUG  AUGCUCGUCA  ACCUCACCCU  AAAUUAUUAG  CAGCAGAACA
121     AAGAGGAAAA  AGGUGCCUGG  UCUUCAGAUA  CGUCAGAAAA  CACAUAGGGA  ACCUAUUCUA
181     CAAUUAACAA  CCCCCAAACU  UUGCAUACAG  GCACCUUACA  AA
```

Fig. 31 (SEQ ID NO:26)

SEQ SACMV BC1_target gene sequence_reverse_RNA: 2760 bases;
Composition   770  A;  454  C;  741  G;  795  U;  0 OTHER
Percentage:   28%  A;  16%  C;  27%  G;  29%  U;  0%OTHER Molecular Weight: 890.71kDa

```
1     UUAUAAUAUG CCUACCGGCG AAAGGUGCAA GCGUUAAGUU UAAAGUAAUU CUUUAAUGUG
61    UUUACGGUAA ACCCCCCGUA GUAUAUUUAA CGGGGGGUAA GGGGGCUAAC GAUCCUUGAA
121   ACUCACGGGG GGCUAACGAG AGCGGAGAGA GAAGAAAGAG AGAUGAUGGUG CACAUCGAAU
181   AAGUGCGGAU AUAUUUGUGG AUUAUUGUAU AGUAAAGUGC UGUGGUGCGC AUUGUAGACG
241   AGGGAAAGGA AAAAAGCGUU AUUCAAGAUG AAAAUAAAGA AACAGAAGCG GAUUAAUCGU
301   GUCCUUAAGU GAAGCUUGAC GAAGAAGCCG CGAAGACAUU CACCAAAUGU AGUGUAGUGG
361   GGUAAGCUGA CAAAAGAAAC AAGCGGCUAA AUAGACUGAA GGAUAGGCGA CGCGCCGGCC
421   AAGUUGUAUA UACUAGGAAC AAGACUAGAG CACACAAUAA GAUAUAUUGU UUACGUAUAU
481   ACGAAGGUAC AGAUGUGCUA UAAAAAGUU GAAACAAGAC UGAAAAUAUG GAGAGCAGAG
541   AGGCAAAUGA UUGGAAACAA AAAAACGAAG UAUCUUACCU GCGGGUUAAA UGGCAGUGUC
601   UGUUAUUAAU GUAGUUGUCG UUUGCGUGGC UCAUGCGUAA UUGUUUGCUA CGACGUGGUU
661   AGUUAGAGGU UAAGGGUCCG AGUAAGCUCG UCCGAUGGUA CGCUGAGUUU CCGGCUACAU
721   ACUUUUAGCU GGUGUAAUAU UAACUUAUGG CUUUGGUCCA GGGUAAAUUG CGUUGACCCA
781   GCCAUAGCA UCUUUAGUCU CUGUUAGCGC AGUCGGAACU GCUGCGUCGA GUCCGUCGUA
841   AGUGAAAGGG GUAGCGAACG UUGCACCUGG AGGUGAUGAA GAGAAGAUGU AUAAAAAGCU
901   AAAGACUUGG AAGGGGAACC UCUUAGUACA UGUCUCAGCU UCUGAGUUUG CAGUAUCUUC
961   CGCACUUUAA GCGUAGGUAG UUCCGGUUCG AGGCUAAUAG UAGCCGGUUU GUAAGGUGCC
1021  UGUAUGCAAA GUUGGGGGU UGUUAAUUGU AGAAUACGUU CCCUAUGUGU UUUCUGACGU
1081  AUCUGAAGAC CAGGCACCUU UUUCCUCUUU GUUCUGCUGC UAAUAAUUUA GGGUGAGGUU
1141  GACGAGCAUC AGUUGUUGGG UAUGGGUGU CCGGGUAGUG GUAGGUAGGU CCGCUUUGUA
1201  CCCGGUGUUC CAGAGUCUAA CCCGAUGGUU CGAGUAACC GGGUCGUGUC GACCUUGUGA
1261  AAGCAAGUGU CAGGUACUCU UACCUGGGUA GCUGUUGUGG UUGCCUGAAU CUGUUGCUGA
1321  GGUGUCUUAU AGGAAUGGUC UUUGAUGUGU CUAAUGUGUG UGGGCUAAAC CUGGGUCCCC
1381  UGAGCUAUAG UGUCCGGGUU AGGCUGAGGC AGAGGUCUUU CCUGGAGCUC UGUGACGAAC
1441  UCUCAUGGUA UUUGUUCACA GAGAUGUUUU AUUUUAGGCU GCGUGGUUCC GUUAACAUUA
1501  UUUGUUAACU AUACAUGGUA UAAACGAAUU UUCGUAUUAG UUUGAUAUAU ACGAAAGUUA
1561  AUUACAAGUA GAGUACAAAG UAAUCAAGUU UGUAUAAGG ACAGUUGUCU GAAUACAGAA
1621  AAAUAAUAGU UGGCUGCAUU AAGCAUGUU UGACGCUUAU GUGUAGUGUG CACCAGGCUG
1681  UAUCGCUAUG GGUGUGUAUU GAGUGAUCAU AUCGCAAGAA UAAAUAUAAA AAUAUCAAUG
1741  GUGGACAUGA UGAUAAUAGG GUAGGAACU UGCUGCUGGU UUAUCCUAUA AAGGGAGGUG
1801  AAUCAGAAGC UGCAUUUGAU UUCCCGAAAA CCUACACUAG AAGUAGGCAG CAAUAUAUAU
1861  UAAAGCUACA GGGUUAUUGC GCUAUGGCCA CUGCCUGCAA AAGGAAGUUG GAUCCGUACG
1921  GCAUGUGCCU AAGUAUAAGG GGCUUGUUGA GUAACUUGCA GCCGUUAUAU GACUGGGGGA
1981  GACCUUGCUU UCCAAAGAAU AGUUGUUCUG UUCGGUACUU CUUCUAUGGG GAGUACCAGC
2041  AAGAGAGAGG GUAUAAUAGU AGUGGUGGCU GAACUGACUG CAACUGCCAG GGUCUUUGGG
2101  AGUUCAAAUU AUUAAAAUAC ACUAGUUGUC UGGAUGGGGG UAAUGGAAGC UAUGGAGCUG
2161  UUCCCUCACU GUGCAUCCUG CAUAUUAGGG GGACAACUCU GUUGAAGUUC CUUCGGGGUA
2221  AUACCUAUAG GAGGUUACUC GCAGCGCAUA UAUCUGGAAA ACCGCUAAGU AUGUGGUUGA
2281  AAGCGCCAUG UGCUCUAAAU CUGCAGACAA AUGGUCUCCA GAAUGCUAUA UGUAUACCAC
2341  AAUGUGCUCG CGGUAUGCCU GAGGAUAUGC CUCAGAAUAU GGGUGCAGAC AUUUGACUUA
2401  UGUAGAACGU AAUUGCUUGC CCUCUGUACG UGUUAUAAAU AUCCUGUUAG GUAUAGGUAA
2461  CAUUUGUGCA CCGCGGAGAA UAUAGGCGUG GAUUUUUAUA UUAGUUAUAC AUGUAUGCAU
2521  GGAUAUAAAA CGCAAAAAUA CCAUCCGGGG UAGUGGAUUG AAACUAACCG UCAUCGUGU
2581  GGAUAUUUUU UACUAUGUG UGUAUCGUUA UUUUAACGGA CAGGUUUAAU CACGUCUUUG
2641  GUGAAUUAUG AGGUACGCAG UGAUGGCUCA GAAGGUCAGA ACGUUAACUA ACCGACUGUA
2701  AUAAAUCACG CACCCCUGGU AACACCCCAG GUAGACGAAA AAGCCCGCGC CGGUAGGCCA
```

Fig. 32 (SEQ ID NO:27)

SEQ SACMV BC1_target region_reverse_RNA: 222 bases;
Composition 40 A; 37 C; 66 G; 79 U; 0 OTHER
Percentage: 18% A; 17% C; 30% G; 36% U; 0%OTHER Molecular Weight: 71.39 kDa

```
1      UUUGUAAGGU GCCUGUAUGC AAAGUUUGGG GGUUGUUAAU UGUAGAAUAG GUUCCCUAUG
61     UGUUUUCUGA CGUAUCUGAA GACCAGGCAC CUUUUUCCUC UUUGUUCUGC UGCUAAUAAU
121    UUAGGGUGAG GUUGACGAGC AUCAGUUGUU GGGUAUUGGG UGUCCGGGUA GUGGUAGGUA
181    GGUCCGCUUU GUACCCGGUG UUCCAGAGUC UAACCCGAUG GU
```

Fig. 33 (SEQ ID NO:28)

SEQ BC1_target region_modified_reverse_RNA: 222 bases;
Composition 40 A; 0 C; 66 G; 116 U; 0 OTHER
Percentage: 18% A; 0% C; 30% G; 52% U; 0%OTHER Molecular Weight: 71.43 kDa

```
1      UGGUAGUUUA AUUUGAGAUU UUGUGGUUUA UGUUUUGUUU GGAUGGAUGG UGAUGGGUUU
61     GUGGGUUAUG GGUUGUUGAU UAUGAGUAGU UGGAGUGGGA UUUAAUAAUU GUUGUUUUGU
121    UUUUUUUUUU UUUAUGGAUU AGAAGUUUAU GUAGUUUUUU GUGUAUUUUU UGGAUAAGAU
181    GUUAAUUGUU GGGGGUUUGA AAUGUAUGUU UGUGGAAUGU UU
```

Fig. 34 (SEQ ID NO:29)

```
SEQ  SACMV BC1_target gene sequence_complement_reverse_RNA: 2760 bases;
Composition  795  A;  741  C;  454  G;  770  U;  0 OTHER
Percentage:   29%  A;  27%  C;  16%  G;  28%  U;  0%OTHER Molecular Weight: 879.81kDa 1     AAUAUUAUAC GGAUGGCCGC UUUCCACGUU CGCAAUUCAA AUUUCAUUAA GAAAUUACAC
61    AAAUGCCAUU UGGGGGGCAU CAUAUAAAUU GCCCCCCAUU CCCCCGAUUG CUAGGAACUU
121   UGAGUGCCCC CCGAUUGCUC UCGCCUCUCU CUUCUUUCUC UCUCUACCAC GUGUAGCUUA
181   UUCACGCCUA UAUAAACACC UAAUAACAUA UCAUUCACG  ACACCACGCG UAACAUCUGC
241   UCCCUUUCCU UUUUUCGCAA UAAGUUCUAC UUUUAUUUCU UUGUCUUCGC CUAAUUAGCA
301   CAGGAAUUCA CUUCGAACUG CUUCUUCGGC GCUUCUGUAA GUGGUUUACA UCACAUCACC
361   CCAUUCGACU GUUUUCUUUG UUCGCCGAUU UAUCUGACUU CCUAUCCGCU GCGCGGCCGG
421   UUCAACAUAU AUGAUCCUUG UUCUGAUCUC GUGUGUUAUU CUAUAUAACA AAUGCAUAUA
481   UGCUUCCAUG UCUACACGAU AUUUUUCAA  CUUUGUUCUG ACUUUAUAC  CUCUCGUCUC
541   UCCGUUUACU AACCUUUGUU UUUUGCUUC  AUAGAAUGGA CGCCCAAUUU ACCGUCACAG
601   ACAAUAAUUA CAUCAACAGC AAACGCACCG AGUACGCAUU AACAAACGAU GCUGCACCAA
661   UCAAUCUCCA AUUCCAGGC  UCAUUCGAGC AGGCUACCAU GCGACUCAAA GGCCGAUGUA
721   UGAAAAUCGA CCACAUUAUA AUUGAAUACC GAAACCAGGU CCCAUUUAAC GCAACUGGGU
781   CGGUUAUCGU AGAAAUCAGA GACAAUCGCG UCAGCCUUGA CGACGCAGCU CAGGCAGCAU
841   UCACUUUCCC CAUCGCUUGC AACGUGGACC UCCACUACUU CUCUUCUACA UAUUUUUCGA
901   UUUCUGAACC UUCCCCUUGG AGAAUCAUGU ACAGAGUCGA AGACUCAAAC GUCAUAGAAG
961   GCGUGAAAUU CGCAUCCAUC AAGGCCAAGC UCCAGUUAUC AUCGGCCAAA CAUUCCACGG
1021  ACAUACGUUU CAAACCCCCA ACAAUUAACA UCUUAUCCAA GGGAUACACA AAAGACUGCA
1081  UAGACUUCUG GUCCGUGGAA AAAGGAGAAA CAAGACGACG AUUAUUAAAU CCCACUCCAA
1141  CUGCUCGUAG UCAACAACCC AUAACCCACA GGCCCAUCAC CAUCCAUCCA GGCGAAACAU
1201  GGGCCACAAG GUCUCAGAUU GGGCUACCAA GCUCAUUAGG CCCAGCACAG CUGGAACACU
1261  UUCGUUCACA GUCCAUGAGA AUGGACCCAU CGACAACACC AACGGACUUA GACAACGACU
1321  CCACAGAAUA UCCUUACCAG AAACUACACA GAUUACACAC ACCCGAUUUG GACCCAGGGG
1381  ACUCGAUAUC ACAGGCCCAA UCGACUCCG  UCUCCAGAAA GGACCUCGAG ACACUGCUUG
1441  AGAGUACCAU AAACAAGUGU CUCUACAAAA UAAAAUCCGA CGCACCAAGG CAAUUGUAAU
1501  AAACAAUUGA UAUGUACCAU AUUUGCUUAA AAGCAUAAUC AAACUAUAUA UGCUUUCAAU
1561  UAAUGUUCAU CUCAUGUUUC AUUAGUUCAA ACAUAAUUCC UGUCAACACA CUUAUCUCUU
1621  UUUAUUAUCA ACCGACGUAA UUCAGUACAA ACUGCGAAUA CACAUCACAC GUGGUCCGAC
1681  AUAGCGAUAC CCACACAUAA CUCACUAGUA UAGCGUUCUU AUUUAUAUUU UUAUAGUUAC
1741  CACCUGUACU ACUAUUAUCC ACAUCCUUGA ACGACGACCA AAUAGGAUAU UUCCCUCCAC
1801  UUAGUCUUCG ACGUAAACUA AAGGGCUUUU GGAUGUGAUC UUCAUCCGUC GUUAUAUAUA
1861  AUUUCGAUGU CCCAAUAACG CGAUACCGGU GACGGACGUU UUCCUUCAAC CUAGGCAUGC
1921  CGUACACGGA UUCAUAUUCC CCGAACAACU CAUUGAACGU CGGCAAUAUA CUGACCCCCU
1981  CUGGAACGAA AGGUUUCUUA UCAACAAGAC AAGCCAUGAA GAAGAUACCC CUCAUGGUCG
2041  UUCUCUCUCC CAUAUUAUCA UCACCACCGA CUUGACUGAC GUUGACGGUC CCAGAAACCC
2101  UCAAGUUUAA UAAUUUAUG  UGAUCAACAG ACCUACCCCC AUUACCUUCG AUACCUCGAC
2161  AAGGGAGUGA CACGUAGGAC GUAUAAUCCC CCUGUUGAGA CAACUUCAAG GAAGCCCAU
2221  UAUGGAUAUC CUCCAAUGAG CGUCGCUAU  AUAGACCUUU GGCGAUUCA  UACACCAACU
2281  UUCGCGGUAC ACGAGAUUUA GACGUCUGUU UACCAGAGGU CUUACGAUAU ACAUAUGGUG
2341  UUACACGAGC GCCAUACGGA CUCCUAUACG GAGUCUAUA  CCCACGCUG  UAAACUGAAU
2401  ACAUCUUGCA UUAACGAACG GGAGACAUGC ACAAUAUUUA UAGGACAAUC CAUAUCCAUU
2461  GUAAACACGU GGCGCCUCUU AUAUCCGCAC CUAAAAAUAU AAUCAAUAUG UACAUACGUA
2521  CCUAUAUUUU GCGUUUUUAU GGUAGGCCCC AUCACCUAAC UUUGAUUGGC CAGUAGCACA
2581  CCUAUAAAAA UAUGAUACAC ACAUAGCAAU AAAAUUGCCU GUCCAAAUUA GUGCAGAAAC
2641  CACUUAAUAC UCCAUGCGUC ACUACCGAGU CUUCCAGUCU UGCAAUUGAU GGCUGACAU
2701  UAUUUAGUGC GUGGGGACCA UUGUGGGGUC CAUCUGCUUU UCGGGCGCG  GCCAUCCGGU
```

Fig. 35 (SEQ ID NO:30)

SEQ  SACMV BC1_target region_complement_reverse_RNA: 222 bases;
Composition  79   A;  66   C;  37   G;  40   U;  0 OTHER
Percentage:  36%  A;  30%  C;  17%  G;  18%  U;  0%OTHER Molecular Weight: 71.13 kDa

```
1     AAACAUUCCA  CGGACAUACG  UUUCAAACCC  CCAACAAUUA  ACAUCUUAUC  CAAGGGAUAC
61    ACAAAAGACU  GCAUAGACUU  CUGGUCCGUG  GAAAAAGGAG  AAACAAGACG  ACGAUUAUUA
121   AAUCCCACUC  CAACUGCUCG  UAGUCAACAA  CCCAUAACCC  ACAGGCCCAU  CACCAUCCAU
181   CCAGGCGAAA  CAUGGGCCAC  AAGGUCUCAG  AUUGGGCUAC  CA
```

Fig. 36 (SEQ ID NO:31)

SEQ  SACMV Bc1_hairpin_RNA: 183 bases;
Composition  41   A;  30   C;  53   G;  59   U;  0 OTHER
Percentage:  22%  A;  16%  C;  29%  G;  32%  U;  0%OTHER Molecular Weight: 58.98 kDa

```
1     GACCUGGAAG  GGGAUAUGAG  GUCGAAGAAU  CGUUGGUUGG  UACAAUUGUA  CUUGCCCUCG
61    AACUGAAUGA  GGGCAUGCAA  AUGAGGUUCC  CCAUUUUCAU  GGAGUUCUCU  GCAGAUCUUG
121   AUGAACAAUU  UAUUUGUUGG  GGUUGGAGU   UGUCGGAGUU  GAUCUAAUGC  CGCUUCUUUC
181   GAG
```

Fig. 37 (SEQ ID NO:32)

SACMV AC1

SEQ SACMV AC1_Target DNA gene sequence: 2800 bp;
Composition 703 A; 578 C; 724 G; 795 T; 0 OTHER
Percentage: 25% A; 21% C; 26% G; 28% T; 0%OTHER Molecular Weight (kDa): ssDNA: 866.96 dsDNA: 1726.1
ORIGIN

```
1     ACCGGATGGC CGCGCCCGAC AAAGTAGGTG GACCCCATTG GATGACCGCG CCCGTAAAAG
61    AAAGTGGTCC CCACGCACGT GTTGCTGTCG GCCAGTCATA TTCACGCGTG AAAGCCTAGA
121   TATTTGTTTT ATGTCGTTAT AGACTTCGTC GCGAAGTAGT GGAGCGTGTC AACATGTGGG
181   ATCCATTGTT GAATGAGTTC CCCGAGTCTG TGCACGGTTT TCGCTGTATG CTTGCTATTA
241   AATATTTGCA GGCCTTGGAG GAAACCTACG AGCCCAATAC TTTGGGCCAC GATCTAGTCC
301   GTGATCTCAT CGGTGTGATC CGAGCCCGTG ATTATGTCGA AGCGTCCCGC CGATATAATC
361   ATTTCCACTC CCGTCTCGAA GGTGCGTCGA AGGCTGAACT TCGACAGCCC GTTCAGCAGC
421   CGTGCTGCTG TCCCCATTGT CCAAGGCACA AACAAGCGTC GATCATGGAC GTTCCGGCCC
481   ATGTACCGAA AGCCCAGAAT GTACAGAATG TTCAAAAGCC CTGATGTTCC GCGTGGCTGT
541   GAAGGCCCAT GTAAGGTTCA ATCTTATGAA CAGCGAGATG ACGTTAAGCA TACTGGCAGT
601   GTTCGTTGTG TTAGTGATGT CACGCGTGGT TCGGGAATTA CACATAGAGT AGGTAAAAGG
661   TTCTGTATCA AGTCTATATA TGTGTTAGGT AAGATATGGA TGGATGAAAA CATCAAGAAG
721   CAGAACCATA CAAACCAGGT CATGTTCTTC TTAGTCCGTG ACAGAAGGCC CTATGGCAAT
781   AGCCCCATGG ACTTTGGACA GGTTTTTAAT ATGTTTGATA ATGAGCCCAG TACAGCCACT
841   GTGAAGAACG ATCTTAGGGA TAGGTATCGA GTTATGCGGA AGTTTCATGC CACCGTTGTT
901   GGGGGTCCTT CTGGAATGAA GGAGCAGGCT TTGGTGAGGA GATTTTTTAG GATAAATAAT
961   CATGTTGTGT ATAATCACCA GGAGGCAGCT AAGTATGAGA ATCATACAGA GAATGCGTTA
1021  TTGTTGTATA TGGCATGTAC GCATGCCTCT AATCCAGTGT ATGCTACGCT TAAAATACGC
1081  ATCTATTTTT ATGATGCAGT AACAAATTAA TAAAGGTTGA ATTTTATTGC ATGTTGCTCC
1141  GTAACTTGGA GTGTGTTTAG TAATACATCG TACAGAACAT GATCAACAGC TCTGAGTACA
1201  GTGTTAATGG AAATAACGCC TATCATATTT AAATACTTGA GCACTTGATA TTTAAATACT
1261  CTTAAGAAAA GACCAGTCGG AGGCCGTAAG GTCGTCCAGA CCTTGAAGTT GAGAAAACAC
1321  TTGTGAATCC CCAATGCCTT CCTGATGTTG TGGTTGAACC GTATCTGGAG GGTGATGATG
1381  TCGTGGTTCA TGTTCCCTGG CCGCTTGTCG TGGTTGGTGA TGTCGAAATA GAGGGGATTT
1441  GTTATTTCCC AGGTAAAAAC GCCATTCTTT GCTTGAGGCG CAGTGATGAG TTCCCCTGTG
1501  CGAGAATCCA TGGTTGATGC AGTCGATATG GAGATAGAAC GAGCAGCCGC ATTCGAGGTC
1561  TACCCTCCTA CGTCTGAGGG CCCTAGTCTT CGCGGTGCGG TGTTGGACTT TGATGGGCAC
1621  TTGAGAACAA TGCCTCGTGG AGGGTGATGA AGGTTGCATT CTTTAAAGCC CAGGCTTTAA
1681  GGGACTGGTT CTTTTCCTCG TCCAGAAACT CTTTATATGA TGATGTCGGT CCTGGATTGC
1741  ATAGGAAGAT AGTGGGAATG CCGCCTTTAA TTTGAATCGG CTTCCCGTAC TTGGTATTGC
1801  TTTGCCAGTC CCTTTGGGCC CCCATGAATT CTTTGAAGTG CTTGAGGTAA TGGGGGTCGA
1861  CGTCATCAAT GACGTTGTAC CATGCGTCGT TGCTGTAAAC CTTTGGACTG AGATCCAAAT
1921  GTCCACATAA GTAGTTGTGT GGTCCCAGAG ATCGGGCCCA CATCGTCTTC CCTGTCCTAC
1981  TATCGCCCTC GATGACGATA CTACTCGGTC TCCATGGCCG CGCAGCGAAA CCCATCACGT
2041  TCTCGGAAAC CCAGTCTTCA AGTTCCTCAG GAACATGAGT GAAAGAAGAA GAAAGAAAGG
2101  GAGAAATATA AGGAATCGGA GGCTCCTGAA AAATCCTATC TAAATTGCTA TTTAAATTAT
2161  GAAACTGTAA AACAAAATCC TTTGGGGCTA GTTCCCGGAT TACATTAAGA GCCTCTGTTT
2221  TACTTGCTGC GTTAAGAGCC TTGGCGTAAG CGTCATTGGC GGATTGTTGT CCGCCGCGAG
2281  CAGATCGTCC GTCGATCTGA AACTCGCCCC ATTGGATGGT GTCTCCGTCC TTGTCCAAAT
2341  AGGACTTGAC GTCAGAACTG GATTTAGCTC CCTGAATGTT TGGATGGAAA TGTGTTGACC
2401  TGGAAGGGGA TATGAGGTCG AAGAATCGTT GGTTGGTACA ATTGTACTTG CCCTCGAACT
2461  GAATGAGGGC ATGCAAATGA GGTTCCCCAT TTTCATGGAG TTCTCTGCAG ATCTTGATGA
2521  ACAATTTATT TGTTGGGGTT TGGAGTTGTC GGAGTTGATC TAATGCCGCT TCTTTCGAGA
2581  GAGTGCATTT CGGATACGTG AGGAAATAAT TTTTGGCTTT TATGCTAAAA CGACCAGCCC
2641  TCGGCATTTT CGCTGTCGTA TAGCAATCGG GGGGCACTCA AAGTTCCTAG CAATCGGGGG
2701  AATGGGGGGC AATTTATATG ATGCCCCCCA AATGGCATAT GTGTAATTTT GTGATGAAAT
2761  TTGAATTTCG AACGTGGAAA GCGGCCATCC GTCTAATATT
```

Fig. 38 (SEQ ID NO:33)

```
SEQ  SACMV AC1_Target DNA gene region: 183 bp;
Composition  41   A;  30   C;  53   G;  59   T;  0 OTHER
Percentage:  22%  A;  16%  C;  29%  G;  32%  T;  0%OTHER Molecular Weight (kDa): ssDNA: 56.88     dsDNA: 112.8
ORIGIN
1      GACCTGGAAG GGGATATGAG GTCGAAGAAT CGTTGGTTGG TACAATTGTA CTTGCCCTCG
61     AACTGAATGA GGGCATGCAA ATGAGGTTCC CCATTTTCAT GGAGTTCTCT GCAGATCTTG
121    ATGAACAATT TATTTGTTGG GGTTTGGAGT TGTCGGAGTT GATCTAATGC CGCTTCTTTC
181    GAG
```

Fig. 39 (SEQ ID NO:34)

```
SEQ  SACMV AC1_Target DNA gene region_modified: 183 bp;
Composition  41   A;  0    C;  53   G;  89   T;  0 OTHER
Percentage:  22%  A;  0%   C;  29%  G;  48%

```
SEQ  SACMV AC1_Target DNA gene sequence_complement: 2800 bp;
Composition   795  A;  724

SEQ  SACMV AC1_Target DNA gene region_complement: 183 bp;
Composition  59   A;  53   C;  30   G;  41   T;  0 OTHER
Percentage:  32%  A;  29%  C;  16%  G;  22%  T;  0%OTHER Molecular Weight (kDa): ssDNA: 56.12      dsDNA: 112.8
ORIGIN
1      CTGGACCTTC CCCTATACTC CAGCTTCTTA GCAACCAACC ATGTTAACAT GAACGGGAGC
61     TTGACTTACT CCCGTACGTT TACTCCAAGG GGTAAAAGTA CCTCAAGAGA CGTCTAGAAC
121    TACTTGTTAA ATAAACAACC CCAAACCTCA ACAGCCTCAA CTAGATTACG GCGAAGAAAG
181    CTC

Fig. 42 (SEQ ID NO:37)

```
SEQ  SACMV AC1_Target DNA gene sequence_reverse: 2800 bp;
Composition   703  A;  578  C;  724  G;  795  T;  0 OTHER
Percentage:   25%  A;  21%  C;  26%  G;  28%  T;  0%OTHER Molecular Weight (kDa): ssDNA:  866.96      dsDNA: 1726.1
ORIGIN
1       TTATAATCTG  CCTACCGGCG  AAAGGTGCAA  GCTTTAAGTT  TAAAGTAGTG  TTTTAATGTG
61      TATACGGTAA  ACCCCCCGTA  GTATATTTAA  CGGGGGGTAA  GGGGGCTAAC  GATCCTTGAA
121     ACTCACGGGG  GGCTAACGAT  ATGCTGTCGC  TTTTACGGCT  CCCGACCAGC  AAAATCGTAT
181     TTTCGGTTTT  TAATAAAGGA  GTGCATAGGC  TTTACGTGAG  AGAGCTTTCT  TCGCCGTAAT
241     CTAGTTGAGG  CTGTTGAGGT  TTGGGGTTGT  TTATTTAACA  AGTAGTTCTA  GACGTCTCTT
301     GAGGTACTTT  TACCCCTTGG  AGTAAACGTA  CGGGAGTAAG  TCAAGCTCCC  GTTCATGTTA
361     ACATGGTTGG  TTGCTAAGAA  GCTGGAGTAT  AGGGGAAGGT  CCAGTTGTGT  AAAGGTAGGT
421     TTGTAAGTCC  CTCGATTTAG  GTCAAGACTG  CAGTTCAGGA  TAAACCTGTT  CCTGCCTCTG
481     TGGTAGGTTA  CCCCGCTCAA  AGTCTAGCTG  CCTGCTAGAC  GAGCGCCGCC  TGTTGTTAGG
541     CGGTTACTGC  GAATGCGGTT  CCGAGAATTG  CGTCGTTCAT  TTTGTCTCCG  AGAATTACAT
601     TAGGCCCTTG  ATCGGGGTTT  CCTAAAACAA  AATGTCAAAG  TATTAAATTT  ATCGTTAAAT
661     CTATCCTAAA  AAGTCCTCGG  AGGCTAAGGA  ATATAAAGAG  GGAAAGAAAG  AAGAAGAAAG
721     TGAGTACAAG  GACTCCTTGA  ACTTCTGACC  CAAAGGCTCT  TGCACTACCC  AAAGCGACGC
781     GCCGGTACCT  CTGGCTCATC  ATAGCAGTAG  CTCCGCTAT   CATCCTGTCC  CTTCTGCTAC
841     ACCCGGGCTA  GAGACCCTGG  TGTGTTGATG  AATACACCTG  TAAACCTAGA  GTCAGGTTTC
901     CAAATGTCGT  TGCTGCGTAC  CATGTTGCAG  TAACTACTGC  AGCTGGGGGT  AATGGAGTTC
961     GTGAAGTTTC  TTAAGTACCC  CCGGGTTTCC  CTGACCGTTT  CGTTATGGTT  CATGCCCTTC
1021    GGCTAAGTTT  AATTTCCGCC  GTAAGGGTGA  TAGAAGGATA  CGTTAGGTCC  TGGCTGTAGT
1081    AGTATATTTC  TCAAAGACCT  GCTCCTTTTC  TTGGTCAGGG  AATTTCGGAC  CCGAAATTTC
1141    TTACGTTGGA  AGTAGTGGGA  GGTGCTCGGT  AACAAGAGTT  CACGGGTAGT  TTCAGGTTGT
1201    GGCGTGGCGC  TTCTGATCCC  GGGAGTCTGC  ATCCTCCCAT  CTGGAGCTTA  CGCCGACGAG
1261    CAAGATAGAG  GTATAGCTGA  CGTAGTTGGT  ACCTAAGAGC  GTGTCCCCTT  GAGTAGTGAC
1321    GCGGAGTTCG  TTTCTTACCG  CAAAAATGGA  CCCTTTATTG  TTTAGGGGAG  ATAAAGCTGT
1381    AGTGGTTGGT  GCTGTTCGCC  GGTCCCTTGT  ACTTGGTGCT  GTAGTAGTGG  GAGGTCTATG
1441    CCAAGTTGGT  GTTGTAGTCC  TTCCGTAACC  CCTAAGTGTT  CACAAAAGAG  TTGAAGTTCC
1501    AGACCTGCTG  GAATGCCGGA  GGCTGACCAG  AAAAGAATTC  TCATAAATTT  ATAGTTCACG
1561    AGTTCATAAA  TTTATACTAT  CCGCAATAAA  GGTAATTGTG  ACATGAGTCT  CGACAACTAG
1621    TACAAGACAT  GCTACATAAT  GATTTGTGTC  AGGTTCAATG  CCTCGTTGTA  CGTTATTTTA
1681    AGTTGGAAAT  AATTAAACAA  TGACGTAGTA  TTTTTATCTA  CGCATAAAAT  TCGCATCGTA
1741    TGTGACCTAA  TCTCCGTACG  CATGTACGGT  ATATGTTGTT  ATTGCGTAAG  AGACATACTA
1801    AGAGTATGAA  TCGACGGAGG  ACCACTAATA  TGTGTTGTAC  TAATAAATAG  GATTTTTTAG
1861    AGGAGTGGTT  TCGGACGAGG  AAGTAAGGTC  TTCCTGGGGG  TTGTTGCCAC  CGTACTTTGA
1921    AGGCGTATTG  AGCTATGGAT  AGGGATTCTA  GCAAGAAGTG  TCACCGACAT  GACCCGAGTA
1981    ATAGTTTGTA  TAATTTTTGG  ACAGGTTTCA  GGTACCCCGA  TAACGGTATC  CCGGAAGACA
2041    GTGCCTGATT  CTTCTTGTAC  TGGACCAAAC  ATACCAAGAC  GAAGAACTAC  AAAAGTAGGT
2101    AGGTATAGAA  TGGATTGTGT  ATATATCTGA  ACTATGTCTT  GGAAAATGGA  TGAGATACAC
2161    ATTAAGGGCT  TGGTGCGCAC  TGTAGTGATT  GTGTTGCTTG  TGACGGTCAT  ACGAATTGCA
2221    GTAGAGCGAC  AAGTATTCTA  ACTTGGAATG  TACCCGGAAG  TGTCGGTGCG  CCTTGTAGTC
2281    CCGAAAACTT  GTAAGACATG  TAAGACCCGA  AAGCCATGTA  CCCGGCCTTG  CAGGTACTAG
2341    CTGCGAACAA  ACACGGAACC  TGTTACCCCT  GTCGTCGTGC  CGACGACTTG  CCCGACAGCT
2401    TCAAGTCGGA  AGCTGCGTGG  AAGCTCTGCC  CTCACCTTTA  CTAATATAGC  CGCCCTGCGA
2461    AGCTGTATTA  GTGCCCGAGC  CTAGTGTGGC  TACTCTAGTG  CCTGATCTAG  CACCGGGTTT
2521    CATAACCCGA  GCATCCAAAG  GAGGTTCCGG  ACGTTTATAA  ATTATCGTTC  GTATGTCGCT
2581    TTTGGCACGT  GTCTGAGCCC  CTTGAGTAAG  TTGTTACCTA  GGGTGTACAA  CTGTGCGAGG
2641    TGATGAAGCG  CTGCTTCAGA  TATTGCTGTA  TTTTGTTTAT  AGATCCGAAA  GTGCGCACTT
2701    ATACTGACCG  GCTGTCGTTG  TGCACGCACC  CCTGGTGAAA  GAAAATGCCC  GCGCCAGTAG
2761    GTTACCCCAG  GTGGATGAAA  CAGCCCGCGC  CGGTAGGCCA
```

Fig. 43 (SEQ ID NO:38)

```
SEQ  SACMV AC1_Target DNA gene region_reverse: 183 bp;
Composition  41   A; 30   C; 53   G; 59   T; 0 OTHER
Percentage:  22%  A; 16%  C; 29%  G; 32%  T; 0%OTHER Molecular Weight (kDa): ssDNA: 56.88     dsDNA: 112.8
ORIGIN
1      GAGCTTTCTT CGCCGTAATC TAGTTGAGGC TGTTGAGGTT TGGGGTTGTT TATTTAACAA
61     GTAGTTCTAG ACGTCTCTTG AGGTACTTTT ACCCCTTGGA GTAAACGTAC GGGAGTAAGT
121    CAAGCTCCCG TTCATGTTAA CATGGTTGGT TGCTAAGAAG CTGGAGTATA GGGGAAGGTC
181    CAG
```

Fig. 44 (SEQ ID NO:39)

```
SEQ  SACMV AC1_Target gene sequence_modified_reverse: 183 bp;
Composition  41   A; 0    C; 53   G; 89   T; 0 OTHER
Percentage:  22%  A; 0%  C; 29%  G; 49%  T; 0%OTHER Molecular Weight (kDa): ssDNA: 57.33     dsDNA: 112.8
ORIGIN
1      GAGTTTTTTT TGTTGTAATT TAGTTGAGGT TGTTGAGGTT TGGGGTTGTT TATTTAATAA
61     GTAGTTTTAG ATGTTTTTTG AGGTATTTTT ATTTTTTGGA GTAAATGTAT GGGAGTAAGT
121    TAAGTTTTTG TTTATGTTAA TATGGTTGGT TGTTAAGAAG TTGGAGTATA GGGGAAGGTT
181    TAG
```

Fig. 45 (SEQ ID NO:40)

SEQ SACMV AC1_Target DNA gene sequence_complement_reverse: 2800 bp;
Composition   795 A;  724 C;  578 G;  703 T;  0 OTHER
Percentage:    28% A;  26% C;  21% G;  25% T;  0%OTHER Molecular Weight (kDa): ssDNA: 861.95    dsDNA: 1726.1
ORIGIN
```
1     AATATTAGAC GGATGGCCGC TTTCCACGTT CGAAATTCAA ATTTCATCAC AAAATTACAC
61    ATATGCCATT TGGGGGGCAT CATATAAATT GCCCCCCATT CCCCCGATTG CTAGGAACTT
121   TGAGTGCCCC CCGATTGCTA TACGACAGCG AAAATGCCGA GGGCTGGTCG TTTTAGCATA
181   AAAGCCAAAA ATTATTTCCT CACGTATCCG AAATGCACTC TCTCGAAAGA AGCGGCATTA
241   GATCAACTCC GACAACTCCA AACCCCAACA AATAAATTGT TCATCAAGAT CTGCAGAGAA
301   CTCCATGAAA ATGGGGAACC TCATTTGCAT GCCCTCATTC AGTTCGAGGG CAAGTACAAT
361   TGTACCAACC AACGATTCTT CGACCTCATA TCCCCTTCCA GGTCAACACA TTTCCATCCA
421   AACATTCAGG GAGCTAAATC CAGTTCTGAC GTCAAGTCCT ATTTGGACAA GGACGGAGAC
481   ACCATCCAAT GGGGCGAGTT TCAGATCGAC GGACGATCTG CTCGCGGCGG ACAACAATCC
541   GCCAATGACG CTTACGCCAA GGCTCTTAAC GCAGCAAGTA AAACAGAGGC TCTTAATGTA
601   ATCCGGGAAC TAGCCCCAAA GGATTTTGTT TTACAGTTTC ATAATTTAAA TAGCAATTTA
661   GATAGGATTT TTCAGGAGCC TCCGATTCCT TATATTTCTC CCTTTCTTTC TTCTTCTTTC
721   ACTCATGTTC CTGAGGAACT TGAAGACTGG GTTTCCGAGA ACGTGATGGG TTTCGCTGCG
781   CGGCCATGGA GACCGAGTAG TATCGTCATC GAGGGCGATA GTAGGACAGG GAAGACGATG
841   TGGGCCCGAT CTCTGGGACC ACACAACTAC TTATGTGGAC ATTTGGATCT CAGTCCAAAG
901   GTTTACAGCA ACGACGCATG GTACAACGTC ATTGATGACG TCGACCCCCA TTACCTCAAG
961   CACTTCAAAG AATTCATGGG GGCCCAAAGG GACTGGCAAA GCAATACCAA GTACGGGAAG
1021  CCGATTCAAA TTAAAGGCGG CATTCCCACT ATCTTCCTAT GCAATCCAGG ACCGACATCA
1081  TCATATAAAG AGTTTCTGGA CGAGGAAAAG AACCAGTCCC TTAAAGCCTG GCTTTAAAG
1141  AATGCAACCT TCATCACCCT CCACGAGCCA TTGTTCTCAA GTGCCCATCA AGTCCAACA
1201  CCGCACCGCG AAGACTAGGG CCCTCAGACG TAGGAGGGTA GACCTCGAAT GCGGCTGCTC
1261  GTTCTATCTC CATATCGACT GCATCAACCA TGGATTCTCG CACAGGGGAA CTCATCACTG
1321  CGCCTCAAGC AAAGAATGGC GTTTTTACCT GGGAAATAAC AAATCCCCTC TATTTCGACA
1381  TCACCAACCA CGACAAGCGG CCAGGGAACA TGAACCACGA CATCATCACC CTCCAGATAC
1441  GGTTCAACCA CAACATCAGG AAGGCATTGG GGATTCACAA GTGTTTTCTC AACTTCAAGG
1501  TCTGGACGAC CTTACGCCCT CCGACTGGTC TTTTCTTAAG AGTATTTAAA TATCAAGTGC
1561  TCAAGTATTT AAATATGATA GGCGTTATTT CCATTAACAC TGTACTCAGA GCTGTTGATC
1621  ATGTTCTGTA CGATGTATTA CTAAACACAC TCCAAGTTAC GGAGCAACAT GCAATAAAAT
1681  TCAACCTTTA TTAATTTGTT ACTGCATCAT AAAAATAGAT GCGTATTTTA AGCGTAGCAT
1741  ACACTGGATT AGAGGCATGC GTACATGCCA TATACAACAA TAACGCATTC TCTGTATGAT
1801  TCTCATACTT AGCTGCCTCC TGGTGATTAT ACACAACATG ATTATTTATC CTAAAAAATC
1861  TCCTCACCAA AGCCTGCTCC TTCATTCCAG AAGGACCCCC AACAACGGTG GCATGAAACT
1921  TCCGCATAAC TCGATACCTA TCCCTAAGAT CGTTCTTCAC AGTGGCTGTA CTGGGCTCAT
1981  TATCAAACAT ATTAAAAACC TGTCCAAAGT CCATGGGGCT ATTGCCATAG GCCTTCTGT
2041  CACGGACTAA GAAGAACATG ACCTGGTTTG TATGGTTCTG CTTCTTGATG TTTTCATCCA
2101  TCCATATCTT ACCTAACACA TATATAGACT TGATACAGAA CCTTTTACCT ACTCTATGTG
2161  TAATTCCCGA ACCACGCGTG ACATCACTAA CACAACGAAC ACTGCCAGTA TGCTTAACGT
2221  CATCTCGCTG TTCATAAGAT TGAACCTTAC ATGGGCTTC ACAGCACGC GGAACATCAG
2281  GGCTTTTGAA CATTCTGTAC ATTCTGGGCT TTCGGTACAT GGGCCGGAAC GTCCATGATC
2341  GACGCTTGTT TGTGCCTTGG ACAATGGGGA CAGCAGCACG GCTGCTGAAC GGGCTGTCGA
2401  AGTTCAGCCT TCGACGCACC TTCGAGACGG GAGTGGAAAT GATTATATCG GCGGGACGCT
2461  TCGACATAAT CACGGGCTCG GATCACACCG ATGAGATCAC GGACTAGATC GTGGCCCAAA
2521  GTATTGGGCT CGTAGGTTTC CTCCAAGGCC TGCAAATATT AATAGCAAG CATACAGCGA
2581  AAACCGTGCA CAGACTCGGG GAACTCATTC AACAATGGAT CCCACATGTT GACACGCTCC
2641  ACTACTTCGC GACGAAGTCT ATAACGACAT AAAACAAATA TCTAGGCTTT CACGCGTGAA
2701  TATGACTGGC CGACAGCAAC ACGTGCGTGG GGACCACTTT CTTTTACGGG CGCGGTCATC
2761  CAATGGGGTC CACCTACTTT GTCGGGCGCG GCCATCCGGT
```

Fig. 46 (SEQ ID NO:41)

```
SEQ  SACMV AC1_Target DNA gene region_complement_reverse: 183 bp;
Composition  59   A;  53   C;  30   G;  41   T;  0 OTHER
Percentage:  32%  A;  29%  C;  16%  G;  22%  T;  0%OTHER Molecular Weight (kDa): ssDNA: 56.12      dsDNA: 112.8
ORIGIN
1       CTCGAAAGAA GCGGCATTAG ATCAACTCCG ACAACTCCAA ACCCCAACAA ATAAATTGTT
61      CATCAAGATC TGCAGAGAAC TCCATGAAAA TGGGGAACCT CATTTGCATG CCCTCATTCA
121     GTTCGAGGGC AAGTACAATT GTACCAACCA ACGATTCTTC GACCTCATAT CCCCTTCCAG
181     GTC
```

Fig. 47 (SEQ ID NO:42)

SEQ  SACMV AC1_Target DNA gene sequence_RNA: 2800 bases;
Composition   703  A;  578  C;  724  G;  795  U;  0 OTHER
Percentage:   25%  A;  21%  C;  26%  G;  28%  U;  0%OTHER Molecular Weight: 900.63kDa

```
   1   ACCGGAUGGC CGCGCCCGAC AAAGUAGGUG GACCCCAUUG GAUGACCGCG CCCGUAAAAG
  61   AAAGUGGUCC CCACGCACGU GUUGCUGUCG GCCAGUCAUA UUCACGCGUG AAAGCCUAGA
 121   UAUUUGUUUU AUGUCGUUAU AGACUUCGUC GCGAAGUAGU GGAGCGUGUC AACAUGUGGG
 181   AUCCAUUGUU GAAUGAGUUC CCCGAGUCUG UGCACGGUUU UCGCUGUAUG CUUGCUAUUA
 241   AAUAUUUGCA GGCCUUGGAG GAAACCUACG AGCCCAAUAC UUUGGGCCAC GAUCUAGUCC
 301   GUGAUCUCAU CGGUGUGAUC CGAGCCCGUG AUUAUGUCGA AGCGUCCCGC CGAUAUAAUC
 361   AUUCCACUC CCGUCUCGAA GGUGCGUCGA AGGCUGAACU UCGACAGCCC GUUCAGCAGC
 421   CGUGCUGCUG UCCCCAUUGU CCAAGGCACA AACAAGCGUC GAUCAUGGAC GUUCCGGCCC
 481   AUGUACCGAA AGCCCAGAAU GUACAGAAUG UUCAAAAGCC CUGAUGUUCC GCGUGGCUGU
 541   GAAGGCCCAU GUAAGGUUCA UCUUAUGAA CAGCGAGAUG ACGUUAAGCA UACUGGCAGU
 601   GUUCGUUGUG UUAGUGAUGU CACGCGUGGU UCGGGAAUUA CACAUAGAGU AGGUAAAAGG
 661   UUCUGUAUCA AGUCUAUAUA UGUGUUAGGU AAGAUAUGGA UGGAUGAAAA CAUCAAGAAG
 721   CAGAACCAUA CAAACCAGGU CAUGUUCUUC UUAGUCCGUG ACAGAAGGCC CUAUGGCAAU
 781   AGCCCCAUGG ACUUUGGACA GGUUUUUAAU AUGUUUGAUA AUGAGCCCAG UACAGCCACU
 841   GUGAAGAACG AUCUUAGGGA UAGGUAUCGA GUUAUGCGGA AGUUUCAUGC CACCGUUGUU
 901   GGGGGUCCUU CUGGAAUGAA GGAGCAGGCU UUGGUGAGCA GAUUUUUUAG GAUAAAUAAU
 961   CAUGUUGUGU AUAAUCACCA GGAGGCAGCU AAGUAUGAGA AUCAUACAGA GAAUGCGUUA
1021   UUGUUGUAUA UGGCAUGUAC GCAUGCCUCU AAUCCAGUGU AUGCUACGCU UAAAAUACGC
1081   AUCUAUUUUU AUGAUGCAGU AACAAAUUAA UAAAGGUUGA AUUUUAUUGC AUGUUGCUCC
1141   GUAACUUGGA GUGUGUUUAG UAAUACAUCG UACAGAACAU GAUCAACAGC UCUAGUACA
1201   GUGUUAAUGG AAAUAACGCC UAUCAUAUUU AAAUACUGUA GCACUUGAUA UUUAAAUACU
1261   CUUAAGAAAA GACCAGUCGU AGGCCGUAAG GUCGUCCAGA CCUUGAAGUU GAGAAAACAC
1321   UUGUGAAUCC CCAAUGCCUU CCUGAUGUUG UGGUUGAACC GUAUCUGGAG GGUGAUGAUG
1381   UCGUGGUUCA UGUUCCCUGG CCGCUUGUCC UGGUUGGUGA UGUCGAAAUA GAGGGGAUUU
1441   GUUAUUUCCC AGGUAAAAAC GCCAUUCUUU GCUUGAGGCG CAGUGAUGAG UUCCCCUGUG
1501   CGAGAAUCCA UGGUUGAUGC AGUCGAUAUG GAGAUAGAAC GAGCAGCCGC AUUCGAGGUC
1561   UACCUCCUA CGUCUGAGGG CCCUAGUCUU CGCGGUGCGG UGUUGGACUU UGAUGGGCAC
1621   UUGAGAACAA UGGCUCGUGG AGGGUGAUGA AGGUUGCAUU CUUUAAAGCC CAGGCUUUAA
1681   GGGACUGGUU CUUUUCCUCG UCCAGAAACU CUUUAUAUGA UGAUGUCGGU CCUGGAUUGC
1741   AUAGGAAGAU AGUGGGAAUG CCGCCUUUAA UUUGAAUCGG CUUCCCGUAC UUGGUAUUGC
1801   UUUGCCAGUC CCUUUGGGCC CCCAUGAAUU CUUUGAAGUG CUUGAGGUAA UGGGGGUCGA
1861   CGUCAUCAAU GACGUUGUAC CAUGCGUCGU UGCUGUAAAC CUUUGGACUG AGAUCCAAAU
1921   GUCCACAUAA GUAGUUGUGU GGUCCCAGAG AUCGGGCCCA CAUCGUCUUC CCUGUCCUAC
1981   UAUCGCCCUC GAUGACGAUA CUACUCGGUC UCCAUGGCCG CGCAGCGAAA CCCAUCACGU
2041   UCUCGGAAAC CCAGUCUUCA AGUUCCUCAG GAACAUGAGU GAAAGAAGAA GAAAGAAAGG
2101   GAGAAAUAUA AGGAAUCGGA GGCUCCUGAA AAAUCCUAUC UAAAUUGCUA UUUAAAUUAU
2161   GAAACUGUAA AACAAAAUCC UUUGGGGCUA GUUCCGGAU UACAUUAAGA GCCUCUGUUU
2221   UACUUGCUGC GUUAAGAGCC UUGGCGUAAG CGUCAUUGGC GGAUUGUUGU CCGCCGCGAG
2281   CAGAUCGUCC GUCGAUCUGA AACUCGCCCC AUUGGAUGGU GUCCGUCC UUGUCCAAAU
2341   AGGACUUGAC GUCAGAACUG GAUUUAGCUC CCUGAAUGUU GGAUGGAAA UGUGUUGACC
2401   UGGAAGGGGA UAUGAGGUCG AAGAAUCGUU GGUUGGUACA AUUGUACUUG CCCUCGAACU
2461   GAAUGAGGGC AUGCAAAUGA GGUUCCCCAU UUUCAUGGAG UUCUCUGCAG AUCUUGAUGA
2521   ACAAUUUAUU UGUUGGGGUU UGGAGUUGUC GGAGUUGAUC UAAUGCCGCU UCUUUCGAGA
2581   GAGUGCAUUU CGGAUACGUG AGGAAAUAAU UUUUGUCUUU UAUGCUAAAA CGACCAGCCC
2641   UCGGCAUUUU CGCUGUCGUA UAGCAAUCGG GGGCACUCA AAGUUCUAG CAAUCGGGGG
2701   AAUGGGGGGC AAUUUAUAUG AUGCCCCCCA AAUGGCAUAU GUGUAAUUUU GUGAUGAAAU
2761   UUGAAUUUCG AACGUGGAAA GCGGCCAUCC GUCUAAUAUU
```

Fig. 48 (SEQ ID NO:43)

SEQ   SACMV AC1_Target DNA gene region_RNA: 183 bases;
Composition  41   A;  30    C;  53    G;  59    U;  0 OTHER
Percentage:  22%  A;  16%   C;  29%   G;  32%   U;  0%OTHER Molecular Weight: 58.98 kDa

```
1    GACCUGGAAG GGGAUAUGAG GUCGAAGAAU CGUUGGUUGG UACAAUUGUA CUUGCCCUCG
61   AACUGAAUGA GGGCAUGCAA AUGAGGUUCC CCAUUUUCAU GGAGUUCUCU GCAGAUCUUG
121  AUGAACAAUU UAUUUGUUGG GGUUUGGAGU UGUCGGAGUU GAUCUAAUGC CGCUUCUUUC
181  GAG
```

Fig. 49 (SEQ ID NO:44)

SEQ   SACMV AC1_Target DNA gene region_modified_RNA: 183 bases;
Composition  41   A;  0     C;  53    G;  89    U;  0 OTHER
Percentage:  22%  A;  0%    C;  29%   G;  49%   U;  0%OTHER Molecular Weight: 59.01 kDa

```
1    GAUUUGGAAG GGGAUAUGAG GUUGAAGAAU UGUUGGUUGG UAUAAUUGUA UUUGUUUUUG
61   AAUUGAAUGA GGGUAUGUAA AUGAGGUUUU UUAUUUUUAU GGAGUUUUUU GUAGAUUUUG
121  AUGAAUAAUU UAUUUGUUGG GGUUUGGAGU UGUUGGAGUU GAUUUAAUGU UGUUUUUUUU
181  GAG
```

Fig. 50 (SEQ ID NO:45)

```
SEQ  SACMV AC1_Target gene_complement_RNA: 2800 bases;
Composition  795 A; 724 C; 578 G; 703 U; 0 OTHER
Percentage:  28% A; 26% C; 21% G; 25% U; 0%OTHER Molecular Weight: 896.90kDa 1     UGGCCUACCG GCGCGGGCUG UUUCAUCCAC CUGGGGUAAC CUACUGGCGC GGGCAUUUUC
61    UUUCACCAGG GGUGCGUGCA CAACGACAGC CGGUCAGUAU AAGUGCGCAC UUUCGGAUCU
121   AUAAACAAAA UACAGCAAUA UCUGAAGCAG CGCUUCAUCA CCUCGCACAG UUGUACACCC
181   UAGGUAACAA CUUACUCAAG GGCUCAGAC  ACGUGCCAAA AGCGACAUAC GAACGAUAAU
241   UUAUAAACGU CCGGAACCUC CUUUGGAUGC UCGGGUUAUG AAACCCGGUG CUAGAUCAGG
301   CACUAGAGUA GCCACACUAG GCUCGGGCAC UAAUACAGCU UCGCAGGGCG GCUAUAUUAG
361   UAAAGGUGAG GGCAGAGCUU CCACGCAGCU UCCGACUUGA AGCUGUCGGG CAAGUCGUCG
421   GCACGACGAC AGGGGUAACA GGUUCCGUGU UUGUUCGCAG CUAGUACCUG CAAGGCCGGG
481   UACAUGGCUU UCGGGUCUUA CAUGUCUUAC AAGUUUCGG  GACUACAAGG CGCACCGACA
541   CUUCCGGGUA CAUUCCAAGU UAGAAUACUU GUCGCUCUAC UGCAAUUCGU AUGACCGUCA
601   CAAGCAACAC AAUCACUACA GUGCGCACCA AGCCCUUAAU GUGUAUCUCA UCCAUUUUCC
661   AAGACAUAGU UCAGAUAUAU ACACAAUCCA UUCUAUACCU ACCUACUUUU GUAGUUCUUC
721   GUCUUGGUAU GUUUGGUCCA GUACAAGAAG AAUCAGGCAC UGUCUUCCGG GAUACCGUUA
781   UCGGGGUACC UGAAACCUGU CCAAAAAUUA UACAAACUAU UACUCGGGUC AUGUCGGUGA
841   CACUUCUUGC UAGAAUCCCU AUCCAUAGCU CAAUACGCCU UCAAAGUACG GUGGCAACAA
901   CCCCCAGGAA GACCUUACUU CCUCGUCCGA AACCACUCCU CUAAAAAAUC CUAUUUAUUA
961   GUACAACACA UAUUAGUGGU CCUCCGUCGA UUCAUACUCU UAGUAUGUCU CUUACGCAAU
1021  AACAACAUAU ACCGUACAUG CGUACGGAGA UUAGGUCACA UACGAUGCGA AUUUUAUGCG
1081  UAGAUAAAAA UACUACGUCA UUGUUUAAUU AUUUCCAACU UAAAAUAACG UACAACGAGG
1141  CAUUGAACCU CACACAAAUC AUUAUGUAGC AUGUCUUGUA CUAGUUGUCG AGACUCAUGU
1201  CACAAUUACC UUUAUUGCGG AUAGUAUAAA UUUAUGAACU CGUGAACUAU AAAUUUAUGA
1261  GAAUUCUUUU CUGGUCAGCC UCCGGCAUUC CAGCAGGUCU GGAACUUCAA CUCUUUUGUG
1321  AACACUUAGG GGUUACGGAA GGACUACAAC ACCAACUUGG CAUGACCUC  CCACUACUAC
1381  AGCACCAAGU ACAAGGGACC GGCGAACAGC ACCAACCACU ACAGCUUUAU CUCCCCUAAA
1441  CAAUAAAGGG UCCAUUUUUG CGGUAAGAAA CGAACUCCGC GUCACUACUC AAGGGGACAC
1501  GCUCUUAGGU ACCAACUACG UCAGCUAUAC CUCUAUCUUG CUCGUCGGCG UAAGCUCCAG
1561  AUGGGAGGAU GCAGACUCCC GGGAUCAGAA GCGCCACGCC ACAACCUGAA ACUACCCGUG
1621  AACUCUAACUAU ACCGAGCACC UCCCACUACU UCCAACGUAA GAAAUUUCGU GUCCGAAAUU
1681  CCCUGACCAA GAAAAGGAGC AGGUCUUUGA GAAAUAUACU ACUACAGCCA GGACCUAACG
1741  UAUCCUUCUA UCACCCUUAC GGCGGAAAUU AAACUUAGCC GAAGGGCAUG AACCAUAACG
1801  AAACGUCAG  GGAAACCCGG GGGUACUUAA GAAACUUCAC GAACUCCAUU ACCCCAGCU
1861  GCAGUAGUUA CUGCAACAUG GUACGCAGCA ACGACAUUUG GAAACCUGAC UCUAGGUUUA
1921  CAGGUGUAUU CAUCAACACA CCAGGGUCUC UAGCCCGGGU GUAGCAGAAG GACAGGAUG
1981  AUAGCGGGAG CUACUGCUAU GAUGAGCCAG AGGUACCGGC GCGUCGCUUU GGGUAGUGCA
2041  AGAGCCUUUG GGUCAGAAGU UCAAGGAGUC CUUGUACUCA CUUUCUUCUU CUUUCUUUCC
2101  CUCUUUAUAU UCCUUAGCCU CCGAGGACUU UUUAGGAUAG AUUUAACGAU AAAUUUAAUA
2161  CUUUGACAUU UUGUUUUAGG AAACCCCGAU CAAGGGCCUA AUGUAAUUCU CGGAGACAAA
2221  AUGAACGACG CAAUUCUCGG AACCGCAUUC GCAGUAACCG CCUAACAACA GGCGGCGCUC
2281  GUCUAGCAGG CAGCUAGACU UUGAGCGGGG UAACCUACCA CAGAGGCAGG AACAGGUUUA
2341  UCCUGAACUG CAGUCUUGAC CUAAAUCGAG GGACUUACAA ACCUACCUUU ACACAACUGG
2401  ACCUUCCCCU AUACUCCAGC UUCUUAGCAA CCAACCAUGU UAACAUGAAC GGGAGCUUGA
2461  CUUACUCCCG UACGUUUACU CCAAGGGGUA AAGUACCUC  AAGGACGUC  UAGAACUACU
2521  UGUUAAAUAA ACAACCCCAA ACCUCAACAG CCUCAACUAG AUUACGGCGA AGAAAGCUCU
2581  CUCACGUAAA GCCUAUGCAC UCCUUUAUUA AAAACCGAAA AUACGAUUUU GCUGGUCGGG
2641  AGCCGUAAAA GCGACAGCAU AUCGUUAGCC CCCCGUGAGU UUCAAGGAUC GUUAGCCCCC
2701  UUACCCCCCG UUAAAUAUAC UACGGGGGGU UUACCGUAUA CACAUUAAAA CACUACUUUA
2761  AACUUAAAGC UUGCACCUUU CGCCGGUAGG CAGAUUAUAA
```

Fig. 51 (SEQ ID NO:46)

```
SEQ  SACMV AC1_Target gene region_complement_RNA: 183 bases;
Composition  59   A;  53   C;  30   G;  41   U;  0 OTHER
Percentage:  32%  A;  29%  C;  16%  G;  22%  U;  0%OTHER Molecular Weight: 58.47 kDa 1      CUGGACCUUC CCCUAUACUC CAGCUUCUUA GCAACCAACC AUGUUAACAU GAACGGGAGC
61     UUGACUUACU CCCGUACGUU UACUCCAAGG GGUAAAAGUA CCUCAAGAGA CGUCUAGAAC
121    UACUUGUUAA AUAAACAACC CCAAACCUCA ACAGCCUCAA CUAGAUUACG GCGAAGAAAG
181    CUC
```

Fig. 52 (SEQ ID NO:47)

```
SEQ  SACMV AC1_Target gene sequence_reverse_RNA: 2800 bases;
Composition  703  A; 578  C; 724  G; 795  U; 0 OTHER
Percentage:  25%  A; 21%  C; 26%  G; 28%  U; 0%OTHER Molecular Weight: 900.63kDa 1      UUAUAAUCUG CCUACCGGCG AAAGGUGCAA GCUUUAAGUU UAAAGUAGUG UUUUAAUGUG
61     UAUACGGUAA ACCCCCCGUA GUAUAUUUAA CGGGGGGUAA GGGGGCUAAC GAUCCUUGAA
121    ACUCACGGGG GGCUAACGAU AUGCUGUCGC UUUUACGGCU CCCGACCAGC AAAAUCGUAU
181    UUUCGGUUUU UAAUAAAGGA GUGCAUAGGC UUUACGUGAG AGAGCUUUCU UCGCCGUAAU
241    CUAGUUGAGG CUGUUGAGGU UUGGGGUUGU UUAUUUAACA AGUAGUUCUA GACGUCUCUU
301    GAGGUACUUU UACCCCUUGG AGUAAACGUA CGGGAGUAAG UCAAGCUCCC GUUCAUGUUA
361    ACAUGGUUGG UUGCUAAGAA GCUGGAGUAU AGGGGAAGGU CCAGUUGUGU AAAGGUAGGU
421    UUGUAAGUCC CUCGAUUUAG GUCAAGACUG CAGUUCAGGA UAAACCUGUU CCUGCCUCUG
481    UGGUAGGUUA CCCCGCUCAA AGUCUAGCUG CCUGCUAGAC GAGCGCCGCC UGUUGUUAGG
541    CGGUUACUGC GAAUGCGGUU CCGAGAAUUG CGUCGUUCAU UUUGUCUCCG AGAAUUACAU
601    UAGGCCCUUG AUCGGGGUUU CCUAAAACAA AAUGUCAAAG UAUUAAAUUU AUCGUUAAAU
661    CUAUCCUAAA AAGUCCUCGG AGGCUAAGGA AUAUAAAGAG GGAAAGAAAG AAGAAGAAAG
721    UGAGUACAAG GACUCCUUGA ACUUCUGACC CAAAGGCUCU UGCACUACCC AAAGCGACGC
781    GCCGGUACCU CUGGCUCAUC AUAGCAGUAG CUCCCGCUAU CAUCCUGUCC CUUCUGCUAC
841    ACCCGGGCUA GAGACCCUGG UGUGUUGAUG AAUACACCUG UAAACCUAGA GUCAGGUUUC
901    CAAAUGUCGU UGCUGCGUAC CAUGUUGCAG UAACUACUGC AGCUGGGGGU AAUGGAGUUC
961    GUGAAGUUUC UUAAGUACCC CCGGGUUUCC CUGACCGUUU CGUUAUGGUU CAUGCCCUUC
1021   GGCUAAGUUU AAUUUCCGCC GUAAGGGUGA UAGAAGGAUA CGUUAGGUCC UGGCUGUAGU
1081   AGUAUAUUUC UCAAAGACCU GCUCCUUUUC UUGGUCAGGG AAUUUCGGAC CCGAAAUUUC
1141   UUACGUUGGA AGUAGUGGGA GGUGCUCGGU AACAAGAGUU CACGGGUAGU UUCAGGUUGU
1201   GGCGUGGCGC UUCUGAUCCC GGGAGUCUGC AUCCUCCCAU CUGGAGCUUA CGCCGACGAG
1261   CAAGAUAGAG GUAUAGCUGA CGUAGUUGGU ACCUAAGAGC GUGUCCCCUU GAGUAGUGAC
1321   GCGGAGUUCG UUUCUUACCG CAAAAAUGGA CCCUUUAUUG UUUAGGGGAG AUAAAGCUGU
1381   AGUGGUUGGU GCUGUUCGCC GGUCCCUUGU ACUUGGUGCU GUAGUAGUGG GAGGUCUAUG
1441   CCAAGUUGGU GUUGUAGUCC UUCCGUAACC CCUAAGUGUU CACAAAAGAG UUGAAGUUCC
1501   AGACCUGCUG GAAUGCCGGA GGCUGACCAG AAAAGAAUUC UCAUAAAUUU AUAGUUCACG
1561   AGUUCAUAAA UUUAUACUAU CCGCAAUAAA GGUAAUUGUG ACAUGAGUCU CGACAACUAG
1621   UACAAGACAU GCUACAUAAU GAUUUGUGUG AGGUUCAAUG CCUCGUUGUA CGUUAUUUUA
1681   AGUUGGAAAU AAUUAAACAA UGACGUAGUA UUUUUAUCUA CGCAUAAAAU UCGCAUCGUA
1741   UGUGACCUAA UCUCCGUACG CAUGUACGGU AUAUGUUGUU AUUGCGUAAG AGACAUACUA
1801   AGAGUAUGAA UCGACGGAGG ACCACUAAUA UGUGUUGUAC UAAUAAAUAG GAUUUUUUAG
1861   AGGAGUGGUU UCGGACGAGG AAGUAAGGUC UUCCUGGGGG UUGUUGCCAC CGUACUUUGA
1921   AGGCGUAUUG AGCUAUGGAU AGGGAUUCUA GCAAGAAGUG UCACCGACAU GACCCGAGUA
1981   AUAGUUUGUA UAAUUUUUGG ACAGGUUUCA GGUACCCCGA UAACGGUAUC CCGGAAGACA
2041   GUGCCUGAUU CUUCUUGUAC UGGACCAAAC AUACCAAGAC GAAGAACUAC AAAAGUAGGU
2101   AGGUAUAGAA UGGAUUGUGU AUAUAUCUGA ACUAUGUCUU GGAAAAUGGA UGAGAUACAC
2161   AUUAAGGGCU UGGUGCGCAC UGUAGUGAUU GUGUUGCUUG UGACGGUCAU ACGAAUUGCA
2221   GUAGAGCGAC AAGUAUUCUA ACUUGGAAUG UACCCGGAAG UGUCGGUGCG CCUUGUAGUC
2281   CCGAAAACUU GUAAGACAUG UAAGACCCGA AAGCCAUGUA CCCGGCCUUG CAGGUACUAG
2341   CUGCGAACAA ACACGGAACC UGUUACCCCU GUCGUCGUGC CGACGACUUG CCCGACAGCU
2401   UCAAGUCGGA AGCUGCGUGG AAGCUCUGCC CUCACCUUUA CUAAUAUAGC CGCCCUGCGA
2461   AGCUGUAUUA GUGCCCGAGC CUAGUGUGGC UACUCUAGUG CCUGAUCUAG CACCGGGUUU
2521   CAUAACCCGA GCAUCCAAAG GAGGUUCCGG ACGUUUAUAA AUUAUCGUUC GUAUGUCGCU
2581   UUUGGCACGU GUCUGAGCCC CUUGAGUAAG UUGUUACCUA GGGUGUACAA CUGUGCGAGG
2641   UGAUGAAGCG CUGCUUCAGA UAUUGCUGUA UUUUGUUUAU AGAUCCGAAA GUGCGCACUU
2701   AUACUGACCG GCUGUCGUUG UGCACGCACC CCUGGUGAAA GAAAAUGCCC GCGCCAGUAG
2761   GUUACCCCAG GUGGAUGAAA CAGCCCGCGC CGGUAGGCCA
```

Fig. 53 (SEQ ID NO:48)

SEQ  SACMV AC1_Target gene region_reverse_RNA: 183 bases;
Composition   41   A;   30   C;   53   G;   59   U;   0 OTHER
Percentage:   22%  A;   16%  C;   29%  G;   32%  U;   0%OTHER Molecular Weight: 58.98 kDa

```
1      GAGCUUUCUU CGCCGUAAUC UAGUUGAGGC UGUUGAGGUU UGGGGUUGUU UAUUUAACAA
61     GUAGUUCUAG ACGUCUCUUG AGGUACUUUU ACCCCUUGGA GUAAACGUAC GGGAGUAAGU
121    CAAGCUCCCG UUCAUGUUAA CAUGGUUGGU UGCUAAGAAG CUGGAGUAUA GGGGAAGGUC
181    CAG
```

Fig. 54 (SEQ ID NO:49)

SEQ  SACMV AC1_Target DNA gene region_modified_reverse_RNA: 183 bases;
Composition   41   A;   0    C;   53   G;   89   U;   0 OTHER
Percentage:   22%  A;   0%   C;   29%  G;   49%  U;   0%OTHER Molecular Weight: 59.01 kDa

```
1      GAGUUUUUUU UGUUGUAAUU UAGUUGAGGU UGUUGAGGUU UGGGGUUGUU UAUUUAAUAA
61     GUAGUUUUAG AUGUUUUUUG AGGUAUUUUU AUUUUUUGGA GUAAAUGUAU GGGAGUAAGU
121    UAAGUUUUUG UUUAUGUUAA UAUGGUUGGU UGUUAAGAAG UUGGAGUAUA GGGGAAGGUU
181    UAG
```

Fig. 55 (SEQ ID NO:50)

```
SEQ  SACMV AC1_Target gene sequence_complement_reverse_RNA: 2800 bases;
Composition   795  A;  724  C;  578  G;  703  U;  0 OTHER
Percentage:    28%  A;  26%  C;  21%  G;  25%  U;  0%OTHER Molecular Weight: 896.90kDa 1      AAUAUUAGAC  GGAUGGCCGC  UUUCCACGUU  CGAAAUUCAA  AUUUCAUCAC  AAAAUUACAC
61     AUAUGCCAUU  UGGGGGGCAU  CAUAUAAAUU  GCCCCCCAUU  CCCCCGAUUG  CUAGGAACUU
121    UGAGUGCCCC  CCGAUUGCUA  UACGACAGCG  AAAAUGCCGA  GGGCUGGUCG  UUUUAGCAUA
181    AAAGCCAAAA  AUUAUUCCU   CACGUAUCCG  AAAUGCACUC  UCUCGAAAGA  AGCGGCAUUA
241    GAUCAACUCC  GACAACUCCA  AACCCCAACA  AAUAAAUUGU  UCAUCAAGAU  CUGCAGAGAA
301    CUCCAUGAAA  AUGGGGAACC  UCAUUUGCAU  GCCCUCAUUC  AGUUCGAGGG  CAAGUACAAU
361    UGUACCAACC  AACGAUUCUU  CGACCUCAUA  UCCCCUUCCA  GGUCAACACA  UUUCCAUCCA
421    AACAUUCAGG  GAGCUAAAUC  CAGUUCUGAC  GUCAAGUCCU  AUUUGGACAA  GGACGGAGAC
481    ACCAUCCAAU  GGGGCGAGUU  UCAGAUCGAC  GGACGAUCUG  CUCGCGGCGG  ACAACAAUCC
541    GCCAAUGACG  CUUACGCCAA  GGCUCUUAAC  GCAGCAAGUA  AAACAGAGGC  UCUUAAUGUA
601    AUCCGGGAAC  UAGCCCCAAA  GGAUUUUGUU  UUACAGUUUC  AUAAUUUAAA  UAGCAAUUUA
661    GAUAGGAUUU  UUCAGGAGCC  UCCGAUUCCU  UAUAUUUCUC  CCUUUCUUUC  UUCUUCUUUC
721    ACUCAUGUUC  CUGAGGAACU  UGAAGACUGG  GUUCCGAGA   ACGUGAUGGG  UUUCGCUGCG
781    CGGCCAUGGA  GACCGAGUAG  UAUCGUCAUC  GAGGGCGAUA  GUAGGACAGG  GAAGACGAUG
841    UGGGCCCGAU  CUCUGGGACC  ACACAACUAC  UUAUGUGGAC  AUUUGGAUCU  CAGUCCAAAG
901    GUUUACAGCA  ACGACGCAUG  GUACAACGUC  AUUGAUGACG  UCGACCCCCA  UUACCUCAAG
961    CACUUCAAAG  AAUUCAUGGG  GGCCCAAAGG  GACUGGCAAA  GCAAUACCAA  GUACGGGAAG
1021   CCGAUUCAAA  UUAAGGCGG   CAUUCCCACU  AUCUUCCUAU  GCAAUCCAGG  ACCGACAUCA
1081   UCAUAUAAAG  AGUUUCUGGA  CGAGGAAAAG  AACCAGUCCC  UUAAAGCCUG  GGCUUUAAAG
1141   AAUGCAACCU  UCAUCACCCU  CCACGAGCCA  UUGUUCUCAA  GUGCCCAUCA  AAGUCCAACA
1201   CCGCACCGCG  AAGACUAGGG  CCCUCAGACG  UAGGAGGGUA  GACCUCGAAU  GCGGCUGCUC
1261   GUUCUAUCUC  CAUAUCGACU  GCAUCAACCA  UGGAUUCUCG  CACAGGGGAA  CUCAUCACUG
1321   CGCCUCAAGC  AAAGAAUGGC  GUUUUUACCU  GGGAAAUAAC  AAAUCCCCUC  UAUUUCGACA
1381   UCACCAACCA  CCAAGGAACA  CCAGGGAACA  UGAACCACGA  CAUCAUCACC  CUCCAGAUAC
1441   GGUUCAACCA  CAACAUCAGG  AAGGCAUUGG  GGAUUCACAA  GUGUUUUCUC  AACUUCAAGG
1501   UCUGGACGAC  CUUACGGCCU  CCGACUGGUC  UUUUCUUAAG  AGUAUUUAAA  UAUCAAGUGC
1561   UCAAGUAUUU  AAAUAUGAUA  GGCGUUAUUU  CCAUUAACAC  UGUACUCAGA  GCUGUUGAUC
1621   AUGUUCUGUA  CGAUGUAUUA  CUAAACACAC  UCCAAGUUAC  GGAGCAACAU  GCAAUAAAAU
1681   UCAACCUUUA  UUAAUUGUU   ACUGCAUCAU  AAAAAUAGAU  GCGUAUUUUA  AGCGUAGCAU
1741   ACACUGGAUU  AGAGGCAUGC  GUACAUGCCA  UAUACAACAA  UAACGCAUUC  UCUGUAUGAU
1801   UCUCAUACUU  AGCUGCCUCC  UGGUGAUUAU  ACACAACAUG  AUUAUUUAUC  CUAAAAAAUC
1861   UCCUCACCAA  AGCCUGCUCC  UUCAUUCCAG  AAGGACCCCC  AACAACGGUG  GCAUGAAACU
1921   UCCGCAUAAC  UCGAUACCUA  UCCCUAAGAU  CGUUCUUCAC  AGUGGCUGUA  CUGGGCUCAU
1981   UAUCAAACAU  AUUAAAAACC  UGUCCAAAGU  CCAUGGGGCU  AUUGCCAUAG  GGCCUUCUGU
2041   CACGGACUAA  GAAGAACAUG  ACCUGGUUUG  UAUGGUUCUG  CUUCUUGAUG  UUUUCAUCCA
2101   UCCAUAUCUU  ACCUAACACA  UAUAGACU    UGAUACAGAA  CCUUUUACCU  ACUCUAUGUG
2161   UAAUUCCCGA  ACCACGCGUG  ACAUCACUAA  CACAACGAAC  ACUGCCAGUA  UGCUUAACGU
2221   CAUCUCGCUG  UUCAUAAGAU  UGAACCUUAC  AUGGGCCUUC  ACAGCCACGC  GGAACAUCAG
2281   GGCUUUUGAA  CAUUCUGUAC  AUUCGGGCU   UUCGGUACAU  GGGCCGGAAC  GUCCAUGAUC
2341   GACGCUUGUU  UGUGCCUUGG  ACAAUGGGGA  CAGCAGCACG  GCUGCUGAAC  GGGCUGUCGA
2401   AGUUCAGCCU  UCGACGCACC  UUCGAGACGG  GAGUGGAAAU  GAUUAUACG   GCGGGACGCU
2461   UCGACAUAAU  CACGGGCUCG  GAUCACACCG  AUGAGAUCAC  GGACUAGAUC  GUGGCCCAAA
2521   GUAUUGGGCU  CGUAGGUUUC  CUCCAAGGCC  UGCAAAUAUU  UAAUAGCAAG  CAUACAGCGA
2581   AAACCGUGCA  CAGACUCGGG  AACUCAUUC   AACAAUGGAU  CCCACAUGUU  GACACGCUCC
2641   ACUACUUCGC  GACGAAGUCU  AUAACGACAU  AAAACAAAUA  UCUAGGCUUU  CACGCGUGAA
2701   UAUGACUGGC  CGACAGCAAC  ACGUGCGUGG  GGACCACUUU  CUUUUACGGG  CGCGGUCAUC
2761   CAAUGGGGUC  CACCUACUUU  GUCGGCGCG   GCCAUCCGGU
```

Fig. 56 (SEQ ID NO:51)

SEQ  SACMV AC1_Target gene region_complement_reverse_RNA: 183 bases;
Composition  59   A;  53   C;  30   G;  41   U;  0 OTHER
Percentage:  32%  A;  29%  C;  16%  G;  22%  U;  0%OTHER Molecular Weight: 58.47 kDa

```
1    CUCGAAAGAA GCGGCAUUAG AUCAACUCCG ACAACUCCAA ACCCCAACAA AUAAAUUGUU
61   CAUCAAGAUC UGCAGAGAAC UCCAUGAAAA UGGGGAACCU CAUUUGCAUG CCCUCAUUCA
121  GUUCGAGGGC AAGUACAAUU GUACCAACCA ACGAUUCUUC GACCUCAUAU CCCCUUCCAG
181  GUC
```

Fig. 57 (SEQ ID NO:52)

MSV AC1

SEQ MSV AC1_Target gene DNA sequence: 2690 bp;
Composition  693 A; 632 C; 688 G; 677 T; 0 OTHER
Percentage:  26% A; 23% C; 26% G; 25% T; 0%OTHER Molecular Weight (kDa): ssDNA: 831.72    dsDNA: 1658.4
ORIGIN

```
1     ACCGCGCCTT CTTTTCCTGC GAGGGCCCGG TAGGGACCGA GCGCTTTGAT TTAAAGCCTG
61    GTTCTGCTTT GTATGATTTA TCTAAAGCAG CCCAATCTAA AGAAACCGGT CCCGGGCACT
121   ATAAATTGCC TAACAAGTGC GATTCATTCA TGGATCCACA GAACGCCCTG TATTATCAGC
181   CGCGGGTACC CACAGCAGCT CCGACATCCG GAGGAGTGCC GTGGAGTCGC GTAGGCGAGG
241   TAGCTATTTT GAGCTTTGTT GCATTGATTT GCTTTTACCT GCTTTACCTT TGGGTGCTGA
301   GAGACCTTAT CTTAGTTCTG AAGGCTCGAC AAGGCAGATC CACGGAGGAG CTGATATTTG
361   GTGGACAAGC TGTGGATAGG AGCAACCCTA TCCCTAATCT ACCTTCACCA CCAAGTCAGG
421   GCAATCCCGG GCCATTTGTT CCAGGACGG GATAAGCAAT CAGCCATGTC CACGTCCAAG
481   AGGAAGCGGG GAGATGATTC GAATTGGAAT AAGCGGGTGC CTAAGAAGAA GCCATCTTCA
541   GCTGGGCTGA AGAGGGCTGG AAGCAAGGCC GATAGGCCAT CCCTCCAAAT CCAGACACTC
601   CAGCATGCTG GGACCACCAT GATAACTGTC CCATCCGGAG GAGTATGTGA CCTCATCAAC
661   ACCTATGCCC GAGGATCTGA CGAGGGCCAC CGCCACACCA GCGAGACTCT GACGTACAAG
721   ATCGCCGTCG ACTACCACTT CGTTGCCGAC GCGGCTGCCT GCCGCTACTC CAACACCGGA
781   ACCGGTGTAA TGTGGCTGGT GTATGACACC ACTCCCGGCG GACAAGCTCC GACCCCGCAA
841   ACTATATTTG CCTACCCTGA CACGCTAAAA GCGTGGCCGG CCACATGGAA AGTGAGCCGG
901   GAGCTGTGTC ATCGCTTCGT GGTGAAACGG CGATGGTTGT TCAACATGGA GACCGACGGT
961   CGGATTGGTT CGGATATCCC TCCCTCGAAT ACAAGTTGGA AGCCTTGCAA GCGCAACATC
1021  TACTTCCACA AGTTCACGAG TGGGTTGGGA GTGAGAACGC AGTGGAAGAA TGTAACGGAC
1081  GGAGGAGTTG GTGCCATCCA GAGAGGAGCT CTGTACATGG TCATTGCCCC AGGCAATGGC
1141  CTTACTTTTA CTGCCCATGG GCAGACCCGT CTGTACTTTA AGAGTGTTGG CAACCAGTAA
1201  TGAATAAAAA CTCCGTTTTT ATTATATTTG ATGAATGCTG AAAGCTTACA TTAATATGTC
1261  GTGCGATGGC ACGAAAAAAC ACACGCAAAC AATACAGGGG GGTAGTCGGC GGGCGGCTAA
1321  GGGTGGTGCT CGGCGGGCAG AACATCGAAA AATCAAGATC TATATGAATT ACACTTCCTC
1381  CGTAGGAGGA AGCACAGGGG GAGAATACCA CTTCTCCCCC GGCGACATAA TGTAAATGAC
1441  GCAGTTTGCC TCGAAATACT CCAGCTGCCC TGGAGTCATT TCCTTCATCC AATCTTCATC
1501  CGAGTTGGCG AGGATTATTG TAGGCTTAGA CTTCTTCTGC ACCTTTTTCT TCTTACCATA
1561  CTTGGGGTTT ACAATGAAAT CCCTCTGACA GCCAACTAAC TGTTTCCAAC AAGGACAGAA
1621  TTTAAACGGA ATATCATCTA CGATGTTGTA GATTGCGTCT TCGTTGTATG AAGACCAATC
1681  AACATTATTT TGCCAGTAAT TATGAACCCC TAGGCTTCTG GCCCAAGTAG ATTTTCCGGT
1741  TCTTGTTGGG CCGACGATGT AGAGGCTCTG CTTTCTTGAT CTTTCATCTG ATGACTGGAT
1801  ACAGAATCCA TCCATTGGAG GTCAGAAATT GCATCCTCGA GGGTATAACA GGTAGGTTGA
1861  AGGAGCATGT AAGCTTCGGG ACTAACCTGG AAGATGTTAG GCTGGAGCCA ATCGTTGATT
1921  GACTCATTAC AAAGTAAATC AGGTGAGGAG GGTGGATGAG GATTGGTGAA CTCTTCCTGA
1981  ATCTCAGGAA AAAGTTATT TGCAGAGTAT TCAAAATACT GCAATTTTGT GGACCAATCA
2041  AAGGGGAGCT CTTTCTGGAT CATGGAGGAG TACTCTTCTT TGGAGGTAGC GTGTGAAATA
2101  ATGTCTCGCA TTATTTCATC TTTAGAAGGC TTTTTTTCCT TTACCTCTGA ATCAGATTTT
2161  CCTAGGAAGG GGGACTTCCT AGGAATGAAA GTACCTCTCT CAAACACAGC CAGAGGTTCC
2221  TTGAGAATGT AATCCCTCAC TCTGTTAACT GACTTGGCAC TCTGAATATT TGGGTGAAAC
2281  CCATTTATAT CAAAGAACCT TGAGTCAGAT ATCCTTATCG GCTTCTCTGG CTGAAGCAAT
2341  GCATGTAAAT GCAAACTTCC ATCTTTATGT GCCTCTCGGG CACATAGAAT ATATTTGGGA
2401  ATCCAACGAA CGACGAGCTC CCAGATCATC TGACAGGCGA TTTCAGGATT TTCTGGACAC
2461  TTTGGATAGG TTAGGAACGT GTTAGCGTTC CTGTGTGAGA ACTGACGGTT GGATGAGGAG
2521  GAGGCCATAG CCGACGACGG AGGTTGAGGC TGAGGGATGG CAGACTGGGA GCTCCAAACT
2581  CTATAGTATA CCCGTGCGCC TTCGAAATCC GCCGCTCCAT TGTCTTATAG TGGTTGTAAA
2641  TGGGCCGGAC CGGGCCGGCC CAGCAGGAAA AGAAGGCGCG CACTAATATT
```

Fig. 58 (SEQ ID NO:53)

```
SEQ  MSV AC1_Target gene DNA region: 246 bp;
Composition   74   A;  40    C;  68    G;  64    T;  0 OTHER
Percentage:  30%   A; 16%    C; 28%    G; 26%    T;  0%OTHER Molecular Weight (kDa): ssDNA: 76.55       dsDNA: 151.6
ORIGIN
1       TCCATCCATT GGAGGTCAGA AATTGCATCC TCGAGGGTAT AACAGGTAGG TTGAAGGAGC
61      ATGTAAGCTT CGGGACTAAC CTGGAAGATG TTAGGCTGGA GCCAATCGTT GATTGACTCA
121     TTACAAAGTA AATCAGGTGA GGAGGGTGGA TGAGGATTGG TGAACTCTTC CTGAATCTCA
181     GGAAAAAGCT TATTTGCAGA GTATTCAAAA TACTGCAATT TTGTGGACCA ATCAAAGGGG
241     AGCTCT
```

Fig. 59 (SEQ ID NO:54)

```
SEQ  MSV AC1_Target gene DNA region_modified: 246 bp;
Composition   74   A;   0    C;  68    G; 104    T;  0 OTHER
Percentage:  30%   A;  0%    C; 28%    G; 42%    T;  0%OTHER Molecular Weight (kDa): ssDNA: 76.55       dsDNA: 151.6
ORIGIN
1       TTTATTTATT GGAGGTTAGA AATTGTATTT TTGAGGGTAT AATAGGTAGG TTGAAGGAGT
61      ATGTAAGTTT TGGGATTAAT TTGGAAGATG TTAGGTTGGA GTTAATTGTT GATTGATTTA
121     TTATAAAGTA AATTAGGTGA GGAGGGTGGA TGAGGATTGG TGAATTTTTT TTGAATTTTA
181     GGAAAAAGTT TATTTGTAGA GTATTTAAAA TATTGTAATT TTGTGGATTA ATTAAAGGGG
241     AGTTTT
```

Fig. 60 (SEQ ID NO:55)

```
SEQ  MSV AC1_Target gene DNA sequence_complement: 2690 bp;
Composition   677  A;  688  C;  632  G;  693  T;  0 OTHER
Percentage:    25%  A;  26%  C;  23%  G;  26%  T;  0%OTHER Molecular Weight (kDa): ssDNA: 829.33    dsDNA: 1658.4
ORIGIN
1       TGGCGCGGAA  GAAAAGGACG  CTCCCGGGCC  ATCCCTGGCT  CGCGAAACTA  AATTTCGGAC
61      CAAGACGAAA  CATACTAAAT  AGATTTCGTC  GGGTTAGATT  TCTTTGGCCA  GGGCCCGTGA
121     TATTTAACGG  ATTGTTCACG  CTAAGTAAGT  ACCTAGGTGT  CTTGCGGGAC  ATAATAGTCG
181     GCGCCCATGG  GTGTCGTCGA  GGCTGTAGGC  CTCCTCACGG  CACCTCAGCG  CATCCGCTCC
241     ATCGATAAAA  CTCGAAACAA  CGTAACTAAA  CGAAATGGA   CGAAATGGAA  ACCCACGACT
301     CTCTGGAATA  GAATCAAGAC  TTCCGAGCTG  TTCCGTCTAG  GTGCCTCCTC  GACTATAAAC
361     CACCTGTTCG  ACACCTATCC  TCGTTGGGAT  AGGGATTAGA  TGGAAGTGGT  GGTTCAGTCC
421     CGTTAGGGCC  CGGTAAACAA  GGTCCGTGCC  CTATTCGTTA  GTCGGTACAG  GTGCAGGTTC
481     TCCTTCGCCC  CTCTACTAAG  CTTAACCTTA  TTCGCCCACG  GATTCTTCTT  CGGTAGAAGT
541     CGACCCGACT  TCTCCCGACC  TTCGTTCCGG  CTATCCGGTA  GGGAGGTTTA  GGTCTGTGAG
601     GTCGTACGAC  CCTGGTGCTA  CTATTGACAG  GGTAGGCCTC  CTCATACACT  GGAGTAGTTG
661     TGGATACGGG  CTCCTAGACT  GCTCCCGTTG  GCGGTGTGGT  CGCTCTGAGA  CTGCATGTTC
721     TAGCGGCAGC  TGATGGTGAA  GCAACGGCTG  CGCCGACGGA  CGGCGATGAG  GTTGTGGCCT
781     TGGCCACATT  ACACCGACCA  CATACTGTGG  TGAGGGCCGC  CTGTTCGAGG  CTGGGGCGTT
841     TGATATAAAC  GGATGGGACT  GTGCGATTTT  CGCACCGGCC  GGTGTACCTT  TCACTCGGCC
901     CTCGACACAG  TAGCGAAGCA  CCACTTTGCC  GCTACCAACA  AGTTGTACCT  CTGGCTGCCA
961     GCCTAACCAA  GCCTATAGGG  AGGGAGCTTA  TGTTCAACCT  TCGGAACGTT  CGCGTTGTAG
1021    ATGAAGGTGT  TCAAGTGCTC  ACCCAACCCT  CACTCTTGCG  TCACCTTCTT  ACATTGCCTG
1081    CCTCCTCAAC  CACGGTAGGT  CTCTCCTCGA  GACATGTACC  AGTAACGGGG  TCCGTTACCG
1141    GAATGAAAAT  GACGGGTACC  CGTCTGGGCA  GACATGAAAT  TCTCACAACC  GTTGGTCATT
1201    ACTTATTTTT  GAGGGCAAAA  TAATATAAAC  TACTTACGAC  TTTCGAATGT  AATTATACAG
1261    CACGCTACCG  TGCTTTTTTG  TGTGCGTTTG  TTATGTCCCC  CCATCAGCCG  CCCGCCGATT
1321    CCCACCACGA  GCCGCCCGTC  TTGTAGCTTT  TTAGTTCTAG  ATATACTTAA  TGTGAAGGAG
1381    GCATCCTCCT  TCGTGTCCCC  CTCTTATGGT  GAAGAGGGGG  CCGCTGTATT  ACATTTACTG
1441    CGTCAAACGG  AGCTTTATGA  GGTCGACGGG  ACCTCAGTAA  AGGAAGTAGG  TTAGAAGTAG
1501    GCTCAACCGC  TCCTAATAAC  ATCCGAATCT  GAAGAAGACG  TGGAAAAAGA  AGAATGGTAT
1561    GAACCCCAAA  TGTTACTTTA  GGGAGACTGT  CGGTTGATTG  ACAAAGGTTG  TTCCTGTCTT
1621    AAATTTGCCT  TATAGTAGAT  GCTACAACAT  CTAACGCAGA  AGCAACATAC  TTCTGGTTAG
1681    TTGTAATAAA  ACGGTCATTA  ATACTTGGGG  ATCCGAAGAC  CGGGTTCATC  TAAAAGGCCA
1741    AGAACAACCC  GGCTGCTACA  TCTCCGAGAC  GAAAGAACTA  GAAAGTAGAC  TACTGACCTA
1801    TGTCTTAGGT  AGGTAACCTC  CAGTCTTTAA  CGTAGGAGCT  CCCATATTGT  CCATCCAACT
1861    TCCTCGTACA  TTCAAGCCC   TGATTGGACC  TTCTACAATC  CGACCTCGGT  TAGCAACTAA
1921    CTGAGTAATG  TTTCATTTAG  TCCACTCCTC  CCACCTACTC  CTAACCACTT  GAGAAGGACT
1981    TAGAGTCCTT  TTTCGAATAA  ACGTCTCATA  AGTTTTATGA  CGTTAAAACA  CCTGGTTAGT
2041    TTCCCCTCGA  GAAAGACCTA  GTACCTCTCC  ATGAGAAGAA  ACCTCCATCG  CACACTTTAT
2101    TACAGAGCGT  AATAAAGTAG  AAATCTTCCG  AAAAAAAGGA  AATGGAGACT  TAGTCTAAAA
2161    GGATCCTTCC  CCCTGAAGGA  TCCTTACTTT  CATGGAGAGA  GTTTGTGTCG  GTCTCCAAGG
2221    AACTCTTACA  TTAGGGAGTG  AGACAATTGA  CTGAACCGTG  AGACTTATAA  ACCCACTTTG
2281    GGTAAATATA  GTTCTTGGA   ACTCAGTCTA  TAGGAATAGC  CGAAGAGACC  GACTTCGTTA
2341    CGTACATTTA  CGTTTGAAGG  TAGAAATACA  CGGAGAGCCC  GTGTATCTTA  TATAAACCCT
2401    TAGGTTGCTT  GCTGCTCGAG  GGTCTAGTAG  ACTGTCCGCT  AAAGTCCTAA  AAGACCTGTG
2461    AAACCTATCC  AATCCTTGCA  CAATCGCAAG  GACACACTCT  TGACTGCCAA  CCTACTCCTC
2521    CTCCGGTATC  GGCTGCTGCC  TCCAACTCCG  ACTCCCTACC  GTCTGACCCT  CGAGGTTTGA
2581    GATATCATAT  GGGCACGCGG  AAGCTTTAGG  CGGCGAGGTA  ACAGAATATC  ACCAACATTT
2641    ACCCGGCCTG  GCCCGGCCGG  GTCGTCCTTT  TCTTCCGCGC  GTGATTATAA
```

Fig. 61 (SEQ ID NO:56)

SEQ  MSV AC1_Target gene DNA region_complement: 246 bp;
Composition   64   A;   68    C;  40   G;  74   T;  0 OTHER
Percentage:   26%  A;   28%   C;  16%  G;  30%  T;  0%OTHER Molecular Weight (kDa): ssDNA: 75.34      dsDNA: 151.6
ORIGIN
1      AGGTAGGTAA CCTCCAGTCT TTAACGTAGG AGCTCCCATA TTGTCCATCC AACTTCCTCG
61     TACATTCGAA GCCCTGATTG GACCTTCTAC AATCCGACCT CGGTTAGCAA CTAACTGAGT
121    AATGTTTCAT TTAGTCCACT CCTCCCACCT ACTCCTAACC ACTTGAGAAG GACTTAGAGT
181    CCTTTTTCGA ATAAACGTCT CATAAGTTTT ATGACGTTAA AACACCTGGT TAGTTTCCCC
241    TCGAGA Fig. 62 (SEQ ID NO:57)

```
SEQ  MSV AC1_Target gene DNA sequence_reverse: 2690 bp;
Composition  693  A;  632  C;  688  G;  677  T;  0 OTHER
Percentage:   26%  A;  23%  C;  26%  G;  25%  T;  0%OTHER Molecular Weight (kDa): ssDNA: 831.72    dsDNA: 1658.4
ORIGIN
1       TTATAATCAC  GCGCGGAAGA  AAAGGACGAC  CCGGCCGGGC  CAGGCCGGGT  AAATGTTGGT
61      GATATTCTGT  TACCTCGCCG  CCTAAAGCTT  CCGCGTGCCC  ATATGATATC  TCAAACCTCG
121     AGGGTCAGAC  GGTAGGGAGT  CGGAGTTGGA  GGCAGCAGCC  GATACCGGAG  GAGGAGTAGG
181     TTGGCAGTCA  AGAGTGTGTC  CTTGCGATTG  TGCAAGGATT  GGATAGGTTT  CACAGGTCTT
241     TTAGGACTTT  AGCGGACAGT  CTACTAGACC  CTCGAGCAGC  AAGCAACCTA  AGGGTTTATA
301     TAAGATACAC  GGGCTCTCCG  TGTATTTCTA  CCTTCAAACG  TAAATGTACG  TAACGAAGTC
361     GGTCTCTTCG  GCTATTCCTA  TAGACTGAGT  TCCAAGAAAC  TATATTTACC  CAAAGTGGGT
421     TTATAAGTCT  CACGGTTCAG  TCAATTGTCT  CACTCCCTAA  TGTAAGAGTT  CCTTGGAGAC
481     CGACACAAAC  TCTCTCCATG  AAAGTAAGGA  TCCTTCAGGG  GAAGGATCC   TTTTAGACTA
541     AGTCTCCATT  TCCTTTTTTT  CGGAAGATTT  CTACTTTATT  ACGCTCTGTA  ATAAAGTGTG
601     CGATGGAGGT  TTCTTCTCAT  GGAGAGGTAC  TAGGTCTTTC  TCGAGGGGAA  ACTAACCAGG
661     TGTTTTAACG  TCATAAAACT  TATGAGACGT  TTATTCGAAA  AAGGACTCTA  AGTCCTTCTC
721     AAGTGGTTAG  GAGTAGGTGG  GAGGAGTGGA  CTAAATGAAA  CATTACTCAG  TTAGTTGCTA
781     ACCGAGGTCG  GATTGTAGAA  GGTCCAATCA  GGGCTTCGAA  TGTACGAGGA  AGTTGGATGG
841     ACAATATGGG  AGCTCCTACG  TTAAAGACTG  GAGGTTACCT  ACCTAAGACA  TAGGTCAGTA
901     GTCTACTTTC  TAGTTCTTTC  GTCTCGGAGA  TGTAGCAGCC  GGGTTGTTCT  TGGCCTTTTA
961     GATGAACCCG  GTCTTCGGAT  CCCCAAGTAT  TAATGACCGT  TTTATTACAA  CTAACCAGAA
1021    GTATGTTGCT  TCTGCGTTAG  ATGTTGTAGC  ATCTACTATA  AGGCAAATTT  AAGACAGGAA
1081    CAACCTTTGT  CAATCAACCG  ACAGTCTCCC  TAAAGTAACA  TTTGGGGTTC  ATACCATTCT
1141    TCTTTTTCCA  CGTCTTCTTC  AGATTCGGAT  GTTATTAGGA  GCGGTTGAGC  CTACTTCTAA
1201    CCTACTTCCT  TTACTGAGGT  CCCGTCGACC  TCATAAAGCT  CCGTTTGACG  CAGTAAATGT
1261    AATACAGCGG  CCCCCTCTTC  ACCATAAGAG  GGGGACACGA  AGGAGGATGC  CTCCTTCACA
1321    TTAAGTATAT  CTAGAACTAA  AAAGCTACAA  GACGGGCGGC  TCGTGGTGGG  AATCGGCGGG
1381    CGGCTGATGG  GGGGACATAA  CAAACGCACA  CAAAAAAGCA  CGGTAGCGTG  CTGTATAATT
1441    ACATTCGAAA  GTCGTAAGTA  GTTTATATTA  TTTTGCCCTC  AAAAATAAGT  AATGACCAAC
1501    GGTTGTGAGA  ATTTCATGTC  TGCCCAGACG  GGTACCCGTC  ATTTTCATTC  CGGTAACGGA
1561    CCCCGTTACT  GGTACATGTC  TCGAGGAGAG  ACCTACCGTG  GTTGAGGAGG  CAGGCAATGT
1621    AAGAAGGTGA  CGCAAGAGTG  AGGGTTGGGT  GAGCACTTGA  ACACCTTCAT  CTACAACGCG
1681    AACGTTCCGA  AGGTTGAACA  TAAGCTCCCT  CCCTATAGGC  TTGGTTAGGC  TGGCAGCCAG
1741    AGGTACAACT  TGTTGGTAGC  GGCAAAGTGG  TGCTTCGCTA  CTGTGTCGAG  GGCCGAGTGA
1801    AAGGTACACC  GGCCGGTGCG  AAAATCGCAC  AGTCCCATCC  GTTTATATCA  AACGCCCCAG
1861    CCTCGAACAG  GCGGCCCTCA  CCACAGTATG  TGGTCGGTGT  AATGTGGCCA  AGGCCACAAC
1921    CTCATCGCCG  TCCGTCGGCG  CAGCCGTTGC  TTCACCATCA  GCTGCCGCTA  GAACATGCAG
1981    TCTCAGAGCG  ACCACACCGC  CAACGGGAGC  AGTCTAGGAG  CCCGTATCCA  CAACTACTCC
2041    AGTGTATGAG  GAGGCCTACC  CTGTCAATAG  TACCACCAGG  GTCGTACGAC  CTCACAGACC
2101    TAAACCTCCC  TACCGGATAG  CCGGAACGAA  GGTCGGGAGA  AGTCGGGTCG  ACTTCTACCG
2161    AAGAAGAATC  CGTGGGCGAA  TAAGGTTAAG  CTTAGTAGAG  GGGCGAAGGA  GAACCTGCAC
2221    CTGTACCGAC  TAACGAATAG  GGCACGGACC  TTGTTTACCG  GGCCCTAACG  GGACTGAACC
2281    ACCACTTCCA  TCTAATCCCT  ATCCCAACGA  GGATAGGTGT  CGAACAGGTG  GTTTATAGTC
2341    GAGGAGGCAC  CTAGACGGAA  CAGCTCGGAA  GTCTTGATTC  TATTCCAGAG  AGTCGTGGGT
2401    TTCCATTTCG  TCCATTTTCG  TTTAGTTACG  TTGTTTCGAG  TTTTATCGAT  GGAGCGGATG
2461    CGCTGAGGTG  CCGTGAGGAG  GCCTACAGCC  TCGACGACAC  CCATGGGCGC  CGACTATTAT
2521    GTCCCGCAAG  ACACCTAGGT  ACTTACTTAG  CGTGAACAAT  CCGTTAAATA  TCACGGGCCC
2581    TGGCCAAAGA  AATCTAACCC  GACGAAATCT  ATTTAGTATG  TTTCGTCTTG  GTCCGAAATT
2641    TAGTTTCGCG  AGCCAGGGAT  GGCCCGGGAG  CGTCCTTTTC  TTCCGCGCCA
```

Fig. 63 (SEQ ID NO:58)

SEQ MSV AC1_Target gene DNA region_reverse: 246 bp;
Composition  74   A;  40   C;  68   G;  64   T;  0 OTHER
Percentage:  30%  A;  16%  C;  28%  G;  26%  T;  0%OTHER Molecular Weight (kDa): ssDNA: 76.55    dsDNA: 151.6
ORIGIN
1       TCTCGAGGGG AAACTAACCA GGTGTTTTAA CGTCATAAAA CTTATGAGAC GTTTATTCGA
61      AAAAGGACTC TAAGTCCTTC TCAAGTGGTT AGGAGTAGGT GGGAGGAGTG GACTAAATGA
121     AACATTACTC AGTTAGTTGC TAACCGAGGT CGGATTGTAG AAGGTCCAAT CAGGGCTTCG
181     AATGTACGAG GAAGTTGGAT GGACAATATG GGAGCTCCTA CGTTAAAGAC TGGAGGTTAC
241     CTACCT

Fig. 64 (SEQ ID NO:59)

SEQ MSV AC1_Target gene DNA region_modified_reverse: 246 bp;
Composition  74   A;  0    C;  68   G;  104  T;  0 OTHER
Percentage:  30%  A;  0%   C;  28%  G;  42%  T;  0%OTHER Molecular Weight (kDa): ssDNA: 77.15    dsDNA: 151.6
ORIGIN
1       TTTTGAGGGG AAATTAATTA GGTGTTTTAA TGTTATAAAA TTTATGAGAT GTTTATTTGA
61      AAAAGGATTT TAAGTTTTTT TTAAGTGGTT AGGAGTAGGT GGGAGGAGTG GATTAAATGA
121     AATATTATTT AGTTAGTTGT TAATTGAGGT TGGATTGTAG AAGGTTTAAT TAGGGTTTTG
181     AATGTATGAG GAAGTTGGAT GGATAATATG GGAGTTTTTA TGTTAAAGAT TGGAGGTTAT
241     TTATTT

Fig. 65 (SEQ ID NO:60)

```
SEQ  MSV AC1_Target gene DNA sequence_complement_reverse: 2690 bp;
Composition  677 A;  688 C;  632 G;  693 T;  0 OTHER
Percentage:   25% A;  26% C;  23% G;  26% T;  0%OTHER Molecular Weight (kDa): ssDNA: 829.33    dsDNA: 1658.4
ORIGIN
1      AATATTAGTG CGCGCCTTCT TTTCCTGCTG GGCCGGCCCG GTCCGGCCCA TTTACAACCA
61     CTATAAGACA ATGGAGCGGC GGATTTCGAA GGCGCACGGG TATACTATAG AGTTTGGAGC
121    TCCCAGTCTG CCATCCCTCA GCCTCAACCT CCGTCGTCGG CTATGGCCTC CTCCTCATCC
181    AACCGTCAGT TCTCACACAG GAACGCTAAC ACGTTCCTAA CCTATCCAAA GTGTCCAGAA
241    AATCCTGAAA TCGCCTGTCA GATGATCTGG GAGCTCGTCG TTCGTTGGAT TCCCAAATAT
301    ATTCTATGTG CCCGAGAGGC ACATAAAGAT GGAAGTTTGC ATTTACATGC ATTGCTTCAG
361    CCAGAGAAGC CGATAAGGAT ATCTGACTCA AGGTTCTTTG ATATAAATGG GTTTCACCCA
421    AATATTCAGA GTGCCAAGTC AGTTAACAGA GTGAGGGATT ACATTCTCAA GGAACCTCTG
481    GCTGTGTTTG AGAGAGGTAC TTTCATTCCT AGGAAGTCCC CCTTCCTAGG AAAATCTGAT
541    TCAGAGGTAA AGGAAAAAAA GCCTTCTAAA GATGAAATAA TGCGAGACAT TATTTCACAC
601    GCTACCTCCA AGAAGAGTA CCTCTCCATG ATCCAGAAAG AGCTCCCCTT TGATTGGTCC
661    ACAAAATTGC AGTATTTTGA ATACTCTGCA AATAAGCTTT TTCCTGAGAT TCAGGAAGAG
721    TTCACCAATC CTCATCCACC CTCCTCACCT GATTTACTTT GTAATGAGTC AATCAACGAT
781    TGGCTCCAGC CTAACATCTT CCAGGTTAGT CCCGAAGCTT ACATGCTCCT TCAACCTACC
841    TGTTATACCC TCGAGGATGC AATTTCTGAC CTCCAATGGA TGGATTCTGT ATCCAGTCAT
901    CAGATGAAAG ATCAAGAAAG CAGAGCCTCT ACATCGTCGG CCCAACAAGA ACCGGAAAAT
961    CTACTTGGGC CAGAAGCCTA GGGGTTCATA ATTACTGGCA AAATAATGTT GATTGGTCTT
1021   CATACAACGA AGACGCAATC TACAACATCG TAGATGATAT TCCGTTTAAA TTCTGTCCTT
1081   GTTGGAAACA GTTAGTTGGC TGTCAGAGGG ATTTCATTGT AAACCCCAAG TATGGTAAGA
1141   AGAAAAAGGT GCAGAAGAAG TCTAAGCCTA CAATAATCCT CGCCAACTCG GATGAAGATT
1201   GGATGAAGGA AATGACTCCA GGGCAGCTGG AGTATTTCGA GGCAAACTGC GTCATTTACA
1261   TTATGTCGCC GGGGCAGAAG TGGTATTCTC CCCTGTGCT TCCTCCTACG GAGGAAGTGT
1321   AATTCATATA GATCTTGATT TTTCGATGTT CTGCCCGCCG AGCACCACCC TTAGCCGCCC
1381   GCCGACTACC CCCCTGTATT GTTTGCGTGT GTTTTTTCGT GCCATCGCAC GACATATTAA
1441   TGTAAGCTTT CAGCATTCAT CAAATATAAT AAAACGGGAG TTTTTATTCA TTACTGGTTG
1501   CCAACACTCT TAAAGTACAG ACGGGTCTGC CCATGGGCAG TAAAAGTAAG GCCATTGCCT
1561   GGGGCAATGA CCATGTACAG AGCTCCTCTC TGGATGGCAC CAACTCCTCC GTCCGTTACA
1621   TTCTTCCACT GCGTTCTCAC TCCCAACCCA CTCGTGAACT TGTGGAAGTA GATGTTGCGC
1681   TTGCAAGGCT TCCAACTTGT ATTCGAGGGA GGGATATCCG AACCAATCCG ACCGTCGGTC
1741   TCCATGTTGA ACAACCATCG CCGTTTCACC ACGAAGCGAT GACACAGCTC CCGGCTCACT
1801   TTCCATGTGG CCGGCCACGC TTTTAGCGTG TCAGGGTAGG CAAATATAGT TTGCGGGGTC
1861   GGAGCTTGTC CGCCGGGAGT GGTGTCATAC ACCAGCCACA TTACACCGGT TCCGGTGTTG
1921   GAGTAGCGGC AGGCAGCCGC GTCGGCAACG AAGTGGTAGT CGACGGCGAT CTTGTACGTC
1981   AGAGTCTCGC TGGTGTGGCG GTTGCCCTCG TCAGATCCTC GGGCATAGGT GTTGATGAGG
2041   TCACATACTC CTCCGGATGG GACAGTTATC ATGGTGGTCC CAGCATGCTG GAGTGTCTGG
2101   ATTTGGAGGG ATGGCCTATC GGCCTTGCTT CCAGCCCTCT TCAGCCCAGC TGAAGATGGC
2161   TTCTTCTTAG GCACCCGCTT ATTCCAATTC GAATCATCTC CCCGCTTCCT CTTGGACGTG
2221   GACATGGCTG ATTGCTTATC CCGTGCCTGG AACAAATGGC CCGGGATTGC CTGACTTGG
2281   TGGTGAAGGT AGATTAGGGA TAGGGTTGCT CCTATCCACA GCTTGTCCAC CAAATATCAG
2341   CTCCTCCGTG GATCTGCCTT GTCGAGCCTT CAGAACTAAG ATAAGGTCTC TCAGCACCCA
2401   AAGGTAAAGC AGGTAAAAGC AAATCAATGC AACAAAGCTC AAAATAGCTA CCTCGCCTAC
2461   GCGACTCCAC GGCACTCCTC CGGATGTCGG AGCTGCTGTG GGTACCCGCG GCTGATAATA
2521   CAGGGCGTTC TGTGGATCCA TGAATGAATC GCACTTGTTA GGCAATTTAT AGTGCCCGGG
2581   ACCGGTTTCT TTAGATTGGG CTGCTTTAGA TAAATCATAC AAAGCAGAAC CAGGCTTTAA
2641   ATCAAAGCGC TCGGTCCCTA CCGGGCCCTC GCAGGAAAAG AAGGCGCGGT
```

Fig. 66 (SEQ ID NO:61)

SEQ MSV AC1_Target gene DNA region_complement_reverse: 246 bp;
Composition   64   A;   68   C;   40   G;   74   T;   0 OTHER
Percentage:   26%   A;   28%   C;   16%   G;   30%   T;   0%OTHER Molecular Weight (kDa): ssDNA: 75.34      dsDNA: 151.6
ORIGIN
1       AGAGCTCCCC TTTGATTGGT CCACAAAATT GCAGTATTTT GAATACTCTG CAAATAAGCT
61      TTTTCCTGAG ATTCAGGAAG AGTTCACCAA TCCTCATCCA CCCTCCTCAC CTGATTTACT
121     TTGTAATGAG TCAATCAACG ATTGGCTCCA GCCTAACATC TTCCAGGTTA GTCCCGAAGC
181     TTACATGCTC CTTCAACCTA CCTGTTATAC CCTCGAGGAT GCAATTTCTG ACCTCCAATG
241     GATGGA Fig. 67 (SEQ ID NO:62)

SEQ MSV AC1_Hairpin sequence: 663 bp;
Composition  183   A;   90   C;  150   G;  240   T;   0 OTHER
Percentage:   28%   A;   14%   C;   23%   G;   36%   T;   0%OTHER Molecular Weight (kDa): ssDNA: 205.60     dsDNA: 408.6
ORIGIN
1       AAGCTTGCAT GCAGGCCTCT GCAGTCGACG GGCCCGGGAT CCGATTGATC ACTAGTAGAG
61      TTCTCCTTTG ATTGTTTATA AAATTGTAGT ATTTTGAATA TTTTGTAAAT AAGTTTTTTT
121     TTGAGATTTA GGAAGAGTTT ATTAATTTTT ATTTATTTTT TTATTTGAT TTATTTTGGA
181     ATGAGTTAAT TAATGATTGG TTTTAGTTTA ATATTTTTA GGTTAGTTCT GAAGTTTATA
241     TGTTTTTTTA ATTTATTTGT TATATTTTTG AGGATGTAAT TTCTGATCTC TAATGGATGG
301     ATGATCAAAA TCCGATTTCC ATCCATTGGA GGTCAGAAAT CCATCCATTG GAGGTCAGAA
361     ATCCATCCAT TGGAGGTCAG AAATTGCATC CTCGAGGGTA TAACAGGTAG GTTGAAGGAG
421     CATGTAAGCT TCGGGACTAA CCTGGAAGAT GTTAGGCTGG AGCCAATCGT TGATTGACTC
481     ATTACAAAGT AAATCAGGTG AGGAGGGTGG ATGAGGATTG GTGAACTCTT CCTGAATCTC
541     AGGAAAAAGC TTATTTGCAG AGTATTCAAA ATACTGCAAT TTTGTGGACC AATCAAAGGG
601     GAGCTCTAAT CTAGATGCAT TCGCGAGGTA CCGAGCTCGA ATTCACTGGC CGTCGTTTTA
661     CAA Fig. 68 (SEQ ID NO:63)

```
SEQ  MSV AC1_Target gene DNA sequence_RNA: 2690 bases;
Composition   693  A;  632  C;  688  G;  677  U;  0 OTHER
Percentage:   26%  A;  23%  C;  26%  G;  25%  U;  0%OTHER Molecular Weight: 865.28kDa 1    ACCGCGCCUU CUUUUCCUGC GAGGGCCCGG UAGGGACCGA GCGCUUUGAU UUAAAGCCUG
  61    GUUCUGCUUU GUAUGAUUUA UCUAAAGCAG CCCAAUCUAA AGAAACCGGU CCCGGGCACU
 121    AUAAAUUGCC UAACAAGUGC GAUUCAUUCA UGGAUCCACA GAACGCCCUG UAUUAUCAGC
 181    CGCGGGUACC CACAGCAGCU CCGACAUCCG GAGGAGUGCC GUGGAGUCGC GUAGGCGAGG
 241    UAGCUAUUUU GAGCUUUGUU GCAUUGAUUU GCUUUUACCU GCUUUACCUU GGGGUGCUGA
 301    GAGACCUUAU CUUAGUUCUG AAGGCUCGAC AAGGCAGAUC CACGGAGGAG CUGAUAUUUG
 361    GUGGACAAGC UGUGGAUAGG AGCAACCCUA UCCCUAAUCU ACCUUCACCA CCAAGUCAGG
 421    GCAAUCCCGG GCCAUUUGUU CCAGGCACGG GAUAAGCAAU CAGCCAUGUC CACGUCCAAG
 481    AGGAAGCGGG GAGAUGAUUC GAAUUGGAAU AAGCGGGUGC CUAAGAAGAA GCCAUCUUCA
 541    GCUGGGCUGA AGAGCGGCUGG AAGCAAGGCC GAUAGGCCAU CCCUCCAAAU CCAGACACUC
 601    CAGCAUGCUG GGACCACCAU GAUAACUGUC CAUCCGGAG GAGUAUGUGA CCUCAUCAAC
 661    ACCUAUGCCC GAGGAUCUGA CGAGGGCAAC CGCCACACCA GCGAGACUCU GACGUACAAG
 721    AUCGCCGUCG ACUACCACUU CGUUGCCGAC GCGGCUGCCU GCCGCUACUC CAACACCGGA
 781    ACCGGUGUAA UGUGGCUGGU GUAUGACACC ACUCCCGGCG GACAAGCUCC GACCCCGCAA
 841    ACUAUAUUUG CCUACCCUGA CACGCUAAAA GCGUGGCCGG CCACAUGGAA AGUGAGCCGG
 901    GAGCUGUGUC AUCGCUUCGU GGUGAAACGG CGAUGGUUGU CAACAUGGA GACCGACGGU
 961    CGGAUUGGUU CGGAUAUCCC UCCCUCGAAU ACAAGUUGGA AGCCUUGCAA GCGCAACAUC
1021    UACUUCCACA AGUUCACGAG UGGGUUGGGA GUGAGAACGC AGUGGAAGAA UGUAACGGAC
1081    GGAGGAGUUG GUGCCAUCCA GAGAGGAGCU CUGUACAUGG UCAUUGCCCC AGGCAAUGGC
1141    CUUACUUUUA CUGCCCAUGG GCAGACCCGU CUGUACUUUA AGAGUGUUGG CAACCAGUAA
1201    UGAAUAAAAA CUCCCGUUUU AUUAUAUUUG AUGAAUGCUG AAAGCUUACA UUAAUAUGUC
1261    GUGCGAUGGC ACGAAAAAAC ACACGCAAAC AAUACAGGGG GGUAGUCGGC GGGCGGCUAA
1321    GGGUGGUGCU CGGCGGGCAG AACAUCGAAA AAUCAAGAUC UAUAUGAAUU ACACUUCCUC
1381    CGUAGGAGGA AGCACAGGGG GAGAAUACCA CUUCUCCCCC GGCGACAUAA UGUAAAUGAC
1441    GCAGUUUGCC UCGAAAUACU CCAGCUGCCC UGGAGUCAUU UCCUUCAUCC AAUCUUCAUC
1501    CGAGUUGGCG AGGAUUAUUG UAGGCUUAGA CUUCUUCUGC ACCUUUUUCU UCUUACCAUA
1561    CUUGGGGUUU ACAAUGAAAU CCCUCUGACA GCCAACUAAC UGUUUCCAAC AAGGACAGAA
1621    UUUAAACGGA AUAUCAUCUA CGAUGUUGUA GAUUGCGUCU UCGUUGUAUG AAGACCAAUC
1681    AACAUUAUUU UGCCAGUAAU UAUGAACCCC UAGGCUUCUG GCCCAAGUAG AUUUUCCGGU
1741    UCUUGUUGGG CCGACGAUGU AGAGGCUCUG CUUUCUUGAU CUUUCAUCUG AUGACUGGAU
1801    ACAGAAUCCA UCCAUUGGAG GUCAGAAAUU GCAUCCUCGA GGGUAUAACA GGUAGGUUGA
1861    AGGAGCAUGU AAGCUUCGGG ACUAACCUGG AAGAUGUUAG GCUGGAGCCA AUCGUUGAUU
1921    GACUCAUUAC AAAGUAAAUC AGGUGAGGAG GGUGGAUGAG GAUUGGUGAA CUCUUCCUGA
1981    AUCUCAGGAA AAAGCUUAUU UGCAGAGUAU UCAAAAUACU GCAAUUUUGU GGACCAAUCA
2041    AAGGGGAGCU CUUUCUGGAU CAUGGAGAGG UACUCUUCUU UGGAGGUAGC GUGUGAAAUA
2101    AUGUCUCGCA UUAUUCAUC UUUAGAAGGC UUUUUUUCCU UUACCUCUGA AUCAGAUUUU
2161    CCUAGGAAGG GGGACUUCCU AGGAAUGAAA GUACCUCUCU CAAACACAGC CAGAGGUUCC
2221    UUGAGAAUGU AAUCCCUCUG UCUGUAAUCG GACUUGGCAC UCUGAAUAUU UGGGUGAAAC
2281    CCAUUUAUAU CAAAGAACCU UGAUCAGAU AUCCUUAUCG GCUUCUCUGG CUGAAGCAAU
2341    GCAUGUAAAU GCAAACUUCC AUCUUUAUGU GCCUCUCGGG CACAUAGAAU AUAUUUGGGA
2401    AUCCAACGAA CGACGAGCUC CCAGAUCAUC UGACAGGCGA UUUCAGGAUU UUCUGGACAC
2461    UUUGGAUAGG UUAGGAACGU GUUAGCGUUC CUGUGUGAGA ACUGACGGUU GGAUGAGGAG
2521    GAGGCCAUAG CCGACGACGG AGGUUGAGGC UGAGGAUGG CAGACUGGGA GCUCCAAACU
2581    CUAUAGUAUA CCCGUGCGCC UUCGAAAUCC GCCGCUCCAU UGUCUUAUAG UGGUUGUAAA
2641    UGGGCCGGAC CGGGCCGGCC CAGCAGGAAA AGAAGGCGCG CACUAAUAUU
```

Fig. 69 (SEQ ID NO:64)

```
SEQ  MSV AC1_Target gene DNA region_RNA: 246 bases;
Composition   74   A;  40   C;  68   G;  64   U;  0 OTHER
Percentage:   30%  A;  16%  C;  28%  G;  26%  U;  0%OTHER Molecular Weight: 79.59 kDa 1     UCCAUCCAUU  GGAGGUCAGA  AAUUGCAUCC  UCGAGGGUAU  AACAGGUAGG  UUGAAGGAGC
61    AUGUAAGCUU  CGGGACUAAC  CUGGAAGAUG  UUAGGCUGGA  GCCAAUCGUU  GAUUGACUCA
121   UUACAAAGUA  AAUCAGGUGA  GGAGGGUGGA  UGAGGAUUGG  UGAACUCUUC  CUGAAUCUCA
181   GGAAAAAGCU  UAUUUGCAGA  GUAUUCAAAA  UACUGCAAUU  UUGUGGACCA  AUCAAAGGGG
241   AGCUCU
```

Fig. 70 (SEQ ID NO:65)

```
SEQ  MSV AC1_Target gene DNA region_modified_RNA: 246 bases;
Composition   74   A;  0    C;  68   G;  104  U;  0 OTHER
Percentage:   30%  A;  0%   C;  28%  G;  42%  U;  0%OTHER Molecular Weight: 79.63 kDa 1     UUUAUUUAUU  GGAGGUUAGA  AAUUGUAUUU  UUGAGGGUAU  AAUAGGUAGG  UUGAAGGAGU
61    AUGUAAGUUU  UGGGAUUAAU  UUGGAAGAUG  UUAGGUUGGA  GUUAAUUGUU  GAUUGAUUUA
121   UUAUAAAGUA  AAUUAGGUGA  GGAGGGUGGA  UGAGGAUUGG  UGAAUUUUUU  UUGAAUUUUA
181   GGAAAAAGUU  UAUUUGUAGA  GUAUUAAAAA  UAUUGUAAUU  UUGUGGAUUA  AUUAAAGGGG
241   AGUUUU
```

Fig. 71 (SEQ ID NO:66)

```
SEQ  MSV AC1_Target gene DNA sequence_complement_RNA: 2690 bases;
Composition    677  A;  688  C;  632   G;  693   U;  0 OTHER
Percentage:    25%  A;  26%  C;  23%   G;  26%   U;  0%OTHER Molecular Weight: 862.67kDa 1    UGGCGCGGAA GAAAAGGACG CUCCCGGGCC AUCCCUGGCU CGCGAAACUA AAUUUCGGAC
  61    CAAGACGAAA CAUACUAAAU AGAUUUCGUC GGGUUAGAUU UCUUUGGCCA GGGCCCGUGA
 121    UAUUUAACGG AUUGUUCACG CUAAGUAAGU ACCAGGUGU  CUUGCGGGAC AUAAUAGUCG
 181    GCGCCCAUGG GUGUCGUCGA GGCUGUAGGC CUCCUCACGG CACCUCAGCG CAUCCGCUCC
 241    AUCGAUAAAA CUCGAAACAA CGUAACUAAA CGAAAUGGA  CGAAAUGGAA ACCCACGACU
 301    CUCUGGAAUA GAAUCAAGAC UUCCGAGCUG UUCCGUCUAG GUGCCUCCUC GACUAUAAAC
 361    CACCUGUUCG ACACCUAUCC UCGUUGGGAU AGGGAUUAGA UGGAAGUGGU GGUUCAGUCC
 421    CGUUAGGGCC CGGUAAACAA GGUCCGUGCC CUAUUCGUUA GUCGGUACAG GUGCAGGUUC
 481    UCCUUCGCCC CUCUACUAAG CUUAACCUUA UUCGCCCACG GAUUCUUCUU CGGUAGAAGU
 541    CGACCCGACU UCUCCCGACC UUCGUUCCGG CUAUCCGGUA GGGAGGUUUA GGUCUGUGAG
 601    GUCGUACGAC CCUGGUGGUA CUAUUGACAG GGUAGGCCUC CUCAUACACU GGAGUAGUUG
 661    UGGAUACGGG CUCCUAGACU GCUCCCGUUG GCGGUGUGGU CGCUCUGAGA CUGCAUGUUC
 721    UAGCGGCAGC UGAUGGUGAA GCAACGGCUG CGCCGACGGA CGGCGAUGAG GUUGUGGCCU
 781    UGGCCACAUU ACACCGACCA CAUACUGUGG UGAGGGCCGC CUGUUCGAGG CUGGGGCGUU
 841    UGAUAUAAAC GGAUGGGACU GUGCGAUUUU CGCACCGGCC GGUGUACCUU UCACUCGGCC
 901    CUCGACACAG UAGCGAAGCA CCACUUUGCC GCUACCAACA AGUUGUACCU CUGGCUGCCA
 961    GCCUAACCAA GCCUAUAGGG AGGGAGCUUA UGUUCAACCU UCGGAACGUU CGCGUUGUAG
1021    AUGAAGGUGU UCAAGUGCUC ACCCAACCCU CACUCUUGCG UCACCUUCUU ACAUUGCCUG
1081    CCUCCUCAAC CACGGUAGGU CUCUCCUCGA GACAUGUACC AGUAACGGGG UCCGUUACCG
1141    GAAUGAAAAU GACGGGUACC CGUCGGGCA  GACAUGAAAU UCUCACAACC GUUGGUCAUU
1201    ACUUAUUUUU GAGGGCAAAA UAAUAUAAAC UACUUACGAC UUUCGAAUGU AAUUAUACAG
1261    CACGCUACCG UGCUUUUUUG UGUGCGUUUG UUAUGUCCCC CCAUCGCCG  CCCGCCGAUU
1321    CCCACCACGA GCCGUCCCGUC UUGUAGCUUU UUAGUUCUAG AUAUACUUAA UGUGAAGGAG
1381    GCAUCCUCCU UCGUGUCCCC CUCUUAUGGU GAAGAGGGGG CCGCUGUAUU ACAUUUACUG
1441    CGUCAAACGG AGCUUUAUGA GGUCGACGGG ACCUCAGUAA AGGAAGUAGG UUAGAAGUAG
1501    GCUCAACCGC UCCUAAUAAC AUCCGAAUCU GAAGAAGACG UGGAAAAGA  AGAAUGGUAU
1561    GAACCCCAAA UGUUACUUUA GGGAGACUGU CGGUUGAUUG ACAAAGGUUG UUCCUGUCUU
1621    AAAUUUGCCU AUAGUAGAU  GCUACAACAU CUAACGCAGA AGCAACAUAC UUCUGGUUAG
1681    UUGUAAUAAA ACGGUCAUUA AUACUUGGGG AUCCGAAGAC CGGGUUCAUC UAAAAGGCCA
1741    AGAACAACCC GGCUGCUACA UCUCCGAGAC GAAAGAACUA GAAAGUAGAC UACUGACCUA
1801    UGUCUUAGGU AGGUAACCUC CAGUCUUUAA CGUAGGAGCU CCCAUAUUGU CCAUCCAACU
1861    UCCUCGUACA UUCGAAGCCC UGAUUGGACC UUCUACAAUC CGACCUCGGU UAGCAACUAA
1921    CUGAGUAAUG UUUCAUUUAG UCCACUCCUC CCACCUACUC CUAACCACUU GAGAAGGACU
1981    UAGAGUCCUU UUUCGAAUAA ACGUCUCAUA AGUUUAUGA  CGUUAAAACA CCUGGUUAGU
2041    UUCCCCUCGA GAAAGACCUA GUACCUCUCC AUGAGAACAA ACCUCCAUCG CACACUUUAU
2101    UACAGAGCGU AAUAAAGUAG AAAUCUUCCG AAAAAAAGGA AAUGGAGACU UAGUCUAAAA
2161    GGAUCCUUCC CCCUGAAGGA UCCUUACUUU CAUGGAGAGA GUUUGUGUCG GUCUCCAAGG
2221    AACUCUUACA UUAGGGAGUG AGACAAUUGA CUGAACCGUG AGACUUAUAA ACCCACUUUG
2281    GGUAAAUAUA GUUUCUUGGA ACUCAGUCUA UAGGAAUAGC CGAAGAGACC GACUUCGUUA
2341    CGUACAUUUA CGUUUGAAGG UAGAAAUACA CGGAGAGCCC GUGUAUCUUA UAUAAACCCU
2401    UAGGUUGCUU GCUGCUCGAG GGUCUAGUAG ACUGUCCGCU AAAGUCCUAA AAGACCUGUG
2461    AAACCUAUCC AAUCCUUGCA CAAUCGCAAG GACACACUCU UGACUGCCAA CCUACUCCUC
2521    CUCCGGUAUC GGCUGCUGCC UCCAACUCCG ACUCCUACC  GUCUGACCCU CGAGGUUUGA
2581    GAUAUCAUAU GGGCACGCGG AAGCUUUAGG CGGCGAGGUA ACAGAAUAUC ACCAACAUUU
2641    ACCCGGCCUG GCCCGGCCGG UCGUCCUUU  UCUUCCGCGC GUGAUUAUAA
```

Fig. 72 (SEQ ID NO:67)

```
SEQ  MSV AC1_Target gene DNA region_complement_RNA: 246 bases;
Composition   64   A;  68   C;  40   G;  74   U;  0 OTHER
Percentage:  26%   A;  28%  C;  16%  G;  30%  U;  0%OTHER Molecular Weight: 78.24 kDa 1     AGGUAGGUAA CCUCCAGUCU UUAACGUAGG AGCUCCCAUA UUGUCCAUCC AACUUCCUCG
61    UACAUUCGAA GCCCUGAUUG GACCUUCUAC AAUCCGACCU CGGUUAGCAA CUAACUGAGU
121   AAUGUUUCAU UUAGUCCACU CCUCCCACCU ACUCCUAACC ACUUGAGAAG GACUUAGAGU
181   CCUUUUUCGA AUAAACGUCU CAUAAGUUUU AUGACGUUAA AACACCUGGU UAGUUUCCCC
241   UCGAGA
```

Fig. 73 (SEQ ID NO:68)

```
SEQ  MSV AC1_Target gene DNA sequence_reverse_RNA: 2690 bases;
Composition  693 A; 632 C; 688 G; 677 U; 0 OTHER
Percentage:  26% A; 23% C; 26% G; 25% U; 0%OTHER Molecular Weight: 865.28kDa 1    UUAUAAUCAC GCGCGGAAGA AAAGGACGAC CCGGCCGGGC CAGGCCGGGU AAAUGUUGGU
  61    GAUAUUCUGU UACCUCGCCG CCUAAAGCUU CCGCGUGCCC AUAUGAUAUC UCAAACCUCG
 121    AGGGUCAGAC GGUAGGGAGU CGGAGUUGGA GGCAGCAGCC GAUACCGGAG GAGGAGUAGG
 181    UUGGCAGUCA AGAGUGUGUC CUUGCGAUUG UGCAAGGAUU GGAUAGGUUU CACAGGUCUU
 241    UUAGGACUUU AGCGGACAGU CUACUAGACC CUCGAGCAGC AAGCAACCUA AGGGUUUAUA
 301    UAAGAUACAC GGGCUCUCCG UGUAUUUCUA CCUUCAAACG UAAAUGUACG UAACGAAGUC
 361    GGUCUCUUCG GCUAUUCCUA UAGACUGAGU UCCAAGAAAC UAUAUUUACC CAAAGUGGGU
 421    UUAUAAGUCU CACGGUUCAG UCAAUUGUCU CACUCCCUAA UGUAAGAGUU CCUUGGAGAC
 481    CGACACAAAC UCUCUCCAUG AAAGUAAGGA UCCUUCAGGG GGAAGGAUCC UUUUAGACUA
 541    AGUCUCCAUU UCCUUUUUUU CGGAAGAUUU CUACUUUAUU ACGCUCUGUA AUAAAGUGUG
 601    CGAUGGAGGU UUCUUCUCAU GGAGAGGUAC UAGGUCUUUC UCGAGGGGAA ACUAACCAGG
 661    UGUUUUAACG UCAUAAAACU AUGAGACGU UUAUUCGAAA AAGGACUCUA AGUCCUUCUC
 721    AAGUGGUUAG GAGUAGGUGG GAGGAGUGGA CUAAAUGAAA CAUUACUCAG UUAGUUGCUA
 781    ACCGAGGUCG GAUUGUAGAA GGUCCAAUCA GGGCUUCGAA UGUACGAGGA AGUUGGAUGG
 841    ACAAUAUGGG AGCUCCUACG UUAAAGACUG GAGGUUACCU ACCUAAGACA UAGGUCAGUA
 901    GUCUACUUUC UAGUUCUUUC GUCUCGGAGA UGUAGCAGCC GGGUUGUUCU UGGCCUUUUA
 961    GAUGAACCCG GUCUUCGGAU CCCCAAGUAU UAAUGACCGU UUUAUUACAA CUAACCAGAA
1021    GUAUGUUGCU UCUGCGUUAG AUGUUGUAGC AUCUACUAUA AGGCAAAUUU AAGACAGGAA
1081    CAACCUUUGU CAAUCAACCG ACAGUCUCCC UAAAGUAACA UUUGGGGUUC AUACCAUUCU
1141    UCUUUUUCCA CGUCUUCUUC AGAUUCGGAU GUUAUUAGGA GCGGUUGAGC CUACUUCUAA
1201    CCUACUUCCU UUACUGAGGU CCCGUCGACC UCAUAAAGCU CCGUUUGACG CAGUAAAUGU
1261    AAUACAGCGG CCCCCUCUUC ACCAUAAGAG GGGACACGA AGGAGGAUGC CUCCUUCACA
1321    UUAAGUAUAU CUAGAACUAA AAAGCUACAA GACGGGCGGC UCGUGGUGGG AAUCGGCGGG
1381    CGGCUGAUGG GGGGACAUAA CAAACGCACA CAAAAAGCA CGGUAGCGUG CUGUAUAAUU
1441    ACAUUCGAAA GUCGUAAGUA GUUUAUAUUA UUUUGCCCUC AAAAAUAAGU AAUGACCAAC
1501    GGUUGUGAGA AUUUCAUGUC UGCCCAGACG GGUACCGUC AUUUCAUUC CGGUAACGGA
1561    CCCCGUUACU GGUACAUGUC UCGAGGAGAG ACCUACCGUG GUUGAGGAGG CAGGCAAUGU
1621    AAGAAGGUGA CGCAAGAGUG AGGGUUGGGU GAGCACUUGA ACACCUUCAU CUACAACGCG
1681    AACGUUCCGA AGGUUGAACA UAAGCUCCCU CCCUAUAGGC UUGGUUAGGC UGGCAGCCAG
1741    AGGUACAACU UGUUGGUAGC GGCAAAGUGG UGCUUCGCUA CUGUGUCGAG GGCCGAGUGA
1801    AAGGUACACC GGCCGGUGCG AAAAUCGCAC AGUCCCAUCC GUUUAUAUCA AACGCCCCAG
1861    CCUCGAACAG GCGGCCCUCA CCACAGUAUG UGGUCGGUGU AAUGUGGCCA AGGCACAAC
1921    CUCAUCGCCG UCCGUCGGCG CAGCCGUUGC UUCACCAUCA GCUGCCGCUA GAACAUGCAG
1981    UCUCAGAGCG ACCACACCGC CAACGGGAGC AGUCUAGGAG CCCGUAUCCA CAACUACUCC
2041    AGUGUAUGAG GAGGCCUACC CUGUCAAUAG UACCACCAGG GUCGUACGAC CUCACAGACC
2101    UAAACCUCCC UACCGGAUAG CCGGAACGAA GGUCGGGAGA GUCGGGUCG ACUUCUACCG
2161    AAGAAGAAUC CGUGGGCGAA UAAGGUUAAG CUUAGUAGAG GGGCGAAGGA GAACCUGCAC
2221    CUGUACCGAC UAACGAAUAG GGCACGGACC UUGUUUACCG GGCCCUAACG GGACUGAACC
2281    ACCACUUCCA UCUAAUCCCU AUCCCAACGA GGAUAGGUGU CGAACAGGUG GUUUAUAGUC
2341    GAGGAGGCAC CUAGACGGAA CAGCUCGGAA GUCUUGAUUC UAUUCCAGAG AGUCUGGGU
2401    UUCCAUUUCG UCCAUUUUCG UUUAGUUACG UUGUUUCGAG UUUUAUCGAU GGAGCGGAUG
2461    CGCUGAGGUG CCGUGAGGAG GCCUACAGCC UCGACGACAC CCAUGGGCGC CGACUAUUAU
2521    GUCCGCAAG ACACCUAGGU ACUUACUUAG CGUAACAAU CCGUUAAAUA UCACGGGCCC
2581    UGGCCAAAGA AAUCUAACCC GACGAAAUCU AUUUAGUAUG UUUCGUCUUG GUCCGAAAUU
2641    UAGUUUCGCG AGCCAGGGAU GGCCCGGGAG CGUCCUUUUC UUCCGCGCCA
```

Fig. 74 (SEQ ID NO:69)

```
SEQ  MSV AC1_Target gene DNA region_reverse_RNA: 246 bases;
Composition  74  A; 40   C; 68   G; 64   U; 0 OTHER
Percentage:  30% A; 16%  C; 28%  G; 26%  U; 0%OTHER Molecular Weight: 79.59 kDa 1    UCUCGAGGGG AAACUAACCA GGUGUUUUAA CGUCAUAAAA CUUAUGAGAC GUUUAUUCGA
 61    AAAAGGACUC UAAGUCCUUC UCAAGUGGUU AGGAGUAGGU GGGAGGAGUG GACUAAAUGA
121    AACAUUACUC AGUUAGUUGC UAACCGAGGU CGGAUUGUAG AAGGUCCAAU CAGGGCUUCG
181    AAUGUACGAG GAAGUUGGAU GGACAAUAUG GGAGCUCCUA CGUUAAAGAC UGGAGGUUAC
241    CUACCU
```

Fig. 75 (SEQ ID NO:70)

```
SEQ  MSV AC1_Target gene DNA region_modified_reverse_RNA: 246 bases;
Composition  74  A; 0    C; 68   G; 104  U; 0 OTHER
Percentage:  30% A; 0%   C; 28%  G; 42%  U; 0%OTHER Molecular Weight: 79.63 kDa 1    UUUUGAGGGG AAAUUAAUUA GGUGUUUUAA UGUUAUAAAA UUUAUGAGAU GUUUAUUUGA
 61    AAAAGGAUUU UAAGUUUUUU UUAAGUGGUU AGGAGUAGGU GGGAGGAGUG GAUUAAAUGA
121    AAUAUUAUUU AGUUAGUUGU UAAUUGAGGU UGGAUUGUAG AAGGUUUAAU UAGGGUUUUG
181    AAUGUAUGAG GAAGUUGGAU GGAUAAUAUG GGAGUUUUUA UGUUAAAGAU UGGAGGUUAU
241    UUAUUU
```

Fig. 76 (SEQ ID NO:71)

SEQ  MSV AC1_Target gene DNA sequence_complement_reverse_RNA: 2690 bases;
Composition   677 A;  688 C;  632 G;  693 U;  0 OTHER
Percentage:   25% A;  26% C;  23% G;  26% U;  0%OTHER Molecular Weight: 862.67kDa

```
1       AAUAUUAGUG CGCGCCUUCU UUUCCUGCUG GGCCGGCCCG GUCCGGCCCA UUUACAACCA
61      CUAUAAGACA AUGGAGCGGC GGAUUUCGAA GGCGCACGGG UAUACUAUAG AGUUUGGAGC
121     UCCCAGUCUG CCAUCCCUCA GCCUCAACCU CCGUCGUCGG CUAUGGCCUC CUCCUCAUCC
181     AACCGUCAGU UCUCACACAG GAACGCUAAC ACGUUCCUAA CCUAUCCAAA GUGUCCAGAA
241     AAUCCUGAAA UCGCCUGUCA GAUGAUCUGG GAGCUCGUCG UUCGUUGGAU UCCCAAAUAU
301     AUUCUAUGUG CCCGAGAGGC ACAUAAAGAU GGAAGUUUGC AUUUACAUGC AUUGCUUCAG
361     CCAGAGAAGC CGAUAAGGAU AUCUGACUCA AGGUUCUUUG AUAUAAAUGG GUUUCACCCA
421     AAUAUUCAGA GUGCCAAGUC AGUUAACAGA GUGAGGGAUU ACAUUCUCAA GGAACCUCUG
481     GCUGUGUUUG AGAGAGGUAC UUUCAUUCCU AGGAAGUCCC CCUUCCUAGG AAAAUCUGAU
541     UCAGAGGUAA AGGAAAAAAA GCCUUCUAAA GAUGAAAAUA UGCGAGACAU UAUUUCACAC
601     GCUACCUCCA AAGAAGAGUA CCUCUCCAUG AUCCAGAAAG AGCUCCCCUU UGAUUGGUCC
661     ACAAAAUUGC AGUAUUUUGA AUACUCUGCA AAUAAGCUUU UCCUGAGAU UCAGGAAGAG
721     UUCACCAAUC CUCAUCCACC CUCCUCACCU GAUUUACUUU GAAUGAGUC AAUCAACGAU
781     UGGCUCCAGC CUAACAUCUU CCAGGUUAGU CCCGAAGCUU ACAUGCUCCU UCAACCUACC
841     UGUUAUACCC UCGAGGAUGC AAUUCUGAC CUCCAAUGGA UGGAUUCUGU AUCCAGUCAU
901     CAGAUGAAAG AUCAAGAAAG CAGAGCCUCU ACAUCGUCGG CCCAACAAGA ACCGGAAAAU
961     CUACUUGGGC CAGAAGCCUA GGGGUUCAUA AUUACUGGCA AAAUAAUGUU GAUUGGUCUU
1021    CAUACAACGA AGACGCAAUC UACAACAUCG UAGAUGAUAU UCCGUUUAAA UUCUGUCCUU
1081    GUUGGAAACA GUUAGUUGGC UGUCAGAGGG AUUUCAUUGU AAACCCCAAG UAUGGUAAGA
1141    AGAAAAAGGU GCAGAAGAAG UCUAAGCCUA CAAUAAUCCU CGCCAACUCG GAUGAAGAUU
1201    GGAUGAAGGA AAUGACUCCA GGGCAGCUGG AGUAUUCGA GGCAAACUGC GUCAUUUACA
1261    UUAUGUCGCC GGGGGAGAAG UGGUAUUCUC CCCCUGUGCU UCCUCCUACG GAGGAAGUGU
1321    AAUUCAUAUA GAUCUUGAUU UUCGAUGUU CUGCCCGCCG AGCACCACCC UUAGCCGCCC
1381    GCCGACUACC CCCCUGUAUU GUUUGCGUGU GUUUUUUCGU GCCAUCGCAC GACAUAUUAA
1441    UGUAAGCUUU CAGCAUUCAU CAAAUAUAAU AAAACGGGAG UUUUUAUUCA UUACUGGUUG
1501    CCAACACUCU UAAAGUACAG ACGGGUCUGC CCAUGGGCAG UAAAAGUAAG GCCAUUGCCU
1561    GGGGCAAUGA CCAUGUACAG AGCUCCUCUC UGGAUGGCAC CAACUCCUCC GUCCGUUACA
1621    UUCUUCCACU GCGUUCUCAC UCCCAACCCA CUCGUGAACU GUGGAAGUA GAUGUUGCGC
1681    UUGCAAGGCU UCCAACUUGU AUUCGAGGGA GGGAUAUCCG AACCAAUCCG ACCGUCGGUC
1741    UCCAUGUUGA ACAACCAUCG CCGUUUCACC ACGAAGCGAU GACACAGCUC CCGGCUCACU
1801    UUCCAUGUGG CCGGCCACGC UUUUAGCGUG UCAGGGUAGG CAAAUAUAGU UUGCGGGGUC
1861    GGAGCUUGUC CGCCGGGAGU GGUGUCAUAC ACCAGCCACA UUACACCGGU UCCGGUGUUG
1921    GAGUAGCGGC AGGCAGCCGC GUCGGCAACG AAGUGGUAGU CGACGGCGAU CUUGUACGUC
1981    AGAGUCUCGC UGGUGUGGCG GUUGCCCUCG UCAGAUCCUC GGGCAUAGGU GUUGAUGAGG
2041    UCACAUACUC CUCCGGAUGG GACAGUUAUC AUGGUGGUCC CAGCAUGCUG GAGUGUCUGG
2101    AUUUGGAGGG AUGGCCUAUC GGCCUUGCUU CCAGCCCUCU CAGCCCAGC UGAAGAUGGC
2161    UUCUUCUUAG GCACCCGCUU AUUCCAAUUC GAAUCAUCUC CCCGCUUCCU CUUGGACGUG
2221    GACAUGGCUG AUUGCUUAUC CCGUGCCUGG AACAAAUGGC CGGGAUUGC CUGACUUGG
2281    UGGUGAAGGU AGAUUAGGGA UAGGGUUGCU CCUAUCCACA GCUUGCCAC CAAAUAUCAG
2341    CUCCUCCGUG GAUCUGCCUU GUCGAGCCUU CAGAACUAAG AUAAGGUCUC UCAGCACCCA
2401    AAGGUAAAGC AGGUAAAAGC AAAUCAAUGC AACAAAGCUC AAAAUAGCUA CCUCGCCUAC
2461    GCGACUCCAC GGCACUCCUC CGGAUGUCGG AGCUGCUGUG GGUACCCGCG GCUGAUAAUA
2521    CAGGGCGUUC UGUGGAUCCA UGAAUGAAUC GCACUUGUUA GGCAAUUUAU AGUGCCCGGG
2581    ACCGGUUUCU UUAGAUGGG CUGCUUUAGA UAAAUCAUAC AAAGCAGAAC CAGGCUUUAA
2641    AUCAAAGCGC UCGGUCCCUA CCGGGCCCUC GCAGGAAAAG AAGGCGCGGU
```

Fig. 77 (SEQ ID NO:72)

```
SEQ  MSV AC1_Target gene DNA region_complement_reverse_RNA: 246 bases;
Composition   64   A;   68   C;   40   G;   74   U;   0 OTHER
Percentage:   26%  A;   28%  C;   16%  G;   30%  U;   0%OTHER Molecular Weight: 78.24 kDa 1    AGGUAGGUAA CCUCCAGUCU UUAACGUAGG AGCUCCCAUA UUGUCCAUCC AACUUCCUCG
 61    UACAUUCGAA GCCCUGAUUG GACCUUCUAC AAUCCGACCU CGGUUAGCAA CUAACUGAGU
121    AAUGUUUCAU UUAGUCCACU CCUCCACCU ACUCCUAACC ACUUGAGAAG GACUUAGAGU
181    CCUUUUUCGA AUAAACGUCU CAUAAGUUUU AUGACGUUAA AACACCUGGU UAGUUUCCCC
241    UCGAGA
```

Fig. 78 (SEQ ID NO:73)

```
SEQ  MSV AC1_Hairpin sequence_RNA: 663 bp;
Composition   183  A;   90   C;   150  G;   240  U;   0 OTHER
Percentage:   28%  A;   14%  C;   23%  G;   36%  U;   0%OTHER Molecular Weight: 212.85kDa 1    AAGCUUGCAU GCAGGCCUCU GCAGUCGACG GGCCCGGGAU CCGAUUGAUC ACUAGUAGAG
 61    UUCUCCUUUG AUUGUUUAUA AAAUUGUAGU AUUUUGAAUA UUUUGUAAAU AAGUUUUUUU
121    UUGAGAUUUA GGAAGAGUUU AUUAAUUUUU AUUUAUUUUU UUUAUUUGAU UUAUUUUGGA
181    AUGAGUUAAU UAAUGAUUGG UUUUAGUUUA AUAUUUUUJA GGUUAGUUCU GAAGUUUAUA
241    UGUUUUUUUA AUUUAUUUGU UAUAUUUUUG AGGAUGUAAU UUCUGAUCUC UAAUGGAUGG
301    AUGAUCAAAA UCCGAUUUCC AUCCAUUGGA GGUCAGAAAU CCAUCCAUUG GAGGUCAGAA
361    AUCCAUCCAU UGGAGGUCAG AAAUUGCAUC UCGAGGGUA UAACAGGUAG GUUGAAGGAG
421    CAUGUAAGCU UCGGGACUAA CCUGGAAGAU GUUAGGCUGG AGCCAAUCGU UGAUUGACUC
481    AUUACAAAGU AAAUCAGGUG AGGAGGGUGG AUGAGGAUUG GUGAACUCUU CCUGAAUCUC
541    AGGAAAAAGC UUAUUGCAG AGUAUUCAAA AUACUGCAAU UUUGUGGACC AAUCAAAGGG
601    GAGCUCUAAU CUAGAUGCAU UCGCGAGGUA CCGAGCUCGA AUUCACUGGC CGUCGUUUUA
661    CAA
```

Fig. 79 (SEQ ID NO:74)

SACMV AC1 - Hairpin sequences

```
SEQ  SACMV AC1_Hairpin sequence: 384 bp;
Composition   145  A;   88   C;   46   G;   105  T;   0 OTHER
Percentage:   38%  A;   23%  C;   12%  G;   27%  T;   0%OTHER Molecular Weight (kDa):  ssDNA: 117.87    dsDNA: 236.7
ORIGIN
  1    CTCGAAAGAA GCGGCATTAG ATCAACTCCG ACAACTCCAA ACCCCAACAA ATAAATTGTT
 61    CATCAAGATC TGCAGAGAAC TCCATGAAAA TGGGGAACCT CATTTGCATG CCCTCATTCA
121    GTTCGAGGGC AAGTACAATT GTACCAACCA ACGATTCTTC GACCTCATAT CCCCTTCCAG
181    GTCAATCGGA TCTGACCTGG AAGAGGATAT GAAGTCGAAG AATCATTAAT TAATACAATT
241    ATACTTACCC TCAAACTAAA TAAAAACATA CAAATAAAAT TCCCCCATTT TCATAAAATT
301    CTCTACAAAT CTTAATAAAC AATTTATTTA TTAAAATTTA AAATTATCAA AATTAATCTA
361    ATGCCACTTC TTTCGAGACT AGTC
```

Fig. 80 (SEQ ID NO:75)

```
SEQ  SACMV AC1_Hairpin sequence: 384 bp;
Composition  145  A;  88   C;  46   G;  105  T;  0 OTHER
Percentage:   38%  A;  23%  C;  12%  G;  27%  T;  0%OTHER Molecular Weight (kDa): ssDNA: 117.87    dsDNA: 236.7
ORIGIN
1    CTCGAAAGAA GCGGCATTAG ATCAACTCCG ACAACTCCAA ACCCCAACAA ATAAATTGTT
61   CATCAAGATC TGCAGAGAAC TCCATGAAAA TGGGGAACCT CATTTGCATG CCCTCATTCA
121  GTTCGAGGGC AAGTACAATT GTACCAACCA ACGATTCTTC GACCTCATAT CCCCTTCCAG
181  GTCAATCGGA TCTGACCTGG AAGAGGATAT GAAGTCGAAG AATCATTAAT TAATACAATT
241  ATACTTACCC TCAAACTAAA TAAAAACATA CAAATAAAAT TCCCCCATTT TCATAAAATT
301  CTCTACAAAT CTTAATAAAC AATTTATTTA TTAAAATTTA AAATTATCAA AATTAATCTA
361  ATGCCACTTC TTTCGAGACT AGTC
```

Fig. 81 (SEQ ID NO:76)

# USE OF DOUBLE STRANDED RNA HAIRPIN DUPLEXES IN GENE SILENCING

CROSS-REFERENCE TO RELATED APPLICATIONS

This application is the U.S. National Phase application of PCT International Application No. PCT/IB2008/050316, filed Jan. 29, 2008, and claims priority of South African Patent Application No. 2007/00815, filed Jan. 29, 2007, both of which are incorporated herein by reference.

BACKGROUND OF THE INVENTION

THIS INVENTION relates to gene silencing. More particularly the invention relates to use of double-stranded RNA hairpin duplexes in gene silencing.

Short hairpin RNAs (shRNAs) expressed from RNA Pol II and Pol III promoters can be used to silence target genes. shRNAs are expressed in the nucleus, and like microRNAs (miRNAs), are shuttled to the cytoplasm where the RNA interference (RNAi) machinery produces small interfering RNA (siRNAs). Typically, shRNAs include double stranded RNA (dsRNA) duplexes of up to 30 base pairs (bp) or nucleotides, which limits the number of functional siRNAs that can be generated from the hairpin precursor.

Long ds RNA hairpins (IhRNAs) and dsRNA duplexes can also be processed by the RNAi machinery into functional siRNAs. Typically, IhRNAs and dsRNA duplexes contain at least three DICER cleavage events and are therefore about 60 bp to 66 bp or longer.

Importantly, IhRNAs are capable of generating different siRNAs, and the number of different targeted siRNAs that are generated is directly proportional to the length of the dsRNA duplex (i.e. the IhRNA). Apart from targeting a greater genetic sequence, multiple siRNAs simultaneously target different sites, preventing the possible generation of mutant variants (i.e. for viral and cancer gene sequences) which may "escape" the targeted effects of siRNAs. Mutational escape is a phenomenon observed frequently for studies using shRNAs and siRNAs against viral targets and is not only limited to the target sequence but also to flanking sequences which affect local RNA secondary structures.

There are difficulties in cloning IdsRNA hairpins, however. Additionally, long dsRNA duplexes that are used in mammalian cells are known to activate the non-specific interferon response system in mammalian cells (e.g. PKR and Rnase L pathways). These difficulties in cloning and the immunostimulatory effect have limited the wide-spread application of long hairpins for gene silencing in mammalian and other cells. The major difficulties with long directly inverted repeats are the formation of cruciform junctions which cause genetic instability. This could lead to the rearrangement or splicing of the DNA constructs as the cell's recombination machinery can recognize cruciforms as Holliday junctions which are substrates for homologous recombination.

SUMMARY OF THE INVENTION

According to a first embodiment of the invention, there is provided a DNA polynucleotide comprising:
  a modified sequence of a target gene or a part thereof, wherein all or a substantial portion of any one type of nucleotide in the target gene sequence or the part thereof has been chemically modified to another type of nucleotide; and
  a complementary sequence of the unmodified target gene or the part thereof;
  wherein either one of the modified sequence or the complementary sequence is in a reverse orientation to the other sequence; and
  wherein the RNA sequence transcribed from the DNA polynucleotide forms a duplex between the modified sequence and the complementary sequence so that a long double stranded RNA (IdsRNA) duplex forms between the modified and complementary sequences with base pair mismatches where the nucleotides have been modified, the IdsRNA duplex being capable of inhibiting expression of the target gene.

The nucleotide modifications may be modifications of cytosine to thymine nucleotides, and the proportion of nucleotide modifications may be about one in every four to 10 nucleotides.

A further nucleotide sequence may be provided between the modified and complementary sequences, the further nucleotide sequence forming a hairpin loop in the RNA sequence between the modified and complementary sequences.

The target gene may be selected from the group consisting of metazoan, plant and viral genes. The metazoan genes may include mammalian, insect and nematode genes. In particular, the target gene may be a BC1 or AC1 gene from South African cassava mosaic virus (SACMV).

When the target gene is the SACMV BC1 gene, the modified sequence may comprise the nucleic acid sequence set forth in any one of SEQ ID NOs: 13, 16, 17 or 18, or a sequence which is at least 80% identical thereto; and the complementary fragment may comprise a nucleic acid sequence set forth in any one of SEC) ID NOs: 14, 15, 19 or 20, or a sequence which is at least 80% identical thereto. For example, the polynucleotide may include the sequence set forth in SEQ ID NO: 21.

When the target gene is the SACMV AC1 gene, the modified sequence may comprise the nucleic acid sequence set forth in any one of SEQ ID NOs: 33, 34, 35, 38, 39 or 40, or a sequence which is at least 80% identical thereto; and the complementary sequence may comprise a nucleic acid sequence set forth in any one of SEQ ID NOs: 36, 37, 41 or 42, or a sequence which is at least 80% identical thereto. For example, the polynucleotide may include the sequence set forth in SEQ ID NO: 53.

The modified and complementary sequences may each consist of more than 60 nucleotides.

The modified and complementary sequences may each consist of more than 80 nucleotides.

The modified and complementary sequences may each consist of more than 100 nucleotides.

Strand-specific amplification may be used to amplify the modified and complementary sequences, so as to ensure that the correct strand of the target gene is amplified.

According to a second embodiment of the invention, there is provided a RNA polynucleotide corresponding to the DNA polynucleotide described above.

The nucleotide modifications in the modified sequence may be cytosine to uracil modifications, and the base pair mismatches may be G:U mismatches.

The modified sequence may be set forth in any one of SEQ ID NOs: 22, 23, 24, 27, 28 or 29, or a sequence which is at least 80% identical thereto, and the complementary sequence may be set forth in any one of SEQ ID NOs: 25, 26, 30 or 31, or a sequence which is at least 80% identical thereto. For example, the RNA polynucleotide may comprise the sequence set forth in SEQ ID NO: 32.

The modified sequence may be set forth in any one of SEQ ID NOs: 43, 44, 45, 48, 49 or 50, or a sequence which is at least 80% identical thereto, and the complementary sequence may be set forth in any one of SEQ ID NOs: 46, 47, 51 or 52, or a sequence which is at least 80% identical thereto. For example, the RNA polynucleotide may comprise the sequence set forth in SEQ ID NO: 54.

According to a third embodiment of the invention, there is provided a long double stranded RNA (IdsRNA) duplex that inhibits the expression of a target gene, the IdsRNA duplex comprising:
- a modified sequence of the target gene or a part thereof, wherein all or a substantial portion of any one type of nucleotide in the target gene sequence or the part thereof has been chemically modified to another type of nucleotide; and
- a complementary sequence of the unmodified target gene or the part thereof;
- wherein the modified and complementary sequences form the IdsRNA duplex with base pair mismatches where the nucleotides have been modified.

The IdsRNA may be substantially as described above, or formed from a DNA or RNA polynucleotide described above.

According to a further embodiment of the invention, there is provided an expression cassette comprising the DNA polynucleotide described above.

The expression cassette may include either an RNA Pol II or an RNA Pol III promoter. The expression cassette may also include a termination signal which is an RNA Pol II or RNA Pol III termination signal.

According to a further embodiment of the invention, there is provided a nucleic acid vector which includes an expression cassette described above.

According to a further embodiment of the invention, there is provided a method of constructing a construct encoding a IdsRNA duplex, the method including:
(i) PCR isolating a coding fragment of a target gene to obtain an untreated PCR product;
(ii) treating at least a fraction of the untreated PCR product with a chemical mutagen, thereby causing chemical mutation of nucleotides of one type to nucleotides of another type so as to obtain a treated PCR product;
(iii) conducting PCR on the treated PCR product to produce a nucleotide sequence with a proportion of mismatched nucleotides compared with the untreated PCR product;
(iv) conducting PCR on the untreated PCR product; and
(v) arranging the treated PCR product from (iii) encoding a sense strand and the untreated PCR product from (iv) encoding an anti-sense strand so that the treated PCR product and untreated PCR product are in a reverse orientation relative to each other.

There may be an intervening loop-encoding sequence between the treated PCR product and untreated PCR product. The intervening hairpin loop-encoding sequence may include at least one restriction site.

The PCR isolation may be by strand-specific PCR.

The method may further including the step of cloning the construct encoding the IdsRNA duplex.

Step (ii) may include subjecting the untreated PCR product to a bisulphite chemical mutagen, typically causing chemical mutation of unmethylated cytosines to thymines and producing a nucleotide sequence with cytosine to uracil mutations in step (iii).

According to a further embodiment of the invention, there is provided a method of silencing a target gene in a metazoan or plant subject, the method including the steps of:

introducing an expression cassette including the DNA polynucleotide described above into the subject; and
causing the expression cassette to express a RNA sequence or a IdsRNA duplex described above, thereby silencing said target gene.

The DNA or RNA polynucleotide or the IdsRNA described above may be used for silencing a target gene.

The DNA or RNA polynucleotide described above may also be used in a method of manufacturing a composition for use in a method of silencing a target gene in a metazoan or plant subject.

BRIEF DESCRIPTION OF THE DRAWINGS

The invention will now be described in more detail, by way of example only, with reference to the accompanying drawings in which:

FIG. 8A shows a 1.5% Agarose gel electrophoresis of BC1 untreated clones. Lane1: O'Generuler 1 Kb Ladder Plus (Fermentas). Lane 3-8: Clones E26 to E21 Hinc II digestion to screen for orientation. Lanes 10-15: Clones E26 to E21 EcoRI and PstI digestion to screen for inserts.

FIG. 8B shows a 1.5% Agarose gel electrophoresis of an MSV AC1 untreated clone. Lane 1: O'Generuler 1 Kb Ladder Plus (Fermentas). Lane 3: Clone G3 EcoRI and XhoI digestion to screen for orientation.

FIG. 8C shows a 1.5% Agarose gel electrophoresis of a pTZ-SACMV AC1 untreated clone. Lane 1: O'Generuler 1 Kb Ladder Plus (Fermentas). Lane2: Clone EcoRI and BgIII digestion to screen for orientation.

FIG. 9A shows a 1% Agarose gel electrophoresis of Clones B4 and E22 digestion. Lane1: O'Generuler 1 Kb Ladder Plus (Fermentas). Lanes 3-4: Clone B4 (BC1 treated with sodium bisulfite) digestion with ScaI and BgIII. Lane 6-7: Clone E22 (BC1 untreated) digestion with ScaI and BamHI.

FIG. 9B shows a 1% Agarose gel electrophoresis of Clones F3 and G3 digestion. Lane1: O'Generuler 1 Kb Ladder Plus (Fermentas). Lanes 3-4: Clone G3 (MSV AC1 untreated) digestion with ScaI and BamHI. Lane 6-7: Clone E22 (MSV AC1 treated with sodium bisulfite) digestion with ScaI and BgIII.

FIG. 9C shows a 1% Agarose gel electrophoresis of pTZ-SACMV AC1 clone. Lane1 & 3: O'Generuler 1 Kb Ladder Plus (Fermentas). Lane 2: AC1 treated clone digestion with ScaI and BgIII. Lane 4: AC1 untreated clone digestion with ScaI and BamHI.

FIG. 10A shows a 1% Agarose gel electrophoresis of BC1 hp clones. Lane1: O'Generuler 1 Kb Ladder Plus (Fermentas). Lanes 3-7: BC1 hp clones 8-4 cut with XhoI and XbaI.

FIG. 10B shows a 1% Agarose gel electrophoresis of MSV AC1 hp clones. Lane1: O'Generuler 1 Kb Ladder Plus (Fermentas). Lanes 3-7: MSV hp clones 1-6 cut with XbaI and SalI.

FIG. 10C shows a 1% Agarose gel electrophoresis of pTZ-SACMV AC1 hp clone. Lane1: O'Generuler 1 Kb Ladder Plus (Fermentas). Lanes 2 pTZ-SACMV AC1 hp clone cut with Pst1.

FIG. 12 shows the BC1 ORF sequence and the MSV AC1 ORF sequence with targeted area underlined.

FIG. 13 shows a SACMV AC1 sequence with target area indicated.

FIG. 16 shows SACMV BC1 target gene sequence.

FIG. 17 shows SACMV BC1 target gene region only.

FIG. 18 shows SACMV BC1 modified target gene region (i.e. a C to G modification)

FIG. 19 shows the complement of SACMV BC1 target gene sequence.

FIG. 20 shows complement of SACMV BC1 target gene region only.

FIG. 21 shows SACMV BC1 target gene sequence in reverse.

FIG. 22 shows SACMV BC1 target gene region in reverse.

FIG. 23 shows the modified target region of the SACMV BC1 gene in reverse.

FIG. 24 shows the reverse complement of the target gene sequence of the SACMV BC1 gene.

FIG. 25 shows the reverse complement of the target gene region of the SACMV BC1 gene.

FIG. 26 shows the SACMV BC1 hairpin sequence.

FIG. 27 shows the RNA sequence of the SACMV BC1 target gene.

FIG. 28 shows the RNA sequence of the SACMV BC1 target gene region.

FIG. 29 shows the RNA sequence of the modified SACMV BC1 target gene region.

FIG. 30 shows the RNA sequence of the complementary SACMV BC1 target gene.

FIG. 31 shows the RNA sequence of the complementary SACMV BC1 target region.

FIG. 32 shows the RNA sequence of the SACMV BC1 target gene in reverse.

FIG. 33 shows the RNA sequence of the SACMV BC1 target region in reverse.

FIG. 34 shows the RNA sequence of the modified SACMV BC1 target region in reverse.

FIG. 35 shows the RNA sequence of the reverse complement of the SACMV BC1 target gene.

FIG. 36 shows the RNA sequence of the reverse complement of the SACMV BC1 target gene region.

FIG. 37 shows the RNA sequence of the SACMV BC1 hairpin.

FIG. 38 shows SACMV AC1 target gene sequence.

FIG. 39 shows SACMV AC1 target gene region only.

FIG. 40 shows SACMV AC1 modified target gene region (i.e. a C to G modification)

FIG. 41 shows the complement of SACMV AC1 target gene sequence.

FIG. 42 shows complement of SACMV AC1 target gene region only.

FIG. 43 shows SACMV AC1 target gene sequence in reverse.

FIG. 44 shows SACMV AC1 target gene region in reverse.

FIG. 45 shows the modified target region of the SACMV AC1 gene in reverse.

FIG. 46 shows the reverse complement of the target gene sequence of the SACMV AC1 gene.

FIG. 47 shows the reverse complement of the target gene region of the SACMV AC1 gene.

FIG. 48 shows the RNA sequence of the SACMV AC1 target gene.

FIG. 49 shows the RNA sequence of the SACMV AC1 target gene region.

FIG. 50 shows the RNA sequence of the modified SACMV AC1 target gene region.

FIG. 51 shows the RNA sequence of the complementary SACMV AC1 target gene.

FIG. 52 shows the RNA sequence of the complementary SACMV AC1 target region.

FIG. 53 shows the RNA sequence of the SACMV AC1 target gene in reverse.

FIG. 54 shows the RNA sequence of the SACMV AC1 target region in reverse.

FIG. 55 shows the RNA sequence of the modified SACMV AC1 target region in reverse.

FIG. 56 shows the RNA sequence of the reverse complement of the SACMV AC1 target gene.

FIG. 57 shows the RNA sequence of the reverse complement of the SACMV AC1 target gene region.

FIG. 58 shows MSV AC1 target gene sequence.

FIG. 59 shows MSV AC1 target gene region only.

FIG. 60 shows MSV AC1 modified target gene region (i.e. a C to G modification)

FIG. 61 shows the complement of MSV AC1 target gene sequence.

FIG. 62 shows complement of MSV AC1 target gene region only.

FIG. 63 shows MSV AC1 target gene sequence in reverse.

FIG. 64 shows MSV AC1 target gene region in reverse.

FIG. 65 shows the modified target region of the MSV AC1 gene in reverse.

FIG. 66 shows the reverse complement of the target gene sequence of the MSV AC1 gene.

FIG. 67 shows the reverse complement of the target gene region of the MSV AC1 gene.

FIG. 68 shows the MSV AC1 hairpin sequence.

FIG. 69 shows the RNA sequence of the MSV AC1 target gene.

FIG. 70 shows the RNA sequence of the MSV AC1 target gene region.

FIG. 71 shows the RNA sequence of the modified MSV AC1 target gene region.

FIG. 72 shows the RNA sequence of the complementary MSV AC1 target gene.

FIG. 73 shows the RNA sequence of the complementary MSV AC1 target region.

FIG. 74 shows the RNA sequence of the MSV AC1 target gene in reverse.

FIG. 75 shows the RNA sequence of the MSV AC1 target region in reverse.

FIG. 76 shows the RNA sequence of the modified MSV AC1 target region in reverse.

FIG. 77 shows the RNA sequence of the reverse complement of the MSV AC1 target gene.

FIG. 78 shows the RNA sequence of the reverse complement of the MSV AC1 target gene region.

FIG. 79 shows the RNA sequence of the MSV AC1 hairpin.

FIG. 80 shows the SACMV AC1 hairpin sequence.

FIG. 81 shows the RNA sequence of the SACMV AC1 hairpin.

DETAILED DESCRIPTION OF THE INVENTION

Figure 1:
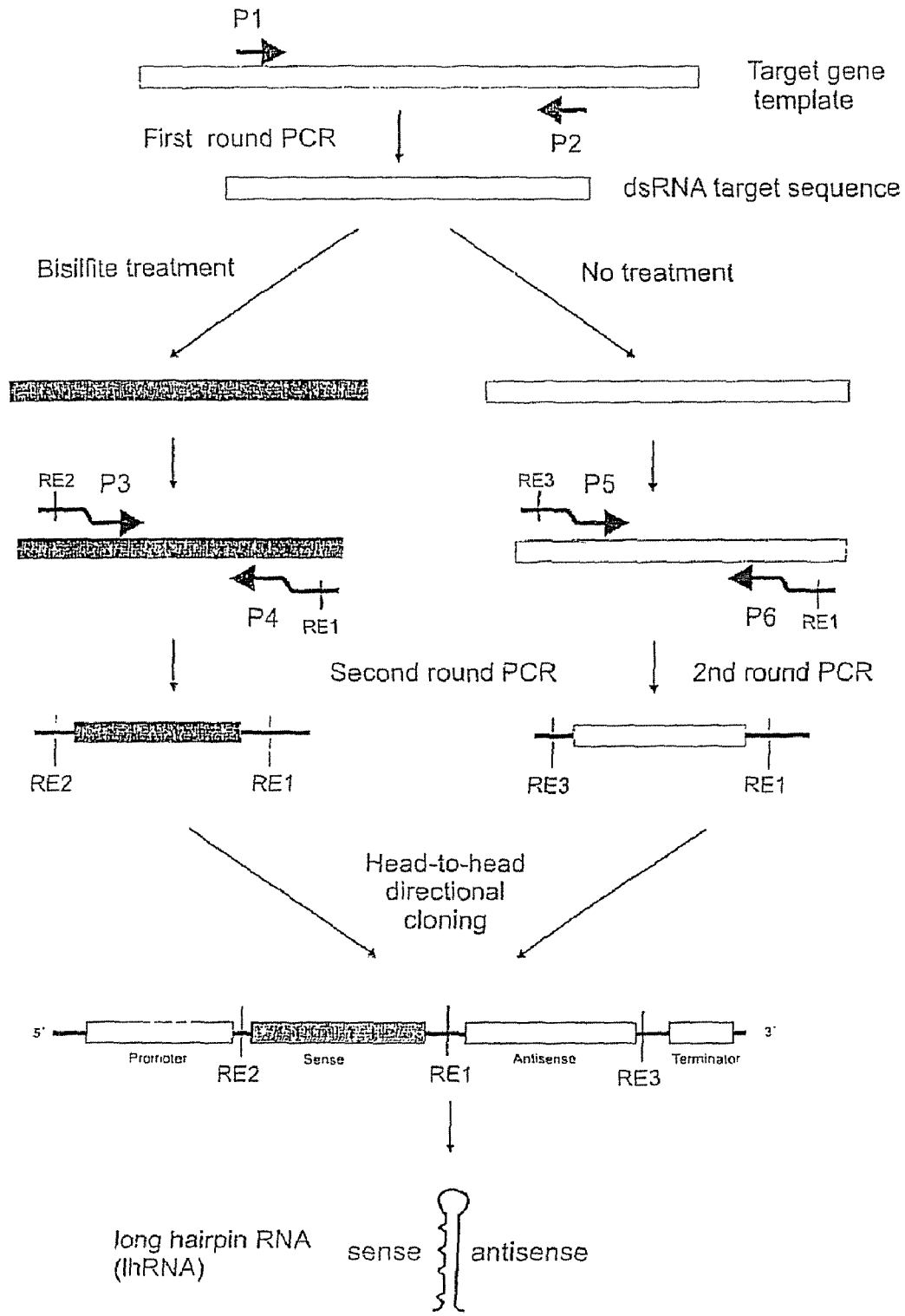
FIG. 1 is a schematic illustration of the procedure for generation of long-hairpin RNAs (IhRNAs) that contain sense sequence changes to produce G:U mismatches in the dsRNA duplex. PCR primers are indicated as P1-P6 and the restriction enzyme digestion sites are shown as RE1-RE3.

Long double stranded RNA (IdsRNA) duplexes having mismatched base pairs are described herein.

Although IdsRNA duplexes are known, there currently exists a limitation to the ability to produce direct inverted repeats. Current technologies, such as intron-spliced hairpin constructs, are used as these are more stable than inverted repeats, but may be less effective. DNA cassettes for the expression of hairpin RNA of a length between 20 bp and 65 bp have included the use of synthetic oligonucleotides to make up the DNA cassette. However, this approach severely limits the size of the expressed long hairpin RNA that can be generated.

An alternative approach of generating IhRNAs by PCR of the desired target fragments and then cloning is hampered by the complementarity of the PCR amplified nucleotide sequences making up the stem of the RNA hairpin which result in cruciform structures that are difficult to clone. One method of preventing the formation of these structures is the use of long intron loops between the stem nucleotide sequences which are spliced out of the RNA transcript after transcription, leaving the dsRNA duplex.

The method of the present invention provides for the use of PCR amplified nucleotide sequences making up the stem of the RNA hairpin that contain mismatched bases, on average every 4 to 6 or 10 base pairs, although this will depend on the C:T content of the DNA and the duration and condition under which the DNA is chemically treated. The mismatched bases are generally introduced in the sense strand, ensuring that the formation of cruciform structures are less favorable, but leaving the anti-sense strand with sequence identity to the target sequence, thereby ensuring that RNAi inhibition of expression of the target gene can occur.

The IdsRNA duplexes of the present invention may be used in mammalian cells without stimulation of the non-specific interferon response.

The mismatched bases in the IdsRNA duplex are typically G:U mismatches, although any non-Watson-Crick pairing including wobble (i.e. where the mismatched base pairing is less stable than that of conventional A:U or G:C bonding), such as purine-purine or pyramidine-pyramidine base pairs may also be used. The mismatches result from the modification or substitution of some of the nucleotides in the IdsRNA duplex, such as by modifying a cytosine to uracil (GU base pairs are seemingly more stable than UG base pairs. The stability of UG base pairs is the same as the stability of AU/UA base pairs. GU base pairs are more stable than GC/CG basepairs). It is important to note that these pairings are all possible, but will just cause a greater distortion of the RNA hairpin structure due their varying stabilities. (Giese, M. R., Betschart, K., Dale, T., Riley, C. K., Rowan, C., Sprouse, K. J., Serra, M. J. 1998. *Stability of RNA Hairpins Closed by Wobble Base Pairs. Biochemistry* 37: 1094-1100). In the specific examples below, the mismatched bases in the IdsRNA duplex are produced by chemical mutation of the PCR amplified sense strand of the IdsRNA duplex with sodium bisulphite, although other methods of nucleic acid modification to generate mismatched bases known to those skilled in the art may also be used. Sodium bisulphite modifies unmethylated cytosines to thymines so that upon transcription, the mismatched nucleotide sequence includes cytosine to uracil mutations. It is also possible to completely synthesize a nucleotide fragment expressing the IdsRNA duplex such that there are mismatched bases in the sense strand.

C to T mutations were optimized for maximum stability and not G to As, using strand specific PCR primers.

The target gene may be selected from any organism. In addition, the IdsRNA duplexes may be used to silence genes from pathogens infecting these organisms, such as bacteria and viruses. For example, siRNAs have been used in the inhibition of genes from a number of pathogens, including human immunodeficiency virus (HIV), hepatitus virus C (HCV), hepatitus B virus (HBV) and influenza virus. In addition, siRNAs have been tested for inhibition of oncogenes in cancer treatment as well as against transposable elements, rogue elements and contagious genes.

Transgenic plants may be produced to express IdsRNA duplexes that inhibit expression of pathogen genes thereby generating a plant resistant to that pathogen, for example by targeting genes from cassava mosaic virus (e.g. BC1) or maize streak virus (e.g. AC1). The plant may also be capable of generating transgenic progeny that will be resistant to the pathogen. It is also possible to engineer tissue-specific expression, such as in the leaves of the plant, so that the dsRNA duplex is only expressed locally. Silencing constructs can also be expressed transiently.

Knock-out of genes in various organisms by IdsRNA may produce novel phenotypes that may be used commercially or for scientific research.

The target genes should be selected so that they do not have sequence identity to host genes that are not required to be silenced. Although the whole gene may be selected, it is also possible to use only a part of the target gene for generating dsRNA duplexes, such as a region of the target gene that is conserved between different strains or variants of the organism to be targeted, thereby limiting the effect of mutational escape from siRNA. It is not required that there be 100% sequence identity with the target sequence for the anti-sense strand of the dsRNA duplex to generate siRNAs that function. Typically, sequences with about 95%, about 90% or even about 80% sequence identity will be sufficient for the generated siRNAs to bind to and initiate silencing of the target sequence. The dsRNA duplex must be generated from an open reading frame, preferably an exon. In the specific examples below, the target region was selected on the basis of these preferred requirements.

The ability to generate multiple siRNAs from a single IdsRNA duplex provides for the possibility of simultaneously targeting different sites, preventing the possible generation of mutant variants (i.e. for viral and cancer gene sequences) which may "escape" the targeted effects of siRNAs.

The length of the nucleotide fragments making up the stem of the IdsRNA duplex can be from 60 nucleotides, and more preferably from 80 nucleotides or greater than 100 nucleotides, and may even be as large as it is possible to PCR amplify a nucleotide fragment. Currently, the typical maximum size is approximately 9 000 bp in length, although as the technology for PCR amplification improves this may increase in length. In addition, although it is currently prohibitively expensive to completely synthesize nucleotides that can be cloned to express IdsRNA duplexes, the cost of DNA synthesis is reducing and it is possible that this method may be used as an alternative to PCR amplification of the target gene fragments.

Although in the specific examples, there is a loop-encoding sequence between the nucleotide fragments making up the head-to-head construct of from 6 bp to 10 bp, the length of the loop sequence is not material to the transcription of or function of the IdsRNA duplex. As has been indicated above, the loop sequence may be over 1000 bp, such as in the case of intron, but it is also possible that no loop sequence is included, or that the loop sequence does not include an intron (e.g. it may include one or more restriction sites). Where a RNA transcript comprising complementary nucleotide fragments that can form a stem is expressed without a loop sequence included, a four-base loop would typically naturally form.

The specific examples provide for PCR amplification of a selected part of the target gene, followed by treatment of a portion of the PCR product generated with bisulphite to yield the modified PCR product with base pair mismatches compared with the unmodified product. These modified and unmodified fragments are then cloned into a standard commercially available vector, such that the fragments are arranged head-to-head or tail-to-tail with either the 3' or 5' ends, respectively, of the fragments oriented towards each other, with an intervening loop-encoding sequence. The cloned head-to-head construct can then be amplified by typical plasmid amplification. It is also possible to clone these products into alternative vectors known to those skilled in the art, such as cosmids or bacteriophage vectors.

It is possible to also isolate and mutate these fragments from restriction digest and not amplify.

The vector into which the head-to-head arrangement is cloned contains a promoter and a terminator sequence operably linked to the head-to-head arrangement in the specific examples, thereby forming an expression cassette for transcribing the IdsRNA duplex in the host cell.

The 35S CaMV promoter, which is a Pol II promoter, and is the most widely used promoter in plant transformation studies was used for the plants in this study. It has been shown that the 35S CaMV promoter works better in dicotyledonous plants than it does in monocotyledonous plants. An example of another Pol II promoter used in plant transformation is the rice ubiquitin promoter, which gives better expression in monocot plants (Wang, J., Oard, J. H., Rice ubiquitin promoters: deletion analysis and potential usefulness in plant transformation systems. Plant Cell Reports 22: 129-234). The terminator used in this study is the octopine synthase (OCS) terminator. Unfortunately, the actual terminator elements are poorly characterized and understood at this time, so the entire OCS gene is used to ensure proper termination and processing. Pol III promoters and terminators have also been used for the expression of artificial miRNAs in plants (Qu, J., Ye, J., Fang, R. 2007. *Artificial MicroRNA-mediated virus resistance in plants. Journal of Virology* 81: 6690-6699). Alternative promoters known to those skilled in the art for expression of RNA transcripts may also be used. The vector may also include further elements for selection, such as antibiotic resistance genes (e.g. kanamycin) or blue-white screening (e.g. β-galactosidase gene).

Once the expression cassettes encoding the IdsRNA duplex according to the invention have been generated, they may be introduced into the subject selected for silencing of the target gene of interest. As indicated above, the subject may be any organism or organism part in which the RNAi process functions to silence target gene expression.

The expression cassette may be introduced into the subject by varying methods of introduction known to a person skilled in the art, depending on the organism to be treated. For example, in plants the expression cassette may be introduced into the plant with the use of *Agrobacterium* transformed with a plasmid expressing the IdsRNA duplex, or plasmids expressing the IdsRNA duplex may be coated onto gold particles and bombarded into parts of the plant such as the leaves. These may then be propagated into new plants from leaf calluses, or expression of the IdsRNA may be allowed to occur in situ in the leaves.

In animal cells, the expression cassettes may be transformed into cells in tissue culture allowing expression of the IdsRNA transcript, or they may be introduced in vivo into animals or specific organs of the animal. There are many known methods for introduction of expression vectors into animal cells in tissue culture (e.g. $CaCl_2$ transfection and liposome transfection) as well as into animals (e.g. plasmid-coated gold particle bombardment, air gun immunisation or injection) and these may all be used for introduction of the expression cassette expressing the IdsRNA duplex.

The expression cassette, once introduced into the host cell, then provides for transcription of the IdsRNA duplex which is processed by the cells' RNAi machinery into multiple siRNAs that target and silence the target gene. In the case of the specific examples, the siRNAs generated are targeted to the cassava mosaic virus BC1 gene, or to the maize streak virus AC1 gene inhibiting expression.

The present invention is further described by the following examples. Such examples, however, are not to be construed as limiting in any way either the spirit or scope of the invention.

EXAMPLES

Figure 2:
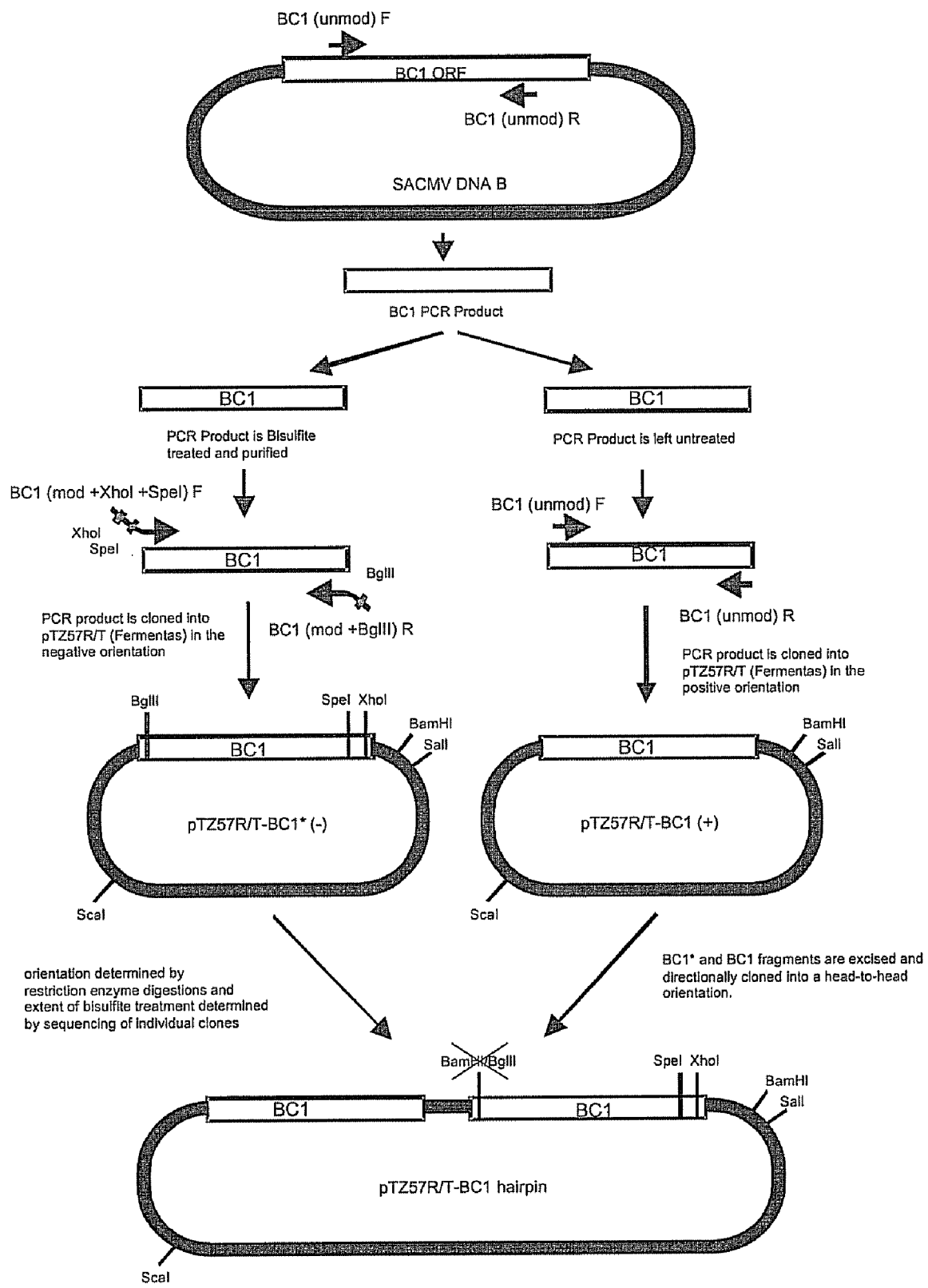
FIG. 2 shows a workflow and methodology for the construction of a head-to-head cassette for the BC1 gene of SACMV. This methodology was applied for the construction of a head-to-head cassette for the AC1 gene of SACMV. Variations in restriction enzyme sites apply.

The methodology herein describes the cloning of a specific region of the BC1 ORF of SACMV and a specific region of the AC1 ORF of MSV such that the identical fragments are cloned adjacent to each other in a head-to-head orientation (see FIG. 1). The cloning is facilitated by treating one of the fragments with sodium bisulfite prior to re-amplification and sub-cloning in a head-to-head orientation to express a IdsRNA duplex. The IdsRNA duplex is capable of being recognized by plant RNAi pathways to ensure the respective knockdown of SACMV (see FIG. 2) and MSV in infected plants.

Example 1

1.1 South African Cassava Mosaic Virus (SACMV) Targeting

Figure 3:
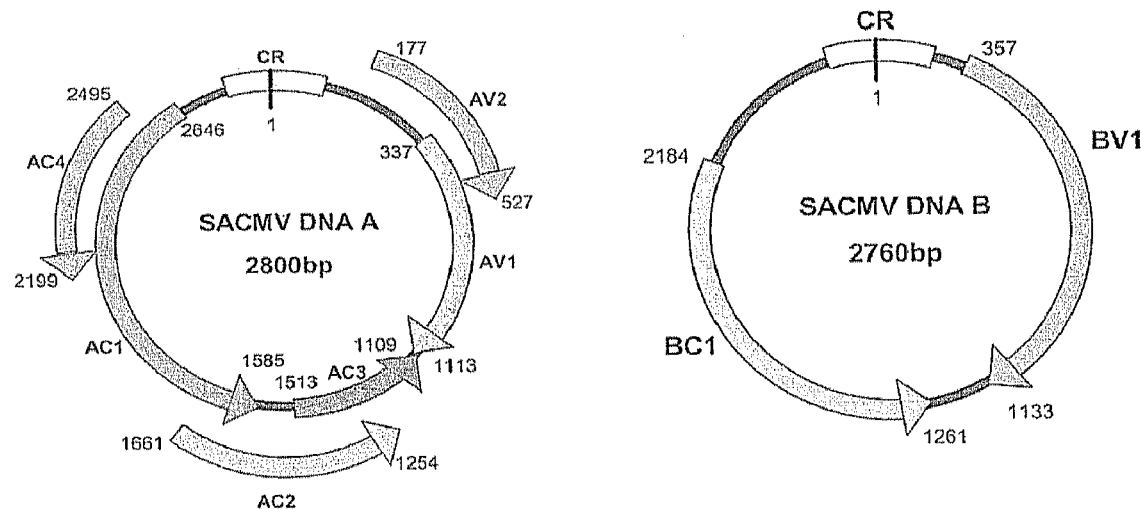
FIG. 3 shows the SACMV DNA A and SACMV DNA B genomes.

PCR primers were designed to amplify a 222 bp region of the BC1 ORF (SEQ ID NO: 1) on the South African Cassava mosaic virus DNA B component (FIGS. 3 and 12). BC1 codes for a long distance movement protein that allows an SACMV infection to spread systemically through a plant.

1.2 Maize Streak Virus (MSV) Targeting

Figure 4:
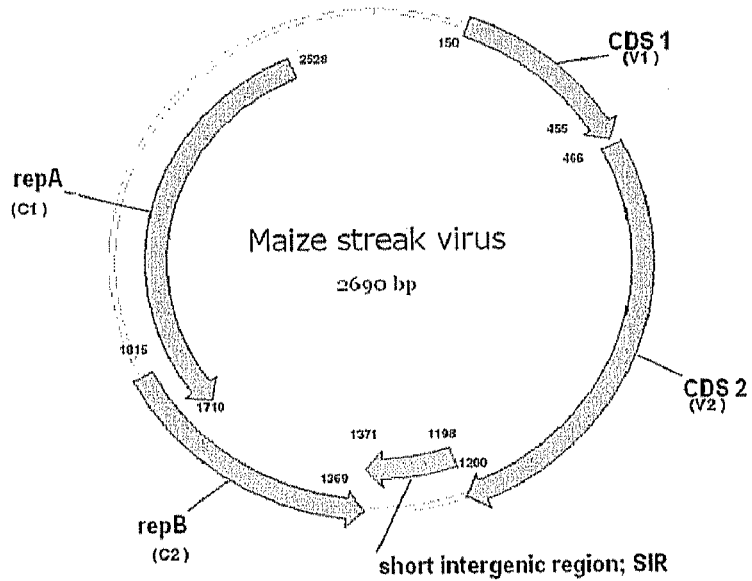
FIG. 4 shows the MSV genome.

PCR primers were designed to amplify a 246 bp region of MSV replication associated protein A (MSV AC1) (SEQ ID NO: 2) (FIGS. 4 and 12). This protein is required for the replication of MSV.

Example 2

2.1 PCR Amplification of Target Sequences

Figure 5A:
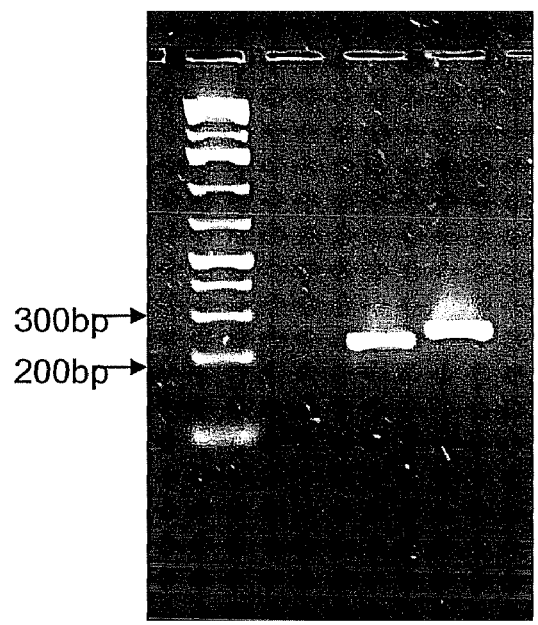
FIG. 5A shows a 1.2% Agarose gel electrophoresis of BC1 and MSV AC1 PCR products. Lane1: O'Generuler 1 Kb Ladder Plus (Fermentas). Lane 3: BC1 PCR Product. Lane 4: MSV AC1 PCR product.
Figure 5B:
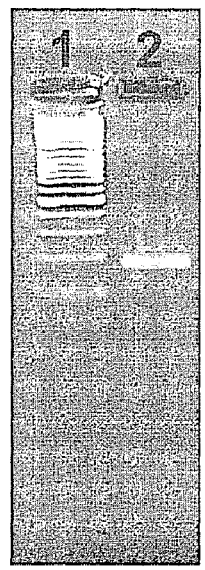
FIG. 5B shows a 1.2% Agarose gel electrophoresis of SACMV AC1 PCR product. Lane1: O'Generuler 1 Kb Ladder Plus (Fermentas). Lane 2: SACMV AC1 PCR Product.

For the amplification of BC1, 400 nmol of the PCR primers BC1 F (unmod) 5' AAACATTCCACGGACATACG 3' (SEQ ID NO: 3) and BC1 R (unmod) 5' TGGTAGCCCAATCT-GAGACCTT 3' (SEQ ID NO: 4) were used with 15.4 ng of SACMV DNA-B template DNA. For the amplification of MSV AC1, 400 nmol of the PCR primers MSV AC1 F (Unmod) 5' AGAGCTCCCCTTTGATTGG 3' (SEQ ID NO: 5) and MSV AC1 R (Unmod) 5' TCCATCCATTGGAGGTCA-GAAAT 3' (SEQ ID NO: 6) were used with 23.28 ng of MSV template DNA. The Triplemaster High Fidelity PCR system (Eppendorf) was used with standard Taq DNA polymerase according to manufacturers recommendations. Reactions were cycled in an Eppendorf thermal cycler at 95° C. for 2 minutes, followed by 30 cycles of 95° C. for 15 seconds, 52° C. for 15 seconds and 72° C. for 15 seconds. A final extension step of 72° C. for 20 minutes was done to allow for the addition of 3' A overhangs to the PCR product. PCR products of the expected sizes were produced (FIG. 5). PCR products were purified using a High Pure PCR Product Purification kit (Roche).

2.2 Modification of PCR Products with Sodium Bisulfite

Depurination of cytosine residues in the PCR products was achieved by applying sodium bisulfite treatment in the EZ DNA Methylation-Gold kit (Zymo Research) to 120 ng BC1, and 360 ng MSV AC1 PCR products respectively. Reactions were set up according to the manufacturers recommendations. Samples were placed in a thermal cycler for 10 minutes at 98° C. to denature dsDNA, and were then methylated at 64° C. BC1 PCR products were depurinated at 4 different time points: 5 minutes, 10 minutes, 15 minutes, and 2.5 hours. MSV AC1 PCR products were methylated for 2.5 hours only, as was recommended by the manufacturer.

2.3 PCR Amplification of Sodium Bisulfite-Treated and Untreated DNA Templates

Sodium bisulfite treated BC1 fragments were amplified using original oligonucleotide primers BC1 F (unmod) and BC1 R (unmod), as well as a second set of modified primers: BC1 F (mod−XhoI+SpeI) 5'GATCCTCGAGACTAG-TAAATATTCTACGGACATACG 3' (SEQ ID NO: 7) and BC1 R (mod−BglII) 5' GATCAGATCTTAGTAGC-CCAATCTAAGACCTTGT 3' (SEQ ID NO: 8). These primers were designed to preferentially bind to the positive strand of the modified DNA template, as well as facilitating future directional cloning steps by introducing restriction endonuclease sites at both the 3' and 5' ends of the PCR product.

Sodium Bisulfite treated MSV AC1 fragments were similarly amplified using the original primers MSV AC1 F (Unmod) and MSV AC1 R (Unmod), as well as a modified primer set: MSV AC1 F (Mod+SpeI) 5' GATCACTAGTAGAGTTCTCC TTTGATTGG 3' (SEQ ID NO: 9) and MSV AC1 R (Mod+ BglIII+BclI) 5' CTAGAGATCTTGATCATCCATCCATTA-GAGATCAGAAAT 3' (SEQ ID NO: 10). PCR amplification was done as described in 2.1.

Figure 6A:
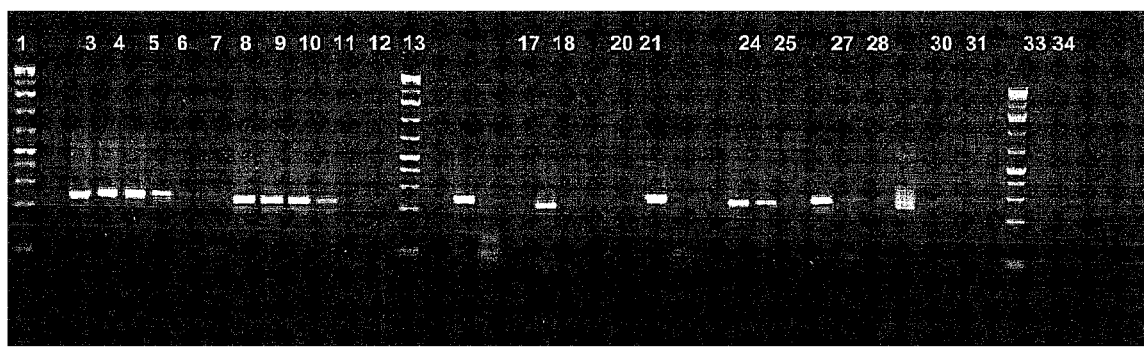
FIG. 6A shows a 1.2% Agarose gel electrophoresis of sodium bisulfite-treated and untreated BC1 and MSV AC1 fragments. Lane1: O'Generuler 1 Kb Ladder Plus (Fermentas). Lane 3: BC1 treated, 5 min, with modified BC1 primers. Lane 4: BC1 Treated 10 min, with modified BC1 primers. Lane 5: BC1 Treated 15 min, with modified BC1 primers. Lane 6: BC1 treated 2.5 hours, with modified BC1 primers. Lanes 7-8: $H_2O$ controls. Lane 9: BC1 treated, 5 min, with unmodified BC1 primers. Lane 10: BC1 Treated 10 min, with unmodified BC1 primers. Lane 11: BC1 Treated 15 min, with unmodified BC1 primers. Lane 12: BC1 treated 2.5 hours, with unmodified BC1 primers. Lane 13: $H_2O$ controls. Lane 17: BC1 untreated, with modified primers. Lane 18: $H_2O$ control. Lane 20: BC1 untreated, with unmodified primers. Lane 21: $H_2O$ control. Lane 24: MSV AC1 treated 2.5 hours, with modified primers. Lane 25: $H_2O$ control. Lane 27: MSV AC1 treated 2.5 hours, with unmodified primers. Lane 28: $H_2O$ control. Lane 30: MSV AC1 untreated, with modified primers. Lane 31: $H_2O$ control. Lane 33: MSV AC1 untreated, with unmodified primers. Lane 34: $H_2O$ control.
Figure 6B:
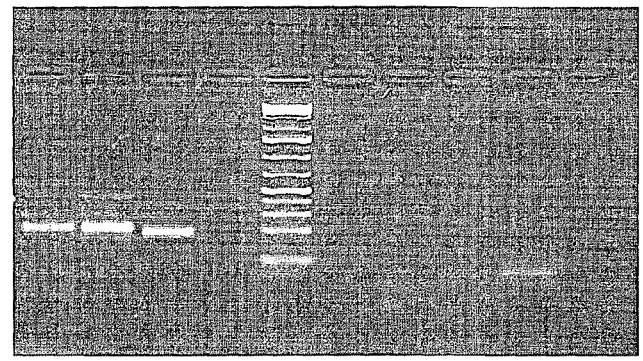
FIG. 6B shows a 1.2% Agarose gel electrophoresis of sodium bisulfite-treated and untreated SACMV AC1 fragments. Lane 1: AC1 treated 2.5 hours, with modified AC1 primers. Lane 2: AC1 untreated, with modified AC1 primers. Lane 3: AC1 treated 2.5 hours, with unmodified AC1 primers. Lane 4: O'Generuler 1 Kb Ladder Plus (Fermentas). Lane 5: $H_2O$ control with modified AC1 primers. Lane 6: $H_2O$ control with unmodified AC1 primers.

It was observed that the modified primers as well as the original primers were able to efficiently amplify both the sodium bisulfite treated and untreated BC1 and MSV AC1 fragments (FIG. 6).

Example 3

3.1 Cloning of PCR Products

The treated PCR products were purified using a High Pure PCR Product Purification kit (Roche), and cloned into pTZ57R (Fermentas) using the InsT/A Clone PCR product cloning kit (Fermentas). Reactions were set up as recommended by the manufacturer; 39.96 ng (+/−0.54 pmol ends) of the BC1 PCR product (sodium bisulfite treated and untreated, respectively) was added to 165 ng linear pTZ57R (0.54 pmol ends), and 44.28 ng (+/−0.54 pmol ends) of the MSV AC1 PCR product (sodium bisulfite treated and untreated, respectively) was added to 165 ng linear pTZ57R (0.54 pmol ends). The ligation mixes were incubated at 22° C. for a minimum of 1 hour, after which they were used to transform competent DH5a cells. The competent cells were initially stored at −70° C., and were thawed on ice. Following this, 15 μl of the ligation mix was added to 50 μl of competent cells and incubated on ice for 20 minutes.

Cells were then heat shocked by placing them at 42° C. for 90 seconds, and then placing them on ice 2 minutes. The transformed cells were then spread plated onto LB agar plates containing 100 μg/ml Ampicillin, as well as X-Gal and IPTG for blue/white screening. Plates were incubated at 37° C. overnight, after which white colonies were selected and inoculated into 3 ml LB broth containing 100 μg/ml Ampicillin. After incubating this at 37° C. overnight, alkaline lysis DNA minipreps were done using a High Pure Plasmid Miniprep kit (Roche).

3.2 Screening of Clones

Restriction analysis was done on presumptive BC1 and MSV AC1 treated and untreated clones to screen for inserts and orientation. The BC1 (bisulfite treated) clones were screened using EcoRI and XhoI, whereas the untreated clones were screened by digestion with HincII. The MSV AC1 (bisulfite treated) clones were screened using EcoRI and BglII, whereas the untreated clones were screened by digestion with EcoRI and XhoI.

Figure 7:
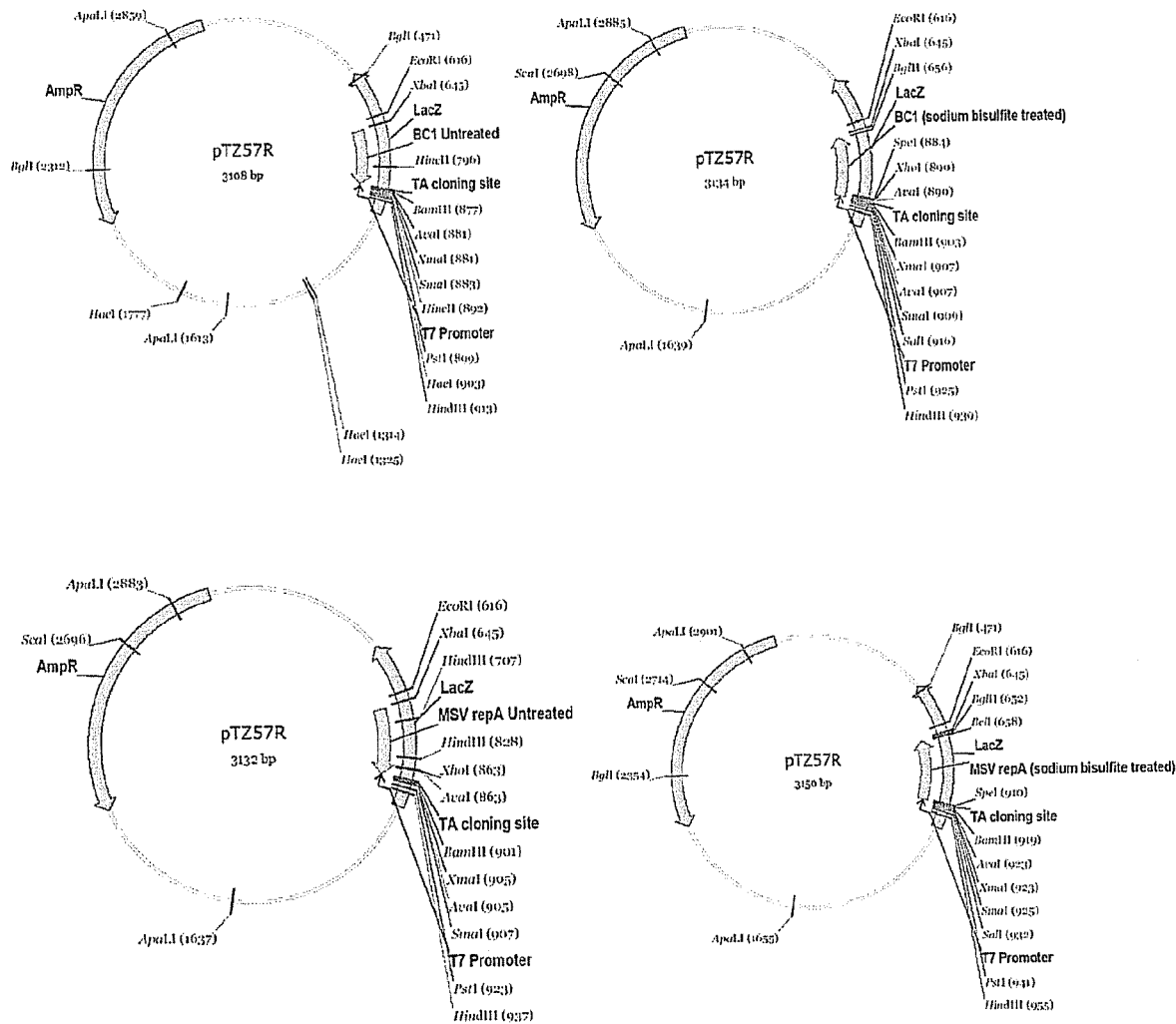
FIG. 7 shows a pTZ57R plasmid containing either BC1 or MSV AC1 inserts in the required orientations. This diagram was used as a basis for orientation screening.

Bisulfite treated clones that were presumptively in the right orientation were sequenced, and untreated clones were digested again to confirm orientation. FIG. 7 illustrates pTZ57R containing inserts in the right orientation.

3.2.1 BC1 and MSV AC1 Bisulfite Treated Clones—Sequencing

No correlation was found between incubation time and methylation of Cs, and the BC1 samples appeared to have been methylated to the maximum extent after 5 minutes. Clone A1 has an insert in the wrong orientation, and cannot be used. Clone D1 has guanine to adenine changes, which was caused by the PCR primers randomly amplifying the negative strand of the template DNA during the first round of PCR, thereby selecting the wrong strand. Methylation appears to be a random process, as a multiple alignment of clones A1, B4, C3 showed no distinct pattern of residues that had been changed.

Clone B4 was selected to be used in the construction of the BC1 hairpin, as it had a sufficient number of depurinations.

3.2.2 BC1 and MSV rep A Untreated Clones—Further Screening

TABLE 1

Sequencing results

| Clone name | Description | Cytosine to Thymine changes* | Guanine to Adenine changes | Correct Orientation |
|---|---|---|---|---|
| A1 | BC1 treated 5 min | 42 | 0 | N |
| B4 | BC1 treated 10 min | 39 | 0 | Y |
| C3 | BC1 treated 15 min | 39 | 0 | Y |
| D1 | BC1 treated 2.5 h | 0 | 7 | Y |
| F3 | MSV AC1 treated 2.5 h | 58 | 0 | Y |

*There are a total of 70 cytosine residues in the BC1 fragment

Numerous BC1 and MSV AC1 clones were screened for orientation by digestion with restriction endonucleases as mentioned before.

Clones E21 to E26 (BC1 untreated) were found to all be in the right orientation, and have an insert of the right size. Similarly, clone G3 (MSV AC1 untreated) was in the right orientation (FIG. 8 FIG. 3).

Example 4

4. Construction of Hairpins From Selected Clones.

In order to construct the hairpins from the selected clones. BC1 and MSV AC1 clones (sodium bisulfite treated), were digested with ScaI and BgIII. Similarly, the untreated clones were digested with ScaI and BamHI. Agarose gel electophoresis was used to separate the resulting fragments.

For clone B4, the 2042 bp fragment (top fragment) was excised from the gel and purified using the MinElute Gel Extraction kit (Qiagen). For clone E22, the 1312 bp fragment (lower fragment) was excised and purified. Similarly, for clone F3, the 2066 bp fragment (top fragment) was excised, and for clone G3 the 1337 bp fragment (lower fragment) was excised and purified.

Figure 11:
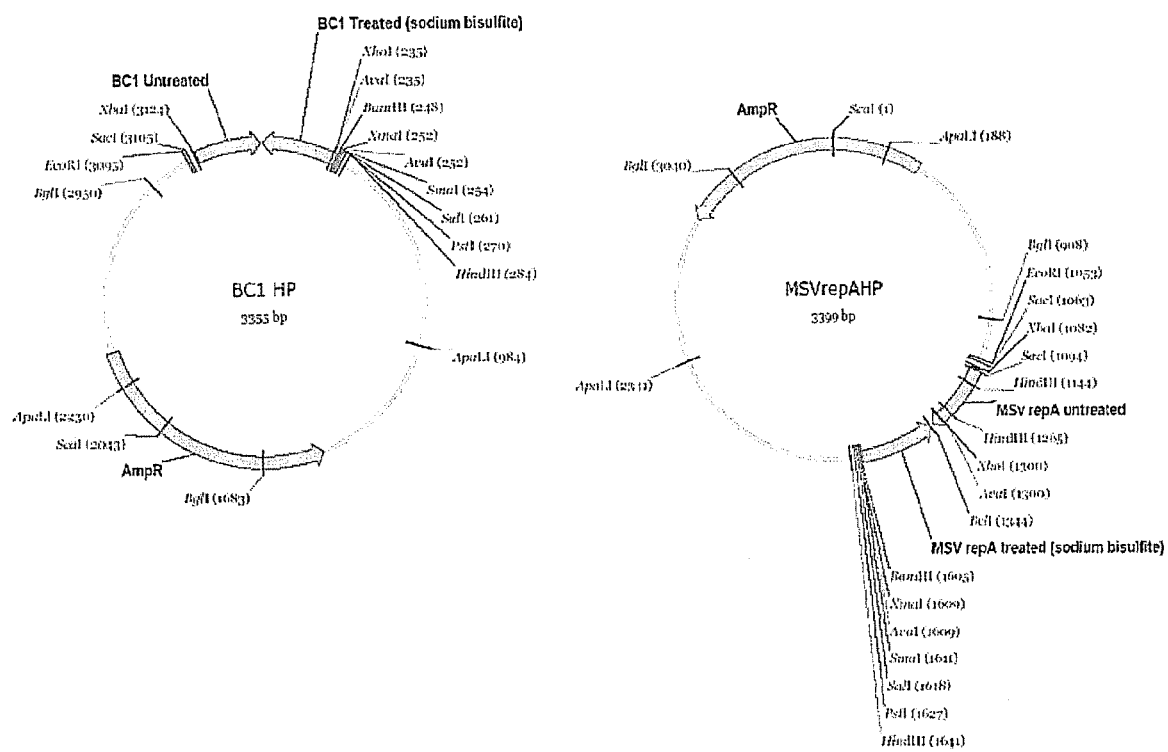
FIG. 11 shows a pTZ57R plasmid containing the double-insert in a head-to-head orientation.
Figure 14:
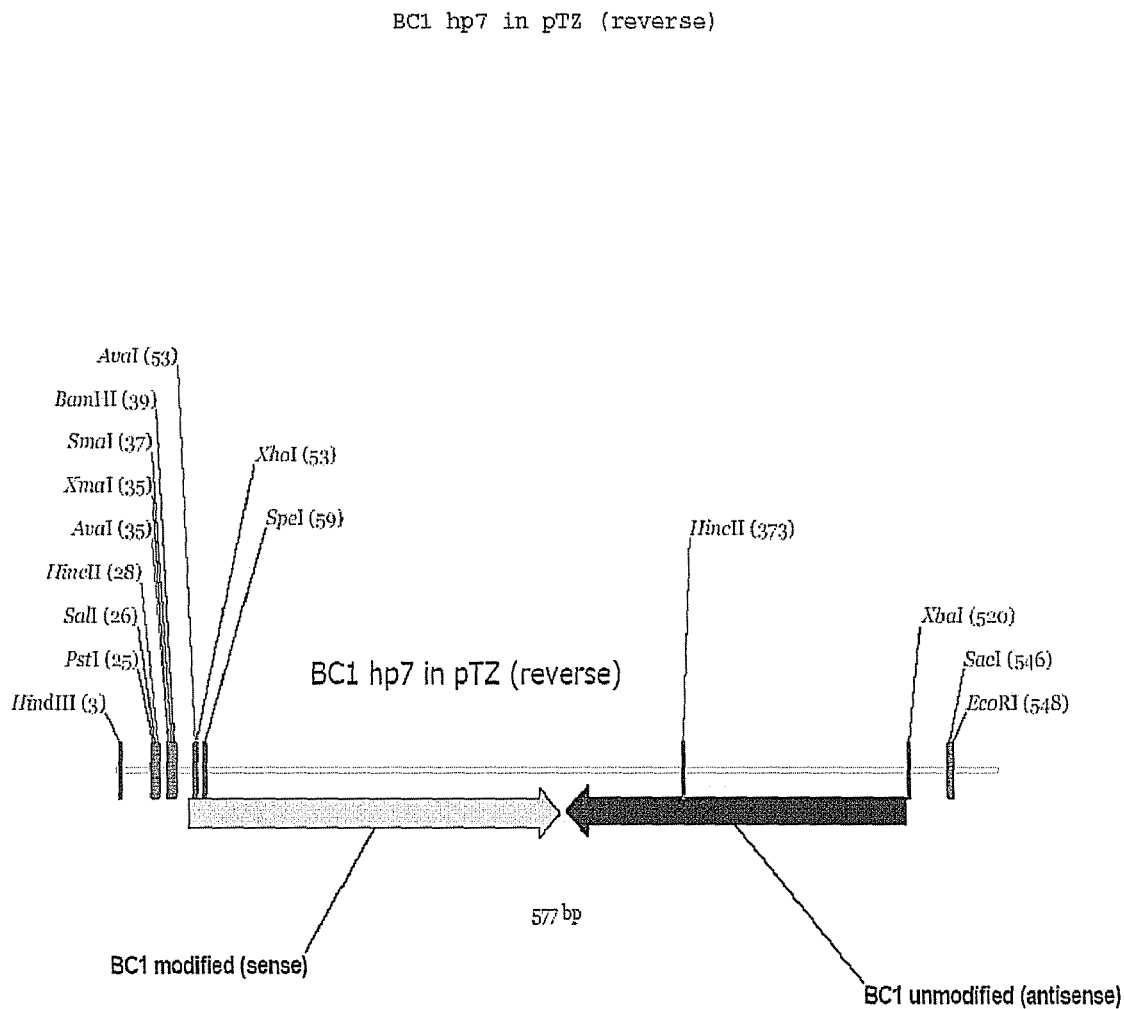
FIG. 14 shows SACMV BC1 in reverse.
Figure 15:
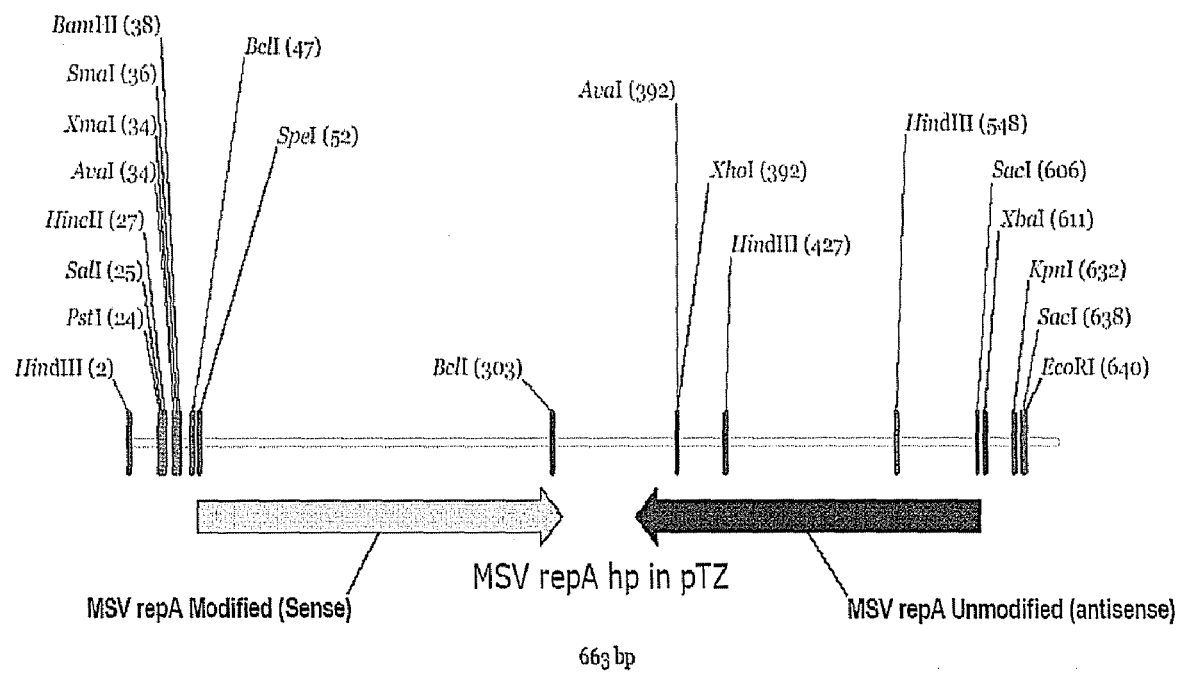
FIG. 15 shows MSV BC1 in reverse.

Approximately 50 ng of each modified fragment was added with 50 ng of each unmodified fragment, respectively, to a ligation mix containing 1× ligation buffer, PEG 4000 and T4 DNA Polymerase (Fermentas). The mixture was incubated at 22° C. for a minimum of 1 hour, after which competent cells were transformed as described previously and plated. Presumptive BC1 hp clones were screened by restriction digestion with XhoI and XbaI. Presumptive MSV AC1 hp clones were screened by digestion with XbaI and SalI (FIG. 11).

The digestions showed that possible hairpins of the expected sizes are present. BC1 hp7 and MSV hp 3 were selected for further construction of the silencing cassette. Their fragments (FIG. 10) were excised from the gel and purified for later cloning into the vector pART 7.

Currently, experiments are underway to screen for siRNAs processed from the SACMV hairpin cassettes in transgenic *Nicotiana benthamiana* and cassava. Transgenic plants will be challenged with SACMV to determine knockdown of AC1 and BC1 and the effect of putative silencing on viral load. The applicant anticipates that plant lines expressing siRNAs derived from the mismatched IdsRNA hairpins will have reduced viral loads apon infection with SACMV. It is anticipated that the stability of the mismatched IdsRNAs will be comparable to that of long intron-spliced dsRNA in plants and will be more effective than perfectly matched inverted repeats. The stability of long intron-spliced inverted repeats is largely dependent upon the G:C content of the target gene, and therefore in the method described here, an increased stability can be achieved independently of the G:C content due to the nature of mutations described.

While the invention has been described in detail with respect to specific embodiments thereof, it will be appreciated by those skilled in the art that various alterations, modifications and other changes may be made to the invention without departing from the spirit and scope of the present invention. It is therefore intended that the claims cover or encompass all such modifications, alterations and/or changes.

SEQUENCE LISTING

```
<160> NUMBER OF SEQ ID NOS: 76

<210> SEQ ID NO 1
<211> LENGTH: 924
<212> TYPE: DNA
<213> ORGANISM: South African cassava mosaic virus
<220> FEATURE:
<221> NAME/KEY: misc_feature
<222> LOCATION: (1)..(924)
<223> OTHER INFORMATION: BC1 ORF

<400> SEQUENCE: 1
caattgttta ttacaattgc cttggtgcgt cggattttat tttgtagaga cacttgttta     60
tggtactctc aagcagtgtc tcgaggtcct ttctggagac ggagtcggat tgggcctgtg    120
atatcgagtc ccctgggtcc aaatcgggtg tgtgtaatct gtgtagtttc tggtaaggat    180
attctgtgga gtcgttgtct aagtccgttg gtgttgtcga tgggtccatt ctcatggact    240
gtgaacgaaa gtgttccagc tgtgctgggc ctaatgagct tggtagccca atctgagacc    300
ttgtggccca tgtttcgcct ggatggatgg tgatgggcct gtgggttatg ggttgttgac    360
```

```
tacgagcagt tggagtggga tttaataatc gtcgtcttgt ttctcctttt tccacggacc    420
agaagtctat gcagtctttt gtgtatccct tggataagat gttaattgtt ggggtttga     480 aacgtatgtc cgtggaatgt ttggccgatg ataatcggag cttggccttg atggatgcga    540
atttcacgcc ttctatgacg tttgagtctt cgactctgta catgattctc caaggggaag    600
gttcagaaat cgaaaaatat gtagaagaga agtagtggag gtccacgttg caagcgatgg    660
ggaaagtgaa tgctgcctga gctgcgtcgt caaggctgac gcgattgtct ctgatttcta    720
cgataaccga cccagttgcg ttaaatggga cctggtttcg gtattcaatt ataatgtggt    780
cgattttcat acatcggcct ttgagtcgca tggtagcctg ctcgaatgag cctgggaatt    840
ggagattgat tggtgcagca tcgtttgtta atgcgtactc ggtgcgtttg ctgttgatgt    900
aattattgtc tgtgacggta aatt                                          924

<210> SEQ ID NO 2
<211> LENGTH: 819
<212> TYPE: DNA
<213> ORGANISM: Maise Streak Virus
<220> FEATURE:
<221> NAME/KEY: misc_feature
<222> LOCATION: (1)..(819)
<223> OTHER INFORMATION: AC1

<400> SEQUENCE: 2
ctaggcttct ggcccaagta gattttccgg ttcttgttgg gccgacgatg tagaggctct     60
gctttcttga tctttcatct gatgactgga tacagaatcc atccattgga ggtcagaaat    120
tgcatcctcg agggtataac aggtaggttg aaggagcatg taagcttcgg gactaacctg    180
gaagatgtta ggctggagcc aatcgttgat tgactcatta caaagtaaat caggtgagga    240
gggtggatga ggattggtga actcttcctg aatctcagga aaaagcttat tgcagagta     300 ttcaaaatac tgcaattttg tggaccaatc aaaggggagc tctttctgga tcatggagag    360
gtactcttct ttggaggtag cgtgtgaaat aatgtctcgc attatttcat ctttagaagg    420 cttttttttcc tttacctctg aatcagattt tcctaggaag ggggacttcc taggaatgaa    480
agtacctctc tcaaacacag ccagaggttc cttgagaatg taatccctca ctctgttaac    540
tgacttggca ctctgaatat ttgggtgaaa cccatttata tcaaagaacc ttgagtcaga    600
tatccttatc ggcttctctg gctgaagcaa tgcatgtaaa tgcaaacttc catctttatg    660
tgcctctcgg gcacatagaa tatatttggg aatccaacga acgacgagct cccagatcat    720
ctgacaggcg atttcaggat tttctggaca ctttggatag gttaggaacg tgttagcgtt    780
cctgtgtgag aactgacggt tggatgagga ggaggccat                           819

<210> SEQ ID NO 3
<211> LENGTH: 20
<212> TYPE: DNA
<213> ORGANISM: Artificial Sequence
<220> FEATURE:
<223> OTHER INFORMATION: Primer : BC1 F
<220> FEATURE:
<221> NAME/KEY: primer_bind
<222> LOCATION: (1)..(20)
<223> OTHER INFORMATION: Primer : BC1 F

<400> SEQUENCE: 3
aaacattcca cggacatacg                                                 20

<210> SEQ ID NO 4
<211> LENGTH: 22
```

```
<212> TYPE: DNA
<213> ORGANISM: Artificial Sequence
<220> FEATURE:
<223> OTHER INFORMATION: Primer : BC1 R
<220> FEATURE:
<221> NAME/KEY: primer_bind
<222> LOCATION: (1)..(22)
<223> OTHER INFORMATION: Primer : BC1 R

<400> SEQUENCE: 4
tggtagccca atctgagacc tt                                             22

<210> SEQ ID NO 5
<211> LENGTH: 19
<212> TYPE: DNA
<213> ORGANISM: Artificial Sequence
<220> FEATURE:
<223> OTHER INFORMATION: Primer : MSV AC1 F
<220> FEATURE:
<221> NAME/KEY: primer_bind
<222> LOCATION: (1)..(19)
<223> OTHER INFORMATION: Primer : MSV AC1 F

<400> SEQUENCE: 5
agagctcccc tttgattgg                                                 19

<210> SEQ ID NO 6
<211> LENGTH: 23
<212> TYPE: DNA
<213> ORGANISM: Artificial Sequence
<220> FEATURE:
<223> OTHER INFORMATION: Primer : MSV AC1 R
<220> FEATURE:
<221> NAME/KEY: primer_bind
<222> LOCATION: (1)..(23)
<223> OTHER INFORMATION: Primer : MSV AC1 R

<400> SEQUENCE: 6
tccatccatt ggaggtcaga aat                                            23

<210> SEQ ID NO 7
<211> LENGTH: 36
<212> TYPE: DNA
<213> ORGANISM: Artificial Sequence
<220> FEATURE:
<223> OTHER INFORMATION: Primer : BC1 F (mod - XhoI+SpeI)
<220> FEATURE:
<221> NAME/KEY: primer_bind
<222> LOCATION: (1)..(36)
<223> OTHER INFORMATION: Primer : BC1 F (mod - XhoI+SpeI)

<400> SEQUENCE: 7
gatcctcgag actagtaaat attctacgga catacg                              36

<210> SEQ ID NO 8
<211> LENGTH: 34
<212> TYPE: DNA
<213> ORGANISM: Artificial Sequence
<220> FEATURE:
<223> OTHER INFORMATION: Primer : BC1 R (mod - BglII)
<220> FEATURE:
<221> NAME/KEY: primer_bind
<222> LOCATION: (1)..(34)
<223> OTHER INFORMATION: Primer : BC1 R (mod - BglII)

<400> SEQUENCE: 8
gatcagatct tagtagccca atctaagacc ttgt                                34

<210> SEQ ID NO 9
<211> LENGTH: 29
```

```
<212> TYPE: DNA
<213> ORGANISM: Artificial Sequence
<220> FEATURE:
<223> OTHER INFORMATION: Primer : MSV AC1 F
<220> FEATURE:
<221> NAME/KEY: primer_bind
<222> LOCATION: (1)..(29)
<223> OTHER INFORMATION: Primer : MSV AC1 F

<400> SEQUENCE: 9
gatcactagt agagttctcc tttgattgg                                      29

<210> SEQ ID NO 10
<211> LENGTH: 39
<212> TYPE: DNA
<213> ORGANISM: Artificial Sequence
<220> FEATURE:
<223> OTHER INFORMATION: Primer: AC1 R (Mod + BglII +BclI)
<220> FEATURE:
<221> NAME/KEY: primer_bind
<222> LOCATION: (1)..(39)
<223> OTHER INFORMATION: Primer: AC1 R (Mod + BglII +BclI)

<400> SEQUENCE: 10
ctagagatct tgatcatcca tccattagag atcagaaat                           39

<210> SEQ ID NO 11
<211> LENGTH: 2760
<212> TYPE: DNA
<213> ORGANISM: South African cassava mosaic virus
<220> FEATURE:
<221> NAME/KEY: misc_feature
<222> LOCATION: (1)..(2760)
<223> OTHER INFORMATION: BC1

<400> SEQUENCE: 11
accggatggc cgcgcccgaa aaagcagatg accccacaa tggtccccac gcactaaata       60
atgtcagcca atcaattgca agactggaag actcggtagt gacgcatgga gtattaagtg     120
gtttctgcac taatttggac aggcaatttt attgctatgt gtgtatcata ttttatagg      180 tgtgctactg gccaatcaaa gttaggtgat ggggcctacc ataaaaacgc aaaatatagg     240
tacgtatgta catattgatt atatttttag gtgcggatat aagaggcgcc acgtgtttac     300
aatggatatg gattgtccta taaatattgt gcatgtctcc cgttcgttaa tgcaagatgt     360
attcagttta cagacgtggg tataagactc cgtataggag tccgtatggc gctcgtgtaa     420
caccatatgt atatcgtaag acctctggta aacagacgtc taaatctcgt gtaccgcgaa     480
agttggtgta tgaatcgcca aaaggtctat atacgcgacg ctcattggag gatatccata    540
atggggcttc cttgaagttg tctcaacagg gggattatac gtcctacgtg tcactccctt    600
gtcgaggtat cgaaggtaat gggggtaggt ctgttgatca cataaaatta ttaaacttga    660
gggtttctgg gaccgtcaac gtcagtcaag tcggtggtga tgataatatg ggagagagaa    720
cgaccatgag gggtatcttc ttcatggctt gtcttgttga taagaaacct ttcgttccag    780
agggggtcag tatattgccg acgttcaatg agttgttcgg ggaatatgaa tccgtgtacg    840
gcatgcctag gttgaaggaa aacgtccgtc accggtatcg cgttattggg acatcgaaat    900
tatatataac gacggatgaa gatcacatcc aaaagccctt tagtttacgt cgaagactaa    960
gtggagggaa atatcctatt tggtcgtcgt tcaaggatgt ggataatagt agtacaggtg   1020
gtaactataa aaatataaat aagaacgcta tactagtgag ttatgtgtgg gtatcgctat   1080 gtcgaccac gtgtgatgtg tattcgcagt ttgtactgaa ttacgtcggt tgataataaa   1140
aagagataag tgtgttgaca ggaattatgt ttgaactaat gaaacatgag atgaacatta   1200
```

```
attgaaagca tatatagttt gattatgctt ttaagcaaat atggtacata tcaattgttt    1260
attacaattg ccttggtgcg tcggatttta ttttgtagag acacttgttt atggtactct    1320
caagcagtgt ctcgaggtcc tttctggaga cggagtcgga ttgggcctgt gatatcgagt    1380
cccctgggtc caaatcgggt gtgtgtaatc tgtgtagttt ctggtaagga tattctgtgg    1440
agtcgttgtc taagtccgtt ggtgttgtcg atgggtccat tctcatggac tgtgaacgaa    1500
agtgttccag ctgtgctggg cctaatgagc ttggtagccc aatctgagac cttgtggccc    1560
atgtttcgcc tggatggatg gtgatgggcc tgtgggttat ggttgttga ctacgagcag    1620 ttggagtggg atttaataat cgtcgtcttg tttctccttt tccacggac cagaagtcta    1680 tgcagtcttt tgtgtatccc ttggataaga tgttaattgt tggggttttg aaacgtatgt    1740
ccgtggaatg tttggccgat gataatcgga gcttggcctt gatggatgcg aatttcacgc    1800
cttctatgac gtttgagtct tcgactctgt acatgattct ccaaggggaa ggttcagaaa    1860
tcgaaaaata tgtagaagag aagtagtgga ggtccacgtt gcaagcgatg gggaaagtga    1920
atgctgcctg agctgcgtcg tcaaggctga cgcgattgtc tctgatttct acgataaccg    1980
acccagttgc gttaaatggg acctggtttc ggtattcaat tataatgtgg tcgattttca    2040
tacatcggcc tttgagtcgc atggtagcct gctcgaatga gcctgggaat tggagattga    2100
ttggtgcagc atcgtttgtt aatgcgtact cggtgcgttt gctgttgatg taattattgt    2160
ctgtgacggt aaattgggcg tccattctat gaagcaaaaa acaaaggtt agtaaacgga    2220 gagacgagag gtataaaagt cagaacaaag ttgaaaaaat atcgtgtaga catgaaagca    2280
tatatgcatt tgttatatag aataacacac gagatcagaa caaggatcat atatgttgaa    2340
ccggccgcgc agcggatagg aagtcagata aatcggcgaa caaagaaaac agtcgaatgg    2400
ggtgatgtga tgtaaaccac ttacagaagc gccgaagaag cagttcgaag tgaattcctg    2460
tgctaattag gcgaagacaa agaaataaaa gtagaactta ttgcgaaaaa aggaaaggga    2520
gcagatgtta cgcgtggtgt cgtgaaatga tatgttatta ggtgtttata taggcgtgaa    2580
taagctacac gtggtagaga gagaaagaag agagaggcga gagcaatcgg ggggcactca    2640
aagttcctag caatcggggg aatggggggc aatttatatg atgcccccca aatggcattt    2700
gtgtaatttc ttaatgaaat ttgaattgcg aacgtggaaa gcggccatcc gtataatatt    2760
```

<210> SEQ ID NO 12
<211> LENGTH: 222
<212> TYPE: DNA
<213> ORGANISM: Artificial Sequence
<220> FEATURE:
<223> OTHER INFORMATION: SACMV BC1_target region (C to T modification)
<220> FEATURE:
<221> NAME/KEY: misc_feature
<222> LOCATION: (1)..(222)
<223> OTHER INFORMATION: SACMV BC1_target region (C to T modification)

<400> SEQUENCE: 12
tggtagccca atctgagacc ttgtggccca tgtttcgcct ggatggatgg tgatgggcct 60
gtgggttatg ggttgttgac tacgagcagt tggagtggga tttaataatc gtcgtcttgt 120
ttctcctttt tccacggacc agaagtctat gcagtctttt gtgtatccct tggataagat 180
gttaattgtt gggggtttga aacgtatgtc cgtggaatgt tt 222

<210> SEQ ID NO 13
<211> LENGTH: 222
<212> TYPE: DNA
<213> ORGANISM: Artificial Sequence

```
<220> FEATURE:
<223> OTHER INFORMATION: SACMV BC1_target region_modified (C to T
      modification)
<220> FEATURE:
<221> NAME/KEY: misc_feature
<222> LOCATION: (1)..(222)
<223> OTHER INFORMATION: SACMV BC1_target region_modified (C to T
      modification)

<400> SEQUENCE: 13
tggtagttta atttgagatt ttgtggttta tgttttgttt ggatggatgg tgatgggttt    60
gtgggttatg ggttgttgat tatgagtagt tggagtggga tttaataatt gttgttttgt   120
tttttttttt tttatggatt agaagtttat gtagtttttt gtgtattttt tggataagat   180
gttaattgtt gggggtttga atgtatgtt tgtggaatgt tt                       222

<210> SEQ ID NO 14
<211> LENGTH: 2760
<212> TYPE: DNA
<213> ORGANISM: South African cassava mosaic virus
<220> FEATURE:
<221> NAME/KEY: misc_feature
<222> LOCATION: (1)..(2760)
<223> OTHER INFORMATION: BC1

<400> SEQUENCE: 14
tggcctaccg gcgcgggctt tttcgtctac ctggggtgtt accagggtg cgtgatttat      60 tacagtcggt tagttaacgt tctgaccttc tgagccatca ctgcgtacct cataattcac    120
caaagacgtg attaaacctg tccgttaaaa taacgataca cacatagtat aaaaatatcc    180
acacgatgac cggttagttt caatccacta ccccggatgg tattttttgcg ttttatatcc   240 atgcatacat gtataactaa tataaaaatc cacgcctata ttctccgcgg tgcacaaatg    300
ttacctatac ctaacaggat atttataaca cgtacagagg gcaagcaatt acgttctaca    360
taagtcaaat gtctgcaccc atattctgag gcatatcctc aggcataccg cgagcacatt    420
gtggtataca tatagcattc tggagaccat ttgtctgcag atttagagca catggcgctt    480
tcaaccacat acttagcggt tttccagata tatgcgctgc gagtaacctc ctataggtat    540
taccccgaag gaacttcaac agagttgtcc ccctaatatg caggatgcac agtgagggaa    600
cagctccata gcttccatta cccccatcca gacaactagt gtatttttaat aatttgaact   660 cccaaagacc ctggcagttg cagtcagttc agccaccact actattatac cctctctctt    720
gctggtactc cccatagaag aagtaccgaa cagaacaact attctttgga aagcaaggtc    780
tcccccagtc atataacggc tgcaagttac tcaacaagcc ccttatactt aggcacatgc    840
cgtacggatc caacttcctt ttgcaggcag tggccatagc gcaataaccc tgtagcttta    900
atatatattg ctgcctactt ctagtgtagg ttttcgggaa atcaaatgca gcttctgatt    960 cacctcccttt ataggataa accagcagca agttcctaca cctattatca tcatgtccac   1020
cattgatatt tttatattta ttcttgcgat atgatcactc aatacacacc catagcgata   1080
cagcctggtg cacactacac ataagcgtca aacatgactt aatgcagcca actattattt   1140
ttctctattc acacaactgt ccttaataca aacttgatta ctttgtactc tacttgtaat   1200
taactttcgt atatatcaaa ctaatacgaa aattcgttta taccatgtat agttaacaaa   1260
taatgttaac ggaaccacgc agcctaaaat aaaacatctc tgtgaacaaa taccatgaga   1320
gttcgtcaca gagctccagg aaagaccctct gcctcagcct aaccccggaca ctatagctca   1380 ggggacccag gttagcccca cacacattag acacatcaaa gaccattcct ataagacacc   1440
tcagcaacag attcaggcaa ccacaacagc tacccaggta agagtacctg acacttgctt   1500
```

```
tcacaaggtc gacacgaccc ggattactcg aaccatcggg ttagactctg gaacaccggg    1560
tacaaagcgg acctacctac cactacccgg acacccaata cccaacaact gatgctcgtc    1620
aacctcaccc taaattatta gcagcagaac aaagaggaaa aaggtgcctg gtcttcagat    1680
acgtcagaaa acacataggg aacctattct acaattaaca accccaaac tttgcataca     1740 ggcaccttac aaaccggcta ctattagcct cgaaccggaa ctacctacgc ttaaagtgcg    1800
gaagatactg caaactcaga agctgagaca tgtactaaga ggttcccctt ccaagtcttt    1860
agctttttat acatcttctc ttcatcacct ccaggtgcaa cgttcgctac ccctttcact    1920
tacgacggac tcgacgcagc agttccgact gcgctaacag agactaaaga tgctattggc    1980
tgggtcaacg caatttaccc tggaccaaag ccataagtta atattacacc agctaaaagt    2040
atgtagccgg aaactcagcg taccatcgga cgagcttact cggaccctta acctctaact    2100
aaccacgtcg tagcaaacaa ttacgcatga gccacgcaaa cgacaactac attaataaca    2160
gacactgcca tttaacccgc aggtaagata cttcgttttt ttgtttccaa tcatttgcct    2220
ctctgctctc catattttca gtcttgtttc aactttttta tagcacatct gtaccttcgt    2280
atatacgtaa acaatatatc ttattgtgtg ctctagtctt gttcctagta tatacaactt    2340
ggccggcgcg tcgcctatcc ttcagtctat ttagccgctt gtttctttg tcagcttacc     2400 ccactacact acatttggtg aatgtcttcg cggcttcttc gtcaagcttc acttaaggac    2460
acgattaatc cgcttctgtt tctttatttt catcttgaat aacgcttttt tcctttccct    2520
cgtctacaat gcgcaccaca gcacttact atacaataat ccacaaatat atccgcactt     2580
attcgatgtg caccatctct ctcttttctc tctctccgct ctcgttagcc ccccgtgagt    2640
ttcaaggatc gttagccccc ttacccccg ttaaatatac tacggggggt ttaccgtaaa     2700
cacattaaag aattacttta aacttaacgc ttgcacccttt cgccggtagg catattataa   2760
```

<210> SEQ ID NO 15
<211> LENGTH: 222
<212> TYPE: DNA
<213> ORGANISM: Artificial Sequence
<220> FEATURE:
<223> OTHER INFORMATION: SACMV BC1_target region_complement
<220> FEATURE:
<221> NAME/KEY: misc_feature
<222> LOCATION: (1)..(222)
<223> OTHER INFORMATION: SACMV BC1_target region_complement

<400> SEQUENCE: 15

```
accatcgggt tagactctgg aacaccgggt acaaagcgga cctacctacc actacccgga     60
cacccaatac ccaacaactg atgctcgtca acctcaccct aaattattag cagcagaaca    120
aagaggaaaa aggtgcctgg tcttcagata cgtcagaaaa cacataggga acctattcta    180
caattaacaa ccccaaaact ttgcatacag gcaccttaca aa                       222
```

<210> SEQ ID NO 16
<211> LENGTH: 2760
<212> TYPE: DNA
<213> ORGANISM: South African cassava mosaic virus
<220> FEATURE:
<221> NAME/KEY: misc_feature
<222> LOCATION: (1)..(2760)
<223> OTHER INFORMATION: BC1

<400> SEQUENCE: 16

```
ttataatatg cctaccggcg aaaggtgcaa gcgttaagtt taaagtaatt ctttaatgtg     60
tttacggtaa accccccgta gtatatttaa cgggggtaa ggggctaac gatccttgaa      120
```

```
actcacgggg ggctaacgag agcggagaga gaagaaagag agagatggtg cacatcgaat      180
aagtgcggat atatttgtgg attattgtat agtaaagtgc tgtggtgcgc attgtagacg      240
agggaaagga aaaagcgtt attcaagatg aaaataaaga aacagaagcg gattaatcgt       300
gtccttaagt gaagcttgac gaagaagccg cgaagacatt caccaaatgt agtgtagtgg      360
ggtaagctga caaagaaac aagcggctaa atagactgaa ggataggcga cgcgccggcc       420
aagttgtata tactaggaac aagactagag cacacaataa gatatattgt ttacgtatat      480
acgaaggtac agatgtgcta taaaaaagtt gaaacaagac tgaaaatatg gagagcagag      540
aggcaaatga ttgaaacaa aaaaacgaag tatcttacct gcgggttaaa tggcagtgtc       600
tgttattaat gtagttgtcg tttgcgtggc tcatgcgtaa ttgtttgcta cgacgtggtt      660
agttagaggt taagggtccg agtaagctcg tccgatggta cgctgagttt ccggctacat      720
acttttagct ggtgtaatat taacttatgg ctttggtcca gggtaaattg cgttgaccca     780
gccaatagca tctttagtct ctgttagcgc agtcggaact gctgcgtcga gtccgtcgta      840
agtgaaaggg gtagcgaacg ttgcacctgg aggtgatgaa gagaagatgt ataaaaagct      900
aaagacttgg aaggggaacc tcttagtaca tgtctcagct tctgagtttg cagtatcttc      960
cgcactttaa gcgtaggtag ttccggttcg aggctaatag tagccggttt gtaaggtgcc     1020
tgtatgcaaa gtttggggt tgttaattgt agaataggtt ccctatgtgt tttctgacgt      1080
atctgaagac caggcacctt tttcctcttt gttctgctgc taataattta gggtgaggtt     1140
gacgagcatc agttgttggg tattgggtgt ccgggtagtg gtaggtaggt ccgctttgta     1200
cccggtgttc cagagtctaa cccgatggtt cgagtaatcc gggtcgtgtc gaccttgtga     1260
aagcaagtgt caggtactct tacctgggta gctgttgtgg ttgcctgaat ctgttgctga     1320
ggtgtcttat aggaatggtc tttgatgtgt ctaatgtgtg tgggctaaac ctgggtcccc     1380
tgagctatag tgtccgggtt aggctgaggc agaggtcttt cctggagctc tgtgacgaac     1440
tctcatggta tttgttcaca gagatgtttt attttaggct gcgtggttcc gttaacatta     1500
tttgttaact atacatggta taaacgaatt ttcgtattag tttgatatat acgaaagtta     1560
attacaagta gagtacaaag taatcaagtt tgtattaagg acagttgtgt gaatagagaa     1620
aaataatagt tggctgcatt aagtcatgtt tgacgcttat gtgtagtgtg caccaggctg     1680
tatcgctatg ggtgtgtatt gagtgatcat atcgcaagaa taaatataaa aatatcaatg     1740
gtggacatga tgataatagg tgtaggaact tgctgctggt ttatcctata agggaggtg      1800 aatcagaagc tgcatttgat ttcccgaaaa cctacactag aagtaggcag caatatatat     1860
taaagctaca gggttattgc gctatggcca ctgcctgcaa aaggaagttg gatccgtacg     1920
gcatgtgcct aagtataagg ggcttgttga gtaacttgca gccgttatat gactggggga     1980
gaccttgctt tccaaagaat agttgttctg ttcggtactt cttctatggg gagtaccagc     2040
aagagagagg gtataatagt agtggtggct gaactgactg caactgccag ggtctttggg     2100
agttcaaatt attaaaatac actagttgtc tggatggggg taatggaagc tatggagctg     2160
ttccctcact gtgcatcctg catattaggg ggacaactct gttgaagttc cttcggggta     2220
atacctatag gaggttactc gcagcgcata tatctggaaa accgctaagt atgtggttga     2280
aagcgccatg tgctctaaat ctgcagacaa atggtctcca gaatgctata tgtataccac     2340
aatgtgctcg cggtatgcct gaggatatgc ctcagaatat gggtgcagac atttgactta     2400
tgtagaacgt aattgcttgc cctctgtacg tgttataaat atcctgttag gtataggtaa     2460
catttgtgca ccgcggagaa tataggcgtg gattttata ttagttatac atgtatgcat      2520
```

```
ggatataaaa cgcaaaaata ccatccgggg tagtggattg aaactaaccg gtcatcgtgt    2580 ggatatttt  atactatgtg tgtatcgtta ttttaacgga caggtttaat cacgtctttg    2640
gtgaattatg aggtacgcag tgatggctca gaaggtcaga acgttaacta accgactgta    2700
ataaatcacg caccccctggt aacaccccag gtagacgaaa aagcccgcgc cggtaggcca    2760

<210> SEQ ID NO 17
<211> LENGTH: 222
<212> TYPE: DNA
<213> ORGANISM: Artificial Sequence
<220> FEATURE:
<223> OTHER INFORMATION: SACMV BC1_target region_reverse
<220> FEATURE:
<221> NAME/KEY: misc_feature
<222> LOCATION: (1)..(222)
<223> OTHER INFORMATION: SACMV BC1_target region_reverse

<400> SEQUENCE: 17
tttgtaaggt gcctgtatgc aaagtttggg ggttgttaat tgtagaatag gttccctatg      60
tgttttctga cgtatctgaa gaccaggcac ctttttcctc tttgttctgc tgctaataat     120
ttagggtgag gttgacgagc atcagttgtt gggtattggg tgtccgggta gtggtaggta     180
ggtccgcttt gtacccggtg ttccagagtc taacccgatg gt                        222

<210> SEQ ID NO 18
<211> LENGTH: 222
<212> TYPE: DNA
<213> ORGANISM: Artificial Sequence
<220> FEATURE:
<223> OTHER INFORMATION: SACMV BC1_target region_modified_reverse
<220> FEATURE:
<221> NAME/KEY: misc_feature
<222> LOCATION: (1)..(222)
<223> OTHER INFORMATION: SACMV BC1_target region_modified_reverse

<400> SEQUENCE: 18
tggtagttta atttgagatt ttgtggttta tgttttgttt ggatggatgg tgatgggttt      60
gtgggttatg ggttgttgat tatgagtagt tggagtggga tttaataatt gttgttttgt     120
tttttttttt tttatggatt agaagtttat gtagtttttt gtgtattttt tggataagat     180
gttaattgtt ggggtttga  aatgtatgtt tgtggaatgt tt                        222

<210> SEQ ID NO 19
<211> LENGTH: 2760
<212> TYPE: DNA
<213> ORGANISM: South African cassava mosaic virus
<220> FEATURE:
<221> NAME/KEY: misc_feature
<222> LOCATION: (1)..(2760)
<223> OTHER INFORMATION: BC1

<400> SEQUENCE: 19
aatattatac ggatggccgc tttccacgtt cgcaattcaa atttcattaa gaaattacac       60
aaatgccatt tgggggggcat catataaatt gcccccccatt ccccgattg ctaggaactt     120 tgagtgcccc ccgattgctc tcgcctctct cttctttctc tctctaccac gtgtagctta     180
ttcacgccta tataaacacc taataacata tcatttcacg acaccacgcg taacatctgc     240 tcccttcct  tttttcgcaa taagttctac ttttatttct ttgtcttcgc ctaattagca     300
caggaattca cttcgaactg cttcttcggc gcttctgtaa gtggtttaca tcacatcacc     360
ccattcgact gttttctttg ttcgccgatt tatctgactt cctatccgct gcgcggccgg     420
ttcaacatat atgatccttg ttctgatctc gtgtgttatt ctatataaca aatgcatata     480
```

```
tgcttccatg tctacacgat attttttcaa ctttgttctg actttttatac ctctcgtctc    540 tccgtttact aacctttgtt tttttgcttc atagaatgga cgcccaattt accgtcacag    600
acaataatta catcaacagc aaacgcaccg agtacgcatt aacaaacgat gctgcaccaa    660
tcaatctcca attcccaggc tcattcgagc aggctaccat gcgactcaaa ggccgatgta    720
tgaaaatcga ccacattata attgaatacc gaaaccaggt cccatttaac gcaactgggt    780
cggttatcgt agaaatcaga gacaatcgcg tcagccttga cgacgcagct caggcagcat    840
tcactttccc catcgcttgc aacgtggacc tccactactt ctcttctaca tattttcga    900 tttctgaacc ttccccttgg agaatcatgt acagagtcga agactcaaac gtcatagaag    960
gcgtgaaatt cgcatccatc aaggccaagc tccgattatc atcggccaaa cattccacgg    1020
acatacgttt caaaccccca acaattaaca tcttatccaa gggatacaca aaagactgca    1080
tagacttctg gtccgtggaa aaggagaaa caagacgacg attattaaat cccactccaa    1140
ctgctcgtag tcaacaaccc ataacccaca ggcccatcac catccatcca ggcgaaacat    1200
gggccacaag gtctcagatt gggctaccaa gctcattagg cccagcacag ctggaacact    1260
ttcgttcaca gtccatgaga atggacccat cgacaacacc aacggactta gacaacgact    1320
ccacagaata tccttaccag aaactacaca gattacacac acccgatttg gacccagggg    1380
actcgatatc acaggcccaa tccgactccg tctccagaaa ggacctcgag acactgcttg    1440
agagtaccat aaacaagtgt ctctacaaaa taaaatccga cgcaccaagg caattgtaat    1500
aaacaattga tatgtaccat atttgcttaa aagcataatc aaactatata tgctttcaat    1560
taatgttcat ctcatgtttc attagttcaa acataattcc tgtcaacaca cttatctctt    1620
tttattatca accgacgtaa ttcagtacaa actgcgaata cacatcacac gtggtccgac    1680
atagcgatac ccacacataa ctcactagta tagcgttctt atttatattt ttatagttac    1740
cacctgtact actattatcc acatccttga acgacgacca aataggatat ttccctccac    1800
ttagtcttcg acgtaaacta aagggctttt ggatgtgatc ttcatccgtc gttatatata    1860
atttcgatgt cccaataacg cgataccggt gacggacgtt ttccttcaac ctaggcatgc    1920
cgtacacgga ttcatattcc ccgaacaact cattgaacgt cggcaatata ctgaccccct    1980
ctggaacgaa aggtttctta tcaacaagac aagccatgaa gaagataccc ctcatggtcg    2040
ttctctctcc catattatca tcaccaccga cttgactgac gttgacggtc ccagaaaccc    2100
tcaagtttaa taattttatg tgatcaacag acctaccccc attaccttcg atacctcgac    2160
aagggagtga cacgtaggac gtataatccc cctgttgaga caacttcaag gaagcccat    2220 tatggatatc ctccaatgag cgtcgcgtat atagaccttt tggcgattca tacaccaact    2280
ttcgcggtac acgagattta gacgtctgtt taccagaggt cttacgatat acatatggtg    2340
ttacacgagc gccatacgga ctcctatacg gagtcttata cccacgtctg taaactgaat    2400
acatcttgca ttaacgaacg ggagacatgc acaaatattta taggacaatc catatccatt    2460
gtaaacacgt ggcgcctctt atatccgcac ctaaaaatat aatcaatatg tacatacgta    2520
cctatatttt gcgtttttat ggtaggcccc atcacctaac tttgattggc cagtagcaca    2580
cctataaaaa tatgatacac acatagcaat aaaattgcct gtccaaatta gtgcagaaac    2640
cacttaatac tccatgcgtc actaccgagt cttccagtct gcaattgat tggctgacat    2700 tatttagtgc gtggggacca ttgtgggtc catctgcttt tcgggcgcg gccatccggt    2760
```

<210> SEQ ID NO 20  
<211> LENGTH: 222

```
<212> TYPE: DNA
<213> ORGANISM: Artificial Sequence
<220> FEATURE:
<223> OTHER INFORMATION: SACMV BC1_target region_complement_reverse
<220> FEATURE:
<221> NAME/KEY: misc_feature
<222> LOCATION: (1)..(222)
<223> OTHER INFORMATION: SACMV BC1_target region_complement_reverse

<400> SEQUENCE: 20
aaacattcca cggacatacg tttcaaaccc ccaacaatta acatcttatc caagggatac      60
acaaaagact gcatagactt ctggtccgtg gaaaaaggag aaacaagacg acgattatta    120
aatcccactc caactgctcg tagtcaacaa cccataaccc acaggcccat caccatccat    180
ccaggcgaaa catgggccac aaggtctcag attgggctac ca                       222

<210> SEQ ID NO 21
<211> LENGTH: 183
<212> TYPE: DNA
<213> ORGANISM: Artificial Sequence
<220> FEATURE:
<223> OTHER INFORMATION: SACMV BC1_hairpin
<220> FEATURE:
<221> NAME/KEY: misc_feature
<222> LOCATION: (1)..(222)
<223> OTHER INFORMATION: SACMV BC1_hairpin

<400> SEQUENCE: 21
gacctggaag gggatatgag gtcgaagaat cgttggttgg tacaattgta cttgccctcg      60
aactgaatga gggcatgcaa atgaggttcc ccattttcat ggagttctct gcagatcttg    120
atgaacaatt tatttgttgg ggtttggagt tgtcggagtt gatctaatgc cgcttctttc    180
gag                                                                 183

<210> SEQ ID NO 22
<211> LENGTH: 2760
<212> TYPE: RNA
<213> ORGANISM: South African cassava mosaic virus
<220> FEATURE:
<221> NAME/KEY: misc_feature
<222> LOCATION: (1)..(2760)
<223> OTHER INFORMATION: BC1 RNA

<400> SEQUENCE: 22
accggauggc cgcgcccgaa aaagcagaug accccacaa uggucccac gcacuaaaua      60 augucagcca aucaauugca agacuggaag acucggauagu gacgcauugga guauuaaguug    120 guuucugcac uaauuggac aggcaauuuu auugcuaugu guguaucaua uuuuuauagg    180
ugugcuacug gccaaucaaa guuaggugau ggggccuacc auaaaaacgc aaaauauagg    240
uacguaugua cauauugauu auauuuuuag gugcggauau aagaggcgcc acguguuuac    300
aauggauaug gauugccua uaaauauugu gcaugcuccc cguucguuaa ugcaagaugu    360
auucaguuua cagacguggg uauaagacuc cguauaggag uccguauggc gcucguguaa    420
caccauaugu auaucguaag accucuggua aacagacguc uaaaucucgu guaccgcgaa    480
aguuggugua ugaaucgcca aaaggucuau aucgcgacg cucauggag gauauccaua    540 auggggcuuc cuugaaguug ucucaacagg gggauuauac guccuacgug ucacucccuu    600 gucgaggua ugaaggcuaaau ggggguaggu cuguugauca cauaaauuua uuaaacuuga    660
ggguuucugg gaccgucaac gucagucaag ucgguggga uguauaauaug ggagagagaa    720 cgaccaugag gggauaucuu cucaugccu gucuuguuga uagaaaccuu uucguuccag    780 aggggucag uauauugccg acguucaaug aguuguucgg ggaauaugaa uccguguacg    840
```

```
gcaugccuag guugaaggaa acguccguc accgguaucg cguuauuggg acaucgaaau    900
uauauauaac gacggaugaa gaucacaucc aaaagcccuu uaguuuacgu cgaagacuaa    960
guggagggaa auauccuauu uggucgucgu ucaaggaugu ggauaauagu aguacaggug   1020
guaacuauaa aaauauaaau aagaacgcua acuagugag uuauguguggg guaucgcuau   1080 gucggaccac gugugaugug uauucgcagu uguacugaa uucgucggu ugauaauaaa    1140 aagagauaag uguguugaca ggauuuaugu ugaacuaau gaaacaugag augaacauua   1200
auugaaagca uauauaguuu gauuaugcuu uuaagcaaau augguacaua ucaauuguuu   1260
auuacaauug ccuuggugcg ucggauuuua uuuuguagag acacuuguuu augguacucu   1320
caagcagugu cucgaggucc uuucggaga cggagucgga uugggccugu gauaucgagu   1380 ccccugggguc caaaucgggu guguguaauc uguguaguuu cgguaagga uauucgugg    1440 agucguuguc uaaguccguu ggguuguucu auggguccau ucucauggac ugugaacgaa   1500
aguguuccag cugugcuggg ccuaaugagc uugguagccc aaucgagac cuuguggccc    1560 auguucgcc uggauggaug gugaugggcc ugggguuau ggguuguuga cuacgagcag    1620 uuggagugggg auuuaauaau cgucgucuug uuucuccuuu uuccacggac cagaagucua   1680
ugcagucuuu uguguauccc uuggauaaga uguuaauugu ugggggguuug aaacguaugu   1740 ccguggaaug uuuggccgau gauaaucgga gcuggccuu gauggaugcg aauuucacgc    1800
cuucuaugac guuugagucu ucgacucugu acaugauucu ccaagggggaa gguucagaaa   1860 ucgaaaaaua uguagaagag aaguagugga gguccacguu gcaagcgaug gggaaaguga   1920
augcugccug agcugcgucg ucaaggcuga cgcgauuguc ucugauuucu acgauaaccg   1980
acccaguugc guuaaauggg accgguuuc gguauucaau auaaugugg ucgauuuuca    2040 uacaucggcc uuugagucgc augguagccu gcucgaauga gccugggaau uggagauuga    2100
uuggugcagc aucguuuguu aaugcguacu cggugcguuu gcguugaug uaauuauugu   2160 cugugacggu aaauugggcg uccauucuau gaagcaaaaa aacaaagguu aguaaacgga   2220
gagacgagag guauaaaagu cagaacaaag uugaaaaau aucguguaga cauggaagca    2280
uauaugcauu uguuauauag aauaacacac gagaucagaa caaggaucau auauguugaa    2340
ccggccgcgc agcggauagg aagucagaua aaucggcgaa caaagaaaac agucgaaugg    2400
ggugauguga uguaaaccac uuacagaagc gccgaagaag caguucgaag ugaauuccug   2460
ugcuaauuag gcgaagacaa agaaauaaaa guagaacuua uugcgaaaaaa aggaaaggga   2520 gcagauguua cgcguggugu cgugaaauga uauguuauua gguguuuaua uaggcgugaa    2580
uaagcuacac gguguagaga gagaaagaag agagaggcga gagcaaucgg ggggcacuca    2640
aaguuccuag caaucggggg aauggggggc aauuuauaug augccccca aauggcauuu     2700 guguaauuuc uuaaugaaau uugaauugcg aacguggaaa gcggccaucc guauaauauu    2760
```

<210> SEQ ID NO 23
<211> LENGTH: 222
<212> TYPE: RNA
<213> ORGANISM: Artificial Sequence
<220> FEATURE:
<223> OTHER INFORMATION: SACMV BC1_Target gene RNA region
<220> FEATURE:
<221> NAME/KEY: misc_feature
<222> LOCATION: (1)..(222)
<223> OTHER INFORMATION: SACMV BC1_Target gene RNA region

<400> SEQUENCE: 23

```
ugguagccca aucugagacc uuguggccca uguuucgccu ggauggaugg ugaugggccu     60
```

```
gugggu uaug   gguuguugac   uacgagcagu   uggagaguggga  uuuaauaaauc   gucgucuugu       120 uucuccuuuu   uccacggacc   agaagucuau   gcagucuuuu    guguaucccu    uggauaagau       180
guuaauuguu   ggggguuuga   aacguauguc   cguggaaugu    uu                             222

<210> SEQ ID NO 24
<211> LENGTH: 222
<212> TYPE: RNA
<213> ORGANISM: Artificial Sequence
<220> FEATURE:
<223> OTHER INFORMATION: SACMV BC1_Target gene RNA region_modified
<220> FEATURE:
<221> NAME/KEY: misc_feature
<222> LOCATION: (1)..(222)
<223> OTHER INFORMATION: SACMV BC1_Target gene RNA region_modified

<400> SEQUENCE: 24
ugguaguuua   auugagauu    uuguggguuua  uguuuuguuu   ggauggaugg    ugauggguuu        60 gugggu uaug   gguguuguau   uaugaguagu   uggagaguggga  uuuaauaauu   guuguuuugu       120
uuuuuuuuuu   uuuauggau    agaaguuuau   guaguuuuu     guguauuuuu   uggauaagau        180
guuaauuguu   ggggguuuga   aauguauguu   uguggaaugu    uu                             222

<210> SEQ ID NO 25
<211> LENGTH: 2760
<212> TYPE: RNA
<213> ORGANISM: South African cassava mosaic virus
<220> FEATURE:
<221> NAME/KEY: misc_feature
<222> LOCATION: (1)..(2760)
<223> OTHER INFORMATION: BC1 RNA

<400> SEQUENCE: 25
uggccuaccg   gcgcgggcuu   uuucgucuac   cugggggguguu  accagggggug   cgugauuuau       60 uacagucggu   uaguuaacgu   ucugaccuuc   ugagccauca    cugcguaccu   cauaauucac        120
caaagacgug   auuaaaccug   uccguuaaaa   uaacgauaca    cacauaguau   aaaaauaucc        180
acacgaugac   cgguuaguuu   caauccacua   ccccggaugg    uauuuuugcg   uuuuauaucc        240
augcauacau   guauaacuaa   uauaaaaauc   cacgccuaua    uucuccgcgg   ugcacaaaug        300
uuaccuauac   cuaacaggau   auuuauaaca   cguacagagg    gcaagcaauu   acguucuaca        360
uaagucaaau   gucugcaccc   auauucugag   gcauauccuc    aggcauaccg   cgagcacauu        420
gugguauaca   uauagcauuc   uggagaccau   uugucugcag    auuuagagca   cauggcgcuu        480
ucaaccacau   acuuagcggu   uuccagauua   uaugcgcugc    gaguaaccuc   cuauagguau        540
uaccccgaag   gaacuucaac   agaguugucc   cccuaauaug    caggaugcac   agugagggaa        600
cagcuccaua   gcuuccauua   cccccaucca   gacaacuagu    guauuuuaau   aauuugaacu        660
cccaaagacc   cuggcaguug   cagcaguuc    agccaccacu    acuauuuauac   ccucucucuu       720 gcugguacuc   cccauagaag   aaguaccgaa   cagaacaacu    auucuuugga   aagcaagguc        780
ucccccaguc   auauaacggc   ugcaaguuac   ucaacaagcc    ccuuauacuu   aggcacaugc        840
cguacggauc   caacuuccuu   uugcaggcag   uggccauagc    gcaauaaccc   cuagcuuua         900 auauauauug   cugccuacuu   cuaguguagg   uuucgggaa     ucaaaugca    gcuucgauu         960 caccucccuu   uauaggauaa   accagcagca   aguuccuaca    ccuauuauca   ucauguccac       1020
cauugauauu   uuuauauuua   uucuugcgau   augcacucu     aauacacacc   cauagcgaua       1080 cagccugguug  cacacuacac   auaagcguca   aacaugacuu   aaugcagcca    acuauuauuu       1140
uucucuauuc   acacaacugu   ccuuaauaca   aacuugauua    cuuuguacuc   uacuuguaau       1200
```

```
uaacuuucgu auauaucaaa cuaauacgaa aauucguuua uaccauguau aguuaacaaa    1260
uaauguuaac ggaaccacgc agccuaaaau aaaacaucuc ugugaacaaa uaccaugaga    1320
guucgucaca gagcuccagg aaagaccucu gccucagccu aacccggaca cuauagcuca    1380
ggggacccag guuuagccca cacacauuag acacaucaaa gaccauuccu auaagacacc    1440
ucagcaacag auucaggcaa ccacaacagc uacccaggua agaguaccug acacuugcuu    1500 ucacaaagguc gacacgaccc ggauuacucg aaccaucggg uuagacucug aacaccggg    1560
```

(Note: the above line per image reads "ucacaaggguc gacacgaccc ggauuacucg aaccaucggg uuagacucug aacaccggg")

```
uacaaagcgg accaccuac cacuacccgg acacccaaua cccaacaacu gaugcucguc    1620
aaccucaccc uaauuauua gcagcagaac aaagaggaaa aaggugccug gucuucagau    1680
acgucagaaa acacauaggg aaccuauucu acaauuaaca accccaaaac uuugcauaca    1740
ggcaccuuac aaaccggcua cuauuagccu cgaaccggaa cuaccacgc uuaaagugcg    1800 gaagauacug caaacucaga agcugagaca uguacuaaga gguuccccuu ccaagucuuu    1860
agcuuuuuau acaucuucuc uucauccauu ccagggcaa cguucgcuac cccuuucacu    1920
uacgacggac ucgacgcagc aguuccgacu gcgcuaacag agacuaaaga ugcuauuggc    1980
ugggucaacg caauuuaccc uggaccaaag ccauaaguua auauuacacc agcuaaaagu    2040
auguagccgg aaacucagcg uaccaucgga cgagcuuacu cggacccuua accucuaacu    2100
aaccacgucg uagcaaacaa uuacgcauga gccacgcaaa cgacaacuac auuaauaaca    2160
gacacugcca uuuaaccccgc agguaagaua cuucguuuuu uguuccaa ucauugccu    2220 cucugcucuc cauauuuuca gucuuguuuc aacuuuuuua uagcacaucu guaccuucgu    2280
auauacguaa acaauauauc uuauugugug cucuagucuu guccuaguaa uauacaacuu    2340
ggccggcgcg ucgccuaucc uucaguacauu uuagccgccu guucucuuuug ucagcuuacc    2400 ccacuacacu acauuuggug aaugucuucg cggcucuuc gucaagcuuc acuuaaggac    2460
acgauuaauc cgcuucuguu ucuuuauuuu caucuugaau aacgcuuuuu uccuuucccu    2520
cgucuacaau gcgcaccaca gcacuuuacu auacaauaau ccacaaauau auccgcacuu    2580
auucgaugug caccaucucu cucuuucuuc ucucuccgcu cucguuagcc ccccgugagu    2640
uucaaggauc guuagccccc uuacccccccg uuaaauauac uacgggggu uuaccguaaa    2700 cacauuaaag aauuacuuua aacuuaacgc uugcaccuuu cgccgguagg cauauuauaa    2760
```

<210> SEQ ID NO 26
<211> LENGTH: 222
<212> TYPE: RNA
<213> ORGANISM: Artificial Sequence
<220> FEATURE:
<223> OTHER INFORMATION: SACMV BC1_Target region complement_RNA
<220> FEATURE:
<221> NAME/KEY: misc_feature
<222> LOCATION: (1)..(222)
<223> OTHER INFORMATION: SACMV BC1_Target region complement_RNA

<400> SEQUENCE: 26

```
accaucgggu uagacucugg aacaccgggu acaaagcgga ccaccuacc acuacccgga     60 cacccaauac ccaacaacug augcucguca acccucaccccu aaauuauuag cagcagaaca    120
aagaggaaaa aggugccugg ucuucagaua cgucagaaaa cacauaggga accauuucua    180
caauuaacaa ccccccaaaacu uugcauacag gcaccuuaca aa                       222
```

<210> SEQ ID NO 27
<211> LENGTH: 2760
<212> TYPE: RNA
<213> ORGANISM: South African cassava mosaic virus
<220> FEATURE:
<221> NAME/KEY: misc_feature
<222> LOCATION: (1)..(2760)
<223> OTHER INFORMATION: BC1 RNA

<400> SEQUENCE: 27

| | | | | | |
|---|---|---|---|---|---|
| uuauaauaug | ccuaccggcg | aaaggugcaa | gcguuaaguu | uaaaguaauu | cuuuaaugug | 60 |
| uuuacgguaa | acccccccgua | guauauuuaa | cggggguaa | ggggcuaac | gauccuugaa | 120 |
| acucacgggg | ggcuaacgag | agcggagaga | gaagaaagag | agagaugguuog | cacaucgaau | 180 |
| aagugcggau | auauuugugg | auuauugau | aguaaagugc | uguggugcgc | auuguagacg | 240 |
| agggaaagga | aaaagcguu | auucaagaug | aaaauaaaga | aacagaagcg | gauuaaucgu | 300 |
| guccuuaagu | gaagcuugac | gaagaagccg | cgaagacauu | caccaaaugu | aguguagugg | 360 |
| gguaagcuga | caaaagaaac | aagcggcuaa | auagacugaa | ggauaggcga | cgcgccggcc | 420 |
| aaguuguaua | uacuaggaac | aagacuagag | cacacaauaa | gauauauugu | uuacguauau | 480 |
| acgaagguac | agaugugcua | uaaaaaaguu | gaaacaagac | ugaaaauaug | gagagcagag | 540 |
| aggcaaauga | uuggaaacaa | aaaaacgaag | uaucuuaccu | gcgggguuaaa | uggcagugue | 600 |
| uguuauuaau | guaguugucg | uuugcguggc | ucaugcguaa | uuguuugcua | cgacugguu | 660 |
| aguuagaggu | uaagggucg | aguaagcucg | uccgauggua | cgcugaguuu | ccggcuacau | 720 |
| acuuuuagcu | gguguaauau | uaacuuaugg | cuuuggucca | ggguaaauug | cguugaccca | 780 |
| gccauaagca | ucuuuagucu | cuguuagcgc | agucggaacu | gcugcgucga | guccgucgua | 840 |
| agugaaaggg | guagcgaacg | uugcaccugg | aggugaugaa | gagaagaugu | auaaaaagcu | 900 |
| aaagacuugg | aaggggaacc | ucuuaguaca | ugucucagcu | ucugaguuug | caguaucuuc | 960 |
| cgcacuuuaa | gcguaggaug | uuccggucg | aggcuaauag | uagccggguuuc | uaaggugcc | 1020 |
| uguaugcaaa | guuggggggu | uguuaauugu | agaauaggu | cccauaugugu | uuucugacgu | 1080 |
| aucugaagac | caggcaccuu | uuccucuuu | guucugcugc | uaauaauuua | gggugaagguu | 1140 |
| gacgagcauc | aguuguugggg | uauugggugu | ccggguagug | guagguaggu | ccgcuuugua | 1200 |
| cccgguguuc | cagagucuaa | cccgauggu | cgaguaaucc | gggucguguc | gaccuuguga | 1260 |
| aagcaagugu | cagguacucu | uaccugggua | gcuguugugg | uugccugaau | cguugcuga | 1320 |
| ggugucuuau | aggaaugguc | uuugaugugu | cuaaugugug | uggggcuaaac | cugggucccc | 1380 |
| ugagcuauag | uguccgggu | aggcugaggc | agaggucuuu | ccuggagcuc | ugugacgaac | 1440 |
| ucucauggua | uuuguucaca | gagauguuuu | auuuuaggcu | gcguguucc | guuaacauua | 1500 |
| uuuguuaacu | auacaugguua | uaaacgaauu | uucguauuag | uuugauauau | acgaaaguua | 1560 |
| auuacaagua | gaguacaaag | uaaucaaguu | uguauuaagg | acaguuguguu | gaauagagaa | 1620 |
| aaauaauagu | uggcugcauu | aagucauguu | ugacgcuuau | guguaguguug | caccaggcug | 1680 |
| uaucgcuaug | ggugguauu | gaguugaucau | aucgcaagaa | uaaauauaaa | aauaucaaug | 1740 |
| guggacauga | ugauaauagg | uguaggaacu | ugcugcuggu | uuaccuaua | aagggagugu | 1800 |
| aaucagaagc | ugcauuugau | ucccgaaaa | ccuacacuag | aaguaggcag | caauauauau | 1860 |
| uaaagcuaca | ggguuauugc | gcuauggcca | cugccugcaa | aaggaaguug | gauccguacg | 1920 |
| gcaugugccu | aaguauaagg | ggcuuuguuga | guaacuugca | gccguuuauau | gacuggggga | 1980 |
| gaccuugcuu | uccaaagaau | aguuguucug | uucgguacuu | cuucuauggg | gaguaccagc | 2040 |
| aagagagagg | guauaauagu | aguggguggcu | gaacugacug | caacugccag | ggucuuuggg | 2100 |
| aguucaaauu | auuaaaauac | acuaguuguc | uggauggggg | uaauggaagc | uauggagcug | 2160 |
| uucccucacu | gugcauccug | cauauuaggg | ggacaacucu | guugaaguuc | cucgggguua | 2220 |

```
auaccuauag gagguuacuc gcagcgcaua uaucuggaaa accgcuaagu auguggunga   2280
aagcgccaug ugcucuaaau cugcagacaa auggucucca gaaugcuaua uguauaccac   2340
aaugugcucg cgguaugccu gaggauaugc cucagaauau gggugcagac auuugacuua   2400
uguagaacgu aauugcuugc ccucuguacg uguuauaaau auccuguuag guauagguaa   2460
cauuugugca ccgcggagaa uauaggcgug gauuuuaua uuaguauac auguaugcau     2520 ggauauaaaa cgcaaaaaua ccauccgggg uaguggauug aaacuaaccg gucaucgugu   2580
ggauauuuuu auacuaugug uauucguua uuuuaacgga cagguuaau cacgucuuug     2640 gugaauuaug agguacgcag ugauggcuca gaaggucaga acguuaacua accgacugua   2700
auaaaucacg caccccuggu aacaccccag guagacgaaa aagcccgcgc cgguaggcca   2760

<210> SEQ ID NO 28
<211> LENGTH: 222
<212> TYPE: RNA
<213> ORGANISM: Artificial Sequence
<220> FEATURE:
<223> OTHER INFORMATION: SACMV BC1_target region_reverse_RNA
<220> FEATURE:
<221> NAME/KEY: misc_feature
<222> LOCATION: (1)..(222)
<223> OTHER INFORMATION: SACMV BC1_target region_reverse_RNA

<400> SEQUENCE: 28
uuuguaaggu gccuguaugc aaaguuuggg gguuguuaau uguagaauag guucccuaug    60
uguuuucuga cguaucugaa gaccaggcac cuuuuuccuc uuuguucugc ugcuaauaau   120
uuagggugag guugacgagc aucaguuguu ggguauuggg uguccgggua gugguaggua   180
gguccgcuuu guaccgggug uuccagaguc uaacccgaug gu                      222

<210> SEQ ID NO 29
<211> LENGTH: 222
<212> TYPE: RNA
<213> ORGANISM: Artificial Sequence
<220> FEATURE:
<223> OTHER INFORMATION: BC1_target region_modified_reverse_RNA
<220> FEATURE:
<221> NAME/KEY: misc_feature
<222> LOCATION: (1)..(222)
<223> OTHER INFORMATION: BC1_target region_modified_reverse_RNA

<400> SEQUENCE: 29
ugguaguuua auugagauu uuguggunua uguuuuguuu ggauggaugg ugauggguuu     60
guggguuaug gguguugau uaugaguagu uggaguggga uuuaauaauu guuguuuugu    120
uuuuuuuuuu uuuauggauu agaaguuuau guaguuuuuu guguauuuuu uggauaagau   180
guuaauuguu gggggguuuga aauguauguu uguggaaugu uu                     222

<210> SEQ ID NO 30
<211> LENGTH: 2760
<212> TYPE: RNA
<213> ORGANISM: South African cassava mosaic virus
<220> FEATURE:
<221> NAME/KEY: misc_feature
<222> LOCATION: (1)..(2760)
<223> OTHER INFORMATION: BC1 RNA

<400> SEQUENCE: 30
aauauuauac ggauggccgc uuccacguu cgcaauucaa auucauuaa gaaauuacac      60 aaaugccauu uggggggcau cauauaaauu gcccccauu ccccgauug cuaggaacuu    120 ugagugcccc ccgauugcuc ucgccucucu cuucuuucuc ucucuaccac guguagcuua   180
```

| | |
|---|---|
| uucacgccua uauaaacacc uaauaacaua ucauuucacg acaccacgcg uaacaucugc | 240 |
| ucccuuuccu uuuuucgcaa uaaguucuac uuuuauuucu ugucuucgc cuaauuagca | 300 |
| caggaauuca cuucgaacug cuucuucggc gcuucuguaa ugguuuaca ucacaucacc | 360 |
| ccauucgacu guuuucuuug uucgccgauu uaucugacuu ccuauccgcu gcgcggccgg | 420 |
| uucaacauau augauccuug uucugaucuc gugugucuauu cuauauaaca aaugcauaua | 480 |
| ugcuuccaug ucuacacgau auuuuuucaa cuuuguucug acuuuuauac cucucgucuc | 540 |
| uccguuuacu aaccuuuguu uuuuugcuuc auagaaugga cgcccaauuu accgucacag | 600 |
| acaauaauua caucaacagc aaacgcaccg aguacgcauu aacaaacgau gcugcaccaa | 660 |
| ucaaucucca auucccaggc ucauucgagc aggcuaccau gcgacucaaa ggccgaugua | 720 |
| ugaaaaucga ccacauuaua auugaauacc gaaaccaggu cccauuuaac gcaacugggu | 780 |
| cgguuaucgu agaaaucaga gacaaucgcg ucagccuuga cgacgcagcu caggcagcau | 840 |
| ucacuuuccc caucgcuugc aacguggacc uccacuacuu cucucuaca uauuuucga | 900 |
| uuucugaacc uuccccuugg agaaucaugu acagagucga agacucaaac gucauagaag | 960 |
| gcgugaaauu cgcauccauc aaggccaagc uccgauuauc aucggccaaa cauuccacgg | 1020 |
| acauacguuu caaaccccca acaauuaaca ucuuauccaa gggauacaca aaagacugca | 1080 |
| uagacuucug guccguggaa aaaggagaaa caagacgacg auuauuaaau cccacuccaa | 1140 |
| cugcucguag ucaacaaccc auaacccaca ggcccaucac cauccauccca ggcgaaacau | 1200 |
| gggccacaag gucucagauu gggcuaccaa gcucauuagg cccagcacag cuggaacacu | 1260 |
| uucguucaca guccaugaga auggacccau cgacaacacc aacggacuua gacaacgacu | 1320 |
| ccacagaaua uccuuaccag aaacuacaca gauuacacac acccgauuug gacccagggg | 1380 |
| acucgauauc acaggcccaa uccgacuccg ucuccagaaa ggaccucgag acacugcuug | 1440 |
| agaguaccau aaaacaagugu cucuacaaaa uaaaauccga cgcaccaagg caauuguaau | 1500 |
| aaacaauuga uauguaccau auuugcuuaa aagcauaauc aaacuauaua gcuuucaau | 1560 |
| uaauguucau cucauguuuc auuaguucaa acauaauucc ugucaacaca cuuaucucuu | 1620 |
| uuuauuauca accgacguaa uucaguacaa acugcgaaua cacaucacac guggucccgac | 1680 |
| auagcgauac ccacacauaa cucacuagua uagcguucuu auuuauauuu uuauaguuac | 1740 |
| caccuguacu acuauuaucc acauccuuga acgacgacca aauaggauau ucccuccac | 1800 |
| uuagucuucg acguaaacua aagggcuuuu ggaugugauc uucauccguc guuauauaua | 1860 |
| auuucgaugu cccaauaacg cgauaccggu gacggacguu uccuucaac cuaggcaugc | 1920 |
| cguacacgga uucauauucc ccgaacaacu cauugaacgu cggcaauaua cugaccccu | 1980 |
| cuggaacgaa agguuucuua ucaacaagac aagccaugaa gaagauaccc cucauggucg | 2040 |
| uucucucucc cauauuauca ucaccaccga cuugacugac guugacgguc ccagaaaccc | 2100 |
| ucaaguuuaa uaauuuuaug ugaucaacag accuaccccc auuaccuucg uaccucgac | 2160 |
| aagggaguga cacguaggac guauaauccc ccuguugaga caacuucaag gaagccccau | 2220 |
| uauggauauc cuccaaugag cgucgcguau auagaccuuu uggcgauuca uacaccaacu | 2280 |
| uucgcgguac acgagauuua gacgucuguu uaccagaggu cuuacgauau acauauggug | 2340 |
| uuacacgagc gccaucggga cuccauacg gagucuaua cccacgucug uaaacugaau | 2400 |
| acaucuugca uuaacgaacg ggagacaugc acaauauuua uaggacaauc cauuccauu | 2460 |
| guaaacacgu ggcgccucuu auauccgcac cuaaaauauu aaucauaug uacauacgua | 2520 |
| ccuauauuuu gcguuuuuau gguaggcccc aucaccuaac uuugauuggc caguagcaca | 2580 |

```
ccuauaaaaa uaugauacac acauagcaau aaaauugccu guccaaauua gugcagaaac    2640
cacuuaauac uccaugcguc acuaccgagu cuuccagucu ugcaauugau uggcugacau    2700
uauuuagugc gugggaccaa uuguggdguc caucugcuuu uucgggcgcg ccauccggu     2760
```

```
<210> SEQ ID NO 31
<211> LENGTH: 222
<212> TYPE: RNA
<213> ORGANISM: Artificial Sequence
<220> FEATURE:
<223> OTHER INFORMATION: SACMV BC1_target region_complement_reverse_RNA
<220> FEATURE:
<221> NAME/KEY: misc_feature
<222> LOCATION: (1)..(222)
<223> OTHER INFORMATION: SACMV BC1_target region_complement_reverse_RNA

<400> SEQUENCE: 31
```

```
aaacauucca cggacauacg uuucaaaccc ccaacaauua acaucuuauc caagggauac    60
acaaaagacu gcauagacuu cgguccgug gaaaaaggag aaacaagacg acgauuauua     120
aaucccacuc caacugcucg uagucaacaa cccauaaccc acaggccau caccauccau     180 ccaggcgaaa caugggccac aaggucucag auugggcuac ca                      222
```

```
<210> SEQ ID NO 32
<211> LENGTH: 183
<212> TYPE: RNA
<213> ORGANISM: Artificial Sequence
<220> FEATURE:
<223> OTHER INFORMATION: SACMV BC1_hairpin_RNA
<220> FEATURE:
<221> NAME/KEY: misc
<222> LOCATION: (1)..(183)
<223> OTHER INFORMATION: SACMV BC1_hairpin_RNA

<400> SEQUENCE: 32
```

```
gaccuggaag gggauaugag gucgaagaau cguuggiuugg uacaauugua cuugcccucg    60
aacugaauga gggcaugcaa augagguucc ccauuuucau ggaguucucu gcagaucuug    120
augaacaauu uauuuguugg gguuggagu ugucggaguu gaucuaaugc cgcuucuuuc     180
gag                                                                   183
```

```
<210> SEQ ID NO 33
<211> LENGTH: 2800
<212> TYPE: DNA
<213> ORGANISM: South African cassava mosaic virus
<220> FEATURE:
<221> NAME/KEY: misc_feature
<222> LOCATION: (1)..(2800)
<223> OTHER INFORMATION: AC1

<400> SEQUENCE: 33
```

```
accggatggc cgcgcccgac aaagtaggtg gacccccattg gatgaccgcg cccgtaaaag    60
aaagtggtcc ccacgcacgt gttgctgtcg gccagtcata ttcacgcgtg aaagcctaga   120
tatttgtttt atgtcgttat agacttcgtc gcgaagtagt ggagcgtgtc aacatgtggg   180
atccattgtt gaatgagttc cccgagtctg tgcacgguttt tcgctgtatg cttgctatta   240
aatatttgca ggccttggag gaaacctacg agcccaatac tttgggccac gatctagtcc   300
gtgatctcat cggtgtgatc cgagcccgtg attatgtcga agcgtcccgc cgatataatc   360
atttccactc ccgtctcgaa ggtgcgtcga aggctgaact tcgacagccc gttcagcagc   420
cgtgctgctg tccccattgt ccaaggcaca acaagcgtc gatcatggac gttccggccc    480
atgtaccgaa agcccagaat gtacagaatg ttcaaaagcc ctgatgttcc gcgtggctgt   540
```

```
gaaggcccat gtaaggttca atcttatgaa cagcgagatg acgttaagca tactggcagt    600
gttcgttgtg ttagtgatgt cacgcgtggt tcgggaatta cacatagagt aggtaaaagg    660
ttctgtatca agtctatata tgtgttaggt aagatatgga tggatgaaaa catcaagaag    720
cagaaccata caaaccaggt catgttcttc ttagtccgtg acagaaggcc ctatggcaat    780
agccccatgg actttggaca ggttttttaat atgtttgata atgagcccag tacagccact    840
gtgaagaacg atcttaggga taggtatcga gttatgcgga agtttcatgc caccgttgtt    900
gggggtcctt ctggaatgaa ggagcaggct ttggtgagga gattttttag gataaataat    960
catgttgtgt ataatcacca ggaggcagct aagtatgaga atcatacaga gaatgcgtta   1020
ttgttgtata tggcatgtac gcatgcctct aatccagtgt atgctacgct aaaaatacgc   1080
atctattttt atgatgcagt aacaaattaa taaaggttga attttattgc atgttgctcc   1140
gtaacttgga gtgtgtttag taatacatcg tacagaacat gatcaacagc tctgagtaca   1200
gtgttaatgg aaataacgcc tatcatattt aaatacttga gcacttgata tttaaatact   1260
cttaagaaaa gaccagtcgg aggccgtaag gtcgtccaga ccttgaagtt gagaaaacac   1320
ttgtgaatcc ccaatgcctt cctgatgttg tggttgaacc gtatctggag ggtgatgatg   1380
tcgtggttca tgttccctgg ccgcttgtcg tggttggtga tgtcgaaata gaggggattt   1440
gttatttccc aggtaaaaac gccattcttt gcttgaggcg cagtgatgag ttcccctgtg   1500
cgagaatcca tggttgatgc agtcgatatg gagatagaac gagcagccgc attcgaggtc   1560
taccctccta cgtctgaggg ccctagtctt cgcggtgcgg tgttggactt tgatgggcac   1620
ttgagaacaa tggctcgtgg agggtgatga aggttgcatt cttttaaagcc caggctttaa   1680 gggactggtt cttttcctcg tccagaaact ctttatatga tgatgtcggt cctggattgc   1740
ataggaagat agtgggaatg ccgcctttaa tttgaatcgg cttcccgtac ttggtattgc   1800
tttgccagtc cctttgggcc cccatgaatt cttttgaagtg cttgaggtaa tgggggtcga   1860
cgtcatcaat gacgttgtac catgcgtcgt tgctgtaaac cttttggactg agatccaaat   1920 gtccacataa gtagttgtgt ggtcccagag atcgggccca catcgtcttc cctgtcctac   1980
tatcgccctc gatgacgata ctactcggtc tccatggccg cgcagcgaaa cccatcacgt   2040
tctcggaaac ccagtcttca agttcctcag gaacatgagt gaaagaagaa gaaagaaagg   2100
gagaaatata aggaatcgga ggctcctgaa aaatcctatc taaattgcta tttaaattat   2160
gaaactgtaa aacaaaatcc tttggggcta gttcccggat tacattaaga gcctctgttt   2220
tacttgctgc gttaagagcc ttggcgtaag cgtcattggc ggattgttgt ccgccgcgag   2280
cagatcgtcc gtcgatctga aactcgcccc attggatggt gtctccgtcc ttgtccaaat   2340
aggacttgac gtcagaactg gatttagctc cctgaatgtt tggatggaaa tgtgttgacc   2400
tggaagggga tatgaggtcg aagaatcgtt ggttggtaca attgtacttg ccctcgaact   2460
gaatgagggc atgcaaatga ggttcccccat tttcatggag ttctctgcag atcttgatga   2520
acaatttatt tgttggggtt tggagttgtc ggagttgatc taatgccgct tctttcgaga   2580
gagtgcattt cggatacgtg aggaaataat ttttggcttt tatgctaaaa cgaccagccc   2640
tcggcatttt cgctgtcgta tagcaatcgg ggggcactca agttcctag caatcgggg    2700 aatgggggca aatttatatg atgccccccca aatggcatat gtgtaatttt gtgatgaaat   2760
ttgaatttcg aacgtggaaa gcggccatcc gtctaatatt                         2800

<210> SEQ ID NO 34
<211> LENGTH: 183
```

```
<212> TYPE: DNA
<213> ORGANISM: Artificial Sequence
<220> FEATURE:
<223> OTHER INFORMATION: SACMV AC1_Target DNA gene region
<220> FEATURE:
<221> NAME/KEY: misc_feature
<222> LOCATION: (1)..(183)
<223> OTHER INFORMATION: SACMV AC1_Target DNA gene region

<400> SEQUENCE: 34
gacctggaag gggatatgag gtcgaagaat cgttggttgg tacaattgta cttgccctcg      60
aactgaatga gggcatgcaa atgaggttcc ccatttttcat ggagttctct gcagatcttg    120
atgaacaatt tatttgttgg ggtttggagt tgtcggagtt gatctaatgc cgcttctttc    180
gag                                                                    183

<210> SEQ ID NO 35
<211> LENGTH: 183
<212> TYPE: DNA
<213> ORGANISM: Artificial Sequence
<220> FEATURE:
<223> OTHER INFORMATION: SACMV AC1_Target DNA gene region_modified
<220> FEATURE:
<221> NAME/KEY: misc_feature
<222> LOCATION: (1)..(183)
<223> OTHER INFORMATION: SACMV AC1_Target DNA gene region_modified

<400> SEQUENCE: 35
gatttggaag gggatatgag gttgaagaat tgttggttgg tataattgta tttgttttttg     60 aattgaatga gggtatgtaa atgaggtttt ttatttttat ggagtttttt gtagattttg    120
atgaataatt tatttgttgg ggtttggagt tgttggagtt gatttaatgt tgttttttttt   180 gag                                                                    183

<210> SEQ ID NO 36
<211> LENGTH: 2800
<212> TYPE: DNA
<213> ORGANISM: South African cassava mosaic virus
<220> FEATURE:
<221> NAME/KEY: misc_feature
<222> LOCATION: (1)..(2800)
<223> OTHER INFORMATION: AC1

<400> SEQUENCE: 36
tggcctaccg gcgcgggctg tttcatccac ctggggtaac ctactggcgc gggcattttc      60
tttcaccagg ggtgcgtgca caacgacagc cggtcagtat aagtgcgcac tttcggatct    120
ataaacaaaa tacagcaata tctgaagcag cgcttcatca cctcgcacag ttgtacaccc    180
taggtaacaa cttactcaag gggctcagac acgtgccaaa agcgacatac gaacgataat    240
ttataaacgt ccggaacctc ctttggatgc tcgggttatg aaacccggtg ctagatcagg    300
cactagagta gccacactag gctcgggcac taatacagct tcgcagggcg gctatattag    360
taaaggtgag ggcagagctt ccacgcagct tccgacttga agctgtcggg caagtcgtcg    420
gcacgacgac aggggtaaca ggttccgtgt tgttcgcag ctagtacctg caaggccggg     480
tacatggctt tcgggtctta catgtcttac aagttttcgg gactacaagg cgcaccgaca    540
cttccgggta cattccaagt tagaatactt gtcgctctac tgcaattcgt atgaccgtca    600
caagcaacac aatcactaca gtgcgcacca agccctaat gtgtatctca tccattttcc     660
aagacatagt tcagatatat acacaatcca ttctatacct acctactttt gtagttcttc    720
gtcttggtat gtttggtcca gtacaagaag aatcaggcac tgtcttccgg gataccgtta    780
tcggggtacc tgaaacctgt ccaaaaatta tacaaactat tactcgggtc atgtcggtga    840
```

```
cacttcttgc tagaatccct atccatagct caatacgcct tcaaagtacg gtggcaacaa      900 ccccaggaa gaccttactt cctcgtccga aaccactcct ctaaaaaatc ctatttatta      960
gtacaacaca tattagtggt cctccgtcga ttcatactct tagtatgtct cttacgcaat     1020
aacaacatat accgtacatg cgtacggaga ttaggtcaca tacgatgcga attttatgcg     1080
tagataaaaa tactacgtca ttgtttaatt atttccaact taaaataacg tacaacgagg     1140
cattgaacct cacacaaatc attatgtagc atgtcttgta ctagttgtcg agactcatgt     1200
cacaattacc tttattgcgg atagtataaa tttatgaact cgtgaactat aaatttatga     1260
gaattctttt ctggtcagcc tccggcattc cagcaggtct ggaacttcaa ctcttttgtg     1320
aacacttagg ggttacggaa ggactacaac accaacttgg catagacctc ccactactac     1380
agcaccaagt acaagggacc ggcgaacagc accaaccact acagctttat ctcccctaaa     1440
caataaaggg tccatttttg cggtaagaaa cgaactccgc gtcactactc aaggggacac     1500
gctcttaggt accaactacg tcagctatac ctctatcttg ctcgtcggcg taagctccag     1560
atgggaggat gcagactccc gggatcagaa gcgccacgcc acaacctgaa actacccgtg     1620
aactcttgtt accgagcacc tcccactact tccaacgtaa gaaatttcgg gtccgaaatt     1680
ccctgaccaa gaaaggagc aggtctttga gaaatatact actacagcca ggacctaacg     1740
tatccttcta tcacccttac ggcggaaatt aaacttagcc gaagggcatg aaccataacg     1800
aaacggtcag ggaaacccgg gggtacttaa gaaacttcac gaactccatt accccccagct    1860 gcagtagtta ctgcaacatg gtacgcagca acgacatttg gaaacctgac tctaggttta     1920
caggtgtatt catcaacaca ccagggtctc tagcccgggt gtagcagaag gacaggatg     1980 atagcgggag ctactgctat gatgagccag aggtaccggc gcgtcgcttt gggtagtgca     2040
agagcctttg ggtcagaagt tcaaggagtc cttgtactca ctttcttctt ctttctttcc     2100
ctctttatat tccttagcct ccgaggactt tttaggatag atttaacgat aaatttaata     2160
ctttgacatt ttgtttttagg aaaccccgat caagggccta atgtaattct cggagacaaa    2220
atgaacgacg caattctcgg aaccgcattc gcagtaaccg cctaacaaca ggcggcgctc     2280
gtctagcagg cagctagact ttgagcgggg taacctacca cagaggcagg aacaggttta    2340
tcctgaactg cagtcttgac ctaaatcgag ggacttacaa acctaccttt acacaactgg     2400
accttcccct atactccagc ttcttagcaa ccaaccatgt taacatgaac gggagcttga     2460
cttactcccg tacgtttact ccaaggggta aaagtacctc aagagacgtc tagaactact     2520
tgttaaataa acaaccccaa acctcaacag cctcaactag attacggcga agaaagctct     2580
ctcacgtaaa gcctatgcac tccttttatta aaaaccgaaa atacgatttt gctggtcggg     2640
agccgtaaaa gcgacagcat atcgttagcc ccccgtgagt ttcaaggatc gttagccccc     2700
ttaccccccg ttaaatatac tacgggggt ttaccgtata cacattaaaa cactactta     2760 aacttaaagc ttgcacccttt cgccggtagg cagattataa                          2800
```

<210> SEQ ID NO 37
<211> LENGTH: 183
<212> TYPE: DNA
<213> ORGANISM: Artificial Sequence
<220> FEATURE:
<223> OTHER INFORMATION: SACMV AC1_Target DNA gene region_complement
<220> FEATURE:
<221> NAME/KEY: misc_feature
<222> LOCATION: (1)..(183)
<223> OTHER INFORMATION: SACMV AC1_Target DNA gene region_complement

<400> SEQUENCE: 37

```
ctggaccttc ccctatactc cagcttctta gcaaccaacc atgttaacat gaacgggagc      60
ttgacttact cccgtacgtt tactccaagg ggtaaaagta cctcaagaga cgtctagaac     120
tacttgttaa ataaacaacc ccaaacctca acagcctcaa ctagattacg gcgaagaaag     180
ctc                                                                   183
```

<210> SEQ ID NO 38
<211> LENGTH: 2800
<212> TYPE: DNA
<213> ORGANISM: South African cassava mosaic virus
<220> FEATURE:
<221> NAME/KEY: misc_feature
<222> LOCATION: (1)..(2800)
<223> OTHER INFORMATION: AC1

<400> SEQUENCE: 38

```
ttataatctg cctaccggcg aaaggtgcaa gctttaagtt taaagtagtg ttttaatgtg      60
tatacggtaa acccccgta gtatatttaa cgggggtaa gggggctaac gatccttgaa      120
actcacgggg ggctaacgat atgctgtcgc ttttacggct cccgaccagc aaaatcgtat     180
tttcggtttt taataaagga gtgcataggc tttacgtgag agagctttct tcgccgtaat     240
ctagttgagg ctgttgaggt ttggggttgt ttatttaaca agtagttcta gacgtctctt     300
gaggtacttt tacccctttgg agtaaacgta cgggagtaag tcaagctccc gttcatgtta     360
acatggttgg ttgctaagaa gctggagtat aggggaaggt ccagttgtgt aaaggtaggt     420
ttgtaagtcc ctcgatttag gtcaagactg cagttcagga taaacctgtt cctgcctctg     480
tggtaggtta ccccgctcaa agtctagctg cctgctagac gagcgccgcc tgttgttagg     540
cggttactgc gaatgcggtt ccgagaattg cgtcgttcat tttgtctccg agaattacat     600
taggcccttg atcggggttt cctaaaacaa aatgtcaaag tattaaattt atcgttaaat     660
ctatcctaaa aagtcctcgg aggctaagga atataaagag ggaaagaaag aagaagaaag     720
tgagtacaag gactccttga acttctgacc caaaggctct tgcactaccc aaagcgacgc     780
gccggtacct ctggctcatc atagcagtag ctcccgctat catcctgtcc cttctgctac     840
acccgggcta gagaccctgg tgtgttgatg aatacacctg taaacctaga gtcaggtttc     900
caaatgtcgt tgctgcgtac catgttgcag taactactgc agctgggggt aatggagttc     960
gtgaagtttc ttaagtaccc ccgggtttcc ctgaccgttt cgttatggtt catgcccttc    1020
ggctaagttt aatttccgcc gtaagggtga tagaaggata cgttaggtcc tggctgtagt    1080
agtatatttc tcaaagacct gctccttttc ttggtcaggg aatttcggac ccgaaatttc    1140
ttacgttgga agtagtggga ggtgctcggt aacaagagtt cacgggtagt ttcaggttgt    1200
ggcgtggcgc ttctgatccc gggagtctgc atcctcccat ctggagctta cgccgacgag    1260
caagatagag gtatagctga cgtagttggt acctaagagc gtgtcccctt gagtagtgac    1320
gcggagttcg tttcttaccg caaaaatgga ccctttattg tttaggggag ataaagctgt    1380
agtggttggt gctgttcgcc ggtcccttgt acttggtgct gtagtagtgg gaggtctatg    1440
ccaagttggt gttgtagtcc ttccgtaacc cctaagtgtt cacaaaagag ttgaagttcc    1500
agacctgctg gaatgccgga ggctgaccag aaaagaattc tcataaattt atagttcacg    1560
agttcataaa tttatactat ccgcaataaa ggtaattgtg acatgagtct cgacaactag    1620
tacaagacat gctacataat gatttgtgtg aggttcaatg cctcgttgta cgttattttta    1680 agttggaaat aattaaacaa tgacgtagta ttttatctta cgcataaaat tcgcatcgta    1740
tgtgacctaa tctccgtacg catgtacggt atatgttgtt attgcgtaag agacatacta    1800
```

-continued

```
agagtatgaa tcgacggagg accactaata tgtgttgtac taataaatag gatttttag   1860 aggagtggtt tcggacgagg aagtaaggtc ttcctggggg ttgttgccac cgtactttga   1920
aggcgtattg agctatggat agggattcta gcaagaagtg tcaccgacat gacccgagta   1980
atagtttgta taatttttgg acaggtttca ggtaccccga taacggtatc ccggaagaca   2040
gtgcctgatt cttcttgtac tggaccaaac ataccaagac gaagaactac aaaagtaggt   2100
aggtatagaa tggattgtgt atatatctga actatgtctt ggaaaatgga tgagatacac   2160
attaagggct tggtgcgcac tgtagtgatt gtgttgcttg tgacggtcat acgaattgca   2220
gtagagcgac aagtattcta acttggaatg tacccggaag tgtcggtgcg ccttgtagtc   2280
ccgaaaactt gtaagacatg taagacccga aagccatgta cccggccttg caggtactag   2340
ctgcgaacaa acacggaacc tgttacccct gtcgtcgtgc cgacgacttg cccgacagct   2400
tcaagtcgga agctgcgtgg aagctctgcc ctcaccttta ctaatatagc cgccctgcga   2460
agctgtatta gtgcccgagc ctagtgtggc tactctagtg cctgatctag caccgggttt   2520
cataacccga gcatccaaag gaggttccgg acgtttataa attatcgttc gtatgtcgct   2580
tttggcacgt gtctgagccc cttgagtaag ttgttaccta gggtgtacaa ctgtgcgagg   2640
tgatgaagcg ctgcttcaga tattgctgta ttttgtttat agatccgaaa gtgcgcactt   2700
atactgaccg gctgtcgttg tgcacgcacc cctggtgaaa gaaaatgccc gcgccagtag   2760
gttaccccag gtggatgaaa cagcccgcgc cggtaggcca                        2800

<210> SEQ ID NO 39
<211> LENGTH: 183
<212> TYPE: DNA
<213> ORGANISM: Artificial Sequence
<220> FEATURE:
<223> OTHER INFORMATION: SACMV AC1_Target DNA gene region_reverse
<220> FEATURE:
<221> NAME/KEY: misc_feature
<222> LOCATION: (1)..(183)
<223> OTHER INFORMATION: SACMV AC1_Target DNA gene region_reverse

<400> SEQUENCE: 39
gagctttctt cgccgtaatc tagttgaggc tgttgaggtt tggggttgtt tatttaacaa     60
gtagttctag acgtctcttg aggtactttt accccttgga gtaaacgtac gggagtaagt    120
caagctcccg ttcatgttaa catggttggt tgctaagaag ctggagtata ggggaaggtc    180
cag                                                                  183

<210> SEQ ID NO 40
<211> LENGTH: 183
<212> TYPE: DNA
<213> ORGANISM: Artificial Sequence
<220> FEATURE:
<223> OTHER INFORMATION: SACMV AC1_Target gene sequence_modified_reverse
<220> FEATURE:
<221> NAME/KEY: misc_feature
<222> LOCATION: (1)..(183)
<223> OTHER INFORMATION: SACMV AC1_Target gene sequence_modified_reverse

<400> SEQUENCE: 40
gagttttttt tgttgtaatt tagttgaggt tgttgaggtt tggggttgtt tatttaataa     60
gtagttttag atgtttttttg aggtattttt atttttgga gtaaatgtat gggagtaagt    120
taagtttttg tttatgttaa tatggttggt tgttaagaag ttggagtata ggggaaggtt    180
tag                                                                  183
```

```
<210> SEQ ID NO 41
<211> LENGTH: 2800
<212> TYPE: DNA
<213> ORGANISM: South African cassava mosaic virus
<220> FEATURE:
<221> NAME/KEY: misc_feature
<222> LOCATION: (1)..(2800)
<223> OTHER INFORMATION: AC1

<400> SEQUENCE: 41
aatattagac ggatggccgc tttccacgtt cgaaattcaa atttcatcac aaaattacac     60
atatgccatt tgggggcat catataaatt gccccccatt ccccgattg ctaggaactt      120 tgagtgcccc ccgattgcta tacgacagcg aaaatgccga gggctggtcg ttttagcata    180
aaagccaaaa attatttcct cacgtatccg aaatgcactc tctcgaaaga agcggcatta    240
gatcaactcc gacaactcca aaccccaaca aataaattgt tcatcaagat ctgcagagaa    300
ctccatgaaa atggggaacc tcatttgcat gccctcattc agttcgaggg caagtacaat    360
tgtaccaacc aacgattctt cgacctcata tccccttcca ggtcaacaca tttccatcca    420
aacattcagg gagctaaatc cagttctgac gtcaagtcct atttggacaa ggacggagac    480
accatccaat ggggcgagtt tcagatcgac ggacgatctg ctcgcggcgg acaacaatcc    540
gccaatgacg cttacgccaa ggctcttaac gcagcaagta aaacagaggc tcttaatgta    600
atccgggaac tagccccaaa ggattttgtt ttacagtttc ataatttaaa tagcaattta    660
gataggattt ttcaggagcc tccgattcct tatatttctc cctttctttc ttcttctttc    720
actcatgttc ctgaggaact tgaagactgg gtttccgaga acgtgatggg tttcgctgcg    780
cggccatgga gaccgagtag tatcgtcatc gagggcgata gtaggacagg gaagacgatg    840
tgggcccgat ctctgggacc acacaactac ttatgtggac atttggatct cagtccaaag    900
gtttacagca acgacgcatg gtacaacgtc attgatgacg tcgacccccca ttacctcaag    960 cacttcaaag aattcatggg ggcccaaagg gactggcaaa gcaataccaa gtacgggaag   1020
ccgattcaaa ttaaaggcgg cattcccact atcttcctat gcaatccagg accgacatca   1080
tcatataaag agtttctgga cgaggaaaag aaccagtccc ttaaagcctg gcttttaaag   1140
aatgcaacct tcatcaccct ccacgagcca ttgttctcaa gtgccatca agtccaaca    1200 ccgcaccgcg aagactaggg ccctcagacg taggagggta gacctcgaat gcggctgctc   1260
gttctatctc catatcgact gcatcaacca tggattctcg cacaggggaa ctcatcactg   1320
cgcctcaagc aaagaatggc gttttttacct gggaaataac aaatcccctc tatttcgaca   1380
tcaccaacca cgacaagcgg ccagggaaca tgaaccacga catcatcacc ctccagatac   1440
ggttcaacca caacatcagg aaggcattgg ggattcacaa gtgttttctc aacttcaagg   1500
tctggacgac cttacggcct ccgactggtc ttttcttaag agtatttaaa tatcaagtgc   1560
tcaagtattt aaatatgata ggcgttattt ccattaacac tgtactcaga gctgttgatc   1620
atgttctgta cgatgtatta ctaaacacac tccaagttac ggagcaacat gcaataaaat   1680 tcaacccttta ttaatttgtt actgcatcat aaaaatagat gcgtattta agcgtagcat   1740 acactggatt agaggcatgc gtacatgcca tatacaacaa taacgcattc tctgtatgat   1800
tctcatactt agctgcctcc tggtgattat acacaacatg attatttatc ctaaaaaatc   1860
tcctcaccaa agcctgctcc ttcattccag aaggaccccc aacaacggtg gcatgaaact   1920
tccgcataac tcgataccta tccctaagat cgttcttcac agtggctgta ctgggctcat   1980
tatcaaacat attaaaaacc tgtccaaagt ccatggggct attgccatag gccttctgt    2040 cacggactaa gaagaacatg acctggtttg tatggttctg cttcttgatg ttttcatcca   2100
```

```
tccatatctt acctaacaca tatatagact tgatacagaa ccttttacct actctatgtg    2160
taattcccga accacgcgtg acatcactaa cacaacgaac actgccagta tgcttaacgt    2220
catctcgctg ttcataagat tgaaccttac atgggccttc acagccacgc ggaacatcag    2280
ggcttttgaa cattctgtac attctgggct ttcggtacat gggccggaac gtccatgatc    2340
gacgcttgtt tgtgccttgg acaatgggga cagcagcacg ctgctgaac gggctgtcga     2400 agttcagcct tcgacgcacc ttcgagacgg gagtggaaat gattatatcg gcgggacgct    2460
tcgacataat cacgggctcg gatcacaccg atgagatcac ggactagatc gtggcccaaa    2520
gtattgggct cgtaggtttc ctccaaggcc tgcaaatatt taatagcaag catacagcga    2580
aaaccgtgca cagactcggg gaactcattc aacaatggat cccacatgtt gacacgctcc    2640
actacttcgc gacgaagtct ataacgacat aaaacaaata tctaggcttt cacgcgtgaa    2700
tatgactggc cgacagcaac acgtgcgtgg ggaccacttt cttttacggg cgcggtcatc    2760
caatggggtc cacctacttt gtcgggcgcg gccatccggt                          2800

<210> SEQ ID NO 42
<211> LENGTH: 183
<212> TYPE: DNA
<213> ORGANISM: Artificial Sequence
<220> FEATURE:
<223> OTHER INFORMATION: SACMV AC1_Target DNA gene
      region_complement_reverse
<220> FEATURE:
<221> NAME/KEY: misc_feature
<222> LOCATION: (1)..(183)
<223> OTHER INFORMATION: SACMV AC1_Target DNA gene
      region_complement_reverse

<400> SEQUENCE: 42
ctcgaaagaa gcggcattag atcaactccg acaactccaa accccaacaa ataaattgtt     60
catcaagatc tgcagagaac tccatgaaaa tggggaacct catttgcatg ccctcattca    120
gttcgagggc aagtacaatt gtaccaacca acgattcttc gacctcatat ccccttccag    180
gtc                                                                  183

<210> SEQ ID NO 43
<211> LENGTH: 2800
<212> TYPE: RNA
<213> ORGANISM: South African cassava mosaic virus
<220> FEATURE:
<221> NAME/KEY: misc_feature
<222> LOCATION: (1)..(2800)
<223> OTHER INFORMATION: AC1 RNA

<400> SEQUENCE: 43
accggauggc cgcgcccgac aaaguaggug daccccauug gaugaccgcg cccguaaaag     60
aaaguggucc ccacgcacgu guugcugucg gccagucaua uucacgcgug aaagccuaga    120
uauuuguuuu augucguuau agacuucguc gcgaaguagu ggagcguguc aacaugggg     180 auccauuguu gaaugaguuc cccgagcucu ugcacgguuu ucgcguauau cuugcuauua    240
aauauuugca ggccuuggag gaaaccuacg agcccaauac uuugggccac gaucuagucc    300
gugaucucau cggugugauc cgagcccgug auuaugucga agcguccgc cgauauaauc     360 auuuccacuc ccgucucgaa ggugcgucga aggcugaacu ucgacagccc guucagcagc    420
cgugcugcug uccccauugu ccaaggcaca aacaagcguc gaucauggac guuccggccc    480
auguaccgaa agcccagaau guacagaaug uucaaaagcc cugauguucc gcguggcugu    540
gaaggcccau guaagguuca aucuuaugaa cagcgagaug acguuaagca uacuggcagu    600
```

```
guucguugug uuagugaugu cacgcguggu ucgggaauua cacauagagu agguaaaagg    660
uucuguauca agucuauaua uguguuaggu aagauaugga uggaugaaaa caucaagaag    720
cagaaccaua caaaccaggu caugucuuc uuaguccgug acagaaggcc cuauggcaau    780
agccccaugg acuuuggaca gguuuuuaau auguugaua augagcccag uacagccacu    840
gugaagaacg aucuuaggga uagguaucga guuaugcgga aguuucaugc caccguuguu    900 gggggucccuu cuggaaugaa ggagcaggcu uggugagga gauuuuuag gauaaauaau    960 cauguugugu auaaucacca ggaggcagcu aaguaugaga aucauacaga gaaugcguua   1020
uuguuguaua uggcauguac gcaugccucu aauccagugu augcuacgcu uaaaauacgc   1080
aucuauuuuu augaugcagu aacaaauuaa uaaagguuga auuuuauugc auguugcucc   1140
guaacuugga gguguuuag uaauacaucg uacagaacau gaucaacagc ucgaguaca    1200 guguuaaugg aaauaacgcc uaucauauuu aaauacuuga gcacuugaua uuuaaauacu   1260
cuuaagaaaa gaccagucgg aggccguaag gucguccaga ccuugaaguu gagaaaacac   1320
uguguaaucc ccaaugccuu ccugauguug ugguugaacc guaucuggag ggugaugaug   1380 ucggguuca uguccccugg ccgcuugucg ugguggguga ugucgaaaua gagggggauuu   1440 guuauuuccc agguaaaaac gccauucuuu gcuugaggcg cagugaugag uucccccugug   1500 cgagaauccg agaauccca ugguugaugc agucgauaug gagauagaac gagcagccgc auucgagguc   1560
uacccuccua cgucugaggg cccagucuu cgcggugcgg uguuggacuu ugaugggcac   1620
uugagaacaa uggcucgugg aggguugauga agguugcauu cuuuaaagcc caggcuuuaa   1680
gggacugguu cuuuuccucg uccagaaacu cuuuauauga ugaugucggu ccuggauugc   1740
auaggaagau aguggggaaug ccgccuuuaa uuugaaucgg cuucccgauc uugguauugc   1800
uuugccaguc ccuuugggcc cccaugaauu cuuugaagug cuugagguaa uggggucgga   1860
cgucaucaau gacguugac caugcgucgu ugcuguaaac cuuggacugg agauccaaau   1920
guccacauaa guaguugugu ggcccagag aucgggccca caucgucuuc ccuguccuac   1980
uaucgcccuc gaugacgaua cuacucggu cucauggcg cgcagcgaaa cccaucacgu   2040
ucucggaaac ccagucuuca aguuccucag gaacaugagu gaaagaagaa gaaagaaagg   2100
gagaaauaua aggaaucgga ggccccugaa aaauccuauc uaaauugcua uuuaaauuau   2160
gaaacuguaa aacaaaaaucc uuuggggcua guucccggau acauuaaga gccucuguuu   2220 uacuugcugc guuaagagcc uuggcguaag cgucauuggc ggauuguugu ccgccgcgag   2280
cagaucgucc gucgaucuga aacucgcccc auuggauggu gucccgucc uuguccaaau   2340 aggacuugac gucagaacug gauuuagcuc ccugaauguu uggaauggaaa uguuguugacc   2400 uggaagggga uaugaggucg aagaaucguu gguuggacua auuguacuug cccucgaacu   2460 gaaugaggge augcaaauga gguucccau uuucauggag uucucugcag aucuugauga   2520
acaauuuauu uguuggggu uggaguuguc ggaguugauc uaaugccgcu ucuuucgaga   2580
gagugcauuu cggauacgug aggaaauaau uuuuggcuuu uaugcuaaaa cgaccagccc   2640
ucggcauuuu cgcugucgua uagcaaucgg ggggcacuca aguuccuag caaucggggg   2700 aaugggggggc aauuuuauaug augccccca aauggcauau uguuaauuuu gugaugaaau   2760
uugaauuucg aacguggaaa gcggccaucc gucuaauauu                        2800
```

<210> SEQ ID NO 44
<211> LENGTH: 183
<212> TYPE: RNA
<213> ORGANISM: Artificial Sequence

```
<220> FEATURE:
<223> OTHER INFORMATION: SACMV AC1_Target DNA gene region_RNA
<220> FEATURE:
<221> NAME/KEY: misc_feature
<222> LOCATION: (1)..()
<223> OTHER INFORMATION: SACMV AC1_Target DNA gene region_RNA

<400> SEQUENCE: 44
gaccuggaag gggauaugag gucgaagaau cguugguugg uacaauugua cuugcccucg      60
aacugaauga gggcaugcaa augagguucc ccauuuucau ggaguucucu gcagaucuug     120
augaacaauu uauuuguugg gguuuggagu ugucggaguu gaucuaaugc cgcuucuuuc     180
gag                                                                   183

<210> SEQ ID NO 45
<211> LENGTH: 183
<212> TYPE: RNA
<213> ORGANISM: Artificial Sequence
<220> FEATURE:
<223> OTHER INFORMATION: SACMV AC1_Target DNA gene region_modified_RNA
<220> FEATURE:
<221> NAME/KEY: misc_feature
<222> LOCATION: (1)..(183)
<223> OTHER INFORMATION: SACMV AC1_Target DNA gene region_modified_RNA

<400> SEQUENCE: 45
gauuuggaag gggauaugag guugaagaau uguggguugg uauaauugua uuuguuuug      60 aauugaauga ggguauguaa augagguuuu uuauuuuuau ggaguuuuuu guagauuuug    120
augaauaauu uauuuguugg gguuuggagu uguuggaguu gauuuaaugu uguuuuuuuu    180
gag                                                                   183

<210> SEQ ID NO 46
<211> LENGTH: 2800
<212> TYPE: RNA
<213> ORGANISM: South African cassava mosaic virus
<220> FEATURE:
<221> NAME/KEY: misc_feature
<222> LOCATION: (1)..(2800)
<223> OTHER INFORMATION: AC1 RNA

<400> SEQUENCE: 46
uggccuaccg gcgcgggcug uuucauccac cuggggguaac cuacuggcgc gggcauuuuc     60
uuucaccagg ggugcgugca caacgacagc cggucaguau aagugcgcac uuucggaucu    120
auaaacaaaa uacagcaaua ucugaagcag cgcuucauca ccucgcacag uuguacaccc    180
uagguaacaa cuuacucaag gggcucagac acgugccaaa agcgacauac gaacgauaau    240
uuauaaacgu ccggaaccuc cuuuggaugc ucggguuaug aaacccggug cuagaucagg    300
cacuagagua gccacacuag gcucgggcac uaauacagcu ucgcagggcg gcuauauuag    360
uaaaggugag ggcagagcuu ccacgcagcu uccgacuuga agcugucggg caagucgucg    420
gcacgacgac aggggguaaca gguuccgugu uguuccgcag cuaguaccug caaggccggg    480
uacauggcuu ucgggucuua caugucuuac aaguuuucgg gacuacaagg cgcaccgaca    540
cuuccgggua cauuccaagu uagaauacuu gucgcucuac ugcaauucgu ugaccguca    600 caagcaacac aaucacuaca gugcgcacca agcccuuaau guguaucuca uccauuuucc    660
aagacauagu ucagauauau acacaauccc uucuauaccu accucuuuu guaguucuuc    720 gucuugguau guuuggucca guacaagaag aaucaggcac ugucuuccgg gauaccguua    780 ucggggguacc ugaaaccugu ccaaaaauua uacaaacuau uacucgggguc augucgguga    840 cacuucuugc uagaaucccu auccauagcu caauacgccu ucaaaguacg guggcaacaa    900
```

```
cccccaggaa gaccuuacuu ccucguccga aaccacuccu cuaaaaaauc cuauuuauua      960
guacaacaca uauuaguggu ccuccgucga uucauacucu uaguaugucu cuuacgcaau     1020
aacaacauau accguacaug cguacggaga uuaggucaca uacgaugcga auuuuaugcg     1080
uagauaaaaa uacuacguca uuguuuaauu auuccaacu uaaaauaacg uacaacgagg      1140
cauugaaccu cacacaaauc auuauguagc augucuugua cuaguugucg agacucaugu     1200
cacaauuacc uuuauugcgg auaguauaaa uuuaugaacu cgugaacuau aaauuuauga     1260
gaauucuuuu cuggucagcc uccggcauuc cagcaggucu ggaacuucaa cucuuuugug     1320
aacacuuagg gguuacggaa ggacuacaac accaacuugg cauagaccuc ccacuacuac     1380
agcaccaagu acaagggacc ggcgaacagc accaaccacu acagcuuuau cuccccuaaa     1440
caauaaaggg uccauuuuug cgguaagaaa cgaacuccgc gucacuacuc aaggggacac     1500
gcucuuaggu accaacuacg ucagcuauac cucuaucuug cucgucggcg uaagcuccag     1560
augggaggau gcagacuccc gggaucagaa gcgccacgcc acaaccugaa acuacccgug     1620
aacucuuguu accgagcacc ucccacuacu ccaacguaa gaaauuucgg guccgaaauu      1680
cccugaccaa gaaaaggagc aggucuuuga gaaauauacu acuacagcca ggaccuaacg     1740
uauccuucua ucacccuuac ggcggaaauu aaacuuagcc gaagggcaug aaccauaacg     1800
aaacggucag ggaaacccgg ggguacuaaa gaaacuucac gaacuccauu accccagcu     1860 gcaguaguua cugcaacaug uacgcagca acgacauuug gaaaccugac ucuagguuua     1920 caggguauu caucaacaca ccagggucuc uagcccgggu guagcagaag ggacaggaug     1980
auagcgggag cuacugcuau gaugagccag agguaccggc gcgucgcuuu ggguagugca     2040
agagccuuug ggucagaagu ucaaggaguc cuugacuaca cuuucuucuu cuuucuuucc     2100
cucuuuauau uccuuagccu ccgaggacuu uuuaggauag auuuaacgau aaauuuaaua     2160
cuuugacauu uuguuuagg aaccccgau caagggccua auguaauucu cggagacaaa      2220
augaacgacg caauucucgg aaccgcauuc gcaguaaccg ccuaacaaca ggcggcgcuc     2280
gucuagcagg cagcuagacu uugagcgggg uaaccuacca cagaggcagg aacagguuua     2340
uccugaacug cagucuugac cuaaaucgag ggacuuacaa accuaccuuu acacaacugg     2400 accuucccu auacccagc uucuuagcaa ccaaccaugu uaacaugaac gggagcuuga      2460
cuuacucccg uacguuuacu ccaaggggua aaguaccuc aagagacguc uagaacuacu      2520
uguuaaauaa acaaccccaa accucaacag cccuaacuag auuacggcga agaaagcucu     2580
cucacguaaa gccaugcac uccuuuauua aaaaccgaaa auacgauuuu gcuggucggg      2640
agccguaaaa gcgacagcau aucguuagcc ccccgugagu uucaaggauc guuagccccc     2700 uuacccccg uuaaauauac uacggggggu uuaccguaua cacauuaaaa cacuacuuua      2760
aacuuaaagc uugcaccuuu cgccgguagg cagauuauaa                           2800
```

<210> SEQ ID NO 47
<211> LENGTH: 183
<212> TYPE: RNA
<213> ORGANISM: Artificial Sequence
<220> FEATURE:
<223> OTHER INFORMATION: SACMV AC1_Target gene region_complement_RNA
<220> FEATURE:
<221> NAME/KEY: misc_feature
<222> LOCATION: (1)..(183)
<223> OTHER INFORMATION: SACMV AC1_Target DNA gene region_modified_RNA

<400> SEQUENCE: 47

```
cuggaccuuc cccuauacuc cagcuucuua gcaaccaacc auguuaacau gaacgggagc     60
```

-continued

| | |
|---|---|
| uugacuuacu cccguacguu uacuccaagg gguaaaagua ccucaagaga cgucuagaac | 120 |
| uacuuguuaa auaaacaacc ccaaaccuca acagccucaa cuagauuacg gcgaagaaag | 180 |
| cuc | 183 |

<210> SEQ ID NO 48
<211> LENGTH: 2800
<212> TYPE: RNA
<213> ORGANISM: South African cassava mosaic virus
<220> FEATURE:
<221> NAME/KEY: misc_feature
<222> LOCATION: (1)..(2800)
<223> OTHER INFORMATION: AC1 RNA

<400> SEQUENCE: 48

| | |
|---|---|
| uuauaaucug ccuaccggcg aaaggugcaa gcuuuaaguu uaaaguagug uuuuaaugug | 60 |
| uauacgguaa accccccgua guauauuuaa cgggggguaa gggggcuaac gauccuugaa | 120 |
| acucacgggg ggcuaacgau augcugucgc uuuuacggcu cccgaccagc aaaaucguau | 180 |
| uuucgguuuu uaauaaagga gugcauaggc uuuacgugag agagcuuucu ucgccguaau | 240 |
| cuaguugagg cuguugaggu uuggguugu uauuuaaca aguaguucua gacgucucuu | 300 |
| gagguacuuu uaccccuugg aguaaacgua cgggaguaag ucaagccccc guucauguua | 360 |
| acaugguugu uugcuaagaa gcuggaguau aggggaaggu ccaguugugu aaaggguaggu | 420 |
| uuguaagucc cucgauuuag gucaagacug caguucagga uaaaccuguu ccugccucug | 480 |
| ugguagguua ccccgcucaa agucuagcug ccugcuagac gagcgccgcc uguuguuagg | 540 |
| cgguuacugc gaaugcgguu ccgagaauug cgucguucau uuugucuccg agaauuacau | 600 |
| uaggcccuug aucggguuu ccuaaaacaa aauguvcaaag uauuaaauuu aucguuaaau | 660 |
| cuauccuaaa aagccucgg aggcuaagga auauaaagag ggaagaaag aagaagaaag | 720 |
| ugaguacaag gacuccuuga acuucugacc caaaggcucu ugcacuaccc aaagcgacgc | 780 |
| gccgguaccu cuggcucauc auagcaguag ucccgcuau cauccugucc cuucugcuac | 840 |
| acccgggcua gagacccugg uguguugaug aauuacaccug uaaaccuaga gucagguuuc | 900 |
| caaaugucgu ugcugcguac cauguugcag uaacuacugc agcuggggu aauggaguuc | 960 |
| gugaaguuuc uuaaguaccc ccggguuucc cugaccguuu cguuaugguu caugcccuuc | 1020 |
| ggcuaaguuu aauuccgcc guaaggguga uagaaggaua cguuaggucc uggcuguagu | 1080 |
| aguauauuuc ucaaagaccu gcuccuuuuc uggucaggg aauucggac ccgaaauuuc | 1140 |
| uuacguugga aguaguggga ggugcucggu aacaagaguu cacggguagu ucagguugu | 1200 |
| ggcguggcgc uucugauccc gggagucugc auccucccau cuggagcuua cgccgacgag | 1260 |
| caagauagag guauagcuga cguaguuggu accuaagagc guguccccuu gaguagugac | 1320 |
| gcggaguucg uuucuuaccg caaaaaugga cccuuuauug uuuaggggag auaaagcugu | 1380 |
| agugguuggu gcuguucgcc ggucccuguu acuggugcu uaguagugg gaggucuaug | 1440 |
| ccaaguuggu guuguaguc uuccguaacc ccuaagucguu cacaaaagag uugaaguucc | 1500 |
| agaccugcug gaaugccgga ggcugaccag aaaagaauuc ucauaaauuu auaguucacg | 1560 |
| aguucauaaa uuuauacuau ccgcaauaaa gguaauugug acaugagucu cgacaacuag | 1620 |
| uacaagacau gcuacauaau gauuugugug agguucaaug cccgcuugua cguuauuuua | 1680 |
| aguggaaau aauuaaacaa ugacguagua uuuuuaucua cgcauaaaau ucgcaucgua | 1740 |
| ugugaccuua ucuccguacg cauguacggu auaugugu auugcguaag agacauacua | 1800 |
| agaguaugaa ucgacggagg accacuaaua uguguuguac uaauaaauag gauuuuuag | 1860 |

```
aggagugguu ucggacgagg aaguaagguc uuccuggggg uuguugccac cguacuuuga      1920
aggcguauug agcuauggau agggauucua gcaagaagug ucaccgacau gacccgagua      1980
auaguuugua uaauuuuugg acagguuuca gguaccccga uaacgguauc ccggaagaca      2040
gugccugauu cuucuuguac uggaccaaac auaccaagac gaagaacuac aaaaguaggu      2100
agguauagaa uggauugugu auauaucuga acuaugucuu ggaaaaugga ugagauacac      2160
auuaagggcu uggugcgcac uguagugauu guguugcuug ugacggucau acgaauugca      2220
guagagcgac aaguauucua acuuggaaug uacccggaag ugucgugcg ccuuguaguc       2280 ccgaaaacuu guaagacaug uaagacccga aagccaugua cccggccuug cagguacuag     2340
cugcgaacaa acacggaacc uguuccccu gucgucgugc cgacgacuug cccgacagcu      2400
ucaagucgga agcugcgugg aagcucugcc cucaccuuua cuaauauagc cgcccugcga     2460
agcuguauua gugcccgagc cuagugugggc uacucuagug ccugaucuag caccggguuu   2520
cauaacccga gcauccaaag gagguuccgg acguuuauaa auuacguuc guaugucgcu      2580 uuuggcacgu gucugagccc cuugaguaag uuguuaccua ggguguacaa cugugcgagg    2640
ugaugaagcg cugcuucaga uauugcugua uuuuguuuau agauccgaaa gugcgcacuu   2700
auacugaccg gcugucguug ugcacgcacc ccuggugaaa gaaaaugccc gcgccaguag    2760
guuaccccag guggaugaaa cagcccgcgc cgguaggcca                           2800

<210> SEQ ID NO 49
<211> LENGTH: 183
<212> TYPE: RNA
<213> ORGANISM: Artificial Sequence
<220> FEATURE:
<223> OTHER INFORMATION: SACMV AC1_Target gene region_reverse_RNA
<220> FEATURE:
<221> NAME/KEY: misc_feature
<222> LOCATION: (1)..(183)
<223> OTHER INFORMATION: SACMV AC1_Target gene region_reverse_RNA

<400> SEQUENCE: 49
gagcuuucuu cgccguaauc uaguugaggc uguugagguu uggggguugu uauuuaacaa       60
guaguucuag acgucucuug agguacuuuu accccuugga guaaacguac gggaguaagu    120
caagcucccg uucauguuaa caugguuggu ugcuaagaag cuggaguaua ggggaagguc    180
cag                                                                  183

<210> SEQ ID NO 50
<211> LENGTH: 183
<212> TYPE: RNA
<213> ORGANISM: Artificial Sequence
<220> FEATURE:
<223> OTHER INFORMATION: SACMV AC1_Target DNA gene
      region_modified_reverse_RNA
<220> FEATURE:
<221> NAME/KEY: misc_feature
<222> LOCATION: (1)..(183)
<223> OTHER INFORMATION: SACMV AC1_Target DNA gene
      region_modified_reverse_RNA

<400> SEQUENCE: 50
gaguuuuuuu uguuguaauu uaguugaggu uguugagguu uggggguugu uauuuaauaa       60
guaguuuuag auguuuuuug agguauuuuu auuuuuugga guaaauguau gggaguaagu    120
uaaguuuuug uuuauguuaa uaugguuggu uguuaagaag uuggaguaua ggggaagguu    180
uag                                                                  183
```

```
<210> SEQ ID NO 51
<211> LENGTH: 2800
<212> TYPE: RNA
<213> ORGANISM: South African cassava mosaic virus
<220> FEATURE:
<221> NAME/KEY: misc_feature
<222> LOCATION: (1)..(2800)
<223> OTHER INFORMATION: AC1 RNA

<400> SEQUENCE: 51
```

| | | | | | |
|---|---|---|---|---|---|
| aauauuagac | ggauggccgc | uuccacguu | cgaaauucaa | auucaucac | aaaauuacac | 60 |
| auaugccauu | uggggggcau | cauauaaauu | gccccccauu | ccccgauug | cuaggaacuu | 120 |
| ugagugcccc | ccgauugcua | uacgacagcg | aaaaugccga | gggcuggucg | uuuuagcaua | 180 |
| aaagccaaaa | auuauuuccu | cacguauccg | aaaugcacuc | ucucgaaaga | agcggcauua | 240 |
| gaucaacucc | gacaacucca | aaccccaaca | aauaaauugu | caucaagau | cugcagagaa | 300 |
| cuccaugaaa | augggaacc | ucauuugcau | gcccucauuc | aguucgaggg | caaguacaau | 360 |
| uguaccaacc | aacgauucuu | cgaccucaua | uccccuucca | ggucaacaca | uuccaucca | 420 |
| aacauucagg | gagcuaaauc | caguucugac | gucaaguccu | auuuugacaa | ggacggagac | 480 |
| accauccauu | ggggcgaguu | ucagaucgac | ggacgaucuc | cucgcggcgg | acaacaaucc | 540 |
| gccaaugacg | cuuacgccaa | ggcucuuaac | gcagcaagua | aaacagaggc | ucuuaaugua | 600 |
| auccgggaac | uagccccaaa | ggauuuguu | uuacaguuuc | auaauuaaaa | uagcaauuua | 660 |
| gauaggauuu | uucaggagcc | uccgauuccu | uauauuucuc | ccuucuuuc | uucuucuuuc | 720 |
| acucauguuc | cugaggaacu | ugaagacugg | guuccgaga | acgugauggg | uuucgcugcg | 780 |
| cggccaugga | gaccgaguag | uaucgucauc | gagggcgaua | guaggacagg | gaagacgaug | 840 |
| uggggcccgau | cucugggacc | acacaacuac | uuaugggac | auuggaucu | caguccaaag | 900 |
| guuuacagca | acgacgcaug | guacaacguc | auugaugacg | ucgaccccca | uuaccucaag | 960 |
| cacuucaaag | aauucauggg | ggcccaaagg | gacuggcaaa | gcaauaccaa | guacgggaag | 1020 |
| ccgauucaaa | uuaaaggcgg | cauucccacu | aucuuccuau | gcaauccagg | accgacauca | 1080 |
| ucauauaaag | aguuucugga | cgaggaaaag | aaccaguccc | uuaaagccug | ggcuuuaaag | 1140 |
| aaugcaaccu | ucaucacccu | ccacgagcca | uguuccuaa | gugcccauca | aguccaaca | 1200 |
| ccgcaccgcg | aagacuaggg | cccucagacg | uaggagggua | gaccucgaau | gcggcugcuc | 1260 |
| guucuaucuc | cauaucgacu | gcaucaacca | uggauucucg | cacaggggaa | ucaucacug | 1320 |
| cgccucaagc | aaagaauggc | guuuuuaccu | gggaaauaac | aaaucccuc | uauuucgaca | 1380 |
| ucaccaacca | cgacaagcgg | ccagggaaca | ugaaccacga | caucaucacc | cuccagauac | 1440 |
| gguucaacca | caacaucagg | aaggcauugg | ggauucacaa | guguuuucuc | aacuucaagg | 1500 |
| ucuggacgac | cuuacggccu | ccgacugguc | uuuucuuaag | aguauuuaaa | uaucaagugc | 1560 |
| ucaaguauuu | aaauaugaua | ggcguuauuu | ccauuaacac | uguacucaga | gcuguugauc | 1620 |
| auguucugua | cgauguauua | cuaaacacac | uccaaguuac | ggagcaacau | gcaauaaaau | 1680 |
| ucaaccuuua | uuaauuuguu | acugcaucau | aaaaauagau | gcguauuuua | agcguagcau | 1740 |
| acacuggauu | agaggcaugc | guacauggca | uauuaacaaca | uaacgcauuc | ucuguaugau | 1800 |
| ucucauacuu | agcugccucc | uggugauuau | acacaacaug | auuauuuauc | cuaaaaaauc | 1860 |
| uccucaccaa | agccugcucc | uucauccag | aaggaccccc | aacaacgguug | gcaugaaacu | 1920 |
| uccgcauaac | ucgauaccua | ucccuaagau | cguucuucac | aguggcugua | cugggcucau | 1980 |
| uaucaaacau | auuaaaaacc | uguccaaagu | ccauggggcu | auugcauag | ggccuucugu | 2040 |
| cacggacuaa | gaagaacaug | accugguuug | uaugguucug | cuucuugaug | uuuucaucca | 2100 |

-continued

```
uccauaucuu accuaacaca uauauagacu ugauacagaa ccuuuuaccu acucuaugug   2160
uaauucccga accacgcgug acaucacuaa cacaacgaac acugccagua ugcuuaacgu   2220
caucucgcug uucauaagau ugaaccuuac augggccuuc acagccacgc ggaacaucag   2280
ggcuuuugaa cauucuguac auucugggcu uucgguacau gggccggaac guccaugauc   2340
gacgcuuguu ugugccuugg acaaugggga cagcagcacg gcugcugaac gggcugucga   2400
aguucagccu ucgacgcacc uucgagacgg gaguggaaau gauuauaucg gcgggacgcu   2460
ucgacauaau cacgggcucg gaucacaccg augagaucac ggacuagauc guggcccaaa   2520
guauugggcu cguagguuuc cuccaaggcc ugcaaauauu uaauagcaag cauacagcga   2580
aaaccgugca cagacucggg gaacucauuc aacaauggau cccacauguu gacacgcucc   2640
acuacuucgc gacgaagucu auaacgacau aaaacaaaua ucuaggcuuu cacgcgugaa   2700
uaugacuggc cgacagcaac acgugcgugg ggaccacuuu cuuuuacggg cgcggucauc   2760 caauggggu c caccuacuuu gucgggcgcg gccauccggu                        2800
```

```
<210> SEQ ID NO 52
<211> LENGTH: 183
<212> TYPE: RNA
<213> ORGANISM: Artificial Sequence
<220> FEATURE:
<223> OTHER INFORMATION: SACMV AC1_Target gene
      region_complement_reverse_RNA
<220> FEATURE:
<221> NAME/KEY: misc_feature
<222> LOCATION: (1)..(183)
<223> OTHER INFORMATION: SACMV AC1_Target gene
      region_complement_reverse_RNA

<400> SEQUENCE: 52
cucgaaagaa gcggcauuag aucaacuccg acaacuccaa accccaacaa auaaauuguu     60
caucaagauc ugcagagaac uccaugaaaa uggggaaccu cauuugcaug cccucauuca    120
guucgagggc aaguacaauu guaccaacca acgauucuuc gaccucauau ccccuuccag    180
guc                                                                  183
```

```
<210> SEQ ID NO 53
<211> LENGTH: 2690
<212> TYPE: DNA
<213> ORGANISM: Maize streak virus
<220> FEATURE:
<221> NAME/KEY: misc_feature
<222> LOCATION: (1)..(2690)
<223> OTHER INFORMATION: AC1

<400> SEQUENCE: 53
accgcgcctt cttttcctgc gagggcccgg tagggaccga gcgctttgat ttaaagcctg     60
gttctgcttt gtatgattta tctaaagcag cccaatctaa agaaaccggt cccgggcact    120
ataaattgcc taacaagtgc gattcattca tggatccaca gaacgccctg tattatcagc    180
cgcgggtacc cacagcagct ccgacatccg gaggagtgcc gtggagtcgc gtaggcgagg    240
tagctatttt gagctttgtt gcattgattt gcttttacct gctttacctt tgggtgctga    300
gagaccttat cttagttctg aaggctcgac aaggcagatc cacggaggag ctgatatttg    360
gtggacaagc tgtggatagg agcaacccta tccctaatct accttcacca ccaagtcagg    420
gcaatcccgg gccatttgtt ccaggcacgg gataagcaat cagccatgtc cacgtccaag    480
aggaagcggg gagatgattc gaattggaat aagcgggtgc ctaagaagaa gccatcttca    540
gctgggctga agagggctgg aagcaaggcc gataggccat ccctccaaat ccagacactc    600
```

```
cagcatgctg ggaccaccat gataactgtc ccatccggag gagtatgtga cctcatcaac    660
acctatgccc gaggatctga cgagggcaac cgccacacca gcgagactct gacgtacaag    720
atcgccgtcg actaccactt cgttgccgac gcggctgcct gccgctactc caacaccgga    780
accggtgtaa tgtggctggt gtatgacacc actcccggcg acaagctcc gaccccgcaa     840 actatatttg cctaccctga cacgctaaaa gcgtggccgg ccacatggaa agtgagccgg    900
gagctgtgtc atcgcttcgt ggtgaaacgg cgatggttgt caacatgga gaccgacggt     960 cggattggtt cggatatccc tccctcgaat acaagttgga agccttgcaa gcgcaacatc   1020
tacttccaca agttcacgag tgggttggga gtgagaacgc agtggaagaa tgtaacggac   1080
ggaggagttg gtgccatcca gagaggagct ctgtacatgg tcattgcccc aggcaatggc   1140
cttactttta ctgcccatgg gcagacccgt ctgtacttta agagtgttgg caaccagtaa    1200
tgaataaaaa ctcccgtttt attatatttg atgaatgctg aaagcttaca ttaatatgtc   1260
gtgcgatggc acgaaaaaac acacgcaaac aatacagggg ggtagtcggc gggcggctaa   1320
gggtggtgct cggcgggcag aacatcgaaa aatcaagatc tatatgaatt acacttcctc   1380
cgtaggagga agcacagggg gagaaatacca cttctccccc ggcgacataa tgtaaatgac   1440
gcagtttgcc tcgaaatact ccagctgccc tggagtcatt tccttcatcc aatcttcatc   1500
cgagttggcg aggattattg taggcttaga cttcttctgc acctttttct tcttaccata   1560
cttggggttt acaatgaaat ccctctgaca gccaactaac tgtttccaac aaggacagaa   1620
tttaaacgga atatcatcta cgatgttgta gattgcgtct tcgttgtatg aagaccaatc   1680
aacattattt tgccagtaat tatgaacccc taggcttctg gcccaagtag attttccggt   1740
tcttgttggg ccgacgatgt agaggctctg ctttcttgat cttcatctg atgactggat    1800 acagaatcca tccattggag gtcagaaatt gcatcctcga gggtataaca ggtaggttga   1860
aggagcatgt aagcttcggg actaacctgg aagatgttag gctggagcca atcgttgatt   1920
gactcattac aaagtaaatc aggtgaggag ggtggatgag gattggtgaa ctcttcctga   1980
atctcaggaa aaagcttatt tgcagagtat tcaaaatact gcaattttgt ggaccaatca   2040
aaggggagct ctttctggat catggagagg tactcttctt tggaggtagc gtgtgaaata   2100
atgtctcgca ttatttcatc tttagaaggc ttttttttcct ttacctctga atcagatttt   2160
cctaggaagg gggacttcct aggaatgaaa gtacctctct caaacacagc cagaggttcc   2220
ttgagaatgt aatccctcac tctgttaact gacttggcac tctgaatatt tgggtgaaac   2280
ccatttatat caaagaacct tgagtcagat atccttatcg gcttctctgg ctgaagcaat   2340
gcatgtaaat gcaaacttcc atctttatgt gcctctcggg cacatagaat atatttggga   2400
atccaacgaa cgacgagctc ccagatcatc tgacaggcga tttcaggatt ttctggacac   2460
tttggatagg ttaggaacgt gttagcgttc ctgtgtgaga actgacggtt ggatgaggag   2520
gaggccatag ccgacgacgg aggttgaggc tgagggatgg cagactggga gctccaaact   2580
ctatagtata cccgtgcgcc ttcgaaatcc gccgctccat tgtcttatag tggttgtaaa   2640
tgggccggac cgggccggcc cagcaggaaa agaaggcgcg cactaatatt             2690
```

<210> SEQ ID NO 54
<211> LENGTH: 246
<212> TYPE: DNA
<213> ORGANISM: Artificial Sequence
<220> FEATURE:
<223> OTHER INFORMATION: MSV AC1_Target gene DNA region
<220> FEATURE:
<221> NAME/KEY: misc_feature

```
<222> LOCATION: (1)..(246)
<223> OTHER INFORMATION: MSV AC1_Target gene DNA region
<400> SEQUENCE: 54
tccatccatt ggaggtcaga aattgcatcc tcgagggtat aacaggtagg ttgaaggagc 60
atgtaagctt cgggactaac ctggaagatg ttaggctgga gccaatcgtt gattgactca 120
ttacaaagta aatcaggtga ggagggtgga tgaggattgg tgaactcttc ctgaatctca 180
ggaaaaagct tatttgcaga gtattcaaaa tactgcaatt ttgtggacca atcaaagggg 240
agctct 246

<210> SEQ ID NO 55
<211> LENGTH: 246
<212> TYPE: DNA
<213> ORGANISM: Artificial Sequence
<220> FEATURE:
<223> OTHER INFORMATION: MSV AC1_Target gene DNA region_modified
<220> FEATURE:
<221> NAME/KEY: misc_feature
<222> LOCATION: (1)..(246)
<223> OTHER INFORMATION: MSV AC1_Target gene DNA region_modified
<400> SEQUENCE: 55
tttatttatt ggaggttaga aattgtattt ttgagggtat aataggtagg ttgaaggagt 60
atgtaagttt tgggattaat ttggaagatg ttaggttgga gttaattgtt gattgattta 120
ttataaagta aattaggtga ggagggtgga tgaggattgg tgaatttttt ttgaatttta 180
ggaaaaagtt tatttgtaga gtatttaaaa tattgtaatt ttgtggatta attaaagggg 240
agtttt 246

<210> SEQ ID NO 56
<211> LENGTH: 2690
<212> TYPE: DNA
<213> ORGANISM: Maize streak virus
<220> FEATURE:
<221> NAME/KEY: misc_feature
<222> LOCATION: (1)..(2690)
<223> OTHER INFORMATION: AC1

<400> SEQUENCE: 56
tggcgcggaa gaaaaggacg ctcccgggcc atccctggct cgcgaaacta aatttcggac 60
caagacgaaa catactaaat agatttcgtc gggttagatt tctttggcca gggcccgtga 120
tatttaacgg attgttcacg ctaagtaagt acctaggtgt cttgcgggac ataatagtcg 180
gcgcccatgg gtgtcgtcga ggctgtaggc ctcctcacgg cacctcagcg catccgctcc 240
atcgataaaa ctcgaaacaa cgtaactaaa cgaaaatgga cgaaatggaa acccacgact 300
ctctggaata gaatcaagac ttccgagctg ttccgtctag gtgcctcctc gactataaac 360
cacctgttcg acacctatcc tcgttgggat agggattaga tggaagtggt ggttcagtcc 420
cgttagggcc cggtaaacaa ggtccgtgcc ctattcgtta gtcggtacag gtgcaggttc 480
tccttcgccc ctctactaag cttaacctta ttcgcccacg gattcttctt cggtagaagt 540
cgacccgact tctcccgacc ttcgttccgg ctatccggta gggaggttta ggtctgtgag 600
gtcgtacgac cctggtggta ctattgacag ggtaggcctc ctcatacact ggagtagttg 660
tggatacggg ctcctagact gctcccgttg gcggtgtggt cgctctgaga ctgcatgttc 720
tagcggcagc tgatggtgaa gcaacggctg cgccgacgga cggcgatgag gttgtggcct 780
tggccacatt acaccgacca catactgtgg tgagggccgc ctgttcgagg ctggggcgtt 840
tgatataaac ggatgggact gtgcgatttt cgcaccggcc ggtgtacctt tcactcggcc 900
```

```
ctcgacacag tagcgaagca ccactttgcc gctaccaaca agttgtacct ctggctgcca    960
gcctaaccaa gcctataggg agggagctta tgttcaacct tcggaacgtt cgcgttgtag   1020
atgaaggtgt tcaagtgctc acccaaccct cactcttgcg tcaccttctt acattgcctg   1080
cctcctcaac cacggtaggt ctctcctcga gacatgtacc agtaacgggg tccgttaccg   1140
gaatgaaaat gacgggtacc cgtctgggca gacatgaaat tctcacaacc gttggtcatt   1200
acttattttt gagggcaaaa taatataaac tacttacgac tttcgaatgt aattatacag   1260
cacgctaccg tgcttttttg tgtgcgtttg ttatgtcccc ccatcagccg cccgccgatt   1320
cccaccacga gccgcccgtc ttgtagcttt ttagttctag atatacttaa tgtgaaggag   1380
gcatcctcct tcgtgtcccc ctcttatggt gaagaggggg ccgctgtatt acatttactg   1440
cgtcaaacgg agctttatga ggtcgacggg acctcagtaa aggaagtagg ttagaagtag   1500
gctcaaccgc tcctaataac atccgaatct gaagaagacg tggaaaaaga agaatggtat   1560
gaaccccaaa tgttacttta gggagactgt cggttgattg acaaaggttg ttcctgtctt   1620
aaatttgcct tatagtagat gctacaacat ctaacgcaga agcaacatac ttctggttag   1680
ttgtaataaa acggtcatta atacttgggg atccgaagac cgggttcatc taaaaggcca   1740
agaacaaccc ggctgctaca tctccgagac gaaagaacta gaaagtagac tactgaccta   1800
tgtcttaggt aggtaacctc cagtctttaa cgtaggagct cccatattgt ccatccaact   1860
tcctcgtaca ttcgaagccc tgattggacc ttctacaatc cgacctcggt tagcaactaa   1920
ctgagtaatg tttcatttag tccactcctc ccacctactc ctaaccactt gagaaggact   1980
tagagtcctt tttcgaataa acgtctcata agttttatga cgttaaaaca cctggttagt   2040
ttcccctcga gaaagaccta gtacctctcc atgagaagaa acctccatcg cacactttat   2100
tacagagcgt aataaagtag aaatcttccg aaaaaaagga aatggagact tagtctaaaa   2160
ggatccttcc ccctgaagga tccttacttt catggagaga gtttgtgtcg gtctccaagg   2220
aactcttaca ttagggagtg agacaattga ctgaaccgtg agacttataa acccactttg   2280
ggtaaatata gtttcttgga actcagtcta taggaatagc cgaagagacc gacttcgtta   2340
cgtacattta cgtttgaagg tagaaataca cggagagccc gtgtatctta tataaaccct   2400
taggttgctt gctgctcgag ggtctagtag actgtccgct aaagtcctaa aagacctgtg   2460
aaacctatcc aatccttgca caatcgcaag gacacactct tgactgccaa cctactcctc   2520
ctccggtatc ggctgctgcc tccaactccg actccctacc gtctgaccct cgaggtttga   2580
gatatcatat gggcacgcgg aagctttagg cggcgaggta acagaatatc accaacattt   2640
acccggcctg gcccggccgg gtcgtccttt tcttccgcgc gtgattataa              2690
```

<210> SEQ ID NO 57
<211> LENGTH: 246
<212> TYPE: DNA
<213> ORGANISM: Artificial Sequence
<220> FEATURE:
<223> OTHER INFORMATION: MSV AC1_Target gene DNA region_complement
<220> FEATURE:
<221> NAME/KEY: misc_feature
<222> LOCATION: (1)..(246)
<223> OTHER INFORMATION: MSV AC1_Target gene DNA region_complement

<400> SEQUENCE: 57

```
aggtaggtaa cctccagtct ttaacgtagg agctcccata ttgtccatcc aacttcctcg     60
tacattcgaa gccctgattg gaccttctac aatccgacct cggttagcaa ctaactgagt    120
aatgtttcat ttagtccact cctcccacct actcctaacc acttgagaag gacttagagt    180
```

```
cctttttcga ataaacgtct cataagtttt atgacgttaa aacacctggt tagtttcccc    240
tcgaga                                                                246

<210> SEQ ID NO 58
<211> LENGTH: 2690
<212> TYPE: DNA
<213> ORGANISM: Maize streak virus
<220> FEATURE:
<221> NAME/KEY: misc_feature
<222> LOCATION: (1)..(2690)
<223> OTHER INFORMATION: AC1

<400> SEQUENCE: 58
ttataatcac gcgcggaaga aaaggacgac ccggccgggc caggccgggt aaatgttggt     60
gatattctgt tacctcgccg cctaaagctt ccgcgtgccc atatgatatc tcaaacctcg    120
agggtcagac ggtagggagt cggagttgga ggcagcagcc gataccggag gaggagtagg    180
ttggcagtca agagtgtgtc cttgcgattg tgcaaggatt ggataggttt cacaggtctt    240
ttaggacttt agcggacagt ctactagacc ctcgagcagc aagcaaccta agggtttata    300
taagatacac gggctctccg tgtatttcta ccttcaaacg taaatgtacg taacgaagtc    360
ggtctcttcg gctattccta tagactgagt tccagaaaac tatatttacc caaagtgggt    420
ttataagtct cacggttcag tcaattgtct cactccctaa tgtaagagtt ccttggagac    480
cgacacaaac tctctccatg aaagtaagga tccttcaggg ggaaggatcc ttttagacta    540
agtctccatt tcctttttt cggaagattt ctactttatt acgctctgta ataaagtgtg     600
cgatggaggt ttcttctcat ggagaggtac taggtctttc tcgagggaa actaaccagg    660 tgttttaacg tcataaaact tatgagacgt ttattcgaaa aaggactcta agtccttctc    720
aagtggttag gagtaggtgg gaggagtgga ctaaatgaaa cattactcag ttagttgcta    780
accgaggtcg gattgtagaa ggtccaatca gggcttcgaa tgtacgagga agttggatgg    840
acaatatggg agctcctacg ttaaagactg gaggttacct acctaagaca taggtcagta    900
gtctactttc tagttctttc gtctcggaga tgtagcagcc gggttgttct tggccttta    960 gatgaacccg gtcttcggat ccccaagtat taatgaccgt tttattacaa ctaaccagaa   1020
gtatgttgct tctgcgttag atgttgtagc atctactata aggcaaattt aagacaggaa   1080
caacctttgt caatcaaccg acagtctccc taaagtaaca tttggggttc ataccattct   1140
tcttttccca cgtcttcttc agattcggat gttattagga gcggttgagc ctacttctaa   1200
cctacttcct ttactgaggt cccgtcgacc tcataaagct ccgtttgacg cagtaaatgt   1260
aatacagcgg cccctcttc accataagag ggggacacga aggaggatgc ctccttcaca   1320
ttaagtatat ctagaactaa aaagctacaa gacgggcggc tcgtggtggg aatcggcggg   1380
cggctgatgg ggggacataa caaacgcaca caaaaagca cggtagcgtg ctgtataatt   1440
acattcgaaa gtcgtaagta gtttatatta ttttgccctc aaaataagt aatgaccaac    1500 ggttgtgaga atttcatgtc tgcccagacg ggtacccgtc attttcattc cggtaacgga   1560
ccccgttact ggtacatgtc tcgaggagag acctaccgtg gttgaggagg caggcaatgt   1620
aagaaggtga cgcaagagtg agggttgggt gagcacttga acaccttcat ctacaacgcg   1680
aacgttccga aggttgaaca taagctccct ccctataggc ttggttaggc tggcagccag   1740
aggtacaact tgttggtagc ggcaaagtgg tgcttcgcta ctgtgtcgag ggccgagtga   1800
aaggtacacc ggccggtgcg aaaatcgcac agtcccatcc gttatatca aacgccccag    1860 cctcgaacag gcggccctca ccacagtatg tggtcggtgt aatgtggcca aggccacaac   1920
```

```
ctcatcgccg tccgtcggcg cagccgttgc ttcaccatca gctgccgcta gaacatgcag    1980
tctcagagcg accacaccgc caacgggagc agtctaggag cccgtatcca caactactcc    2040
agtgtatgag gaggcctacc ctgtcaatag taccaccagg gtcgtacgac ctcacagacc    2100
taaacctccc taccggatag ccggaacgaa ggtcgggaga agtcgggtcg acttctaccg    2160
aagaagaatc cgtgggcgaa taaggttaag cttagtagag gggcgaagga gaacctgcac    2220
ctgtaccgac taacgaatag ggcacggacc ttgtttaccg ggccctaacg ggactgaacc    2280
accacttcca tctaatccct atcccaacga ggataggtgt cgaacaggtg gtttatagtc    2340
gaggaggcac ctagacggaa cagctcggaa gtcttgattc tattccagag agtcgtgggt    2400
ttccatttcg tccattttcg tttagttacg ttgtttcgag ttttatcgat ggagcggatg    2460
cgctgaggtg ccgtgaggag gcctacagcc tcgacgacac ccatgggcgc cgactattat    2520
gtcccgcaag acacctaggt acttacttag cgtgaacaat ccgttaaata tcacgggccc    2580
tggccaaaga aatctaaccc gacgaaatct atttagtatg tttcgtcttg gtccgaaatt    2640
tagtttcgcg agccagggat ggcccgggag cgtcctttc ttccgcgcca                2690

<210> SEQ ID NO 59
<211> LENGTH: 246
<212> TYPE: DNA
<213> ORGANISM: Artificial Sequence
<220> FEATURE:
<223> OTHER INFORMATION: MSV AC1_Target gene DNA region_reverse
<220> FEATURE:
<221> NAME/KEY: misc_feature
<222> LOCATION: (1)..(246)
<223> OTHER INFORMATION: MSV AC1_Target gene DNA region_reverse

<400> SEQUENCE: 59
tctcgagggg aaactaacca ggtgttttaa cgtcataaaa cttatgagac gtttattcga     60
aaaaggactc taagtccttc tcaagtggtt aggagtaggt gggaggagtg gactaaatga    120
aacattactc agttagttgc taaccgaggt cggattgtag aaggtccaat cagggcttcg    180
aatgtacgag gaagttggat ggacaatatg ggagctccta cgttaaagac tggaggttac    240
ctacct                                                               246

<210> SEQ ID NO 60
<211> LENGTH: 246
<212> TYPE: DNA
<213> ORGANISM: Artificial Sequence
<220> FEATURE:
<223> OTHER INFORMATION: MSV AC1_Target gene DNA region_modified_reverse
<220> FEATURE:
<221> NAME/KEY: misc_feature
<222> LOCATION: (1)..(246)
<223> OTHER INFORMATION: MSV AC1_Target gene DNA region_modified_reverse

<400> SEQUENCE: 60
ttttgagggg aaattaatta ggtgttttaa tgttataaaa tttatgagat gtttatttga     60
aaaaggattt taagtttttt ttaagtggtt aggagtaggt gggaggagtg gattaaatga    120
aatattattt agttagttgt taattgaggt tggattgtag aaggttttaat tagggttttg    180 aatgtatgag gaagttggat ggataatatg ggagttttta tgttaaagat tggaggttat    240
ttattt                                                               246

<210> SEQ ID NO 61
<211> LENGTH: 2690
<212> TYPE: DNA
<213> ORGANISM: Maize streak virus
```

<220> FEATURE:
<221> NAME/KEY: misc_feature
<222> LOCATION: (1)..(2690)
<223> OTHER INFORMATION: AC1

<400> SEQUENCE: 61

| | | | | | |
|---|---|---|---|---|---|
| aatattagtg | cgcgccttct | tttcctgctg | ggccggcccg | gtccggccca | tttacaacca | 60 |
| ctataagaca | atggagcggc | ggatttcgaa | ggcgcacggg | tatactatag | agtttggagc | 120 |
| tcccagtctg | ccatccctca | gcctcaacct | ccgtcgtcgg | ctatggcctc | ctcctcatcc | 180 |
| aaccgtcagt | tctcacacag | gaacgctaac | acgttcctaa | cctatccaaa | gtgtccagaa | 240 |
| aatcctgaaa | tcgcctgtca | gatgatctgg | gagctcgtcg | ttcgttggat | tcccaaatat | 300 |
| attctatgtg | cccgagaggc | acataaagat | ggaagtttgc | atttacatgc | attgcttcag | 360 |
| ccagagaagc | cgataaggat | atctgactca | aggttctttg | atataaatgg | gtttcaccca | 420 |
| aatattcaga | gtgccaagtc | agttaacaga | gtgagggatt | acattctcaa | ggaacctctg | 480 |
| gctgtgtttg | agagaggtac | tttcattcct | aggaagtccc | ccttcctagg | aaaatctgat | 540 |
| tcagaggtaa | aggaaaaaaa | gccttctaaa | gatgaaataa | tgcgagacat | tatttcacac | 600 |
| gctacctcca | agaagagta | cctctccatg | atccagaaag | agctccccctt | tgattggtcc | 660 |
| acaaaattgc | agtattttga | atactctgca | aataagcttt | ttcctgagat | tcaggaagag | 720 |
| ttcaccaatc | ctcatccacc | ctcctcacct | gatttacttt | gtaatgagtc | aatcaacgat | 780 |
| tggctccagc | ctaacatctt | ccaggttagt | cccgaagctt | acatgctcct | tcaacctacc | 840 |
| tgttataccc | tcgaggatgc | aatttctgac | ctccaatgga | tggattctgt | atccagtcat | 900 |
| cagatgaaag | atcaagaaag | cagagcctct | acatcgtcgg | cccaacaaga | accggaaaat | 960 |
| ctacttgggc | cagaagccta | ggggttcata | attactggca | aaataatgtt | gattggtctt | 1020 |
| catacaacga | agacgcaatc | tacaacatcg | tagatgatat | tccgtttaaa | ttctgtcctt | 1080 |
| gttggaaaca | gttagttggc | tgtcagaggg | atttcattgt | aaaccccaag | tatggtaaga | 1140 |
| agaaaaaggt | gcagaagaag | tctaagccta | caataatcct | cgccaactcg | gatgaagatt | 1200 |
| ggatgaagga | aatgactcca | gggcagctgg | agtatttcga | ggcaaactgc | gtcatttaca | 1260 |
| ttatgtcgcc | gggggagaag | tggtattctc | cccctgtgct | tcctcctacg | gaggaagtgt | 1320 |
| aattcatata | gatcttgatt | tttcgatgtt | ctgcccgccg | agcaccaccc | ttagccgccc | 1380 |
| gccgactacc | cccctgtatt | gtttgcgtgt | gtttttcgt | gccatcgcac | gacatattaa | 1440 |
| tgtaagcttt | cagcattcat | caaatataat | aaaacgggag | ttttattca | ttactggttg | 1500 |
| ccaacactct | taaagtacag | acgggtctgc | ccatgggcag | taaaagtaag | gccattgcct | 1560 |
| ggggcaatga | ccatgtacag | agctcctctc | tggatggcac | caactcctcc | gtccgttaca | 1620 |
| ttcttccact | gcgttctcac | tcccaaccca | ctcgtgaact | tgtggaagta | gatgttgcgc | 1680 |
| ttgcaaggct | tccaacttgt | attcgaggga | gggatatccg | aaccaatccg | accgtcggtc | 1740 |
| tccatgttga | acaaccatcg | ccgtttcacc | acgaagcgat | gacacagctc | ccggctcact | 1800 |
| ttccatgtgg | ccggccacgc | ttttagcgtg | tcagggtagg | caaatatagt | ttgcggggtc | 1860 |
| ggagcttgtc | cgccgggagt | ggtgtcatac | accagccaca | ttacaccggt | tccggtgttg | 1920 |
| gagtagcggc | aggcagccgc | gtcggcaacg | aagtggtagt | cgacggcgat | cttgtacgtc | 1980 |
| agagtctcgc | tggtgtggcg | gttgcccctcg | tcagatcctc | gggcataggt | gttgatgagg | 2040 |
| tcacatactc | ctccggatgg | gacagttatc | atggtggtcc | cagcatgctg | gagtgtctgg | 2100 |
| atttggaggg | atggcctatc | ggccttgctt | ccagccctct | tcagcccagc | tgaagatggc | 2160 |
| ttcttcttag | gcacccgctt | attccaattc | gaatcatctc | cccgcttcct | cttggacgtg | 2220 |

```
gacatggctg attgcttatc ccgtgcctgg aacaaatggc ccgggattgc cctgacttgg    2280
tggtgaaggt agattaggga tagggttgct cctatccaca gcttgtccac caaatatcag    2340
ctcctccgtg gatctgcctt gtcgagcctt cagaactaag ataaggtctc tcagcaccca    2400
aaggtaaagc aggtaaaagc aaatcaatgc aacaaagctc aaaatagcta cctcgcctac    2460
gcgactccac ggcactcctc cggatgtcgg agctgctgtg ggtacccgcg gctgataata    2520
cagggcgttc tgtggatcca tgaatgaatc gcacttgtta ggcaatttat agtgcccggg    2580
accggtttct ttagattggg ctgctttaga taaatcatac aaagcagaac caggctttaa    2640
atcaaagcgc tcggtcccta ccgggccctc gcaggaaaag aaggcgcggt              2690

<210> SEQ ID NO 62
<211> LENGTH: 246
<212> TYPE: DNA
<213> ORGANISM: Artificial Sequence
<220> FEATURE:
<223> OTHER INFORMATION: MSV AC1_Target gene DNA
      region_complement_reverse
<220> FEATURE:
<221> NAME/KEY: misc_feature
<222> LOCATION: (1)..(246)
<223> OTHER INFORMATION: MSV AC1_Target gene DNA
      region_complement_reverse

<400> SEQUENCE: 62
agagctcccc tttgattggt ccacaaaatt gcagtatttt gaatactctg caaataagct     60
ttttcctgag attcaggaag agttcaccaa tcctcatcca ccctcctcac ctgatttact    120
ttgtaatgag tcaatcaacg attggctcca gcctaacatc ttccaggtta gtcccgaagc    180
ttacatgctc cttcaaccta cctgttatac cctcgaggat gcaatttctg acctccaatg    240
gatgga                                                              246

<210> SEQ ID NO 63
<211> LENGTH: 663
<212> TYPE: DNA
<213> ORGANISM: Artificial Sequence
<220> FEATURE:
<223> OTHER INFORMATION: MSV AC1_Hairpin sequence
<220> FEATURE:
<221> NAME/KEY: misc_feature
<222> LOCATION: (1)..(663)
<223> OTHER INFORMATION: MSV AC1_Hairpin sequence

<400> SEQUENCE: 63
aagcttgcat gcaggcctct gcagtcgacg ggcccgggat ccgattgatc actagtagag     60
ttctcctttg attgtttata aaattgtagt attttgaata tttgtaaat aagttttttt    120 ttgagattta ggaagagttt attaattttt atttattttt tttatttgat ttattttgga   180
atgagttaat taatgattgg ttttagttta atattttta ggttagttct gaagtttata    240
tgttttttta atttatttgt tatattttg aggatgtaat ttctgatctc taatggatgg    300
atgatcaaaa tccgatttcc atccattgga ggtcagaaat ccatccattg gaggtcagaa   360
atccatccat tggaggtcag aaattgcatc ctcgagggta taacaggtag gttgaaggag    420
catgtaagct tcgggactaa cctggaagat gttaggctgg agccaatcgt tgattgactc    480
attacaaagt aaatcaggtg aggagggtgg atgaggattg gtgaactctt cctgaatctc   540
aggaaaaagc ttatttgcag agtattcaaa atactgcaat tttgtggacc aatcaaaggg    600
gagctctaat ctagatgcat tcgcgaggta ccgagctcga attcactggc cgtcgtttta    660
caa                                                                 663
```

<210> SEQ ID NO 64
<211> LENGTH: 2690
<212> TYPE: RNA
<213> ORGANISM: Maize streak virus
<220> FEATURE:
<221> NAME/KEY: misc_feature
<222> LOCATION: (1)..(2690)
<223> OTHER INFORMATION: AC1 RNA

<400> SEQUENCE: 64

```
accgcgccuu cuuuuccugc gagggcccgg uagggaccga gcgcuuugau uuaaagccug     60
guucugcuuu guaugauuua ucuaaagcag cccaaucuaa agaaaccggu cccgggcacu    120
auaaauugcc uaacaagugc gauucauuca uggauccaca gaacgcccug uauuaucagc    180
cgcggguacc cacagcagcu ccgacauccg gaggagugcc guggagucgc guaggcgagg    240
uagcuauuuu gagcuuuguu gcauugauuu gcuuuuaccu gcuuuaccuu ugggugcuga    300
gagaccuuau cuuaguucug aaggcucgac aaggcagauc cacggaggag cugauauuug    360
guggacaagc uguggauagg agcaacccua ucccuaaucu accuucacca ccaagucagg    420
gcaaucccgg gccauuuguu ccaggcacgg gauaagcaau cagccauguc cacguccaag    480
aggaagcggg gagaugauuc gaauuggaau aagcgggugc cuaagaagaa gccaucuuca    540
gcugggcuga agagggcugg aagcaaggcc gauaggccau cccuccaaau ccagacacuc    600
cagcaugcug ggaccaccau gauaacuguc ccauccggag gaguauguga ccucaucaac    660
accuaugccc gaggaucuga cgagggcaac cgccacacca gcgagacucu gacguacaag    720
aucgccgucg acuaccacuu cguugccgac gcggcugccu gccgcuacuc caacaccgga    780
accgguguaa uguggcuggu guaugacacc acucccggcg gacaagcucc gaccccgcaa    840
acuauauuug ccuacccuga cacgcuaaaa gcguggccgg ccacauggaa agugagccgg    900
gagcuguguc aucgcuucgu ggugaaacgg cgaugguugu ucaacaugga gaccgacggu    960
cggauugguu cggauauccc ucccucgaau acaaguugga agccuugcaa gcgcaacauc   1020
uacuuccaca aguucacgag uggguuggga gugagaacgc aguggaagaa uguaacggac   1080
ggaggaguug gugccaucca gagaggagcu cuguacaugg ucauugcccc aggcaauggc   1140
cuuacuuuua cugcccaugg gcagacccgu cuguacuuua agaguguugg caaccaguaa   1200
ugaauaaaaa cucccguuuu auuauauuug augaaugcug aaagcuuaca uuaauauguc   1260
gugcgauggc acgaaaaaac acacgcaaac aauacagggg gguagucggc gggcggcuaa   1320
gggugguguc cggcgggcag aacaucgaaa aaucaagauc uauaugaauu acacuuccuc   1380
cguaggagga agcacagggg gagaauacca cuucuccccc ggcgacauaa uguaaaugac   1440
gcaguuugcc ucgaaauacu ccagcugccc uggagucauu ucccuucauc aaucuucauc   1500
cgaguuggcg aggauuauug uaggcuuaga cuucuucugc accuuuuucu ucuuaccaua   1560 cuuggggguuu acaaugaaau cccucugaca gccaacuaac uguuuccaac aaggacagaa   1620
uuuaaacgga auaucaucua cgauguugua gauugcgucu ucguuguaug aagaccaauc   1680
aacauuauuu ugccaguaau uaugaacccc uaggcuucug gcccaaguag auuuuccggu   1740
ucuuguuggg ccgacgaugu agaggcucug cuuucuugau cuuucaucug augacuggau   1800
acagaaucca uccauuggag gucagaaauu gcauccucga ggguauaaca gguagguuga   1860
aggagcaugu aagcuucggg acuaaccugg aagauguuag gcuggagcca aucguugauu   1920
gacucauuac aaaguaaauc aggugaggag gguggaugag gauuggugaa cucuuccuga   1980
aucucaggaa aaagcuuauu ugcagaguau ucaaaauacu gcaauuuugu ggaccaauca   2040
```

```
aaggggagcu cuuucuggau cauggagagg uacucuucuu uggagguagc gugugaaaua    2100
augucucgca uuauuucauc uuuagaaggc uuuuuuuccu uuaccucuga aucagauuuu    2160
ccuaggaagg gggacuuccu aggaaugaaa guaccucucu caaacacagc cagagguucc    2220
uugagaaugu aauccucac ucuguuaacu gacuggcac ucugaauauu ugggugaaac     2280
ccauuuauau caagaaccu ugagucagau auccuuaucg gcuucucugg cugaagcaau    2340
gcauguaaau gcaaacuucc aucuuuaugu gccucucggg cacauagaau auauuuggga    2400
auccaacgaa cgacgagcuc ccagaucauc ugacaggcga uucaggauu uucuggacac    2460 uuuggauagg uuaggaacgu guuagcguuc cugugugaga acugacgguu ggaugaggag    2520
gaggccauag ccgacgacgg agguugaggc ugggauggg cagacuggga gcuccaaacu    2580
cuauaguaua cccgugcgcc uucgaaaucc gccgcuccau ugucuuauag gguuguaaa    2640 ugggccggac cgggccggcc cagcaggaaa agaaggcgcg cacuaauauu              2690
```

<210> SEQ ID NO 65
<211> LENGTH: 246
<212> TYPE: RNA
<213> ORGANISM: Artificial Sequence
<220> FEATURE:
<223> OTHER INFORMATION: MSV AC1_Target gene DNA region_RNA
<220> FEATURE:
<221> NAME/KEY: misc_feature
<222> LOCATION: (1)..(246)
<223> OTHER INFORMATION: MSV AC1_Target gene DNA region_RNA

<400> SEQUENCE: 65

```
uccauccauu ggaggucaga aauugcaucc ucgagggauu aacagguagg uugaaggagc     60
auguaagcuu cgggacuaac cuggaagaug uuaggcugga gccaaucguu gauugacuca    120
uuacaaagua aaucaggua ggagggugga ugaggauugg ugaacucuuc cugaaucuca    180
ggaaaaagcu uauuugcaga guauucaaaa uacugcaauu uuguggacca aucaaggggg    240
agcucu                                                                246
```

<210> SEQ ID NO 66
<211> LENGTH: 246
<212> TYPE: RNA
<213> ORGANISM: Artificial Sequence
<220> FEATURE:
<223> OTHER INFORMATION: MSV AC1_Target gene DNA region_modified_RNA
<220> FEATURE:
<221> NAME/KEY: misc_feature
<222> LOCATION: (1)..(246)
<223> OTHER INFORMATION: MSV AC1_Target gene DNA region_modified_RNA

<400> SEQUENCE: 66
uuuauuuauu ggagguuaga aauuguauuu uugaggguau aauagguagg uugaaggagu 60
auguaaguuu ugggauuaau uuggaagaug uuagguugga guuaauuguu gauugauuua 120
uuauaaagua aauuagguga ggagggugga ugaggauugg ugaauuuuuu uugaauuuua 180
ggaaaaaguu uauuuguaga guauuuaaaa uauuguaauu uuguggauua auuaaagggg 240
aguuuu 246

<210> SEQ ID NO 67
<211> LENGTH: 2690
<212> TYPE: RNA
<213> ORGANISM: Maize streak virus
<220> FEATURE:
<221> NAME/KEY: misc_feature
<222> LOCATION: (1)..(2690)
<223> OTHER INFORMATION: AC1 RNA

<400> SEQUENCE: 67

```
uggcgcggaa gaaaaggacg cucccgggcc aucccuggcu cgcgaaacua aauuucggac      60
caagacgaaa cauacuaaau agauuucguc ggguuagauu ucuuuggcca gggcccguga     120
uauuuaacgg auuguucacg cuaaguaagu accaggugu  cuugcgggac auaauagucg     180
gcgcccaugg gugucgucga ggcuguaggc cuccucagcg caccucagcg cauccgcucc     240
aucgauaaaa cucgaaacaa cguaacuaaa cgaaaaugga cgaaauggaa acccacgacu     300
cucuggaaua gaaucaagac uuccgagcug uuccgucuag gugccuccuc gacuauaaac     360
caccuguucg acaccuaucc ucguuggau  agggauuaga uggaaguggu gguucagucc     420
cguuagggcc cgguaaacaa gguccgugcc cuauucguua gucggacag  gugcagguuc     480
uccuucgccc cucuacuaag cuuaaccuua uucgcccacg gauucuucuu cgguagaagu     540
cgacccgacu ucucccgacc uucguuccgg cuaccggua  gggagguuua ggucugugag     600
gucguacgac ccuggguggua cuaugacag  gguaggccuc cucauacacu ggaguaguug     660
uggauacggg cuccuagacu gcucccguug gcggugug   cgcucugaga cugcauguuc     720
uagcggcagc ugaugugaa  gcaacggcug cgccgacgga cggcgaugag guuguggccu     780
uggccacauu acaccgacca cauacugug  ugagggccgc cuguucgagg cuggggcguu     840
ugauauaaac ggaugggacu gugcgauuuu cgcaccggcc gguguaccuu cacucggcc      900
cucgacacag uagcgaagca ccacuuugcc gcuaccaaca aguuguaccu cuggcugcca     960
gccuaaccaa gccauaggg  agggagcuua uguucaaccu ucggaacguu cgcguuuag    1020
augaaggugu ucaagugcuc acccaacccu cacucuugcg ucaccuucuu acauugccug    1080
ccuccucaac cacgguaggu cucuccucga gacauguacc aguaacgggg uccguuaccg    1140
gaaugaaaau gacggguacc cgucugggca gacaugaaau ucucacaacc guuggucauu    1200
acuuauuuuu gagggcaaaa uaauauaaac uacuuacgac uuucgaaugu aauuauacag    1260
cacgcuaccg ugcuuuuuug ugugcguuug uuaugucccc ccaucagccg cccgccgauu    1320
cccaccacga gccgcccguc uuguagcuuu uuaguucuag auauacuuaa ugugaaggag    1380
gcauccuccu ucgugucccc cucuuauggu gaagaggggg ccgcuguauu acauuuacug    1440
cgucaaacgg agcuuuauga ggucgacggg accucaguaa aggaaguagg uuagaaguag    1500
gcucaaccgc uccuaauaac auccgaaucu gaagaagacg uggaaaaaga agaaugguau    1560
gaaccccaaa uguuacuuua gggagacugu cgguugauug acaagguug  uuccugucuu    1620
aaauuugccu uauaguagau gcuacaacau cuaacgcaga agcaacauac uucugguuag    1680
uuguaauaaa acggucauua auacuugggg auccgaagac cggguucauc uaaaaggcca    1740
agaacaaccc ggcugcuaca ucuccgagac gaaagaacua gaaaguagac uacugaccua    1800
ugucuuaggu agguaaccuc cagucuuuaa cguaggagcu cccauauugu ccauccaacu    1860
uccucguaca uucgaagccc ugauuggacc uucuacaauc gaccucggu  uagcaacuaa    1920
cugaguaaug uuucauuuag uccacuccuc ccaccuacuc cuaaccacuu gagaaggacu    1980
uagaguccuu uuucgaauaa acgucucaua aguuuauga  cguuaaaaca ccugguuagu    2040
uccccucga  gaaagaccua guaccucucc augagaagaa accuccaucg cacacuuuau    2100
uacagagcgu aauaaaguag aaaucuuccg aaaaaaagga aauggagacu uagucuaaaa    2160
ggauccuucc cccugaagga uccuuacuuu cauggagaga guuugugucg gucuccaagg    2220
aacucuacua uuagggagug agacaauuga cugaaccgug agacuuauaa acccacuuug    2280
gguaaauaua guuucuugga acucagucua uaggaauagc cgaagagacc gacuucguua    2340
```

```
cguacauuua cguuugaagg uagaaauaca cggagagccc guguaucuua uauaaacccu    2400
uagguugcuu gcugcucgag ggucuaguag acguccgcu aaaguccuaa aagaccugug    2460
aaaccuaucc aauccuugca caaucgcaag gacacacucu ugacugccaa ccuacuccuc    2520
cuccgguauc ggcugcugcc uccaacuccg acucccuacc gucugacccu cgagguuuga    2580
gauaucauau gggcacgcgg aagcuuuagg cggcgaggua acagaauauc accaacauuu    2640
acccggccug gcccggccgg gucguccuuu ucuuccgcgc gugauuauaa              2690
```

```
<210> SEQ ID NO 68
<211> LENGTH: 246
<212> TYPE: RNA
<213> ORGANISM: Artificial Sequence
<220> FEATURE:
<223> OTHER INFORMATION: MSV AC1_Target gene DNA region_complement_RNA
<220> FEATURE:
<221> NAME/KEY: misc_feature
<222> LOCATION: (1)..(246)
<223> OTHER INFORMATION: MSV AC1_Target gene DNA region_complement_RNA

<400> SEQUENCE: 68
```

```
agguagguaa ccuccagucu uuaacguagg agcucccaua uugccauccc aacuuccucg     60
uacauucgaa gcccugauug gaccuucuac aauccgaccu cgguuagcaa cuaacugagu    120
aauguuucau uuaguccacu ccucccaccu acuccuaacc acuugagaag gacuuagagu    180
ccuuuuucga auaaacgucu cauaaguuuu ugacguuaa aacaccuggu uaguuucccc    240
ucgaga                                                               246
```

```
<210> SEQ ID NO 69
<211> LENGTH: 2690
<212> TYPE: RNA
<213> ORGANISM: Maize streak virus
<220> FEATURE:
<221> NAME/KEY: misc_feature
<222> LOCATION: (1)..(2690)
<223> OTHER INFORMATION: AC1 RNA

<400> SEQUENCE: 69
```

```
uuauaaucac gcgcggaaga aaaggacgac ccggccgggc caggccgggu aaauguuggu     60
gauauucugu uaccucgccg ccuaaagcuu ccgcgugccc auaugauauc ucaaaccucg    120
agggucagac gguagggagu cggaguugga ggcagcagcc gauaccggag gaggaguagg    180
uuggcaguca agagugguc cuugcgauug ugcaaggauu ggauaggguu cacaggucuu    240
uuaggacuuu agcggacagu cuacuagacc cucgagcagc aagcaaccua aggguuuaua    300
uaagauacac gggcucuccg uguauucua ccuucaaacg uaaauguacg uaacgaaguc    360
ggucucuucg gcuauuccua uagacugagu uccagaaaac uauauuuacc caagugggu    420 uuauaagucu cacgguucag ucaauugucu cacucccuaa uguaagaguu ccuuggagac    480
cgacacaaac ucucuccaug aaaguaagga uccuucaggg ggaaggaucc uuuuagacua    540
agucuccauu uccuuuuuuu cggaagauuu cuacuuuauu acgcucugua auaaagugug    600
cgauggaggu uucuucucau ggagagguac uaggucuuuc ucgagggaa acuaaccagg    660 uguuuaacg ucauaaaacu uaugagacgu uauucgaaa aaggacucua aguccuucuc    720
aagugguuag gaguagguggu gaggaguggg cuaaaugaaa cauucucag uuaguugcua    780 accgaggucg gauuguagaa gguccaauca gggcucgaa uguacgagga aguggauggg    840
acaauauggg agcccuacg uuaaagacug gagguuaccu accuaagaca uaggucagua    900
gucuacuuuc uaguucuuuc gucucggaga uguagcagcc gggguguucu uggccuuuua    960
```

```
gaugaacccg gucuucggau ccccaaguau uaaugaccgu uuuauuacaa cuaaccagaa   1020
guauguugcu ucugcguuag auguuguagc aucuacuaua aggcaaauuu aagacaggaa   1080
caaccuuugu caaucaaccg acagucuccc uaaaguaaca uuuggggguuc auaccauucu   1140 ucuuuuucca cgucuucuuc agauucggau guuauuagga gcgguugagc cuacuucuaa   1200
ccuacuuccu uuacugaggu cccgucgacc ucauaaagcu ccguuugacg caguaaaugu   1260
aauacagcgg cccccucuuc accauaagag ggggacacga aggaggaugc cuccuucaca   1320
uuaaguauau cuagaacuaa aaagcuacaa gacgggcggc ucgugguggg aaucggcggg   1380
cggcugaugg ggggacauaa caaacgcaca caaaaaagca cgguagcgug cuguauaauu   1440
acauucgaaa gucguaagua guuuauauua uuuugcccuc aaaaauaagu aaugaccaac   1500
gguugugaga auuucauguc ugcccagacg gguacccguc auuuucauuc cgguaacgga   1560
ccccguuacu gguacauguc ucgaggagag accuaccgug guugaggagg caggcaaugu   1620
aagaagguga cgcaagagug aggguugggu gagcacuuga acaccuucau cuacaacgcg   1680
aacguuccga agguugaaca uaagcucccu cccuauaggc uugguuaggc uggcagccag   1740
agguacaacu uguugguagc ggcaaagugg ugcuucgcua cugugucgag ggccgaguga   1800
aagguacacc ggccggugcg aaaaucgcac agucccaucc guuuauauca aacgccccag   1860
ccucgaacag gcggcccuca ccacaguaug uggucggugu aauguggcca aggccacaac   1920
cucaucgccg uccgucggcg cagccguugc uucaccauca gcugccgcua gaacaugcag   1980
ucucagagcg accacaccgc caacgggagc agucuaggag cccguaucca caacuacucc   2040
aguguaugag gaggccuacc cugucaauag uaccaccagg gucguacgac cucacagacc   2100
uaaaccuccc uaccggauag ccggaacgaa ggucgggaga agucgggucg acuucuaccg   2160
aagaagaauc cgugggcgaa uaagguuaag cuuaguagag gggcgaagga gaaccugcac   2220
cuguaccgac uaacgaauag ggcacggacc uuguuuaccg ggcccuaacg ggacugaacc   2280
accacuucca ucuaaucccu aucccaacga ggauaggugu cgaacaggug guuuauaguc   2340
gaggaggcac cuagacggaa cagcucggaa gucuugauuc uauuccagag agucgugggu   2400
uuccauuucg uccauuuucg uuuaguuacg uuguuucgag uuuuaucgau ggagcggaug   2460
cgcugaggug ccgugaggag gccuacagcc ucgacgacac ccaugggcgc cgacuauuau   2520
gucccgcaag acaccuaggu acuuacuuag cgugaacaau ccguuaaaua ucacgggccc   2580
uggccaaaga aaucuaaccc gacgaaaucu auuuaguaug uuucgucuug guccgaaauu   2640
uaguuucgcg agccagggau ggcccgggag cguccuuuuc uuccgcgcca              2690
```

<210> SEQ ID NO 70
<211> LENGTH: 246
<212> TYPE: RNA
<213> ORGANISM: Artificial Sequence
<220> FEATURE:
<223> OTHER INFORMATION: MSV AC1_Target gene DNA region_reverse_RNA
<220> FEATURE:
<221> NAME/KEY: misc_feature
<222> LOCATION: (1)..(246)
<223> OTHER INFORMATION: MSV AC1_Target gene DNA region_reverse_RNA

<400> SEQUENCE: 70

```
ucucgagggg aaacuaacca gguguuuuaa cgucauaaaa cuuaugagac guuuauucga     60
aaaaggacuc uaaguccuuc ucaagugguu aggaguaggu gggaggagug gacuaaauga    120
aacauuacuc aguuaguugc uaaccgaggu cggauuguag aagguccaau cagggcuucg    180
aauguacgag gaaguuggau ggacaauaug ggagcuccua cguuaaagac uggagguuac    240
``` cuaccu 246

<210> SEQ ID NO 71
<211> LENGTH: 246
<212> TYPE: RNA
<213> ORGANISM: Artificial Sequence
<220> FEATURE:
<223> OTHER INFORMATION: MSV AC1_Target gene DNA region_modified_reverse_RNA
<220> FEATURE:
<221> NAME/KEY: misc_feature
<222> LOCATION: (1)..(246)
<223> OTHER INFORMATION: MSV AC1_Target gene DNA region_modified_reverse_RNA

<400> SEQUENCE: 71
uuuugagggg aaauuaauua gguguuuuaa uguuauaaaa uuuaugagau guuuauuuga 60
aaaaggauuu uaaguuuuuu uuaagugguu aggaguaggu gggaggagug gauuaaauga 120
aauauuauuu aguuaguugu uaauugaggu uggauuguag aagguuuaau uaggguuuug 180
aauguaugag gaaguuggau ggauaauaug ggaguuuuua uguuaaagau uggagguuau 240
uuauuu 246

<210> SEQ ID NO 72
<211> LENGTH: 2690
<212> TYPE: RNA
<213> ORGANISM: Maize streak virus
<220> FEATURE:
<221> NAME/KEY: misc_feature
<222> LOCATION: (1)..(2690)
<223> OTHER INFORMATION: AC1 RNA

<400> SEQUENCE: 72
aauauuagug cgcgccuucu uuuccugcug ggccggcccg guccggccca uuuacaacca 60
cuauaagaca auggagcggc ggauuucgaa ggcgcacggg uauacuauag aguuuggagc 120
ucccagucug ccaucccuca gccucaaccu ccgucgucgg cuauggccuc cuccucaucc 180
aaccgucagu ucucacacag gaacgcuaac acguuccuaa ccuauccaaa guguccagaa 240
aauccugaaa ucgccuguca gaugaucugg gagcucgucg uucguuggau ucccaaauau 300
auucuaugug cccgagaggc acauaaagau ggaaguuugc auuuacaugc auugcuucag 360
ccagagaagc cgauaaggau aucugacuca agguucuuug auauaaaugg guuucaccca 420
aauauucaga gugccaaguc aguuaacaga gugagggauu acauucucaa ggaaccucug 480
gcuguguuug agagagguac uuucauuccu aggaaguccc ccuuccuagg aaaaucugau 540
ucagagguaa aggaaaaaaa gccuucuaaa gaugaaauaa ugcgagacau uauuucacac 600
gcuaccucca aagaagagua ccucuccaug auccagaaag agcuccccuu ugauugggcc 660
acaaaauugc aguauuuuga auacucugca aauaagcuuu uuccugagau ucaggaagag 720
uucaccaauc cucauccacc cuccucaccu gauuuacuuu guaaugaguc aaucaacgau 780
uggcuccagc cuaacaucuu ccagguuagu cccgaagcuu acaugcuccu ucaaccuacc 840
uguuauaccc ucgaggaugc aauuucugac cuccaaugga uggauucugu auccagucau 900
cagaugaaag aucaagaaag cagagccucu acaucgucgg cccaacaaga accggaaaau 960
cuacuugggc cagaagccua gggguucaua auuacuggca aaauaauguu gauuggucuu 1020
cauacaacga agacgcaauc uacaacaucg uagaugauau uccguuuaaa uucuguccuu 1080
guuggaaaca guuaguuggc ugucagaggg auuucauugu aaaccccaag uaugguaaga 1140
agaaaaaggu gcagaagaag ucuaagccua caauaaaccu cgccaacucg gaugaagauu 1200

```
ggaugaagga aaugacucca gggcagcugg aguauuucga ggcaaacugc gucauuuaca    1260
uuaugucgcc gggggagaag ugguauucuc ccccugugcu uccuccuacg gaggaagugu    1320
aauucauaua gaucuugauu uuucgauguu cugcccgccg agcaccaccc uuagccgccc    1380
gccgacuacc ccccuguauu guuugcgugu guuuuuucgu gccaucgcac gacauauuaa    1440
uguaagcuuu cagcauucau caaauauaau aaaacgggag uuuuuauuca uuacugguug    1500
ccaacacucu uaaaguacag acgggucugc ccaugggcag uaaaaguaag gccauugccu    1560
ggggcaauga ccauguacag agcuccucuc uggauggcac caacuccucc guccguuaca    1620
uucuuccacu gcguucucac ucccaaccca cucgugaacu gauggaagua gauguugcgc    1680
uugcaaggcu uccaacuugu auucgaggga gggauauccg aaccaauccg accgucgguc    1740
uccauguuga acaaccaucg ccguuucacc acgaagcgau gacacagcuc ccggcucacu    1800
uuccaugugg ccggccacgc uuuuagcgug ucagguagg caaauauagu uugcgggguc    1860
ggagcuuguc cgccgggagu gguguagaac accagccaca uuacaccggu uccggugcug    1920
gaguagcggc aggcagccgc gucggcaacg aaguggcagu cgacggcgau cuugacguc    1980 agagucucgc uggcuguggcg guugcccucg ucagcauccuc gggcauaggu guugaugagg    2040
ucacauacuc uccggaaugg gacaguuauc augguggucc cagcaugcug gagugucugg    2100
auuuggaggg augccauauc ggccuugcuu ccagcccucu ucagcccagc ugaagauggc    2160
uucuucuuag gcacccgcuu auuccaauuc gaaucauacuc cccgcuuccu cuuggacgug    2220
gacauggcug auugcuuauc ccgugccugg aacaaauggc ccgggauugc ccugacuugg    2280
uggugaaggu agauuaggga uaggguugcu ccuauccaca gcuuguccac caaauaucag    2340
cuccuccgug gaucugccuu gucgagccuu cagaacuaag auaaggucuc ucagcaccca    2400
aagguaaagc agguaaaagc aaaucaaugc aacaaagcuc aaaauagcua ccucgccuac    2460
gcgacuccac ggcacucuc cggaugucgag agcugcugug gguacccgcg gcugauaaua    2520
cagggcguuc uguggaucca ugaaugaauc gcacuuguua ggcaauuuau agugcccggg    2580
accgguuucu uuagauuggg cugcuuuaga uaaaucauac aaagcagaac caggcuuuaa    2640
aucaaagcgc ucggucccua ccgggcccuc gcaggaaaag aaggcgcggu             2690
```

<210> SEQ ID NO 73
<211> LENGTH: 246
<212> TYPE: RNA
<213> ORGANISM: Artificial Sequence
<220> FEATURE:
<223> OTHER INFORMATION: MSV AC1_Target gene DNA
      region_complement_reverse_RNA
<220> FEATURE:
<221> NAME/KEY: misc_feature
<222> LOCATION: (1)..(246)
<223> OTHER INFORMATION: MSV AC1_Target gene DNA
      region_complement_reverse_RNA

<400> SEQUENCE: 73

```
agguagguaa ccuccagucu uuaacguagg agcucccaua uuguccaucc aacuuccucg     60
uacauucgaa gcccugauug gaccuucuac aauccgaccu cgguuagcaa cuaacugagu    120
aauguuucau uuaguccacu ccucccaccu acuccuaacc acuugagaag gacuuagagu    180
ccuuuuucga auaacgcucu cauaaguuuu augacguuaa aacaccuggu uaguuucccc    240
ucgaga                                                              246
```

<210> SEQ ID NO 74
<211> LENGTH: 663

```
<212> TYPE: RNA
<213> ORGANISM: Artificial Sequence
<220> FEATURE:
<223> OTHER INFORMATION: MSV AC1_Hairpin sequence_RNA
<220> FEATURE:
<221> NAME/KEY: misc_feature
<222> LOCATION: (1)..(663)
<223> OTHER INFORMATION: MSV AC1_Hairpin sequence_RNA
<400> SEQUENCE: 74
aagcuugcau gcaggccucu gcagucgacg ggcccgggau ccgauugauc acuaguagag 60
uucuccuuug auuguuuaua aaauuguagu auuuugaaua uuuuguaaau aaguuuuuuu 120
uugagauuua ggaagaguuu auuaauuuuu auuuauuuuu uuuauuugau uuauuuugga 180
augaguuaau uaaugauugg uuuuaguuua auauuuuuua gguuaguucu gaaguuuaua 240
uguuuuuuua auuuauuugu uauauuuuug aggauguaau uucugaucuc uaauggaugg 300
augaucaaaa uccgauuucc auccauugga ggucagaaau ccauccauug gaggucagaa 360
auccauccau uggaggucag aaauugcauc cucgagggua uaacagguag guugaaggag 420
cauguaagcu ucgggacuaa ccuggaagau guuaggcugg agccaaucgu ugauugacuc 480
auuacaaagu aaaucaggug aggagggugg augaggauug gugaacucuu ccugaaucuc 540
aggaaaaagc uuauuugcag aguauucaaa auacugcaau uuuguggacc aaucaaaggg 600
gagcucuaau cuagaugcau ucgcgaggua ccgagcucga auucacuggc cgucguuuua 660
caa 663

<210> SEQ ID NO 75
<211> LENGTH: 384
<212> TYPE: DNA
<213> ORGANISM: Artificial Sequence
<220> FEATURE:
<223> OTHER INFORMATION: SACMV AC1_Hairpin sequence
<220> FEATURE:
<221> NAME/KEY: misc_feature
<222> LOCATION: (1)..(384)
<223> OTHER INFORMATION: SACMV AC1_Hairpin sequence
<400> SEQUENCE: 75
ctcgaaagaa gcggcattag atcaactccg acaactccaa accccaacaa ataaattgtt 60
catcaagatc tgcagagaac tccatgaaaa tggggaacct catttgcatg ccctcattca 120
gttcgagggc aagtacaatt gtaccaacca acgattcttc gacctcatat ccccttccag 180
gtcaatcgga tctgacctgg aagaggatat gaagtcgaag aatcattaat taatacaatt 240
atacttaccc tcaaactaaa taaaaacata caaataaaat tcccccattt tcataaaatt 300
ctctacaaat cttaataaac aatttattta ttaaaattta aaattatcaa aattaatcta 360
atgccacttc tttcgagact agtc 384

<210> SEQ ID NO 76
<211> LENGTH: 384
<212> TYPE: DNA
<213> ORGANISM: Artificial Sequence
<220> FEATURE:
<223> OTHER INFORMATION: SACMV AC1_Hairpin sequence
<220> FEATURE:
<221> NAME/KEY: misc_feature
<222> LOCATION: (1)..(384)
<223> OTHER INFORMATION: SACMV AC1_Hairpin sequence
<400> SEQUENCE: 76
ctcgaaagaa gcggcattag atcaactccg acaactccaa accccaacaa ataaattgtt 60
catcaagatc tgcagagaac tccatgaaaa tggggaacct catttgcatg ccctcattca 120
```

-continued

```
gttcgagggc aagtacaatt gtaccaacca acgattcttc gacctcatat ccccttccag    180
gtcaatcgga tctgacctgg aagaggatat gaagtcgaag aatcattaat taatacaatt    240
atacttaccc tcaaactaaa taaaaacata caaataaaat tcccccattt tcataaaatt    300
ctctacaaat cttaataaac aatttattta ttaaaattta aaattatcaa aattaatcta    360
atgccacttc tttcgagact agtc                                           384
```

The invention claimed is:

1. A method of constructing a plant expression construct comprising a plant expressible promoter operably linked to a DNA sequence encoding a mismatched long double-stranded RNA (ldsRNA) duplex, the method including the steps of:

(i) amplifying a DNA fragment of a target gene to produce an untreated fragment;

(ii) treating a fraction of the amplified DNA fragment of the target gene with a bisulphite mutagen to produce a treated fragment, thereby causing random chemical mutation of cytosine nucleotides to thymine nucleotides, thus creating a proportion of mismatched bases in the treated fragment compared with the untreated fragment;

(iii) conducting sense strand-specific PCR on the treated fragment from (ii);

(iv) conducting PCR on the untreated fragment from (i);

(v) ligating the PCR amplified dsDNA fragments from (iii) and (iv) in a head-to-head orientation such that the two ligated dsDNA fragments are adjacent and in an inverted orientation to each other with respect to their sense strands; and (vi) operably linking a plant-expressible promoter to the DNA sequence encoding a mismatched ldsRNA duplex of part (v).

2. The method according to claim 1, wherein there is an intervening hairpin loop-encoding sequence between the two ligated dsDNA fragments of (v).

3. The method according to claim 2, wherein the intervening hairpin loop-encoding sequence includes at least one restriction site.

4. The method according to claim 1, further including the step of cloning the construct encoding the ldsRNA duplex and inserting it into an expression cassette.

5. The method according to claim 1, wherein the proportion of mismatched bases in the treated fragment compared with the untreated fragment is one in every four to one in every ten nucleotides.

6. A method of silencing a target gene in a plant, the method including the steps of:

(i) constructing a construct according to the method of claim 1;

(ii) introducing an expression cassette including the construct into the plant; and (iii) causing the expression cassette to express a RNA sequence encoded by the construct which silences said target gene.

7. An isolated DNA polynucleotide encoding an ldsRNA duplex, constructed according to the method of claim 1, comprising a plant-expressible promoter operably linked to:

(i) an unmodified sequence of the antisense strand of the target gene or a part thereof; and (ii) a modified sequence of the sense strand of the target gene or the part thereof, wherein the modified sequence differs from the unmodified sequence in that random cytosine nucleotides in the target gene sequence or the part thereof have been modified to thymine nucleotides by bisulphite mutation;

wherein the modified sequence and the unmodified sequence are in a reverse orientation to each other, and wherein the RNA sequence transcribed from the DNA polynucleotide forms a duplex between the modified sense strand sequence of the target gene and the unmodified antisense strand sequence of the target gene so that a ldsRNA duplex forms between the modified and unmodified sequences with base pair mismatches where the nucleotides have been modified, the ldsRNA duplex being capable of inhibiting expression of the target gene, wherein the target gene is an AC1 or BC1 gene from South African cassava mosaic virus (SACMV), or an AC1 gene from maize streak virus (MSV).

8. The polynucleotide according to claim 7, wherein the proportion of nucleotide modifications is one in every four to one in every ten nucleotides.

9. The polynucleotide according to claim 7, which includes a further nucleotide sequence between the modified and unmodified sequences, the further nucleotide sequence forming a hairpin loop in the RNA sequence between the modified and unmodified sequences.

10. The polynucleotide according to claim 7, wherein the modified sequence comprises the nucleic acid sequence set forth in any one of SEQ ID NOs: 13, 16, 17, 18, 33, 34, 35, 38, 39 and 40.

11. The polynucleotide according to claim 7, wherein the modified sequence comprises the sequence set forth in SEQ ID NO: 21 or SEQ ID NO: 53.

12. The polynucleotide according to claim 7, wherein the modified sequence comprises a nucleic acid sequence at least 80% identical to any one of SEQ ID NOs: 13, 16, 17, 18, 33, 34, 35, 38, 39 and 40.

* * * * *